US009518222B2

(12) United States Patent
Goto et al.

(10) Patent No.: US 9,518,222 B2
(45) **Date of Patent: *Dec. 13, 2016**

(54) LIQUID CRYSTAL COMPOUND, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Mayumi Goto, Ichihara (JP); Hiroyuki Tanaka, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/820,229

(22) Filed: Aug. 6, 2015

(65) Prior Publication Data

US 2016/0046864 A1 Feb. 18, 2016

(30) Foreign Application Priority Data

Aug. 6, 2014 (JP) ................................ 2014-160662

(51) Int. Cl.

*C07C 43/225* (2006.01)
*C07D 213/30* (2006.01)

(Continued)

(52) U.S. Cl.

CPC ........... *C09K 19/322* (2013.01); *C07C 43/225* (2013.01); *C07C 255/54* (2013.01); *C07D 213/30* (2013.01);

(Continued)

(58) Field of Classification Search

CPC ... C09K 19/0446; C09K 19/322; C09K 19/54; C09K 2019/0411; C09K 2019/586; C09K 19/20; C09K 19/32; C09K 19/3066; C09K 19/3458; C09K 19/586; C09K 2019/0466; C09K 2019/323; C09K 2019/3422; C07D 213/30; C07D 309/06; C07D 319/06; C07D 239/26; C07D 239/34; C07D 493/08; C07C 43/202; C07C 43/225

See application file for complete search history.

(56) References Cited

U.S. PATENT DOCUMENTS 5,045,229 A 9/1991 Bartmann et al.
5,728,319 A 3/1998 Matsui et al.

(Continued)

FOREIGN PATENT DOCUMENTS

DE 4006921 A1 9/1990
JP H10204016 A 8/1998
WO 9611897 A1 4/1996

*Primary Examiner* — Shean C Wu
(74) *Attorney, Agent, or Firm* — Hogan Lovells US LLP

(57) ABSTRACT

To provide a liquid crystal compound satisfying at least one physical property such as high stability to light, a high clearing point, low minimum temperature of a liquid crystal phase, small viscosity, suitable optical anisotropy, large dielectric anisotropy, large dielectric constant in a minor-axis direction, suitable elastic constant, excellent compatibility, a liquid crystal composition containing the compound and a liquid crystal display device including the composition. The compound is represented by formula (1):

(1)

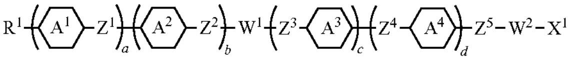

wherein, for example, $R^1$ is alkyl having 1 to 15 carbons, rings $A^1$ to $A^4$ are 1,4-cyclohexylene or 1,4-phenylene, at least one of $Z^1$ to $Z^5$ is —$CF_2O$—, and $X^1$ is fluorine or —$OCF_3$;

$W^1$ is a group represented by formula (1a) or (1b);

(1a)

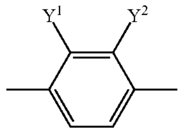

(1b)

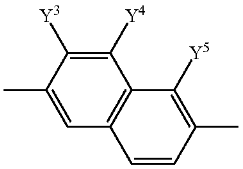

wherein, $Y^1$ to $Y^5$ are fluorine;

$W^2$ is a group represented by formula (1c) or (1d);

(1c)

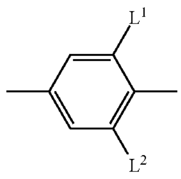

(Continued)

-continued

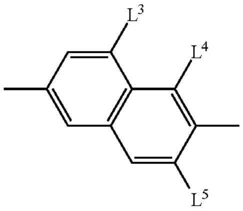

(1d)

wherein, $L^1$ to $L^5$ are fluorine; and a, b, c and d are independently 0 or 1.

15 Claims, No Drawings

(51) Int. Cl.

| | |
|---|---|
| ***C07D 309/06*** | (2006.01) |
| ***C07D 319/06*** | (2006.01) |
| ***C07D 239/26*** | (2006.01) |
| ***C09K 19/32*** | (2006.01) |
| ***C09K 19/34*** | (2006.01) |
| ***C09K 19/54*** | (2006.01) |
| ***C07D 493/08*** | (2006.01) |
| ***C07C 255/54*** | (2006.01) |
| ***C07D 239/34*** | (2006.01) |
| ***C09K 19/20*** | (2006.01) |
| ***C09K 19/30*** | (2006.01) |
| *C09K 19/04* | (2006.01) |

(52) U.S. Cl.

CPC ........... *C07D 239/26* (2013.01); *C07D 239/34* (2013.01); *C07D 309/06* (2013.01); *C07D 319/06* (2013.01); *C07D 493/08* (2013.01); *C09K 19/20* (2013.01); *C09K 19/3066* (2013.01); *C09K 19/32* (2013.01); *C09K 19/3458* (2013.01); *C09K 2019/0466* (2013.01); *C09K 2019/3009* (2013.01); *C09K 2019/3016* (2013.01); *C09K 2019/3025* (2013.01); *C09K 2019/323* (2013.01); *C09K 2019/3422* (2013.01)

(56) References Cited

U.S. PATENT DOCUMENTS

| | | | | |
|---|---|---|---|---|
| 6,007,740 | A | 12/1999 | Andou et al. | |
| 6,548,126 | B1 * | 4/2003 | Sasada et al. ......... | C09K 19/04 428/1.1 |
| 2015/0376502 | A1 * | 12/2015 | Tanaka et al. ..... | C09K 19/3402 252/299.63 |
| 2016/0090532 | A1 * | 3/2016 | Saito et al. ........ | C09K 19/3402 252/299.63 |

* cited by examiner

LIQUID CRYSTAL COMPOUND, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a compound having a difluoromethyleneoxy group, a liquid crystal composition containing the compound and having a nematic phase, and a liquid crystal display device including the composition.

The liquid crystal display device is widely utilized for a display of a personal computer, a television and so forth. The device utilizes optical anisotropy, dielectric anisotropy or the like of the liquid crystal compound. As an operating mode of the liquid crystal display device, a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode, a polymer sustained alignment (PSA) mode and so forth are known.

In such a liquid crystal display device, a liquid crystal composition having suitable physical properties is used. In order to further improve characteristics of the liquid crystal display device, the liquid crystal compound contained in the composition preferably has physical properties described in (1) to (9) below.

(1) High stability to heat, light and so forth, (2) a high clearing point, (3) a low minimum temperature of a liquid crystal phase, (4) small viscosity (η), (5) suitable optical anisotropy (Δn), (6) large dielectric anisotropy (Δ∈), (7) a suitable elastic constant (K), (8) excellent compatibility with other liquid crystal compounds, and (9) a large dielectric constant in a minor axis direction (∈⊥).

An effect of the physical properties of the liquid crystal compound on the characteristics of the device is described below. A compound having the high stability to heat, light and so forth as described in (1) increases a voltage holding ratio of the device. Therefore, a service life of the device becomes long. A compound having the high clearing point as described in (2) extends a temperature range in which the device can be used. A compound having the low minimum temperature of the liquid crystal phase such as a nematic phase or a smectic phase, particularly the low minimum temperature of the nematic phase as described in (3) also extends the temperature range in which the device can be used. A compound having the small viscosity as described in (4) shortens response time of the device.

A compound having the suitable optical anisotropy as described in (5) improves contrast of the device. A compound having a large optical anisotropy or a small optical anisotropy, more specifically, the suitable optical anisotropy is required according to a design of the device. A compound having the large optical anisotropy is suitable when the response time is shortened by decreasing a cell gap of the device. A compound having the large dielectric anisotropy as described in (6) decreases a threshold voltage of the device. Therefore, a power consumption of the device becomes small. On the other hand, a compound having a small dielectric anisotropy shortens the response time of the device by decreasing the viscosity of the composition.

With regard to (7), a compound having the large elastic constant shortens the response time of the device. A compound having a small elastic constant decreases the threshold voltage of the device. Accordingly, the suitable elastic constant is needed depending on the characteristics to be desirably improved. A compound having the excellent compatibility with other liquid crystal compounds as described in (8) is preferred. The reason is that the physical properties of the composition are adjusted by mixing compounds having different physical properties.

Further, an improvement of transmittance in the liquid crystal composition has been strongly required in connection with a demand for achieving a low power consumption and a high definition in the liquid crystal display device in recent years. Above all, the transmittance in the liquid crystal composition used for an FFS mode liquid crystal display device is known to be correlated with the dielectric constant (∈⊥) in the minor axis direction of the liquid crystal composition, and therefore a liquid crystal compound having the large dielectric constant in the minor axis direction as described in (9) is preferred.

A variety of liquid crystal compounds each having a $CF_20$ bonding group have so far been prepared as the compound having the large dielectric anisotropy, and some of the compounds have been practically used. However, in the above compounds, the dielectric constant in the minor axis direction is far from sufficiently large. Under such circumstances, desire has been expressed for development of a compound having excellent physical properties and a suitable balance regarding the physical properties (1) to (9) above, above all, a compound simultaneously having the large dielectric anisotropy (Δ∈) and the large dielectric constant in the minor axis direction.

CITATION LIST

Patent Literature

Patent literature No. 1: WO 1996/011897 A.
Patent literature No. 2: JP H10-204016 A.
Patent literature No. 3: DE 4006921 A.

SUMMARY OF INVENTION

Technical Problem

A first object of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds, and in particular, to provide a compound satisfying the large dielectric anisotropy and the large dielectric constant in the minor axis direction. A second object is to provide a composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in a minor axis direction and a suitable elastic constant. The object is to provide a liquid crystal composition having a suitable balance regarding at least two of the physical properties. A third object is to provide a liquid crystal display device including the composition and having a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition.

in formula (1), $W^2$ is a group represented by formula (1c) or formula (1d);

(1c)

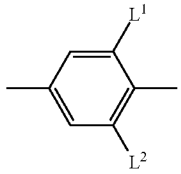

(1)

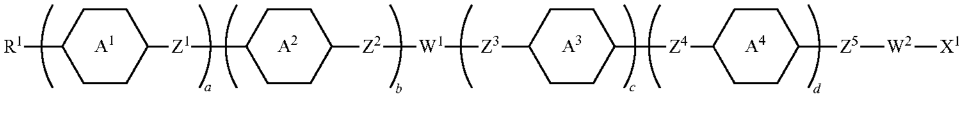

wherein, in formula (1), $R^1$ is alkyl having 1 to 15 carbons, and in the alkyl, at least one of —$CH_2$— may be replaced by —O— or —S—, at least one of —$(CH_2)_2$— may be replaced by —CH═CH—, and in the groups, at least one of hydrogen may be replaced by halogen;

ring $A^1$, ring $A^2$, ring $A^3$ and ring $A^4$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, chroman-2,6-diyl, 2,3-dihydro-1H-indene-2,5-diyl, naphthalene-2,6-diyl, decahydronaphthalene-2,6-diyl or 1,2,3,4-tetrahydronaphthalene2,6-diyl, and at least one of hydrogen directly bonded with the above rings may be replaced by halogen;

$W^1$ is a group represented by formula (1a) or formula (1b);

(1a)

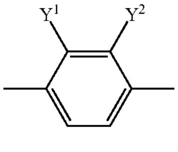

(1b)

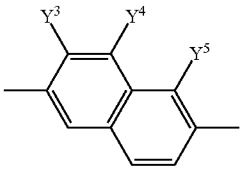

wherein, in formula (1a) and formula (1b), $Y^1$ and $Y^2$ are independently fluorine or chlorine, $Y^3$, $Y^4$ and $Y^5$ are independently hydrogen, fluorine or chlorine, and at least two of $Y^3$, $Y^4$ and $Y^5$ is fluorine or chlorine; and -continued (1d)

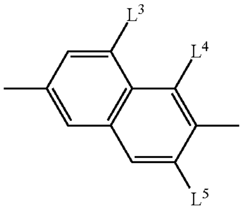

wherein, in formula (1c) and formula (1d), $L^1$, $L^2$, $L^3$, $L^4$ and $L^5$ are independently hydrogen, fluorine, or chlorine; and in formula (1), when $W^1$ is represented by formula (1a) and $W^2$ is represented by formula (1c), at least one of ring $A^1$, ring $A^2$, ring $A^3$ and ring $A^4$ is naphthalene-2,6-diyl in which at least one of hydrogen may be replaced by halogens;

$X^1$ is fluorine, —C≡N, —N═C═S, or alkyl having 1 to 10 carbons in which at least one of hydrogen is replaced by fluorine, alkenyl having 2 to 10 carbon in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;

a, b, c and d are independently 0 or 1, and a sum of a, b, c and d is 0, 1, 2 or 3;

$Z^1$, $Z^2$, $Z^3$, $Z^4$ and $Z^5$ are independently a single bond or alkylene having carbons 1 to 6, and in the alkylene, at least one of —$CH_2$— may be replaced by —O—, —S—, —CO—, or —$SiH_2$—, one or two of —$CH_2CH_2$— may be replaced by —CH═CH— or —C≡C—, and in the divalent groups, at least one of hydrogen may be replaced by fluorine or chlorine; and at least one of $Z^1$ in the case where a is 1, $Z^2$ in the case where b is 1, $Z^3$ in the case where c is 1, $Z^4$ in the case where d is 1, and $Z^5$ is —$CF_2O$—.

Advantageous Effects of Invention

A first advantage of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a suitable elastic constant and an excellent compatibility with other liquid crystal compounds, and in particular, a compound simultaneously having the large dielectric anisotropy and the large dielectric constant in a minor axis direction. A second advantage is provide a composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in a minor axis direction and a suitable elastic constant. A third advantage is to provide a liquid crystal display device including the composition and having a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase and a smectic phase, and also a compound having no liquid crystal phase but being added for adjusting physical properties such as a maximum temperature, a minimum temperature, viscosity and dielectric anisotropy. The compound has a six-membered ring such as 1,4-cyclohexylene and 1,4-phenylene, and rod-like molecular structure. A liquid crystal composition is prepared by mixing such liquid crystal compounds. A ratio (content) of the liquid crystal compounds is expressed in terms of weight percent (% by weight) based on the weight of the liquid crystal composition. An additive such as a polymerizable compound, a polymerization initiator, an optically active compound, an antioxidant, an ultraviolet light absorber, a light stabilizer, a heat stabilizer, an antifoaming agent and a dye is added to the liquid crystal composition, when necessary. A ratio (content) of the additive is expressed in terms of weight percent (% by weight) based on the weight of the liquid crystal composition in a manner similar to the ratio of the liquid crystal compound. Weight parts per million (ppm) may be occasionally used. A Liquid crystal display device is a generic term for a liquid crystal display panel and a liquid crystal display module. The liquid crystal compound, the liquid crystal composition and the liquid crystal display device may be occasionally abbreviated as "compound," "composition" and "device," respectively. A clearing point is a transition temperature between the liquid crystal phase and an isotropic phase in the liquid crystal compound. The minimum temperature of the liquid crystal phase is a transition temperature between a solid and the liquid crystal phase (the smectic phase, the nematic phase or the like) in the liquid crystal compound. A higher limit of a temperature range of the nematic phase is a transition temperature between the nematic phase and the isotropic phase in the liquid crystal composition, and may be occasionally abbreviated as "maximum temperature." A lower limit of the temperature range of the nematic phase may be occasionally abbreviated as "minimum temperature."

A compound represented by formula (1) may be occasionally abbreviated as "compound (1)." The abbreviation may also occasionally apply to a compound represented by formula (2) or the like. In formulas (1) to (15), a symbol such as $A^1$, $B^1$, C or the like surrounded by a hexagonal shape corresponds to ring $A^1$, ring $B^1$, ring $C^1$ or the like, respectively. A symbol of terminal group $R^{11}$ is used for a plurality of compounds. In the compounds, two groups represented by two of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule also applies to a symbol of any other terminal group, ring or the like. In formula (5), when i is 2, two of ring $C^1$ exists. In the compound, two groups represented by two of ring $C^1$ may be identical or different. A same rule also applies to arbitrary two groups when i is larger than 2. A same rule further applies to a symbol of any other ring, bonding group or the like.

An expression "at least one of "A" may be replaced by "B"" means that a position of "A" when the number of "A" is 1 is arbitrary, and that positions thereof can be selected without restriction when the number of "A" is 2 or more. An expression "at least one of A may be replaced by B, C or D" means inclusion of a case where arbitrary A is replaced by B, a case where arbitrary A is replaced by C, and a case where arbitrary A is replaced by D, and also a case where a plurality of A are replaced by at least two of B, C and D. For example, alkyl in which at least one of $—CH_2—$ may be replaced by $—O—$ or $—CH{=}CH—$ includes alkyl, alkenyl, alkoxy, alkoxyalkyl, alkoxyalkenyl and alkenyloxyalkyl. In addition, a case where two of successive $—CH_2—$ is replaced by $—O—$ to form $—O—O—$ is not preferred. In the alkyl or the like, a case where $—CH_2—$ of a methyl part ($—CH_2—H$) is replaced by $—O—$ to form $—O—H$ is not preferred, either.

Then, 2-fluoro-1,4-phenylene means two divalent groups described below. In a chemical formula, fluorine may be leftward (L) or rightward (R). A same rule also applies to an asymmetrical divalent ring such as tetrahydropyran-2,5-diyl.

(L)

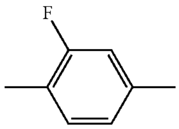

(R)

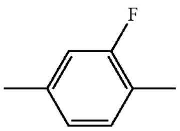

The invention includes the content described in items 1 to 15 below.

Item 1. A compound represented by formula (1):

(1)

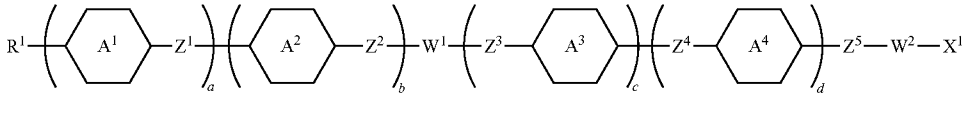

wherein, in formula (1), $R^1$ is alkyl having 1 to 15 carbons, and in the alkyl, at least one of $—CH_2—$ may be replaced by —O— or —S—, at least one of $—(CH_2)_2—$ may be replaced by —CH═CH—, and in the groups, at least one of hydrogen may be replaced by halogen;

ring $A^1$, ring $A^2$, ring $A^3$ and ring $A^4$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, chroman-2,6-diyl, 2,3-dihydro-1H-indene-2,5-diyl, naphthalene-2,6-diyl, decahydronaphthalene-2,6-diyl or 1,2,3,4-tetrahydronaphthalene-2,6-diyl, and at least one of hydrogen directly bonded with the above rings may be replaced by halogen;

$W^1$ is a group represented by formula (1a) or formula (1b);

(1a)

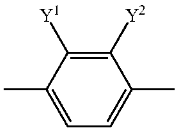

(1b)

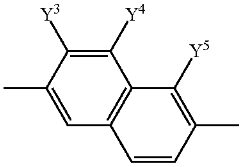

wherein, in formula (1a) and formula (1b), $Y^1$ are $Y^2$ are independently fluorine or chlorine, $Y^3$, $Y^4$ and $Y^5$ are independently hydrogen, fluorine or chlorine, and at least two of $Y^3$, $Y^4$ and $Y^5$ is fluorine or chlorine; and in formula (1), $W^2$ is a group represented by formula (1c) or formula (1d);

(1c)

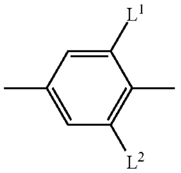

(1d)

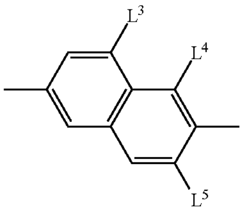

wherein, in formula (1c) and formula (1d), $L^1$, $L^2$, $L^3$, $L^4$ and $L^5$ are independently hydrogen, fluorine or chlorine; and in formula (1), when $W^1$ is represented by formula (1a) and $W^2$ is represented by formula (1c), at least one of ring $A^1$, ring $A^2$, ring $A^3$ and ring $A^4$ is naphthalene-2,6-diyl in which at least one of hydrogen may be replaced by halogen;

$X^1$ is fluorine, —C≡N, —N═C═S, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;

a, b, c and d are independently 0 or 1, and a sum of a, b, c and d is 0, 1, 2 or 3;

$Z^1$, $Z^2$, $Z^3$, $Z^4$ and $Z^5$ are independently a single bond or alkylene having 1-6 carbons, in the alkylene, at least one of $—CH_2—$ may be replaced by —O—, —S—, —CO— or $—SiH_2—$, one or two of $—CH_2CH_2—$ may be replaced by —CH═CH— or —C≡C—, and in the divalent groups, at least one of hydrogen may be replaced by fluorine or chlorine; and at least one of $Z^1$ in the case where a is 1, $Z^2$ in the case where b is 1, $Z^3$ in the case where c is 1, $Z^4$ in the case where d is 1, and $Z^5$ is $—CF_2O—$.

Item 2. The compound according to item 1, wherein, in formula (1) described in item 1, $R^1$ is alkyl having 1 to 15 carbons, alkenyl having 2 to 15 carbons, alkoxy having 1 to 14 carbons or alkenyloxy having 2 to 14 carbons, and in the groups, at least one of hydrogen may be replaced by fluorine;

$X^1$ is fluorine, —C≡N, —N═C═S, $—CH_2F$, $—CHF_2$, $—CF_3$, $—(CH_2)_2—F$, $—CH_2CF_3$, $—CF_2CF_3$, $(CH_2)_3—F$, $CH_2)_2—CF_3$, $CF_2)_3—F$, $(CH_2)_4—F$, $(CH_2)_3CF_3$, $CF_2)_4—F$, $—(CF_2)_5—F$, $—(CF_2)_6—F$, $—(CF_2)_7—F$, $—OCH_2F$, $—OCHF_2$, $—OCF_3$, $—O—(CH_2)_2—F$, $—OCH_2CF_3$, $—OCF_2CF_3$, $—O—(CH_2)_3—F$, $—O—(CH_2)_2—CF_3$, $—O—(CF_2)_3—F$, $—O(CH_2)_4—F$, $—O—(CH_2)_3—CF_3$, $—O—(CF_2)_4—F$, $—O—(CF_2)_5—F$, $—O—(CF_2)_6—F$, —CH═CHF, $—CH═CF_2$, —CF═CHF, $—CF═CF_2$, $—CH═CHCH_2F$, $—CH═CHCF_3$, $—CF═CHCF_3$, $—CF═CFCF_3$, $—(CH_2)_2—CH═CF_2$, $—(CH_2)_2—CF═CF_2$, $—(CH_2)_2—CH═CHCF_3$, $—(CH_2)_2—CF═CHCF_3$ or $—(CH_2)_2—CF═CFCF_3$; and $Z^1$, $Z^2$, $Z^3$, $Z^4$ and $Z^5$ are independently a single bond, $—(CH_2)_2—$, $—(CH_2)_4—$, —COO—, —OCO—, $—CH_2O—$, $—OCH_2—$, $—CF_2O—$, $—OCF_2—$, —CH═CH—, —CF═CF—, $—(CH_2)_2COO—$, $—OCO(CH_2)_2—$, $—(CH_2)_2CF_2O—$, $—OCF_2(CH_2)_2—$, $—(CH_2)_3O—$ or $—O(CH_2)_3—$.

Item 3. The compound according to item 1 or item 2, wherein, in formula (1) described in item 1, $R^1$ is alkyl having 1 to 10 carbons, alkenyl having 2 to 10 carbons, alkoxy having 1 to 9 carbons or alkenyloxy having 2 to 9 carbons, and in the groups, at least one of hydrogen may be replaced by fluorine; and $X^1$ is fluorine, —C≡N, $—CF_3$, $—CHF_2$, $—OCF_3$, $—OCHF_2$, $—CH═CHCF_3$, $—CF═CHCF_3$ or $—CF═CFCF_3$.

Item 4. The compound according to item 1, represented by any one of formulas (1-1) to (1-8):

(1-1)

$R^1—W^1—Z^5—W^2—X^1$ (1-2)

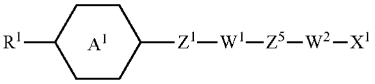

(1-3)

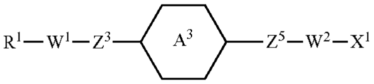

(1-4)

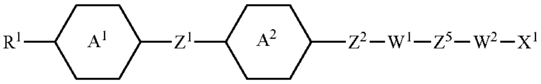

(1-5)

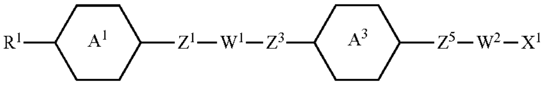

(1-6)

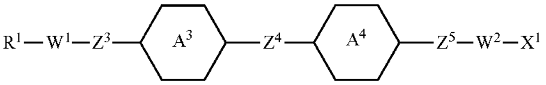

(1-7)

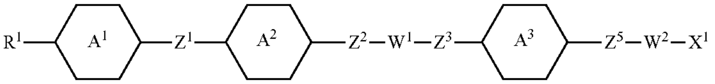

(1-8)

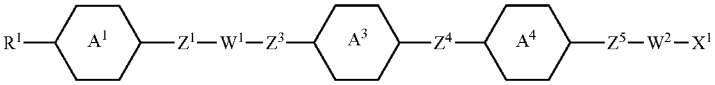

wherein, in formulas (1-1) to (1-8), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one of hydrogen is replaced by fluorine, tetrahydropyran-2,5-diyl or 1,3-dioxane-2,5-diyl, naphthalene-2,6-diyl, or naphthalene-2,6-diyl in which at least one of hydrogen is replaced by fluorine;

$W^1$ is a group represented by formula (1a) or formula (1b);

(1a)

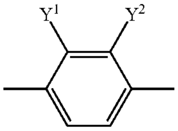

(1b)

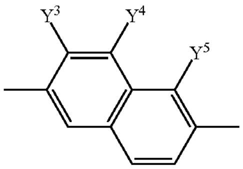

wherein, in formula (1a) and formula (1b), $Y^1$ and $Y^2$ are fluorine, $Y^3$, $Y^4$ and $Y^5$ are independently hydrogen or fluorine, and at least two of $Y^3$, $Y^4$ and $Y^5$ is fluorine; and in formulas (1-1) to (1-8), $W^2$ is a group represented by formula (1c) or formula (1d);

(1c)

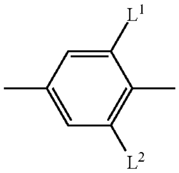

(1d)

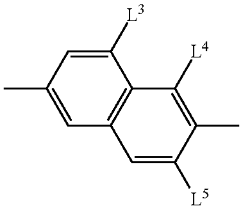

wherein, in formula (1c) and formula (1d), $L^1$, $L^2$, $L^3$, $L^4$ and $L^5$ are independently hydrogen or fluorine; and in formulas (1-1) to (1-8), when $W^1$ is represented by formula (1a) and $W^2$ is represented by formula (1c), at least one of ring $A^1$, ring $A^2$, ring $A^3$ and ring $A^4$ is naphthalene-2,6-diyl in which at least one of hydrogen may be replaced by halogen;

$Z^1$, $Z^2$, $Z^3$, $Z^4$ and $Z^5$ are independently a single bond, $—(CH_2)_2—$, $—(CH_2)_4—$, $—COO—$, $—OCO—$, $—CH_2O—$, $—OCH_2—$, $—CF_2O—$, $—OCF_2—$, $—CH{=}CH—$, $—CF{=}CF—$, $—(CH_2)_2COO—$, $—OCO(CH_2)_2—$, $—(CH_2)_2CF_2O—$, $—OCF_2(CH_2)_2—$, $—(CH_2)_3O—$ or $—O(CH_2)_3—$, and at least one of $Z^1$, $Z^2$, $Z^3$, $Z^4$ and $Z^5$ is $—CF_2O—$; and $X^1$ is fluorine, $—CF_3$, $—CHF_2$, $—OCF_3$ or $—OCHF_2$.

Item 5. The compound according to item 1, represented by any one of formulas (1-9) to (1-29):

(1-9)
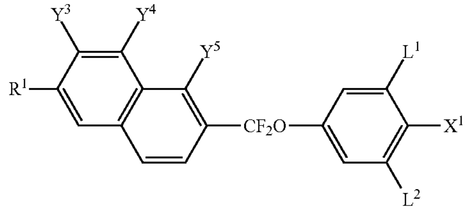
(1-10)
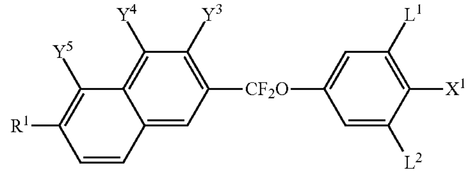
(1-11)
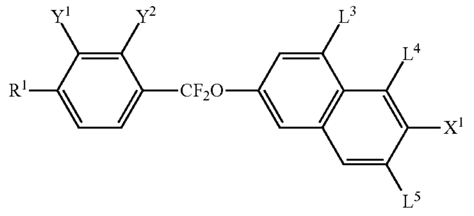
(1-12)
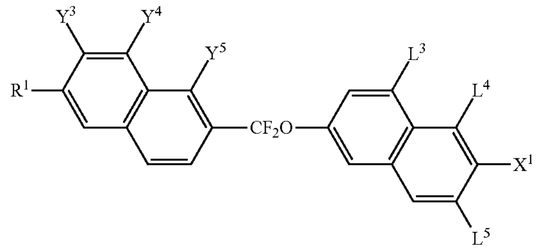
(1-13)
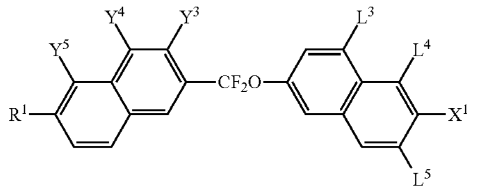
(1-14)
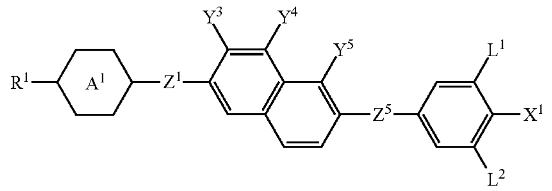
(1-15)
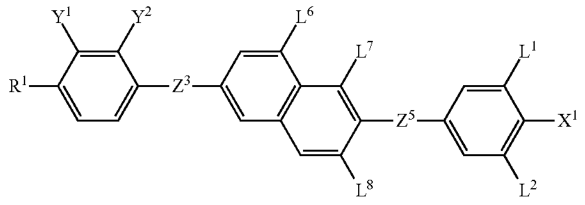
(1-16)
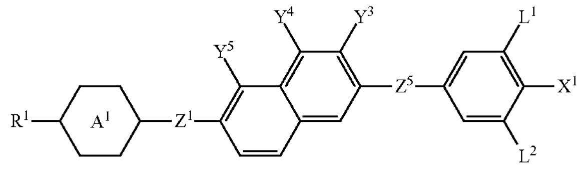
(1-17)
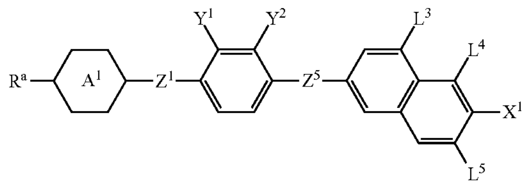
(1-18)
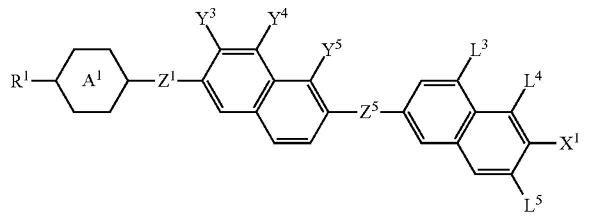
(1-19)
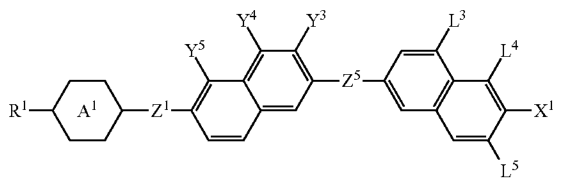
(1-20)
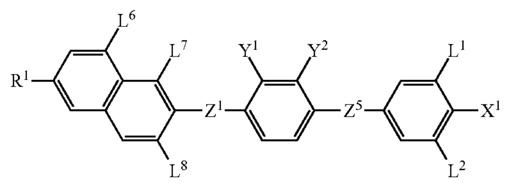
(1-21)
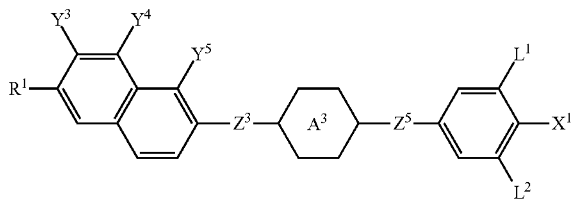
(1-22)
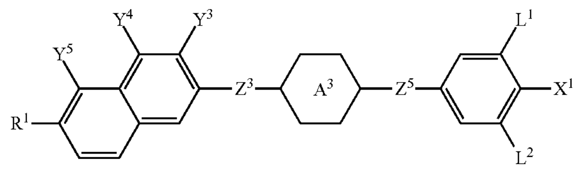

-continued (1-23)

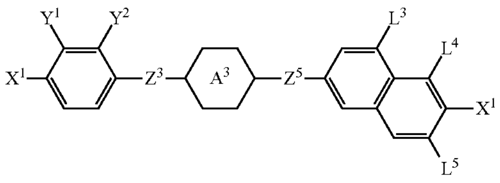

(1-24)

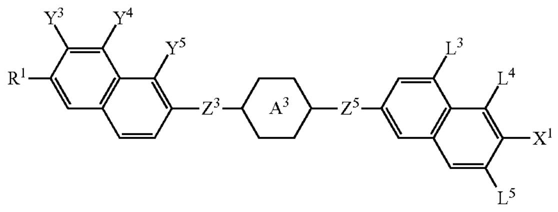

(1-25)

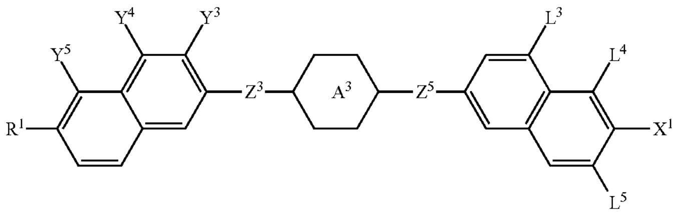

(1-26)

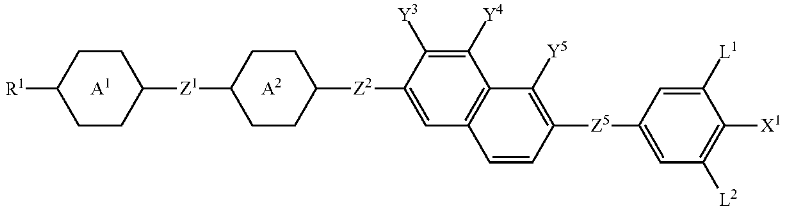

(1-27)

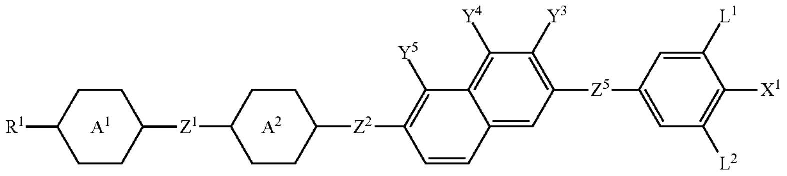

(1-28)

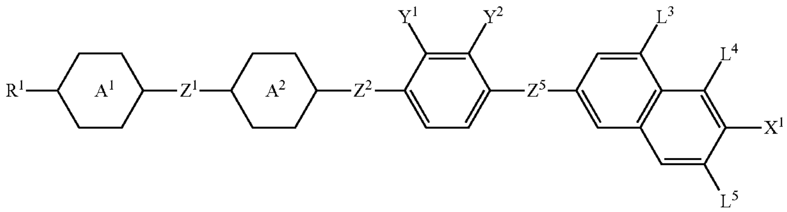

(1-29)

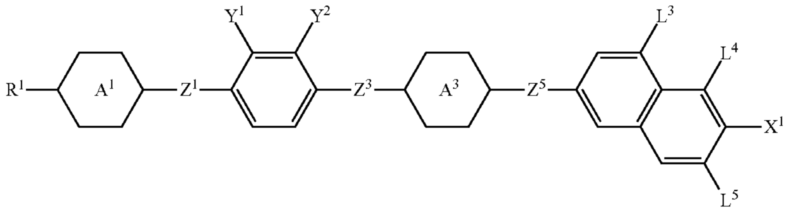

wherein, in formulas (1-9) to (1-29), $R^1$ is alkyl having 1 to 10 carbons or alkenyl having 2 to 10 carbons;

ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$Z^1$, $Z^2$, $Z^3$ and $Z^5$ are independently a single bond, $-(CH_2)_2-$, $-(CH_2)_4-$, $-COO-$, $-OCO-$, $-CH_2O-$, $-OCH_2-$, $-CF_2O-$, $-OCF_2-$, and at least one of $Z^1$, $Z^2$, $Z^3$ and $Z^5$ is $-CF_2O-$;

$X^1$ is fluorine, $-CF_3$ or $-OCF_3$; and $L^1$, $L^2$, $L^3$, $L^4$, $L^5$, $L^6$, $L^7$, $L^8$, $Y^1$, $Y^2$, $Y^3$, $Y^4$ and $Y^5$ are independently hydrogen or fluorine.

Item 6. The compound according to item 1, represented by any one of formulas (1-30) to (1-54):

(1-30)
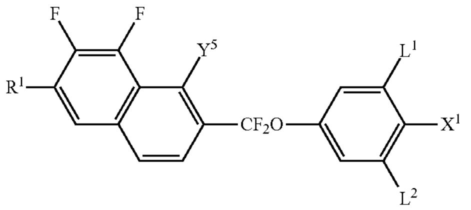
(1-31)
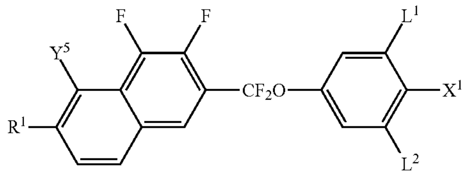
(1-32)
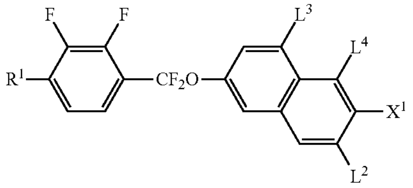
(1-33)
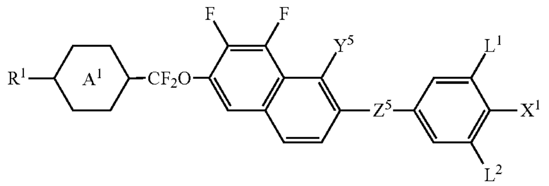
(1-34)
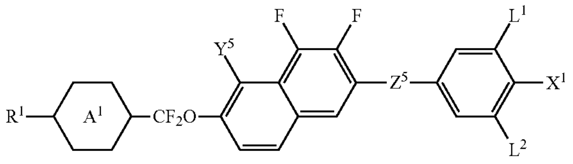
(1-35)
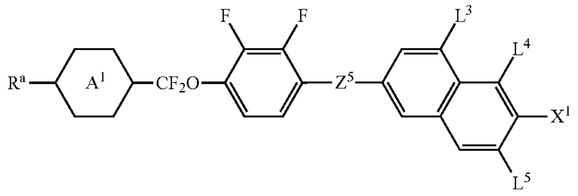
(1-36)
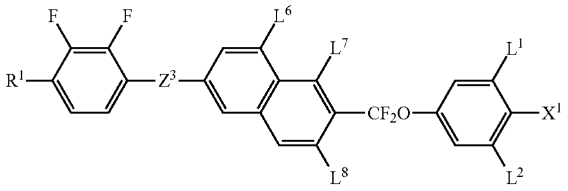
(1-37)
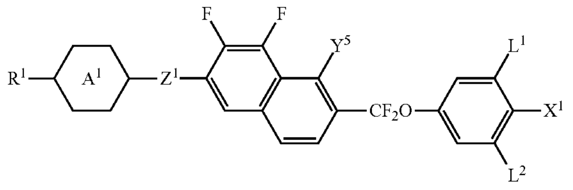
(1-38)
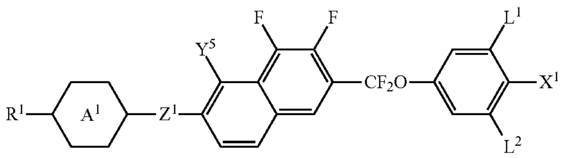
(1-39)
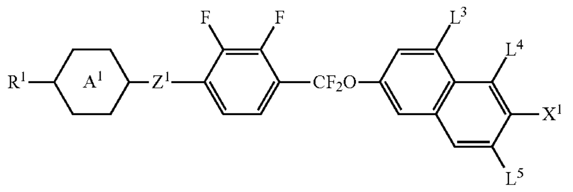
(1-40)
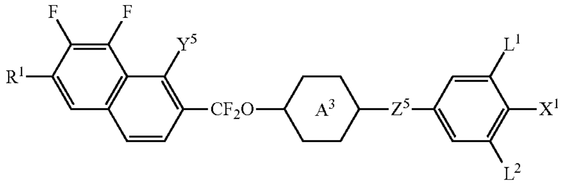
(1-41)
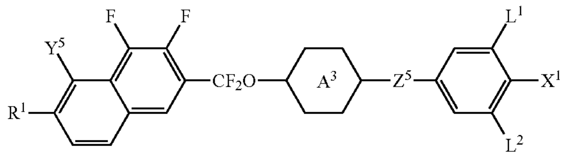
(1-42)
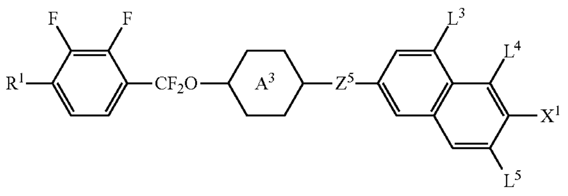
(1-43)
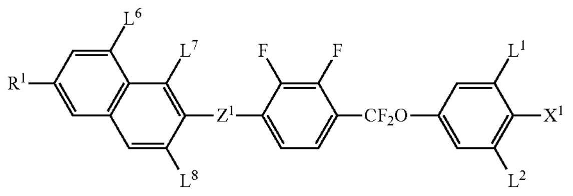

-continued
(1-44)
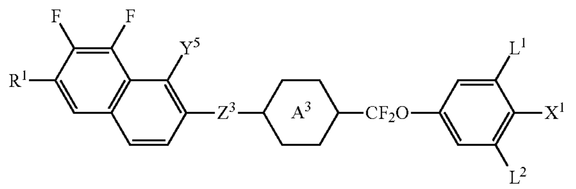
(1-45)
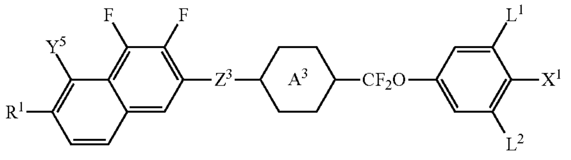
(1-46)
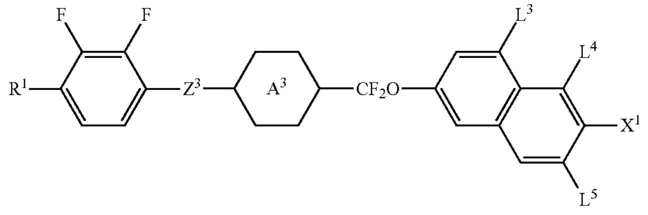
(1-47)
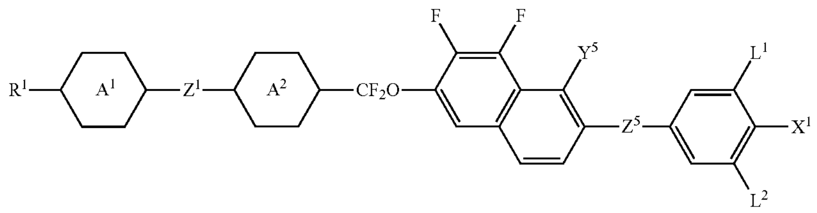
(1-48)
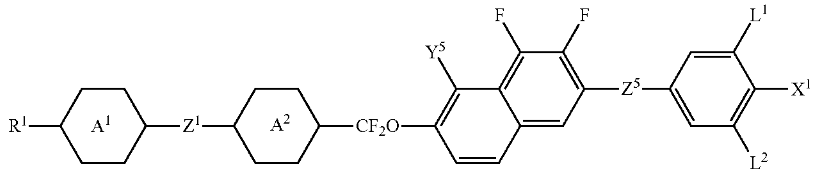
(1-49)
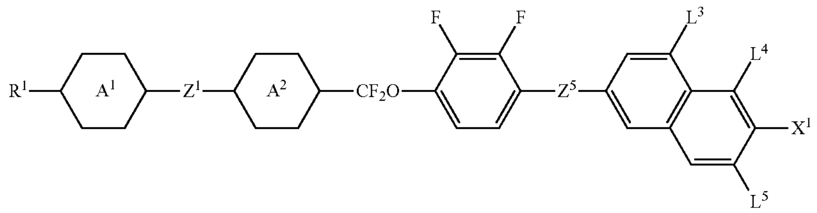
(1-50)
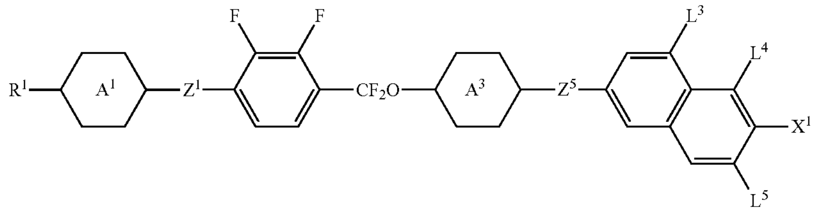
(1-51)
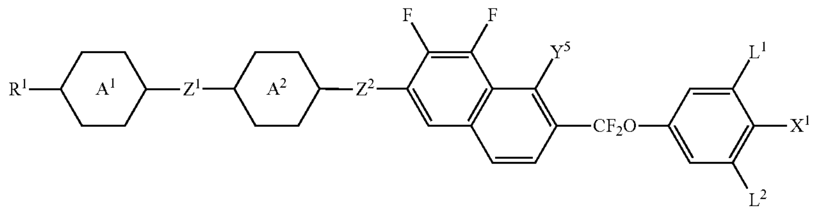

-continued (1-52)

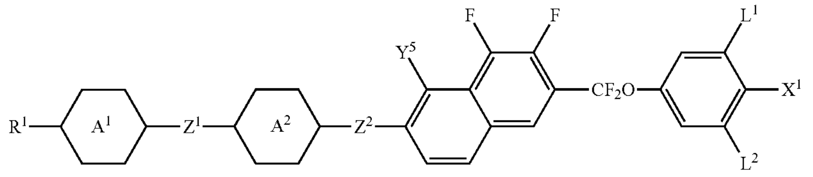

(1-53)

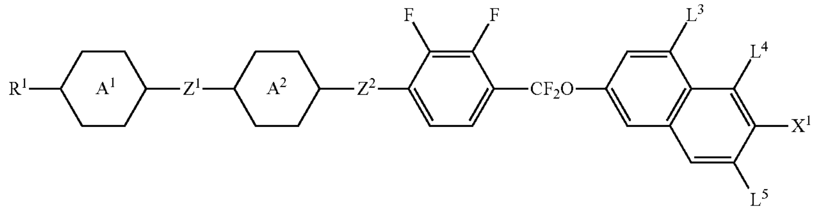

(1-54)

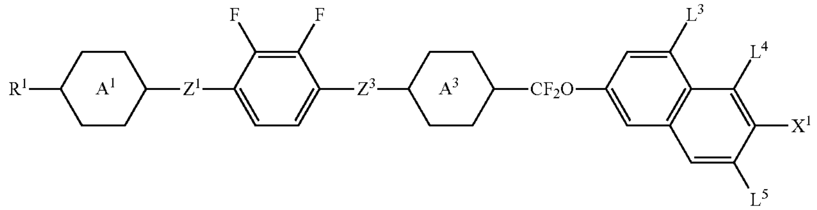

wherein, in formulas (1-30) to (1-54), $R^1$ is alkyl having 1 to 10 carbons or alkenyl having 2 to 10 carbons;

ring $A^1$, ring $A^2$ and ring $A^3$ are independently 1,4-cyclohexylene, 1,4-yclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$Z^1$, $Z^2$, $Z^3$ and $Z^5$ are independently a single bond, $-(CH_2)_2-$, $-COO-$, $-OCO-$, $-CH_2O-$, $-OCH_2-$, $-CF_2O-$ or $-OCF_2-$;

$X^1$ is fluorine, $-CF_3$ or $-OCF_3$; and $L^1$, $L^2$, $L^3$, $L^4$, $L^5$, $L^6$, $L^7$, $L^8$ and $Y^5$ are independently hydrogen or fluorine.

Item 7. The compound according to item 1, represented by any one of formulas (1-55) to (1-78):

(1-55)

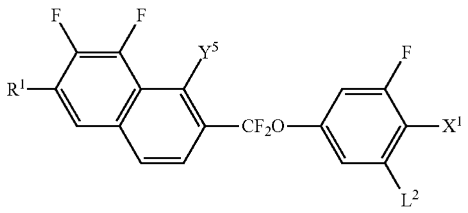

(1-56)

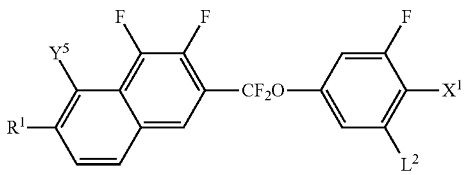

-continued (1-57)

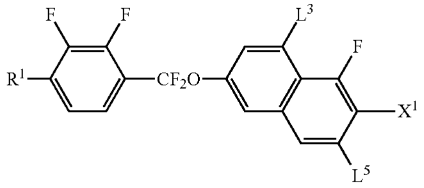

(1-58)

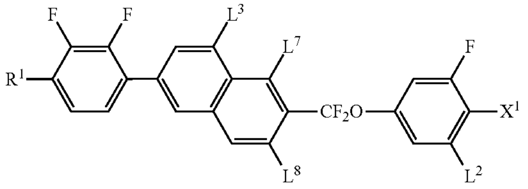

(1-59)

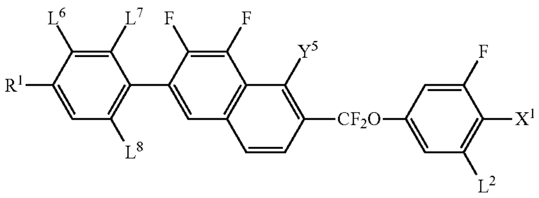

(1-60)

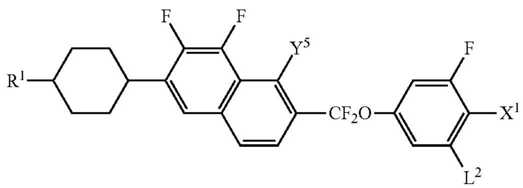

-continued
(1-61)
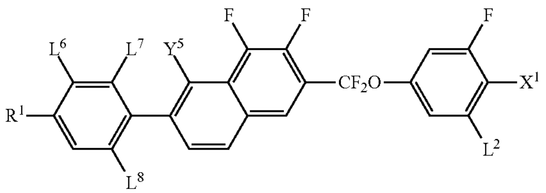
(1-62)
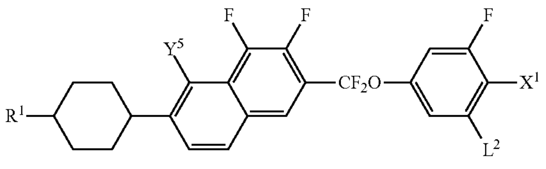
(1-63)
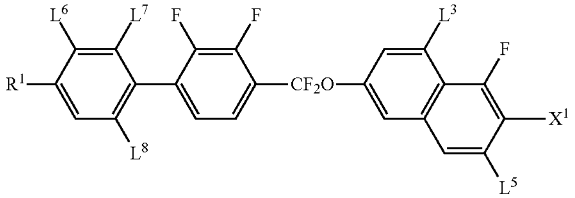
(1-64)
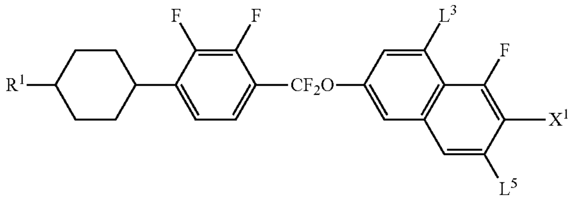
(1-65)
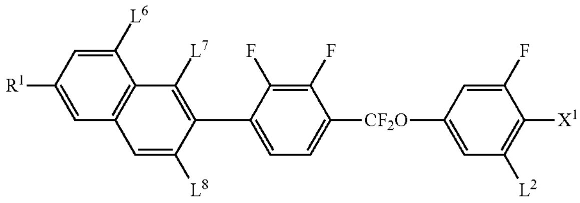
(1-66)
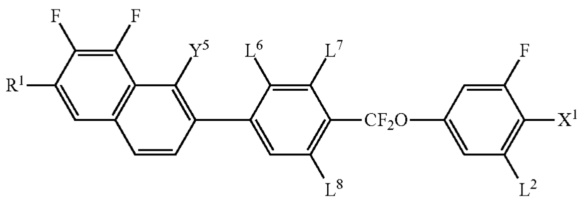
(1-67)
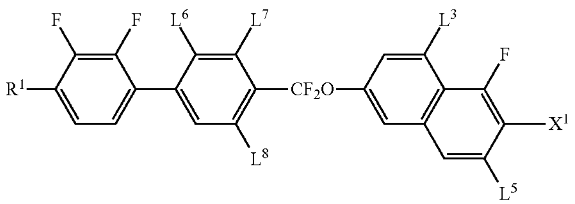
-continued
(1-68)
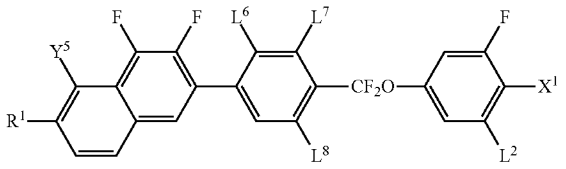
(1-69)
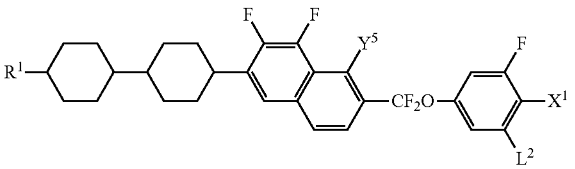
(1-70)
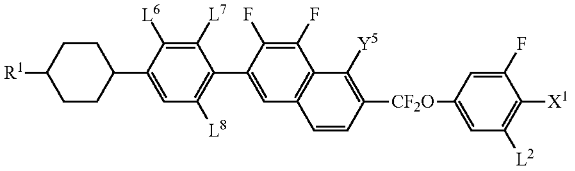
(1-71)
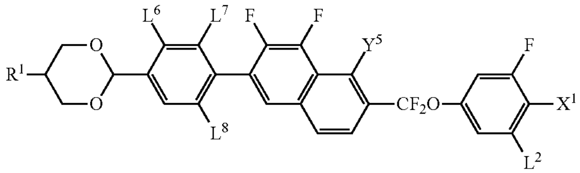
(1-72)
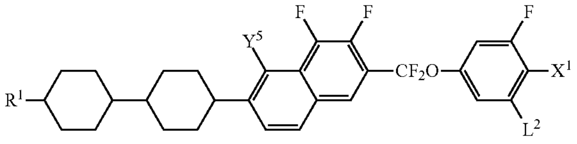
(1-73)
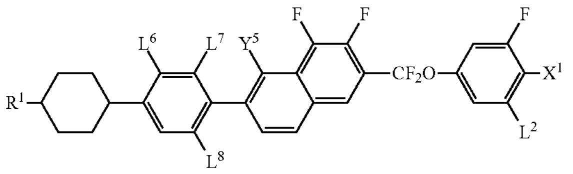
(1-74)
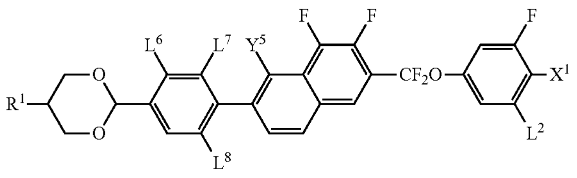
(1-75)
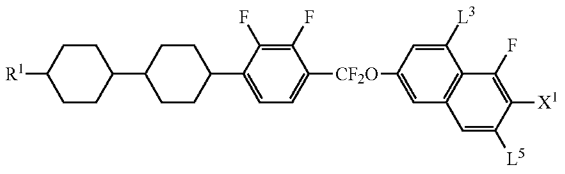

-continued
(1-76)
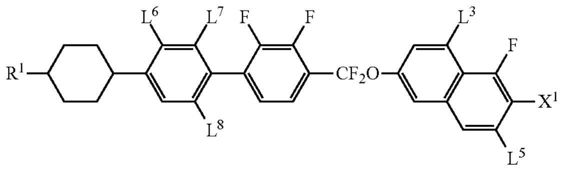
(1-77)
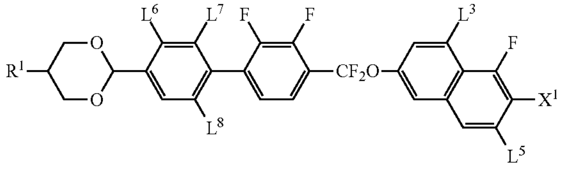
(1-78)
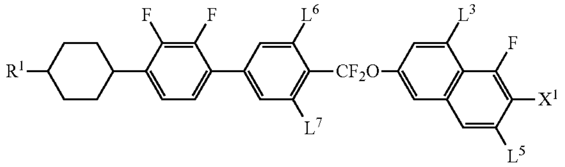
wherein, in formulas (1-55) to (1-78),
$R^1$ is alkyl having 1 to 10 carbons or alkenyl having 2 to 10 carbons;
$X^1$ is fluorine, —$CF_3$ or —$OCF_3$; and
$L^2$, $L^3$, $L^5$, $L^6$, $L^7$, $L^8$ and $Y^5$ are hydrogen or fluorine.
Item 8. The compound according to item 1, represented by any one of formulas (1-79) to (1-98):
(1-79)
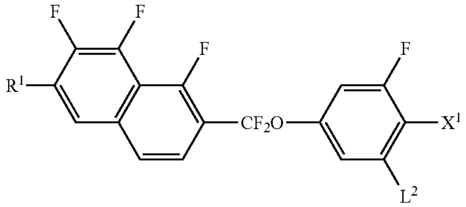
(1-80)
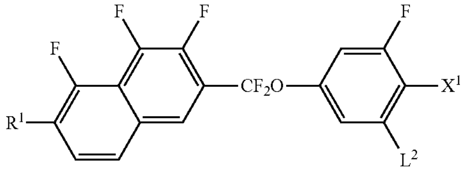
(1-81)
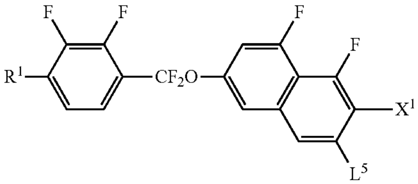
-continued
(1-82)
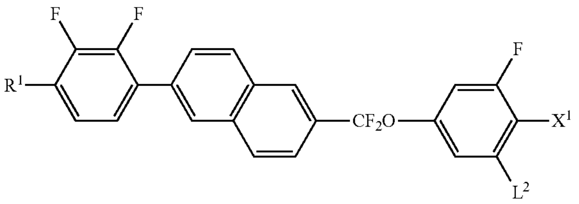
(1-83)
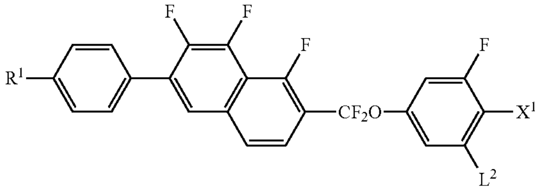
(1-84)
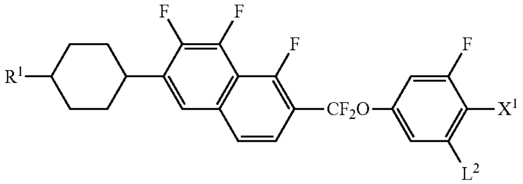
(1-85)
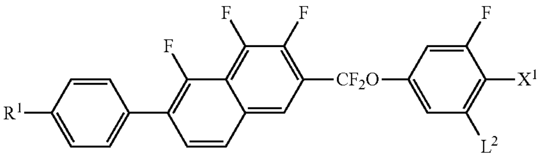
(1-86)
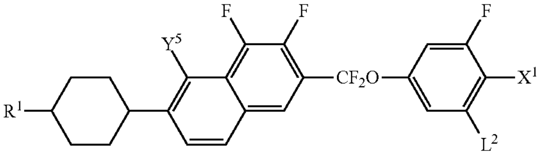
(1-87)
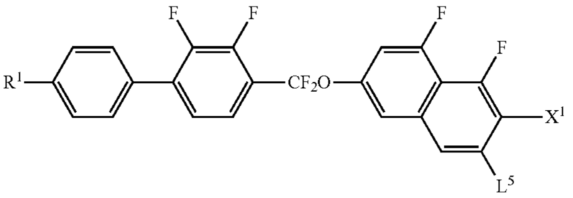
(1-88)
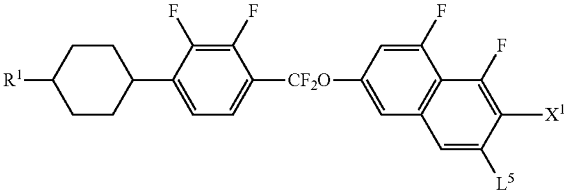

-continued (1-89)

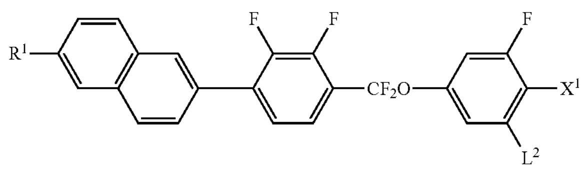

(1-90)

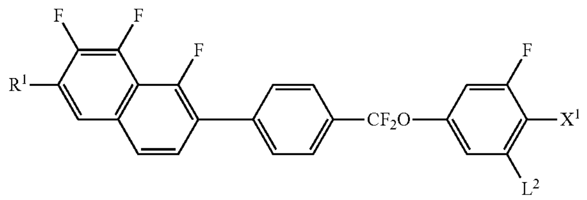

(1-91)

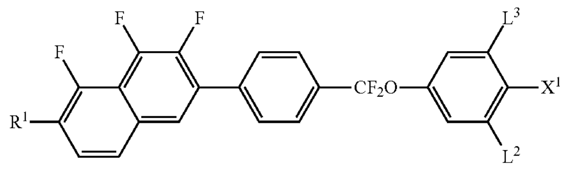

(1-92)

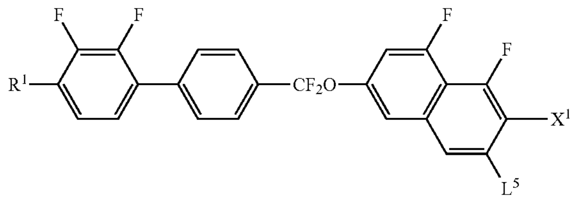

(1-93)

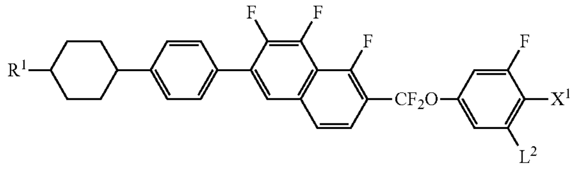

(1-94)

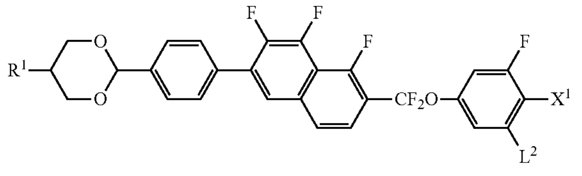

(1-95)

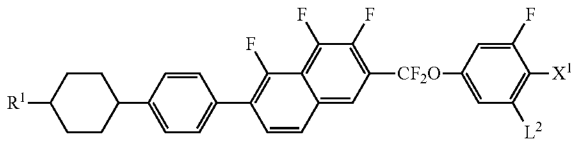

(1-96)

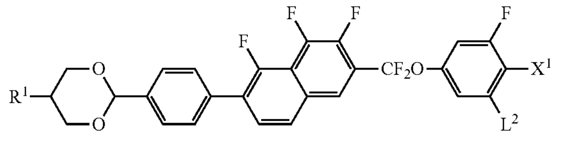

-continued (1-97)

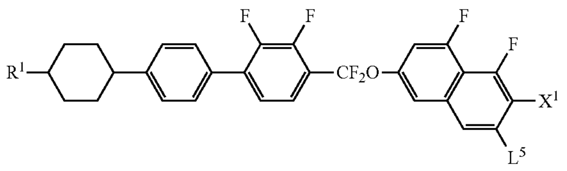

(1-98)

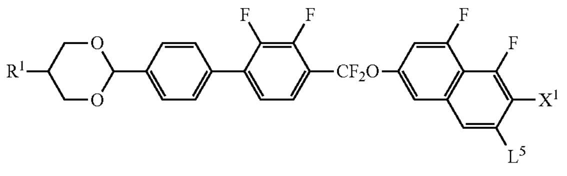

wherein, in formulas (1-79) to (1-98), $R^1$ is alkyl having 1 to 10 carbons or alkenyl having 2 to 10 carbons;

$X^1$ is fluorine, —$CF_3$ or —$OCF_3$; and $L^2$ and $L^5$ are hydrogen or fluorine.

Item 9. A liquid crystal composition containing at least one of compounds represented by any one of items 1 to 8.

Item 10. The liquid crystal composition according to item 9, further containing at least one compound selected from the group of compounds represented by formulas (2) to (4).

(2)

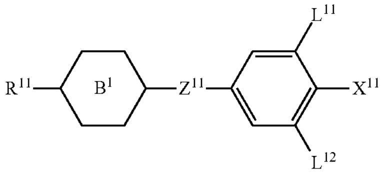

(3)

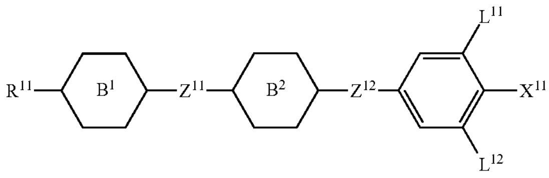

(4)

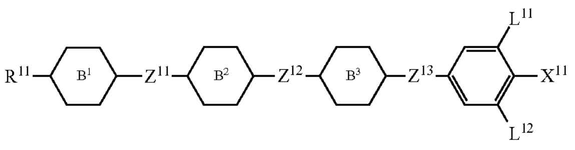

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene, 2-fluoro-1,4-phenylene, 2,5-difluoro-1,4-phenylene, tetrahydropyran-2,5-diyl, 1,3-dioxane-2,5-diyl or pyrimidine-2,5-diyl;

$Z^{11}$, $Z^{12}$ and $Z^{13}$ are independently a single bond, $—CH_2CH_2—$, $—CH{=}CH—$, $—COO—$, $—CF_2O—$, $—OCF_2—$, $—CH_2O—$ or $—(CH_2)_4—$; and $L^{11}$ and $L^{12}$ are independently hydrogen or fluorine.

Item 11. The liquid crystal composition according to any one of items 9 to 10, further containing at least one compound selected from the group of compounds represented by formula (5):

$Z^{14}$ is a single bond, $—CH_2CH_2—$, $—C{\equiv}C—$, $—COO—$, $—CF_2O—$, $—OCF_2—$ or $—CH_2O—$;

$L^{13}$ and $L^{14}$ are independently hydrogen or fluorine; and i is 1, 2, 3 or 4.

Item 12. The liquid crystal composition according to any one of items 9 to 11, further containing at least one compound selected from the group of compounds represented by formulas (6) to (12):

(6)

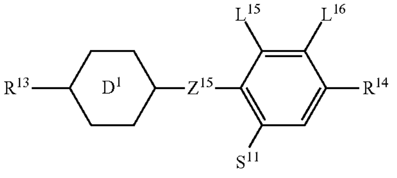

(7)

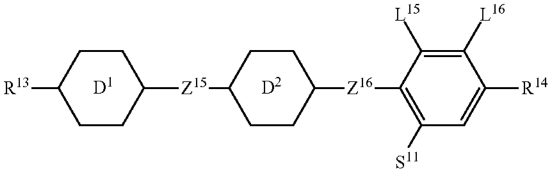

(8)

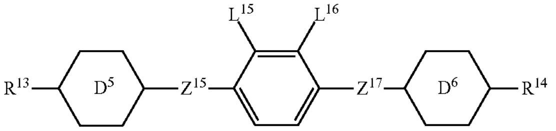

(9)

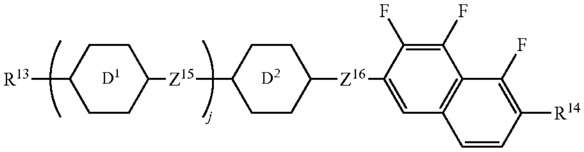

(10)

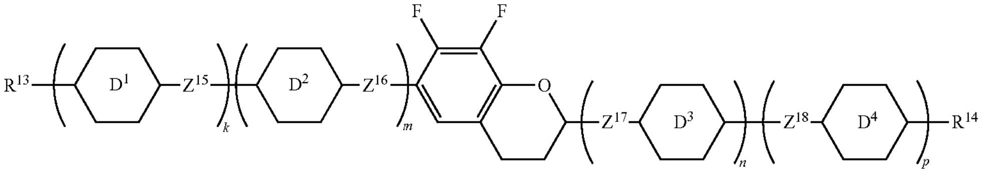

(11)

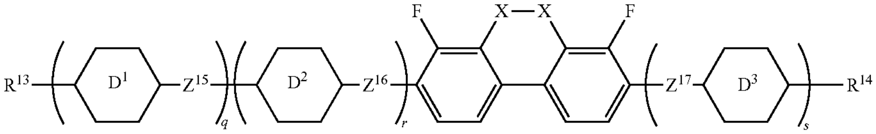

(12)

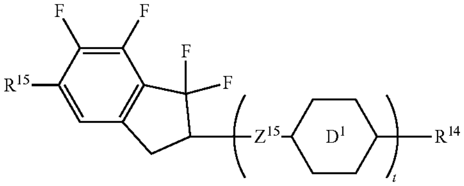

(5)

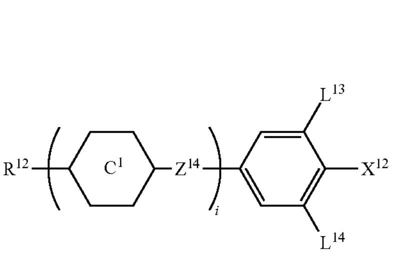

wherein, in formula (5), $R^{12}$ is alkyl having 1 to 10 carbons or alkenyl having 2 to 10 carbons, and in the alkyl and the alkenyl, at least one of hydrogen may be replaced by fluorine and at least one of $—CH_2—$ may be replaced by $—O—$;

$X^{12}$ is $—C{\equiv}N$ or $—C{\equiv}C—C{\equiv}N$;

ring $C^1$ is 1,4-cyclohexylene, 1,4-phenylene, 2-fluoro-1,4-phenylene, 2,5-difluoro-1,4-phenylene, tetrahydropyran-2,5-diyl, 1,3-dioxane-2,5-diyl or pyrimidine-2,5-diyl;

wherein, in formulas (6) to (12), $R^{13}$ and $R^{14}$ are independently alkyl having 1 to 10 carbons or alkenyl having 2 to 10 carbons, and in the alkyl and the alkenyl, at least one of $—CH_2—$ may be replaced by $—O—$;

$R^{15}$ is hydrogen, fluorine, alkyl having 1 to 10 carbons or alkenyl having 2 to 10 carbons, and in the alkyl and the alkenyl, at least one of $—CH_2—$ may be replaced by $—O—$ and at least one of hydrogen may be replaced by fluorine;

$S^{11}$ is hydrogen or methyl;

X is $—CF_2—$, $—O—$ or $—CHF—$;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, $-CH_2CH_2-$, $-COO-$, $-OCF_2-$ or $-OCF_2CH_2CH_2-$;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is independently 1, 2 or 3.

5-position of a ring is replaced by halogen, and therefore has a feature of having both a large dielectric anisotropy and a large dielectric constant in a minor axis direction. A preferred example of compound (1) of the invention is described. A preferred example of a terminal group, a ring structure, a bonding group and a substituent in compound (1) applies also to a subordinate formula of a formula of compound (1).

(1)

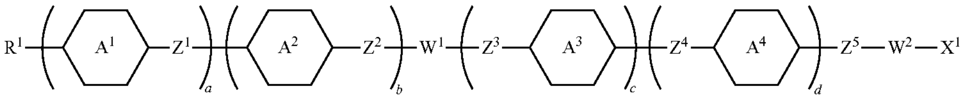

Item 13. The liquid crystal composition according to any one of items 9 to 12, further containing at least one compound selected from the group of compounds represented by formulas (13) to (15):

(13)

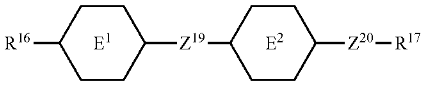

(14)

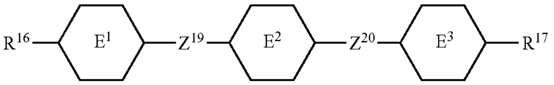

(15)

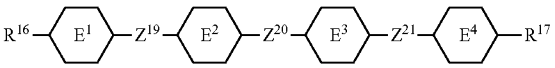

wherein, in formulas (13) to (15), $R^{16}$ and $R^{17}$ are independently alkyl having 1 to 10 carbons or alkenyl having 2 to 10 carbons, and in the alkyl or the alkenyl, at least one of $-CH_2-$ may be replaced by $-O-$, at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, $-CH_2CH_2-$, $-CH{=}CH-$, $-C{\equiv}C-$ or $-COO-$.

Item 14. The liquid crystal composition according to any one of items 9 to 13, further containing at least one of a polymerizable compound, an optically active compound, an antioxidant, an ultraviolet light absorber, a light stabilizer, a heat stabilizer and an antifoaming agent.

Item 15. A liquid crystal display device including the liquid crystal composition according to any one of items 9 to 14.

The compound, the liquid crystal composition and the liquid crystal display device of the invention are described, one by one.

1-1. Compound (1)

Compound (1) of the invention has an electron-withdrawing large polar group as a terminal group, and has 1,4-phenylene in which hydrogen in 2-position and 3-position of a ring are replaced by halogen, or naphthalene-2,6-diyl in which at least two of hydrogen in 3-position, 4-position and wherein, in formula (1), $R^1$ is alkyl having 1 to 15 carbons, and in the alkyl, at least one of $-CH_2-$ may be replaced by $-O-$ or $-S-$, at least one of $-(CH_2)_2-$ may be replaced by $-CH{=}CH-$, and in the groups, at least one of hydrogen may be replaced by halogen.

Examples of such a terminal group $R^1$ include alkyl, alkoxy, alkoxyalkyl, alkoxyalkoxy, alkylthio, alkylthioalkoxy, alkenyl, alkenyloxy, alkenyloxyalkyl, alkoxyalkenyl and alkenylthio. In the groups, at least one of hydrogen may be replaced by halogen. Preferred halogen is fluorine and chlorine. Further preferred halogen is fluorine. The groups have a straight chain or a branched chain, and contain no cyclic group such as cyclohexyl. In the groups, the straight chain is preferred to the branched chain.

A preferred configuration of $-CH{=}CH-$ in the alkenyl depends on a position of a double bond. In alkenyl having the double bond in an odd-numbered position, such as $-CH{=}CHCH_3$, $-CH{=}CHC_2H_5$, $-CH{=}CHC_3H_7$, $-CH{=}CHC_4H_9$, $-C_2H_4CH{=}CHCH_3$ and $-C_2H_4CH{=}CHC_2H_5$, a trans configuration is preferred. In alkenyl having the double bond in an even-numbered position, such as $-CH_2CH{=}CHCH_3$, $-CH_2CH{=}CHC_2H_5$ and $-CH_2CH{=}CHC_3H_7$, a cis configuration is preferred. An alkenyl compound having the preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131, 327.

Examples of alkyl include $-CH_3$, $-C_2H_5$, $-C_3H_7$, $-C_4H_9$, $-C_5H_{11}$, $-C_6H_{13}$, $-C_7H_{15}$, $-C_8H_{17}$, $-C_9H_{19}$, $-C_{10}H_{21}$, $-C_{11}H_{23}$, $-C_{12}H_{25}$, $-C_{13}H_{27}$, $-C_{14}H_{29}$ and $-C_{15}H_{31}$.

Examples of alkoxy include $-OCH_3$, $-OC_2H_5$, $-OC_3H_7$, $-OC_4H_9$, $-OC_5H_{11}$, $-OC_6H_{13}$, $-OC_7H_{15}$, $-OC_8H_{17}$, $-OC_9H_{19}$, $-OC_{10}H_{21}$, $-OC_{11}H_{23}$, $-OC_{12}H_{25}$, $-OC_{13}H_{27}$ and $-OC_{14}H_{29}$.

Examples of alkoxyalkyl include $-CH_2OCH_3$, $-CH_2OC_2H_5$, $-CH_2OC_3H_7$, $-(CH_2)_2-OCH_3$, $-(CH_2)_2-OC_2H_5$, $-(CH_2)_2-OC_3H_7$, $-(CH_2)_3-OCH_3$, $-(CH_2)_4-OCH_3$ and $-(CH_2)_5-OCH_3$.

Examples of alkenyl include $-CH{=}CH_2$, $-CH{=}CHCH_3$, $-CH_2CH{=}CH_2$, $-CH{=}CHC_2H_5$, $-CH_2CH{=}CHCH_3$, $-(CH_2)_2-CH{=}CH_2$, $-CH{=}CHC_3H_7$, $-CH_2CH{=}CHC_2H_5$, $-(CH_2)_2-CH{=}CHCH_3$ and $-(CH_2)_3-CH{=}CH_2$.

Examples of alkenyloxy include $-OCH_2CH{=}CH_2$, $-OCH_2CH{=}CHCH_3$ and $-OCH_2CH{=}CHC_2H_5$.

Examples of alkyl in which at least one of hydrogen is replaced by halogen include $-CH_2F$, $-CHF_2$, $-CF_3$, $-(CH_2)_2-F$, $-CF_2CH_2F$, $-CF_2CHF_2$, $-CH_2CF_3$, $-CF_2CF_3$, $-(CH_2)_3-F$, $-(CF_2)_3-F$, $-CF_2CHFCF_3$, $-CHFCF_2CF_3$, $-(CH_2)_4-F$, $-(CF_2)_4-F$, $-(CH_2)_5-F$, $-(CF_2)_5-F$, $-CH_2Cl$, $-CHCl_2$, $-CCl_3$, $-(CH_2)_2-Cl$, $-CCl_2CH_2Cl$, $-CCl_2CHCl_2$, $-CH_2CCl_3$, $-CCl_2CCl_3$, $-(CH_2)_3-Cl$, $-(CCl_2)_3-Cl$, $-CCl_2CHClCCl_3$, $-CHClCCl_2CCl_3$, $-(CH_2)_4-Cl$, $-(CCl_2)_4-Cl$, $-(CH_2)_5-Cl$ and $-(CCl_2)_5-Cl$.

Examples of alkoxy in which at least one of hydrogen is replaced by halogen include $-OCH_2F$, $-OCHF_2$, $-OCF_3$, $-O-(CH_2)_2-F$, $-OCF_2CH_2F$, $-OCF_2CHF_2$, $-OCH_2CF_3$, $-O-(CH_2)_3-F$, $-O-(CF_2)_3-F$, $-OCF_2CHFCF_3$, $-OCHFCF_2CF_3$, $-O(CH_2)_4-F$, $-(CF_2)_4-F$, $-O-(CH_2)_5-F$, $-CF_2)_5-F$, $-OCH_2Cl$, $-OCHCl_2$, $-OCCl_3$, $-O-(CH_2)_2-Cl$, $-OCCl_2CH_2Cl$, $-OCCl_2CHCl_2$, $-OCH_2CCl_3$, $-O-(CH_2)_3-Cl$, $-O-(CCl_2)_3-Cl$, $-OCCl_2CHClCCl_3$, $-OCHClCCl_2CCl_3$, $-O(CH_2)_4-Cl$, $-O-(CCl_2)_4-Cl$, $-O-(CH_2)_5-Cl$ and $-O-(CCl_2)_5-Cl$.

Examples of alkenyl in which at least one of hydrogen is replaced by halogen include $-CH{=}CHF$, $-CH{=}CF_2$, $-CF{=}CHF$, $-CH{=}CHCH_2F$, $-CH{=}CHCF_3$, $-(CH_2)_2-CH{=}CF_2$, $-CH_2CH{=}CHCF_3$, $-CH{=}CHCF_2CF_3$, $-CH{=}CHCl$, $-CH{=}CCl_2$, $-CCl{=}CHCl$, $-CH{=}CHCH_2Cl$, $-CH{=}CHCCl_3$, $-(CH_2)_2-CH{=}CCl_2$, $-CH_2CH{=}CHCCl_3$ and $-CH{=}CHCCl_2CCl_3$.

Preferred examples of $R^1$ include alkyl having 1 to 15 carbons, alkenyl having 2 to 15 carbons and alkoxy having 2 to 15 carbons. Further preferred examples of $R^1$ include alkyl having 1 to 10 carbons and alkenyl having 2 to 10 carbons. Most preferred examples of $R^1$ include $-CH_3$, $-C_2H_5$, $-C_3H_7$, $-C_4H_9$, $-C_5H_{11}$, $-C_6H_{13}$, $-C_7H_{15}$, $-CH{=}CH_2$, $-CH{=}CHCH_3$, $-CH_2CH{=}CH_2$, $-CH{=}CHC_2H_5$, $-CH_2CH{=}CHCH_3$, $-(CH_2)_2-CH{=}CH_2$, $-CH{=}CHC_3H_7$, $-CH_2CH{=}CHC_2H_5$, $-(CH_2)_2-CH{=}CHCH_3$ and $-(CH_2)_3-CH{=}CH_2$.

In formula (1), ring $A^1$, ring $A^2$, ring $A^3$ and ring $A^4$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, chroman-2,6-diyl, 2,3-dihydro-1H-indene-2,5-diyl, naphthalene-2,6-diyl, decahydronaphthalene-2,6-diyl or 1,2,3,4-tetrahydronaphthalene-2,6-diyl, and at least one of hydrogen directly bonded with the above rings may be replaced by halogen.

Preferred examples of ring $A^1$, ring $A^2$, ring $A^3$ or ring $A^4$ include 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine. A configuration of cis or trans exists in 1,4-cyclohexylene. From a viewpoint of high maximum temperature, a trans configuration is preferred. Preferred examples of 1,4-phenylene in which at least one of hydrogen is replaced by halogen include rings (A-1) to (A-17).

(A-1)

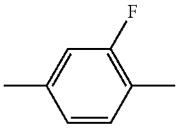

-continued (A-2)

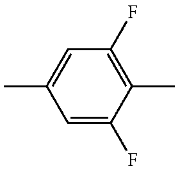

(A-3)

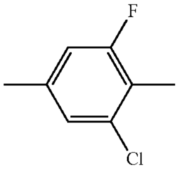

(A-4)

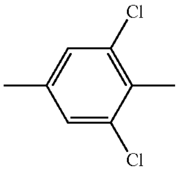

(A-5)

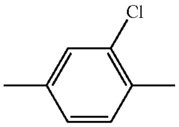

(A-6)

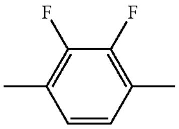

(A-7)

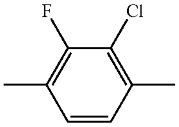

(A-8)

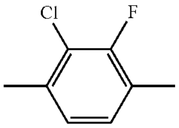

(A-9)

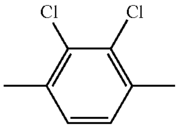

(A-10)

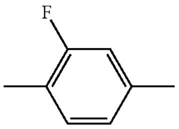

(A-11)

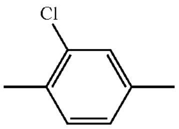

-continued (A-11)
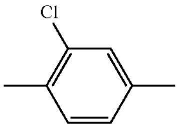

(A-12)
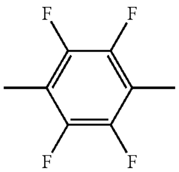

(A-13)
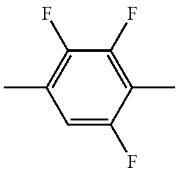

(A-14)
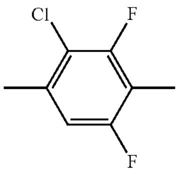

(A-15)
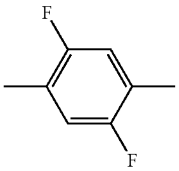

(A-16)
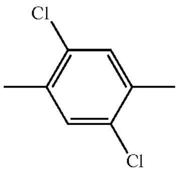

(A-17)
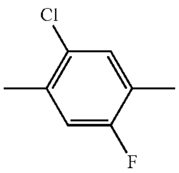

Then, 2-fluoro-1,4-phenylene (A-1) is left-right asymmetrical. In the chemical formula thereof, a case where fluorine is located on a side of a left terminal group (leftward) and a case where fluorine is located on a side of a right terminal group (rightward) exist. Preferred 2-fluoro-1,4-phenylene is rightward (A-1) in order to increase the dielectric anisotropy. A same rule also applies to 2,6-difluoro-1,4-phenylene or the like. Rings (A-1) to (A-9) are further preferred.

Further preferred examples of 1,4-phenylene in which at least one of hydrogen is replaced by halogen include 2-fluoro-1,4-phenylene (A-1), 2,6-difluoro-1,4-phenylene (A-2), 2-chloro-6-fluoro-1,4-phenylene (A-3), 2,3-difluoro-1,4-phenylene (A-6) and 2-chloro-3-fluoro-1,4-phenylene (A-7 and A-8). Most preferred examples of 1,4-phenylene in which at least one of hydrogen is replaced by halogen include 2-fluoro-1,4-phenylene (A-1), 2,6-difluoro-1,4-phenylene (A-2) and 2,3-difluoro-1,4-phenylene (A-6).

Then, 1,3-dioxane-2,5-diyl is left-right asymmetrical. A case where —O— is located on a side of a left terminal group (leftward; A-18) and a case where —O— is located on a side of a right terminal group (rightward; A-19) exist. Preferred 1,3-dioxane-2,5-diyl is rightward (A-19) in order to increase the dielectric anisotropy. In 2,6,7-trioxabicyclo [2.2.2]octane-1,4-diyl (A-20 and A-21), pyrimidine-2,5-diyl (A-22 and A-23) and pyridine-2,5-diyl (A-24 and A-25), —O— is preferably rightward (A-21, A-23 and A-25). In tetrahydropyran-2,5-diyl (A-26 and A-27), from a viewpoint of the large dielectric anisotropy, —O— is preferably rightward (A-27), and from a viewpoint of the large dielectric constant in the minor axis direction, —O— is preferably leftward (A-26).

(A-18)
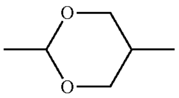

(A-19)
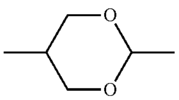

(A-20)
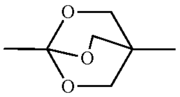

(A-21)
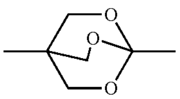

(A-22)
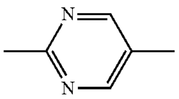

(A-23)
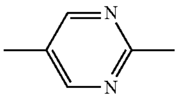

(A-24)
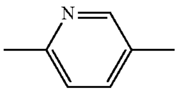

(A-25)
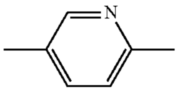

(A-26)
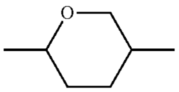

(A-27)
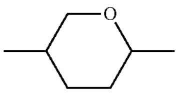

Then, chroman-2,6-diyl, 2,3-dihydro-1H-indene-2,5-diyl, naphthalene-2,6-diyl, decahydronaphthalene-2,6-diyl and 1,2,3,4-tetrahydronaphthalene-2,6-diyl are preferred from a viewpoint of increasing the clearing point.

Further preferred examples of ring $A^1$, ring $A^2$, ring $A^3$ and ring $A^4$ include 1,4-cyclohexylene, 1,4-phenylene, 2-fluoro-1,4-phenylene, 2,6-difluoro-1,4-phenylene, tetrahydropyran-2,5-diyl and 1,3-dioxane-2,5-diyl.

In formula (1), $W^1$ is a group represented by formula (1a) or formula (1b):

(1a)

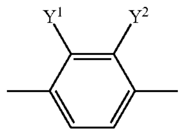

(1b)

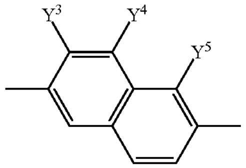

wherein, $Y^1$ and $Y^2$ are independently fluorine or chlorine, $Y^3$, $Y^4$ and $Y^5$ are independently hydrogen, fluorine or chlorine, and at least two of $Y^3$, $Y^4$ and $Y^5$ is fluorine or chlorine. In formula (1a), preferred examples of $Y^1$ and $Y^2$ include a combination in which both $Y^1$ and $Y^2$ are fluorine, and a combination in which one is fluorine and the other is chlorine. Further preferred examples of $Y^1$ and $Y^2$ include a combination in which both $Y^1$ and $Y^2$ are fluorine. In formula (1b), preferred examples of $Y^3$, $Y^4$ and $Y^5$ include a combination in which all of $Y^3$, $Y^4$ and $Y^5$ are fluorine, a combination in which $Y^3$ and $Y^4$ are fluorine and $Y^5$ is hydrogen, a combination in which $Y^4$ and $Y^5$ are fluorine and $Y^3$ is hydrogen, a combination in which $Y^3$ and $Y^4$ are fluorine and $Y^5$ is chlorine, and a combination in which $Y^4$ and $Y^5$ are fluorine and $Y^3$ is chlorine. Further preferred examples of $Y^3$, $Y^4$ and $Y^5$ include a combination in which all of $Y^3$, $Y^4$ and $Y^5$ are fluorine, and a combination in which $Y^3$ and $Y^4$ are fluorine and $Y^5$ is hydrogen.

In formula (1), $W^2$ is a group represented by formula (1c) or formula (1d);

(1c)

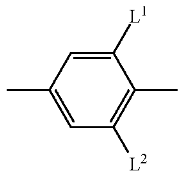

(1d)

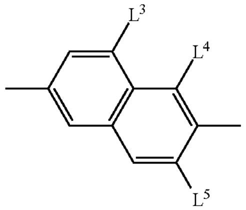

wherein, in formula (1c) and formula (1d), $L^1$, $L^2$, $L^3$, $L^4$ and $L^5$ are independently hydrogen, fluorine or chlorine. In formula (1c), preferred examples of $L^1$ and $L^2$ include a combination in which both $L^1$ and $L^2$ are fluorine, a combination in which one is fluorine and the other is hydrogen, and a combination in which both $L^1$ and $L^2$ are hydrogen. Further preferred examples of $L^1$ and $L^2$ include a combination in which both $L^1$ and $L^2$ are fluorine, and a combination in which one is fluorine and the other is hydrogen. In formula (1d), preferred examples of $L^3$, $L^4$ and $L^5$ include a combination in which all of $L^3$, $L^4$ and $L^5$ are fluorine, a combination in which $L^4$ and $L^5$ are fluorine and $L^3$ is hydrogen, a combination in which $L^3$ and $L^4$ are fluorine and $L^5$ is hydrogen, a combination in which $L^4$ is fluorine and $L^3$ and $L^5$ are hydrogen, and a combination in which all of $L^3$, $L^4$ and $L^5$ are hydrogen. Preferred examples of $L^3$, $L^4$ and $L^5$ include a combination in which all of $L^3$, $L^4$ and $L^5$ are fluorine, a combination in which $L^3$ and $L^4$ are fluorine and $L^5$ is hydrogen, and a combination in which $L^4$ is fluorine and $L^3$ and $L^5$ are hydrogen.

In formula (1), $Z^1$, $Z^2$, $Z^3$, $Z^4$ and $Z^5$ are independently a single bond or alkylene having carbons 1 to 6, and in the alkylene, at least one of $-CH_2-$ may be replaced by $-O-$, $-S-$, $-CO-$ or $-SiH_2-$, one or two of $-CH_2CH_2-$ may be replaced by $-CH{=}CH-$ or $-C{\equiv}C-$, and in the divalent groups, at least one of hydrogen may be replaced by fluorine or chlorine; at least one of, $Z^1$ in the case when a is 1, $Z^2$ in the case when b is 1, $Z^3$ in the case when c is 1, $Z^4$ in the case when d is 1 and $Z^5$, is $-CF_2O-$.

Preferred examples of $Z^1$, $Z^2$, $Z^3$, $Z^4$ and $Z^5$ include a single bond, $-(CH_2)_2-$, $-(CH_2)_4-$, $-COO-$, $-OCO-$, $-CH_2O-$, $-OCH_2-$, $-CF_2O-$, $-OCF_2-$, $-CH{=}CH-$, $-CF{=}CF-$, $-C{\equiv}C-$, $-(CH_2)_2COO-$, $-OCO(CH_2)_2-$, $-(CH_2)_2CF_2O-$, $-OCF_2(CH_2)_2-$, $-(CH_2)_3O-$ or $-O(CH_2)_3-$. Further preferred examples of $Z^1$, $Z^2$, $Z^3$, $Z^4$ and $Z^5$ include a single bond, $-(CH_2)_2-$, $-(CH_2)_4-$, $-COO-$, $-OCO-$, $-CH_2O-$, $-OCH_2-$, $-CF_2O-$ and $-OCF_2-$.

In formula (1), terminal group $X^1$ is fluorine, $-C{\equiv}N$, $-N{=}C{=}S$, alkyl having 1 to 10 carbons in which at least one of hydrogen is replaced by fluorine, alkenyl having 2 to 10 carbons at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine. When $Z^5$ is $-COO-$, ring $W^1$ is a group represented by formula (1a) and ring $W^2$ is a group represented by formula (1c), $X^1$ is fluorine, alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine or alkenyloxy having 2 to 9 carbons in which at least one of hydrogen is replaced by fluorine.

Examples of alkyl in which at least one of hydrogen is replaced by fluorine include $-CH_2F$, $-CHF_2$, $-CF_3$, $-(CH_2)_2-F$, $-CF_2CH_2F$, $-CF_2CHF_2$, $-CH_2CF_3$, $-CF_2CF_3$, $-(CH_2)_3-F$, $-(CF_2)_2-CF_3$, $-CF_2CHFCF_3$, $-CHFCF_2CF_3$, $-(CH_2)_4-F$, $-(CF_2)_3-CF_3$, $-(CH_2)_5-F$ and $-(CF_2)_4-CF_3$.

Examples of alkoxy in which at least one of hydrogen is replaced by fluorine include $-OCH_2F$, $-OCHF_2$, $-OCF_3$, $-O-(CH_2)_2-F$, $-OCF_2CH_2F$, $-OCF_2CHF_2$, $-OCH_2CF_3$, $-O-(CH_2)_3-F$, $-O-(CF_2)_2-CF_3$, $-OCF_2CHFCF_3$, $-OCHFCF_2CF_3$, $-O-(CH_2)_4-F$, $-O-(CF_2)_3-CF_3$, $-O-(CH_2)_5-F$ and $-O-(CF_2)_4-CF_3$.

Examples of alkenyl in which at least one of hydrogen is replaced by fluorine include $-CH{=}CHF$, $-CH{=}CF_2$, $-CF{=}CHF$, $-CF{=}CF_2$, $-CH{=}CHCH_2F$, $-CH{=}CHCF_3$, $-CF{=}CHCF_3$, $-CF{=}CFCF_3$, $-(CH_2)_2-CH=CF_2$, $-(CH_2)_2-CF=CF_2$, $-(CH_2)_2-CH=CHCF_3$, $-(CH_2)_2-CF=CHCF_3$ and $-(CH_2)_2-CF=CFCF_3$.

Preferred examples of $X^1$ include fluorine, $-N=C=S$, $-CH_2F$, $-CHF_2$, $-CF_3$, $-(CH_2)_2-F$, $-CH_2CF_3$, $-CF_2CF_3$, $-(CH_2)_3-F$, $-(CH_2)_2-CF_3$, $-(CF_2)_3-F$, $-(CH_2)_4-F$, $-(CH_2)_3-CF_3$, $-(CF_2)_4-F$, $-(CF_2)_5-F$, $-(CF_2)_6-F$, $-(CF_2)_7-F$, $-OCH_2F$, $-OCHF_2$, $-OCF_3$, $-O-(CH_2)_2-F$, $-OCH_2CF_3$, $-OCF_2CF_3$, $-O-(CH_2)_3-F$, $-O-(CH_2)_2-CF_3$, $-O-(CF_2)_3-F$, $-O(CH_2)_4-F$, $-O-(CH_2)_3-CF_3$, $-O-(CF_2)_4-F$, $-O-(CF_2)_5-F$, $-O-(CF_2)_6-F$, $-CH=CHF$, $-CH=CF_2$, $-CF=CHF$, $-CF=CF_2$, $-CH=CHCH_2F$, $-CH=CHCF_3$, $-CF=CHCF_3$, $-CF=CFCF_3$, $-(CH_2)_2-CH=CF_2$, $-(CH_2)_2-CF=CF_2$, $-(CH_2)_2-CH=CHCF_3$, $-(CH_2)_2-CF=CHCF_3$ and $-(CH_2)_2-CF=CFCF_3$.

Further preferred examples of $X^1$ include fluorine, $-CF_3$, $-OCHF_2$, $-OCF_3$, $-CH=CHCF_3$, $-CF=CHCF_3$ and $-CF=CFCF_3$. Most preferred examples of $X^1$ include fluorine, $-CF_3$ and $-OCF_3$.

In formula (1), a, b, c and d are independently 0 or 1, and a sum of a, b, c and d is 0, 1, 2 or 3. Preferred combinations of a, b, c and d include combinations: (a=b=c=d=0), (a=1, b=c=d=0), (c=1, a=b=d=0), (a=b=1, c=d=0), (a=c=1, b=d=0) and (c=d=1, a=b=0). Further preferred combinations of a, b, c and d include combinations: (a=1, b=c=d=0), (a=b=1, c=d=0) and (a=c=1, b=d=0).

1-2. Physical Properties of Compound (1)

In compound (1), physical properties such as a clearing point, optical anisotropy and dielectric anisotropy can be arbitrarily adjusted by suitably selecting a kind of $R^1$, ring $A^1$ to ring $A^4$, $W^1$, $W^2$, $L^1$ to $L^5$, $Y^1$ to $Y^5$, $Z^1$ to $Z^5$, $X^1$, and a combination of a, b, c and d. Compound (1) may also contain an isotope such as $^2H$ (deuterium) and $^{13}C$ more than an amount of natural abundance respectively, because no significant difference is in the physical properties of the compound. A main effect of a kind of $R^1$ or the like on the physical properties of compound (1) is described below.

When left-terminal group $R^1$ has a straight chain, the temperature range of the liquid crystal phase is wide, and the viscosity is small. When $R^1$ is a branched chain, compatibility with other liquid crystal compounds is good. A compound in which $R^1$ is optically active is useful as a chiral dopant. A reverse twisted domain generated in the liquid crystal display device can be prevented by adding the compound to the composition. A compound in which $R^1$ is not optically active is useful as a component of the composition. When $R^1$ is alkenyl, a preferred configuration depends on a position of a double bond. An alkenyl compound having the preferred configuration has a small viscosity, a high maximum temperature or a wide temperature range of the liquid crystal phase. When $R^1$ is alkoxy, compound (1) has the high maximum temperature.

When all of ring $A^1$ to ring $A^4$ are 1,4-cyclohexylene, the clearing point is high and the viscosity is small. When at least one of ring $A^1$ to ring $A^4$ is 1,4-phenylene or 1,4-phenylene in which at least one of hydrogen is replaced by halogen, the optical anisotropy is comparatively large and an orientational order parameter is comparatively large. When all of ring $A^1$ to ring $A^4$ are 1,4-phenylene, 1,4-phenylene in which at least one of hydrogen is replaced by halogen, pyrimidine-2,5-diyl, pyridine-2,5-diyl or a combination thereof, the optical anisotropy is particularly large. When at least one of ring $A^1$ to ring $A^4$ is 2-fluoro-1,4-phenylene, 2-chloro-1,4-phenylene, 2,6-difluoro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl, the dielectric anisotropy is large. When at least one of ring $A^1$ to ring $A^4$ is 2,3-difluoro-1,4-phenylene, 2,3-dichloro-1,4-phenylene, 2-chloro-3-fluoro-1,4-phenylene, tetrahydropyran-2,5-diyl 1,3-dioxane-2,5-diyl, 7,8-difluorochroman-2,6-diyl or 1,1,6,7-tetrafluoro-2,3-dihydro-1H-indene-2,5-diyl, the dielectric constant in the minor axis direction is large.

When $W^1$ is a group represented by formula (1a) and both $Y^1$ and $Y^2$ are fluorine, the clearing point is high and a chemical stability is high. When $W^1$ is a group represented by formula (1b), the optical anisotropy is large. When $W^1$ is a group represented by formula (1b) and all of $Y^3$, $Y^4$ and $Y^5$ are fluorine, the dielectric constant in the minor axis direction is particularly large.

When $W^2$ is a group represented by formula (1c) and both $L^1$ and $L^2$ are hydrogen, the clearing point is high. When $W^2$ is a group represented by formula (1c) and either $L^1$ or $L^2$ is fluorine, the dielectric anisotropy is comparatively large, the dielectric constant in the minor axis direction is large and compatibility with other liquid crystal compounds is good. When $W^2$ is a group represented by formula (1c) and both L and $L^2$ are fluorine, the dielectric anisotropy is particularly large. When $W^1$ is a group represented by formula (1d), the optical anisotropy is large. When $W^1$ is a group represented by formula (1d) and all of $L^3$, $L^4$ and $L^5$ are fluorine, the dielectric anisotropy is significantly large.

When bonding groups $Z^1$ to $Z^5$ are a single bond, $-CH_2CH_2-$, $-CH=CH-$ or $-CF_2O-$, the viscosity is small. When $Z^1$ to $Z^5$ are $-CH=CH-$, $-CH_2O-$ or $-OCH_2-$, the temperature range of the liquid crystal phase is wide and an elastic constant (K) is large. When $Z^1$ to $Z^5$ are a single bond, $-CH=CH-$, $-C\equiv C-$, $-COO-$, $-OCO-$ or $-CF=CF-$, the clearing point is high. When $Z^1$ to $Z^5$ are $-CH=CH-$, $-C\equiv C-$ or $-CF=CF-$, the optical anisotropy is large. When $Z^1$ to $Z^5$ are $-CF_2O-$ or $-COO-$, the dielectric anisotropy is large. When $Z^1$ to $Z^5$ are $-CH_2CH_2-$, $-CH_2O-$ or $-OCH_2-$, the dielectric anisotropy in the minor axis direction is large. When $Z^1$ to $Z^5$ are a single bond, $-CH_2CH_2-$, $-CH_2O-$ or $-OCH_2-$, the chemical stability is high.

When $X^1$ is fluorine, $-C\equiv N$, $-N=C=S$, $-CF_3$, $-CF=CHF$, $-CH=CHCF_3$, $-CF=CHCF_3$ or $-CF=CFCF_3$, the dielectric anisotropy is particularly large. When $X^1$ is $-C\equiv N$, $-N=C=S$, $-CH=CHF$, $-CH=CF_2$, $-CF=CHF$, $-CF=CF_2$, $-CH=CHCH_2F$, $-CH=CHCF_3$, $-CF=CHCF_3$ or $-CF=CFCF_3$, the clearing point is high and the optical anisotropy is large. When $X^1$ is fluorine, $-OCH_2F$, $-OCHF_2$ or $-OCF_3$, the compatibility with other liquid crystal compounds is good. When $X^1$ is fluorine, $-CF_3$, $-CF_2CF_3$, $-(CF_2)_3-F$, $-(CF_2)_4-F$, $-(CF_2)_5-F$, $-(CF_2)_6-F$, $-(CF_2)_7-F$, $-OCF_3$, $-OCF_2CF_3$, $-O-(CF_2)_3-F$, $-O-(CF_2)_4-F$, $-O-(CF_2)_5-F$ or $-O-(CF_2)_6-F$, the chemical stability is high.

When a combination of a, b, c and d is (a=b=c=d=0), the compatibility with other liquid crystal compounds is good and the viscosity is small. When a combination of a, b, c and d is (a=1, b=c=d=0) or (c=1, a=b=d=0), the compatibility with other liquid crystal compounds is good, the dielectric anisotropy is large and the dielectric constant in the minor axis direction is particularly large. When a combination of a, b, c and d is (a=b=1, c=d=0), the clearing point is high, the dielectric anisotropy is large and the dielectric constant in the minor axis direction is large. When a combination of a, b, c and d is (a=c=1, b=d=0), the dielectric anisotropy is large and the compatibility with other liquid crystal compounds is good. When a combination of a, b, c and d is (a=b=c=1, d=0) or (a=1, b=c=d=0), the clearing point is particularly high and the dielectric anisotropy is large.

As described above, a compound having objective physical properties can be obtained by suitably selecting a kind of ring structure, a terminal group, a bonding group or the like. Accordingly, compound (1) is useful as the component of the liquid crystal composition used for the liquid crystal display device having a mode such as a PC, TN, STN, ECB, OCB, IPS, FFS, or VA mode.

1-3. Preferred Compound

Preferred examples of compound (1) include compounds represented by formulas (1-1) to (1-8).

(1-1)

$$R^1—W^1—Z^5—W^2—X^1$$

(1-2)

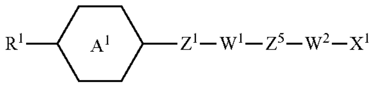

(1-3)

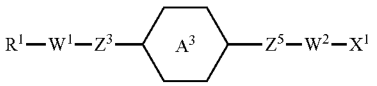

(1-4)

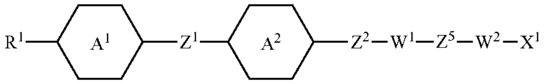

(1-5)

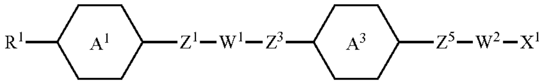

(1-6)

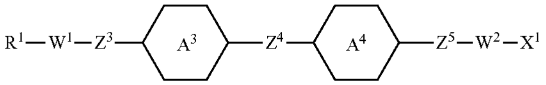

(1-7)

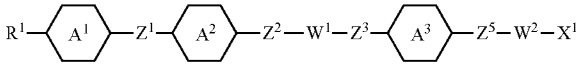

(1-8)

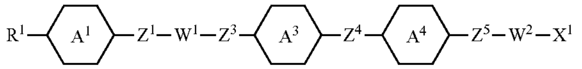

In formulas (1-1) to (1-8), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$W^1$ is a group represented by formula (1a) or formula (1b);

(1a)

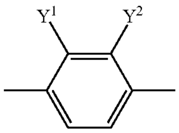

(1b)

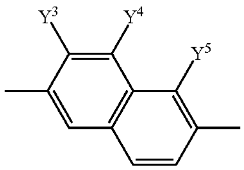

wherein, in formulas (1a) to (1b), $Y^1$ and $Y^2$ are fluorine, $Y^3$, $Y^4$ and $Y^5$ are independently hydrogen or fluorine, and at least two of $Y^3$, $Y^4$ and $Y^5$ is fluorine; and in formulas (1-1) to (1-8), $W^2$ is a group represented by formula (1c) or formula (1d).

(1c)

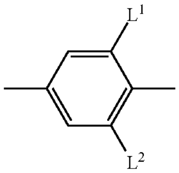

(1d)

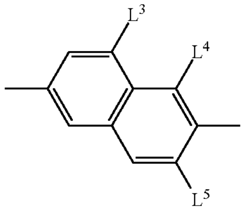

In formulas (1a) to (1b), $L^1$, $L^2$, $L^3$ $L^4$ and $L^5$ are independently hydrogen or fluorine; and in formulas (1-1) to (1-8), $Z^1$, $Z^2$, $Z^3$, $Z^4$ and $Z^5$ are independently a single bond, $—(CH_2)_2—$, $—CH_2O—$, $—OCH_2—$, $—(CH_2)_4—$, $—(CH_2)_2CF_2O—$ or $—OCH_2CF_2O—$, and at least one of $Z^1$, $Z^2$, $Z^3$, $Z^4$ and $Z^5$ is $—(CH_2)_2—$, $—CH_2O—$, $—OCH_2—$, $—(CH_2)_4—$, $—(CH_2)_2CF_2O—$ or $—OCH_2CF_2O—$; and $X^1$ is fluorine, $—CF_3$, $—CHF_2$, $—OCF_3$ or $—OCHF_2$.

(1-9)

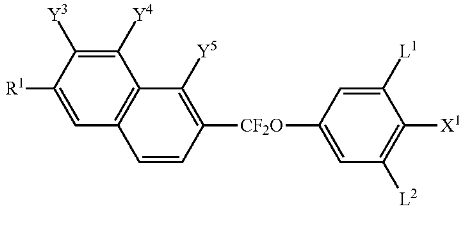

(1-10)

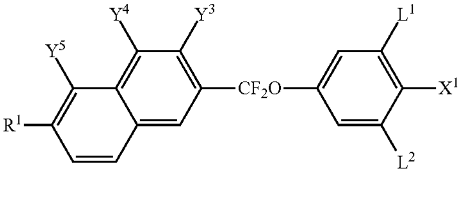

-continued
(1-11)
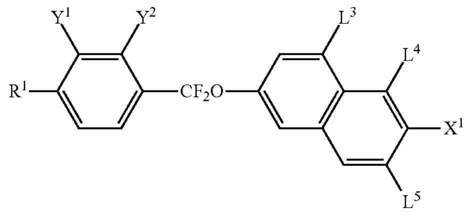
(1-12)
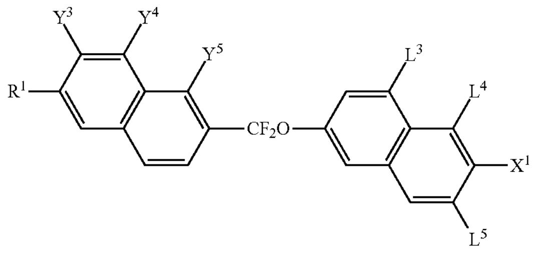
(1-13)
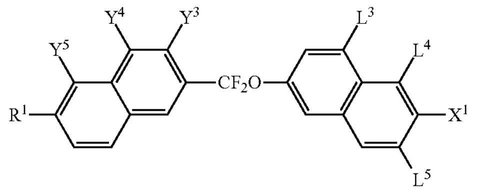
(1-14)
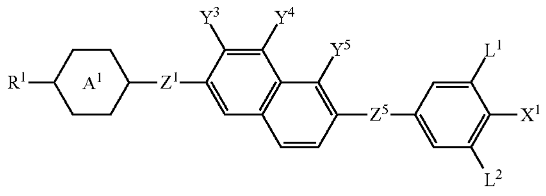
(1-15)
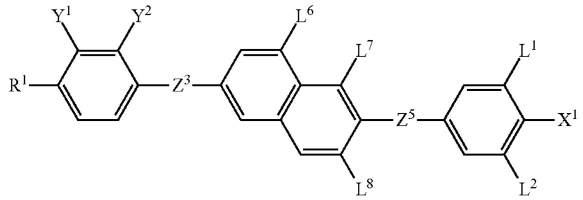
(1-16)
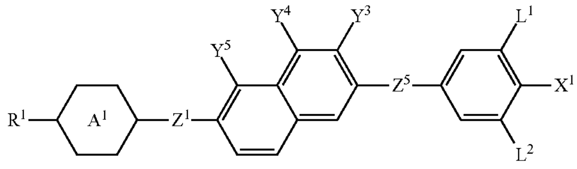
(1-17)
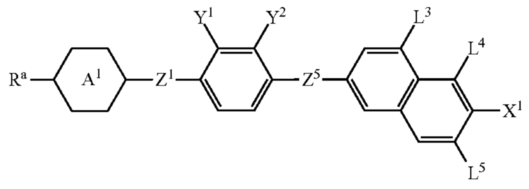
(1-18)
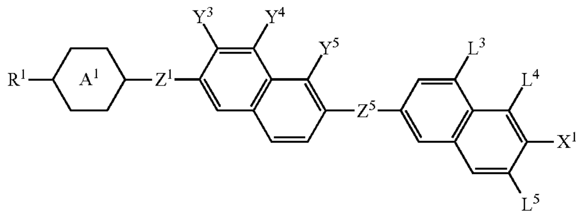
(1-19)
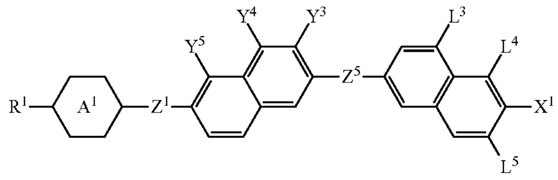
(1-20)
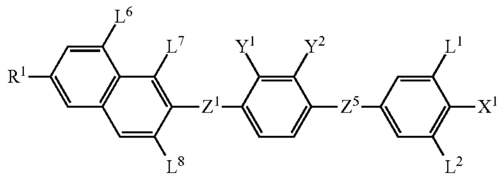
(1-21)
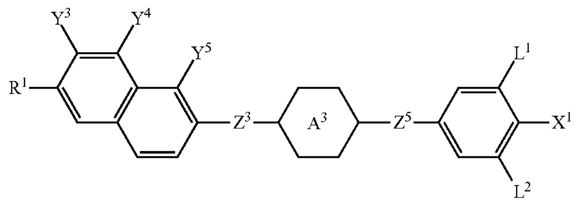
(1-22)
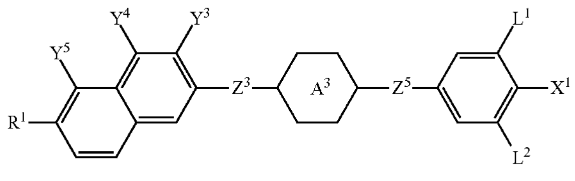
(1-23)
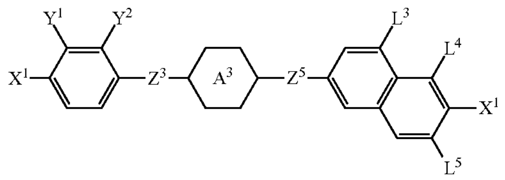
(1-24)
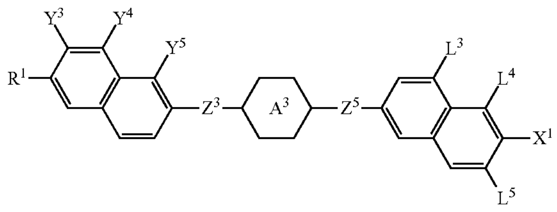

-continued (1-25)

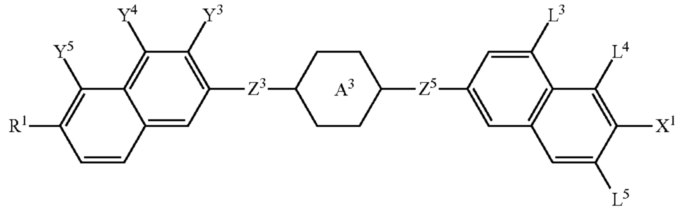

(1-26)

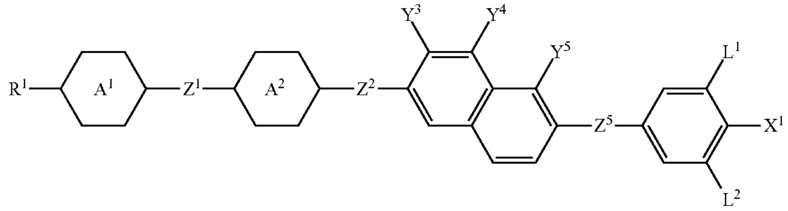

(1-27)

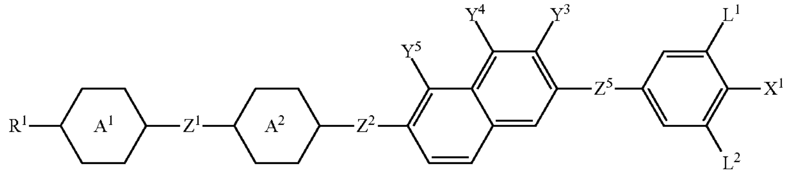

(1-28)

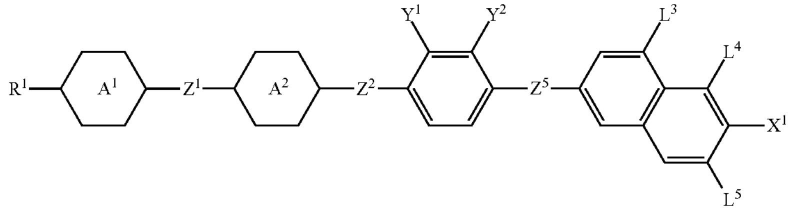

(1-29)

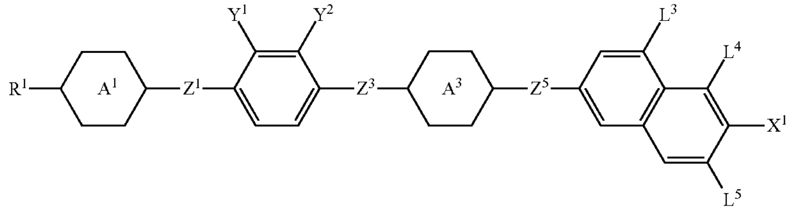

Further preferred examples of compound (1) include compounds represented by formulas (1-9) to (1-29).

In formulas (1-9) to (1-29), $R^1$ is alkyl having 1 to 10 carbons or alkenyl having 2 to 10 carbons;

ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$Z^1$, $Z^2$, $Z^3$ and $Z^5$ are independently a single bond, $-(CH_2)_2-$, $-(CH_2)_4-$, $-COO-$, $-OCO-$, $-CH_2O-$, $-OCH_2-$, $-CF_2O-$ and $-OCF_2-$, and at least one of $Z^1$, $Z^2$, $Z^3$ and $Z^5$ is $-CF_2O-$;

$X^1$ is fluorine, $-CF_3$ or $-OCF_3$; and $L^1$, $L^2$, $L^3$, $L^4$, $L^5$, $L^6$, $L^7$, $L^8$, $Y^1$, $Y^2$, $Y^3$, $Y^4$ and $Y^5$ are independently hydrogen or fluorine.

Still further preferred examples of compound (1) include compounds represented by formulas (1-30) to (1-54).

(1-30)

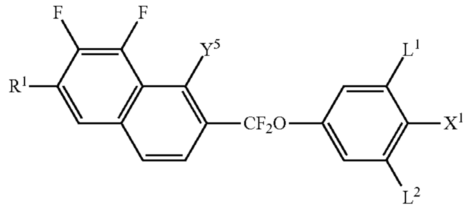

(1-31)

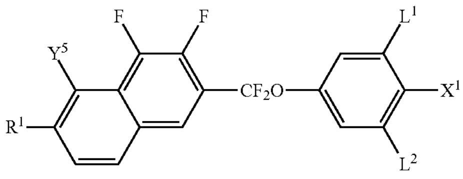

-continued
(1-32)
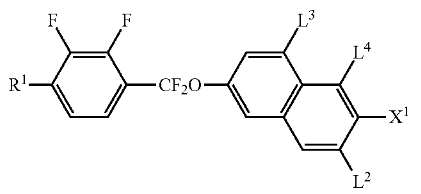
(1-33)
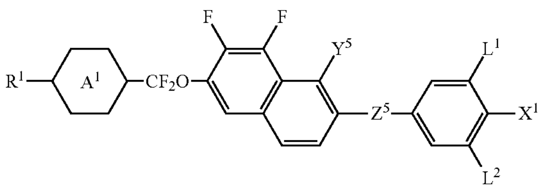
(1-34)
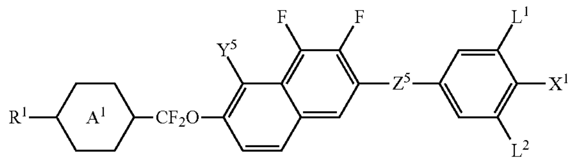
(1-35)
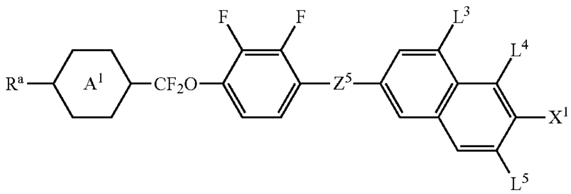
(1-36)
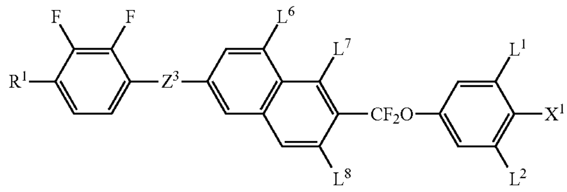
(1-37)
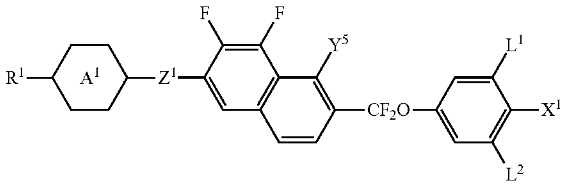
(1-38)
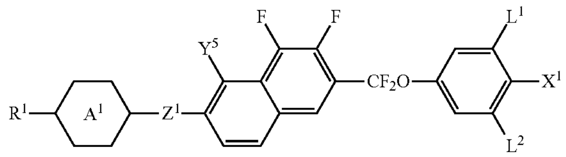
(1-39)
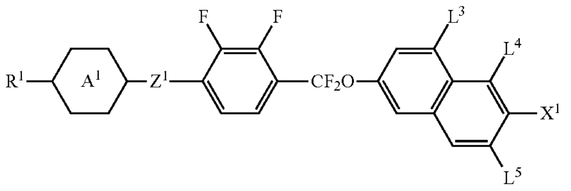
(1-40)
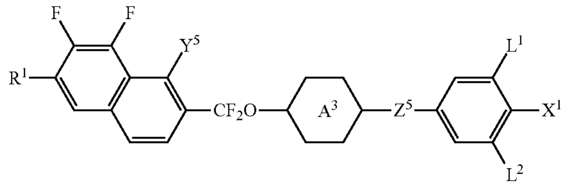
(1-41)
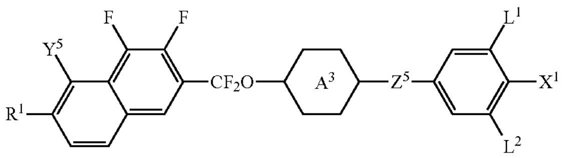
(1-42)
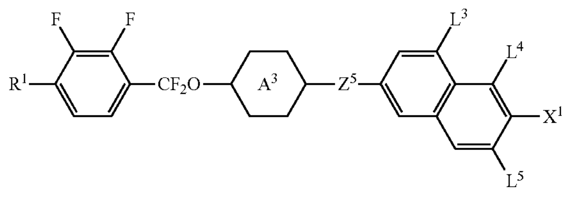
(1-43)
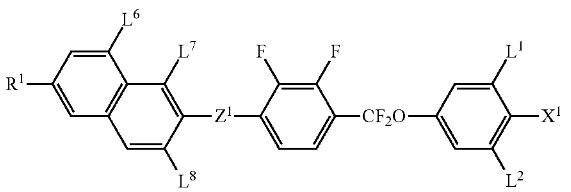
(1-44)
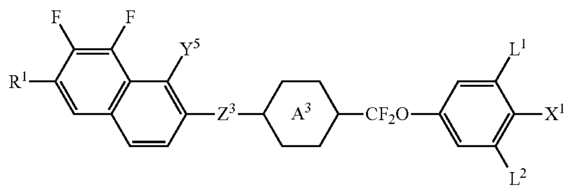
(1-45)
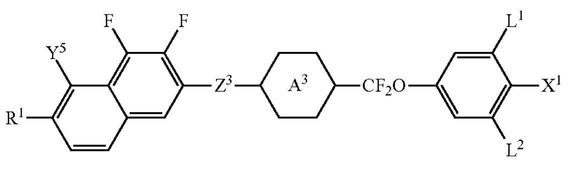

-continued
(1-46)
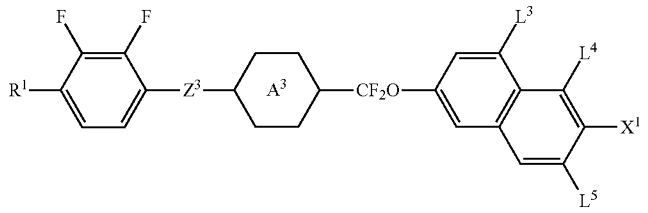
(1-47)
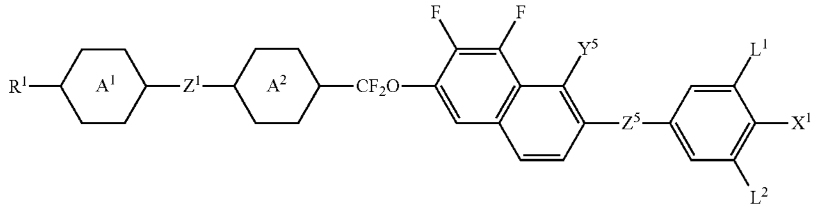
(1-48)
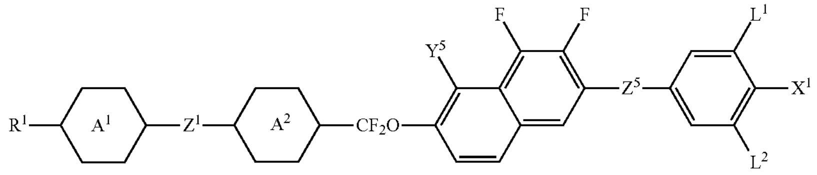
(1-49)
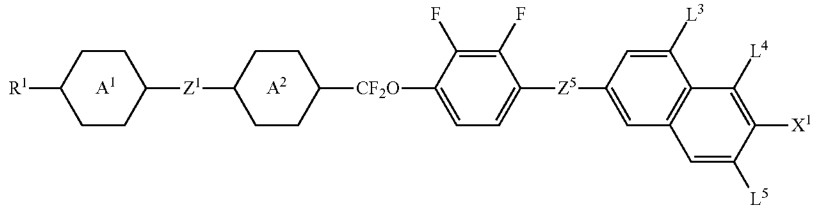
(1-50)
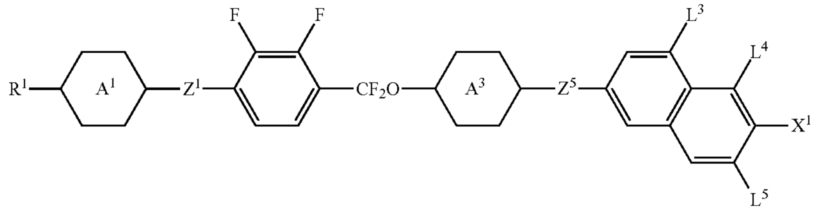
(1-51)
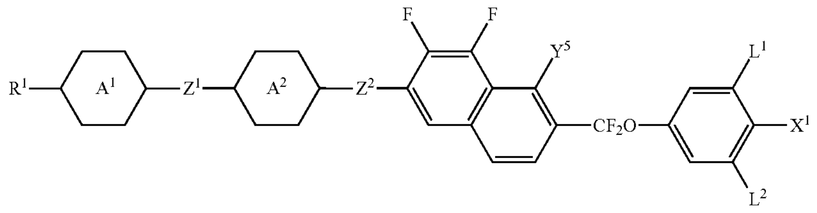
(1-52)
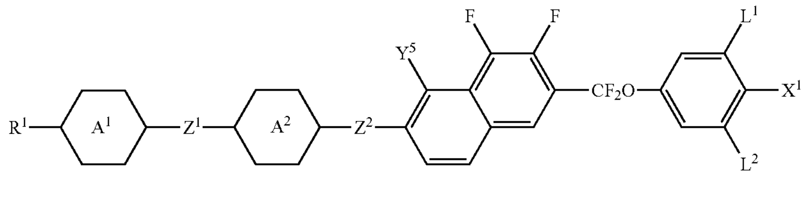

-continued (1-53)

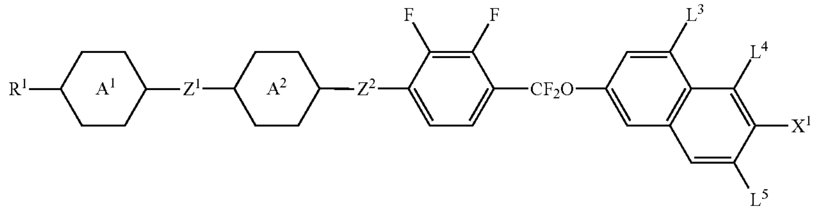

(1-54)

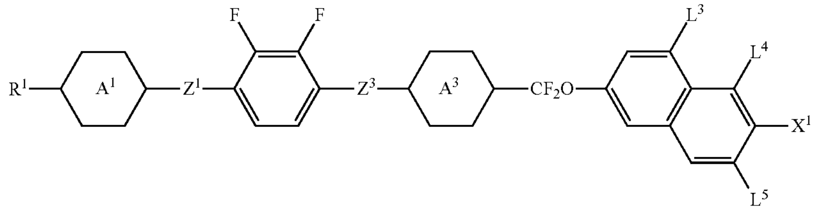

In formulas (1-30) to (1-54), $R^1$ is alkyl having 1 to 10 carbons or alkenyl having 2 to 10 carbons; ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$Z^1$, $Z^2$, $Z^3$ and $Z^5$ are independently a single bond, $-(CH_2)_2-$, $-COO-$, $-OCO-$, $-CH_2O-$, $-OCH_2-$, $-CF_2O-$ and $-OCF_2-$;

$X^1$ is fluorine, $-CF_3$ or $-OCF_3$; and $L^1$, $L^2$, $L^3$, $L^4$, $L^5$, $L^6$, $L^7$, $L^8$ and $Y^5$ are independently hydrogen or fluorine.

Most preferred examples of compound (1) include compounds represented by formulas (1-55) to (1-78).

(1-55)

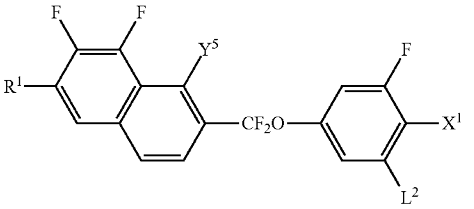

(1-56)

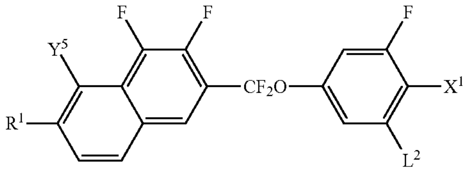

(1-57)

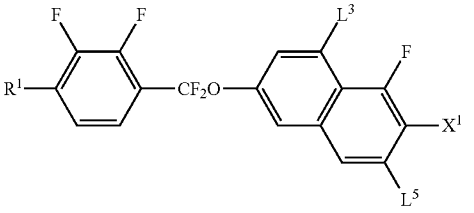

(1-58)

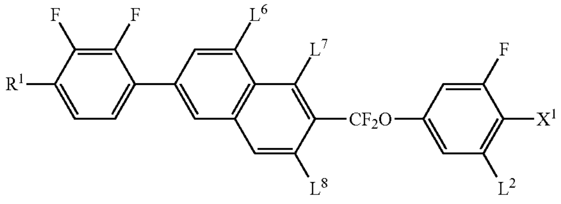

(1-59)

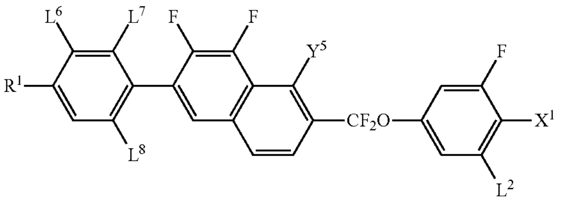

(1-60)

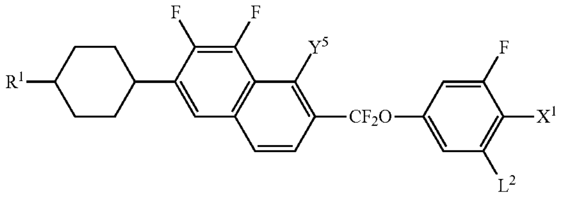

(1-61)

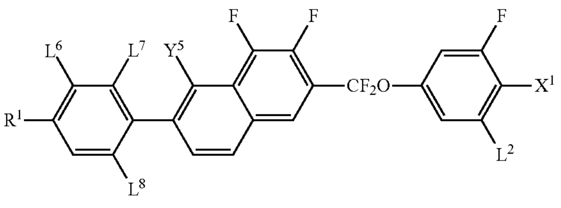

(1-62)

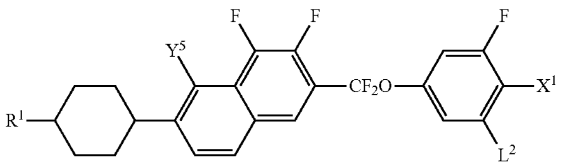

-continued
(1-63)
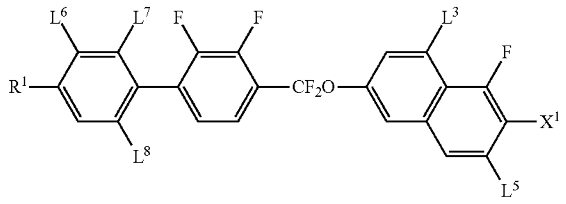
(1-64)
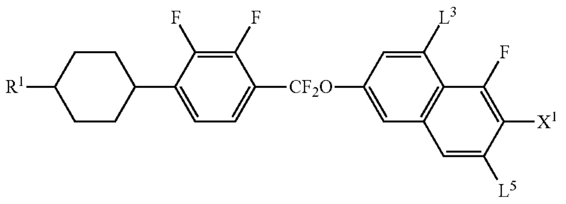
(1-65)
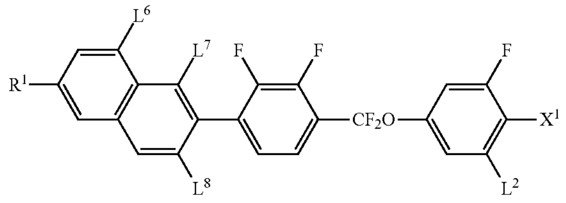
(1-66)
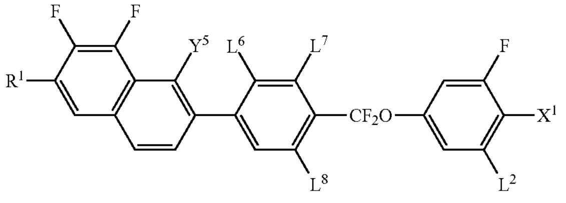
(1-67)
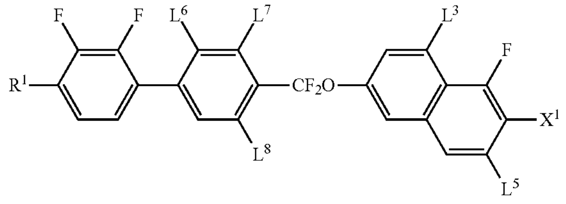
(1-68)
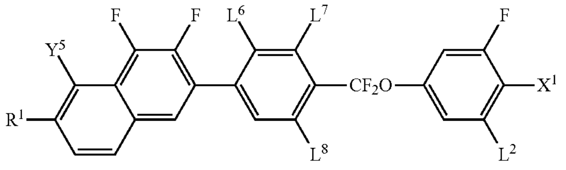
(1-69)
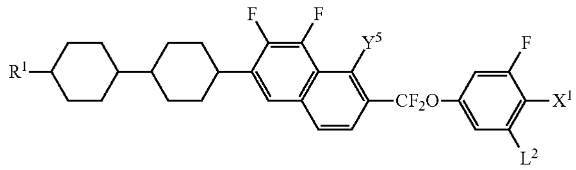
(1-70)
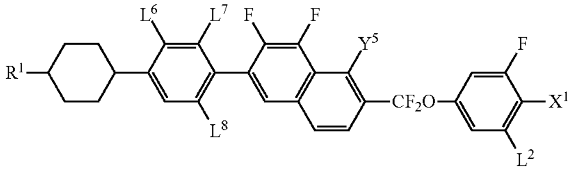
(1-71)
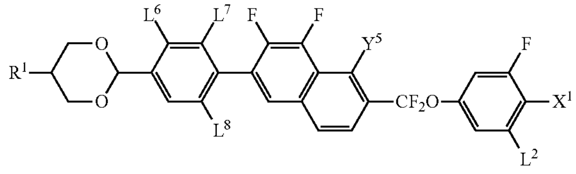
(1-72)
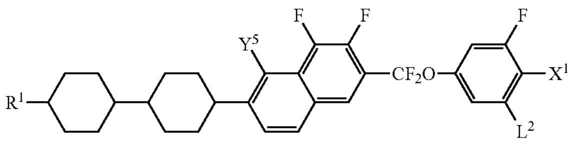
(1-73)
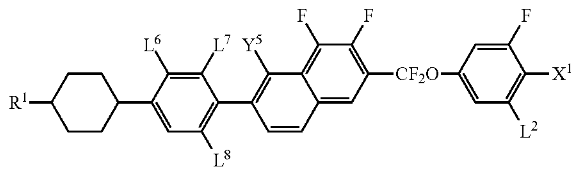
(1-74)
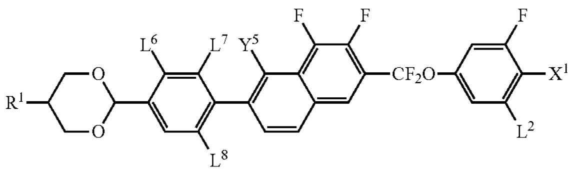
(1-75)
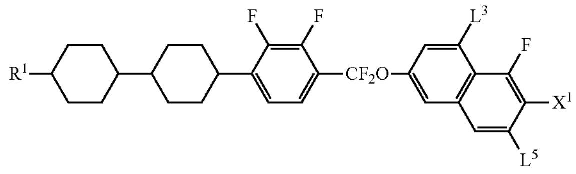
(1-76)
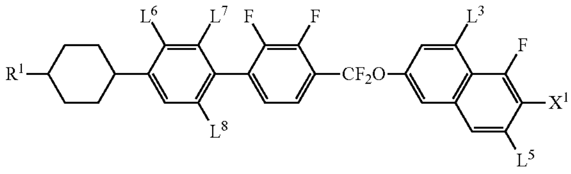

-continued
(1-77)
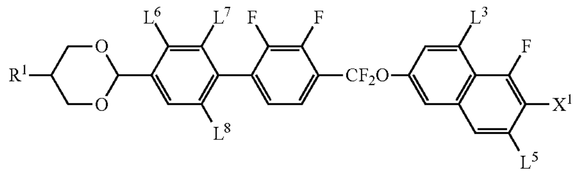
(1-78)
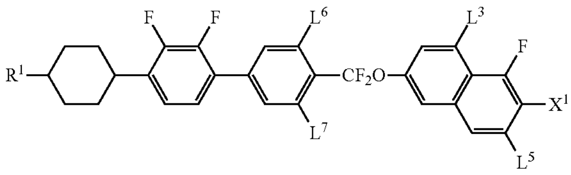
In formulas (1-55) to (1-78), $R^1$ is alkyl having 1 to 10 carbons or alkenyl having 2 to 10 carbons; $X^1$ is fluorine, $—CF_3$ or $—OCF_3$; and $L^2$, $L^3$, $L^5$, $L^6$, $L^7$, $L^8$ and $Y^5$ are hydrogen or fluorine.
Compounds represented by formulas (1-79) to (1-98), among formulas (1-55) to (1-78), are further preferred.
(1-79)
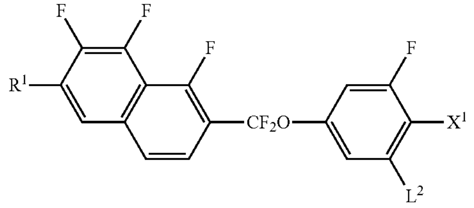
(1-80)
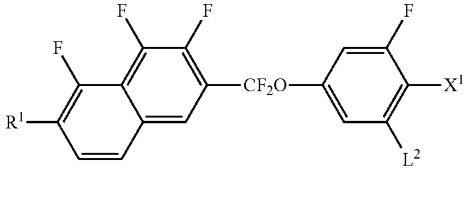
(1-81)
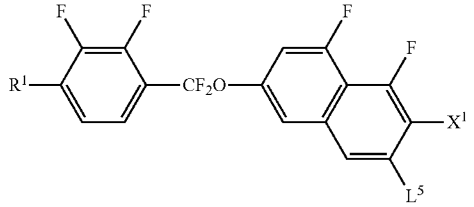
(1-82)
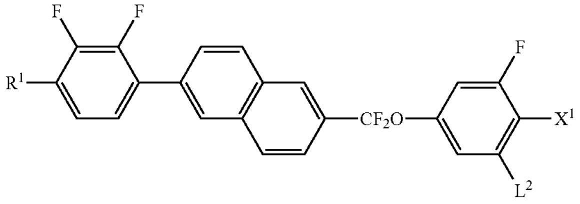
(1-83)
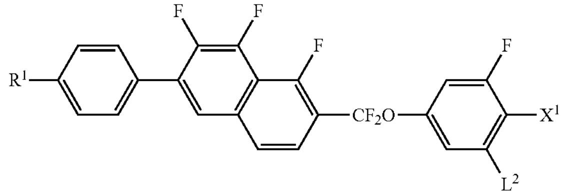
(1-84)
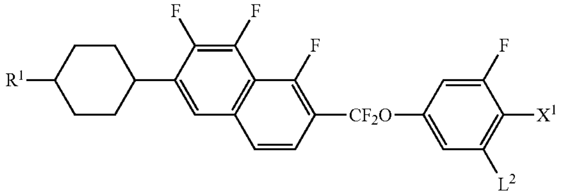
(1-85)
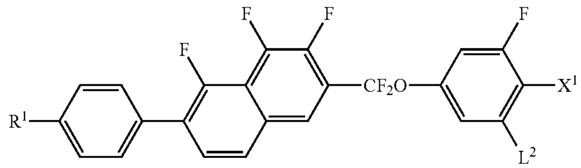
(1-86)
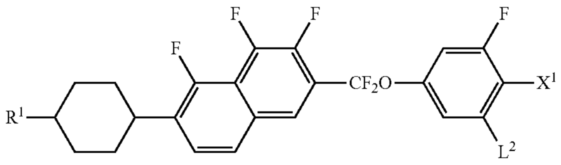
(1-87)
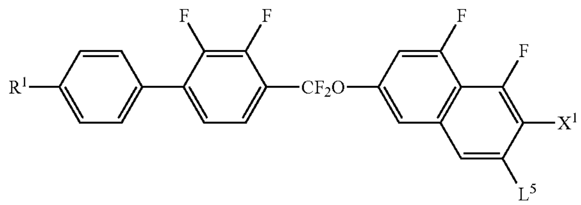
(1-88)
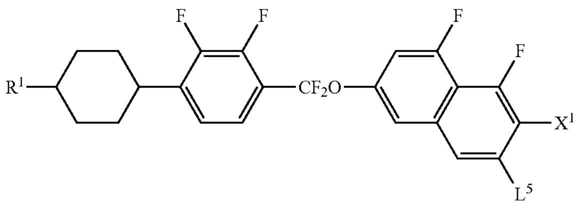

-continued (1-89)

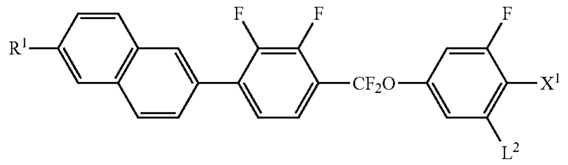

(1-90)

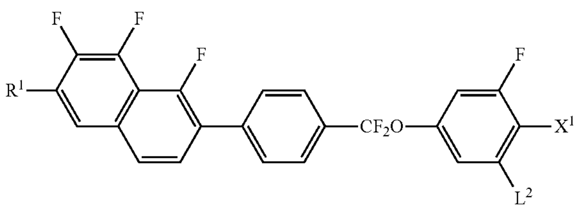

(1-91)

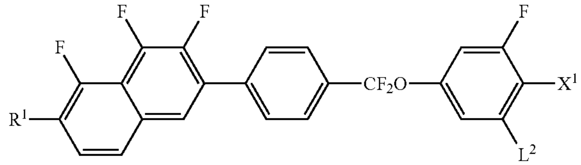

(1-92)

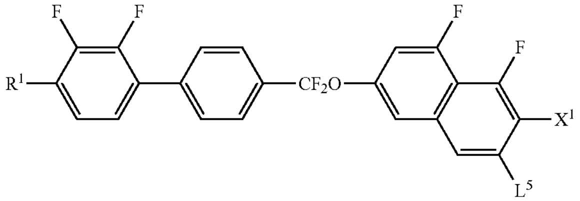

(1-93)

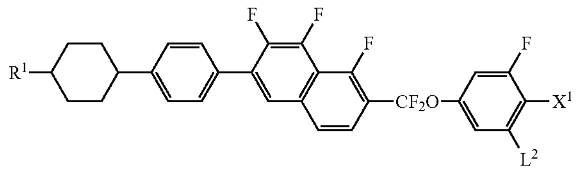

(1-94)

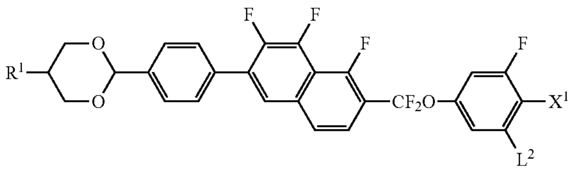

(1-95)

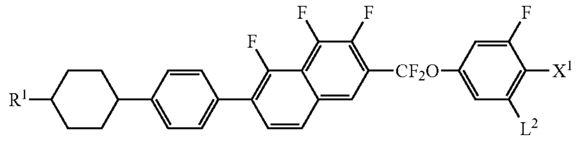

(1-96)

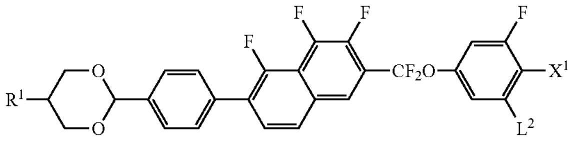

(1-97)

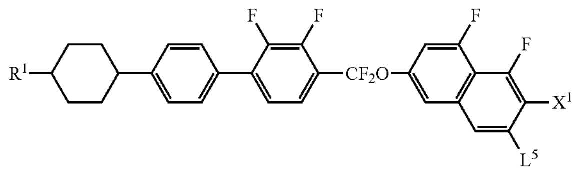

(1-98)

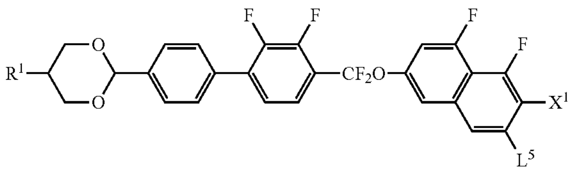

In formulas (1-79) to (1-98), $R^1$ is alkyl having 1 to 10 carbons or alkenyl having 2 to 10 carbons; $X^1$ is fluorine, $—CF_3$ or $—OCF_3$; and $L^2$ and $L^5$ are hydrogen or fluorine.

1-4. Synthesis of Compound (1)

A synthetic method of compound (1) is described. Compound (1) can be synthesized by suitably combining methods in synthetic organic chemistry. A method of introducing an objective terminal group, ring and bonding group into a starting material is described in books such as “Organic Syntheses” (John Wiley & Sons, Inc.), “Organic Reactions” (John Wiley & Sons, Inc.), “Comprehensive Organic Synthesis” (Pergamon Press) and “New Experimental Chemistry Course (Shin Jikken Kagaku Koza in Japanese)” (Maruzen Co., Ltd.).

1-4-1. Formation of a Bonding Group

An example of the method of forming a single bond in compound (1) is as described in a scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to (1G) correspond to compound (1) or an intermediate of compound (1).

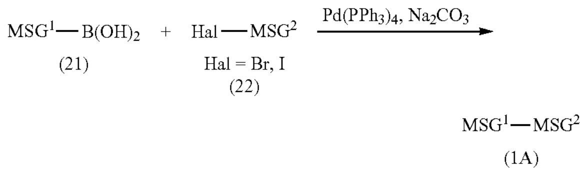

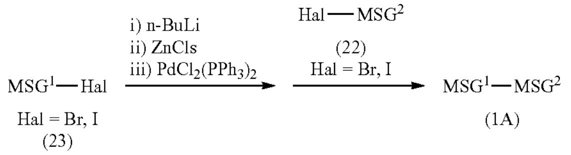

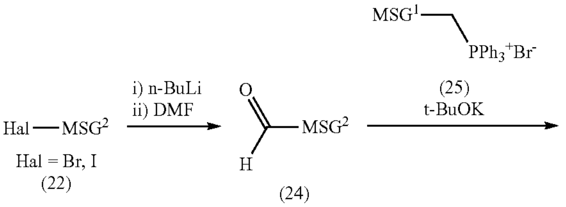

-continued
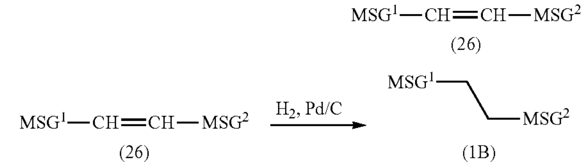
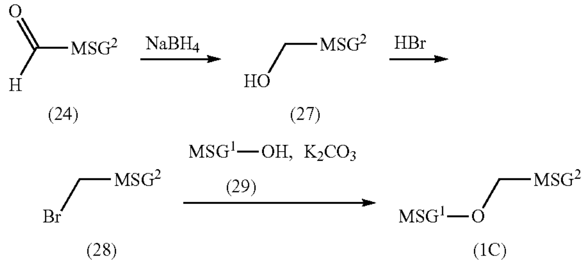
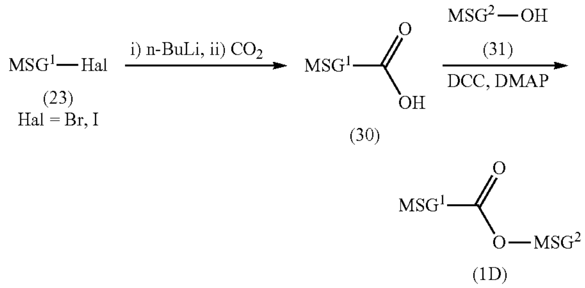
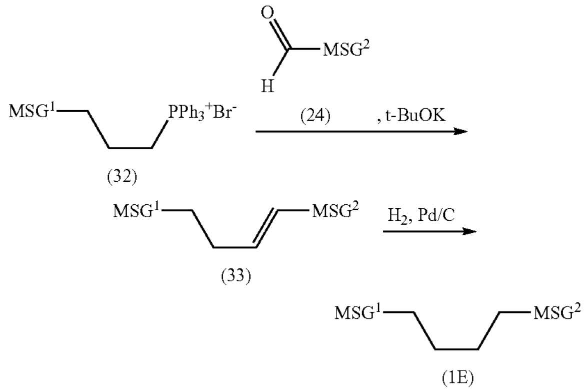
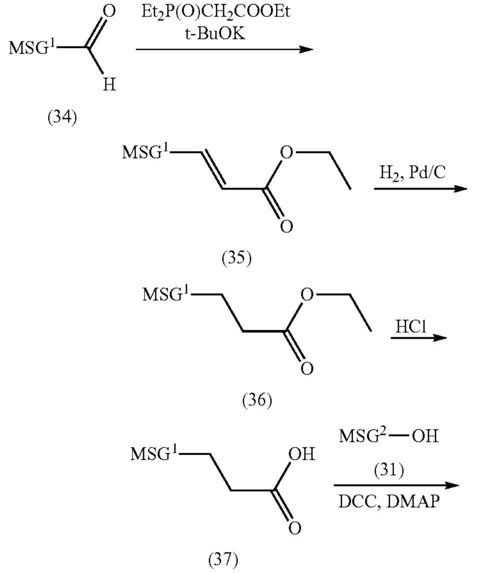
-continued
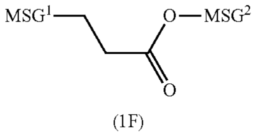
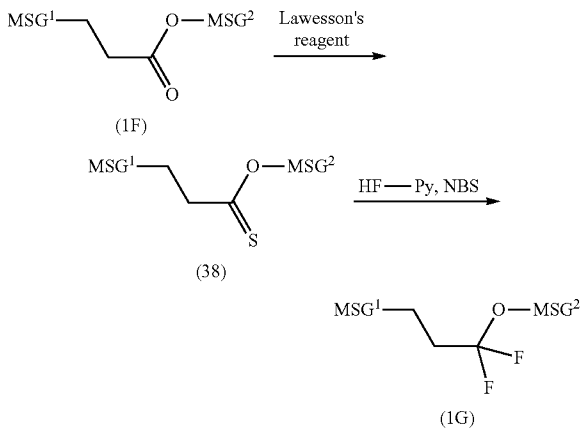
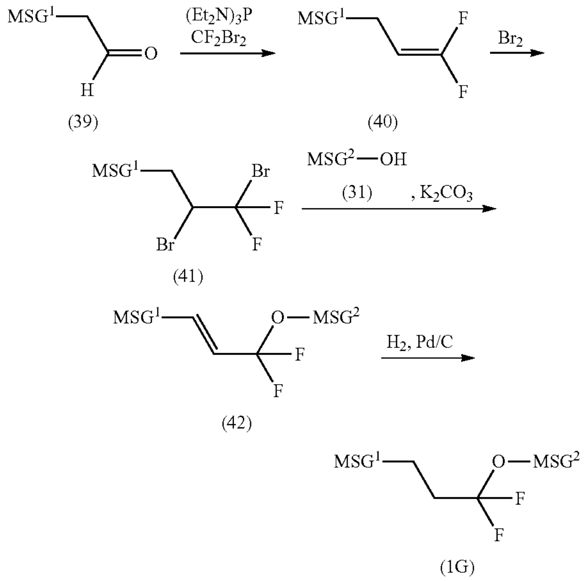
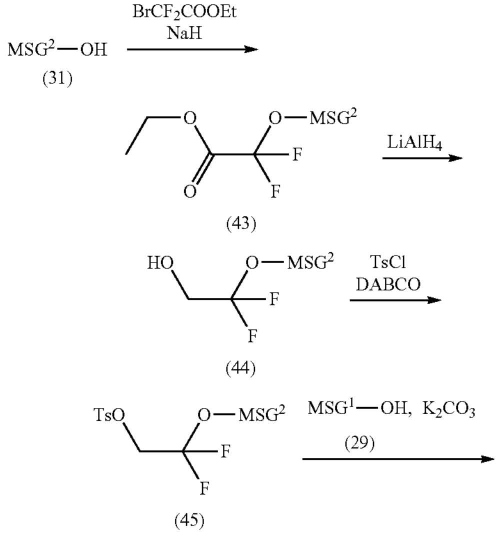

-continued

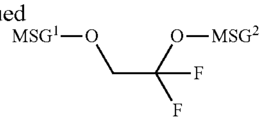

(1H)

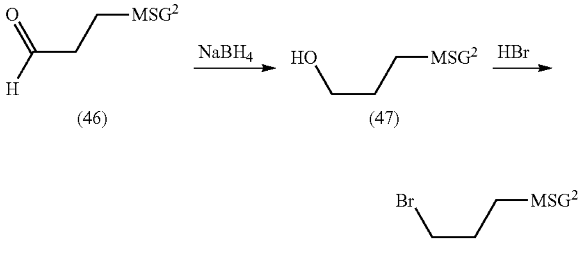

(46) (47)

(48)

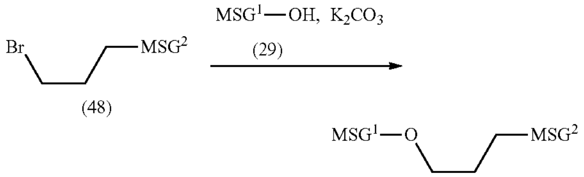

(48)

(1I)

(I) Formation of Single Bond

Compound (1A) is prepared by allowing arylboronic acid (21) to react with compound (22) in the presence of carbonate and a tetrakis(triphenylphosphine)palladium as catalyst. The compound (1A) can also be prepared by allowing compound (23) to react with n-butyllithium, and subsequently with zinc chloride, and allowing the resulting product to react with compound (22) in the presence of a dichlorobis(triphenylphosphine)palladium as catalyst.

(II) Formation of $—CH_2CH_2—$

Aldehyde (24) is prepared by allowing compound (22) to react with n-butyllithium, and subsequently with N,N-dimethylformamide (DMF). Compound (26) is prepared by allowing phosphorus ylide obtained by allowing phosphonium salt (25) to react with potassium tert-butoxide to react with aldehyde (24). Compound (1B) is prepared by hydrogenating compound (26) in the presence of palladium carbon catalyst.

(III) Formation of $—OCH_2—$ and $—CH_2O—$

Compound (27) is obtained by reducing compound (24) with sodium borohydride. Compound (28) is obtained by brominating compound (27) by hydrobromic acid. Compound (28) is allowed to react with compound (29) in the presence of potassium carbonate to form compound (1C). A compound having $—CH_2O—$ is also obtained according to the method.

(IV) Formation of —COO— and —OCO—

Carboxylic acid (30) is obtained by allowing compound (23) to react with n-butyllithium and subsequently with carbon dioxide. Compound (1G) having —COO— is prepared by dehydrating carboxylic acid (30) and phenol (31) in the presence of 1,3-dicyclohexylcarbodiimide (DDC) and 4-dimethylaminopyridine (DMAP). A compound having —OCO— is also prepared according to the method.

(V) Formation of $—(CH_2)_4—$

Compound (1E) is prepared by using phosphonium salt (32) according to the method described in section (II).

(VI) Formation of $—(CH_2)_2COO—$

Compound (35) is obtained by acting diethylphosphoethyl acetate and potassium tert-butoxide on aldehyde (34). Compound (36) is obtained by hydrogenating compound (35) in the presence of palladium carbon catalyst, and subsequently carboxylic acid (37) is obtained by hydrolyzing compound (36). Compound (1F) is obtained by condensing carboxylic acid (37) and phenol (31) in the presence of DDC and DMAP.

(VII) Formation of $—(CH_2)_2CF_2O—$

Compound (38) is obtained by thionating compound (1F) with Lawesson's reagent. Compound (1G) having $—(CH_2)_2CF_2O—$ is obtained from fluorinating compound (38) by a hydrogen fluoride-pyridine complex and N-bromosuccinimide (NBS). Compound (1G) is also obtained by difluoromethylation, bromination, etherification and hydrogenation, one by one, from compound (39).

(VIII) Formation of $—OCH_2CF_2O—$

Compound (43) is obtained by etherifying phenol (31) and ethyl bromodifluoroacetate in the presence of NaH. Then, alcohol (44) is obtained by reducing compound (43) with lithium aluminum hydride. Compound (45) is obtained by tosylating alcohol (44) with p-toluenesulfonyl chloride and 1,4-diazabicyclo[2.2.2]octane (DABCO), and subsequently compound (45) is allowed to react with compound (29) in the presence of potassium carbonate to prepare compound (1H).

(IX) Formation of $—O(CH_2)_3—$ and $—(CH_2)_3O—$

Compound (1I) is prepared by using aldehyde (46) according to the method described in section (III). A compound having $—(CH_2)_3O—$ is prepared according to the method.

1-4-2. Formation of Ring $A^1$ and Ring $A^2$

With regard to a ring such as 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl and pyridine-2,5-diyl, a starting material thereof is commercially available or a synthetic method thereof is well known.

1-4-2. Synthesis Example

An example of a method of preparing compound (1) is as described below. In the compounds, $R^1$, ring $A^1$ to ring $A^4$, $Z^1$ to $Z^5$, $W^1$, $W^2$, $Y^1$ to $Y^5$, $L^1$ to $L^5$, $X^1$, a, b, c and d are defined in a manner identical with the definitions in item 1 described above.

Compound (1-101) in which $Z^5$ is $—CF_2O—$ in formula (1) can be prepared according to the method described below. Compound (50) is obtained by acting propanedithiol and trifluoromethanesulfonic acid on compound (49) prepared according to a known method. Then, compound (1-101) can be derived from compound (51) obtained according to a known method by being allowed to react with compound (50) using triethylamine, hydrogen fluoride-triethylamine complex and bromine. In addition, a compound in which a=1 and $Z^1$ is $—CF_2O—$, a compound in which b=1 and $Z^2$ is $—CF_2O—$, a compound in which c=1 and $Z^3$ is $—CF_2O—$, and a compound in which d=1 and $Z^4$ is $—CF_2O—$ can also be prepared by the similar method.

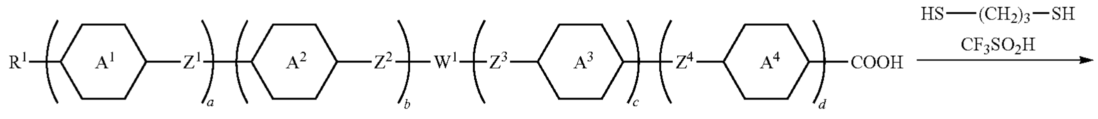

(49)

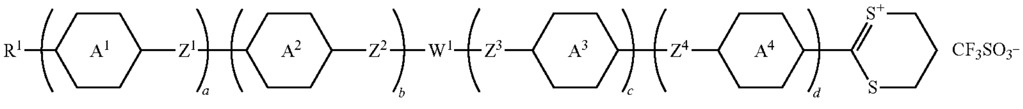

(50)

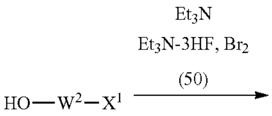

(51)

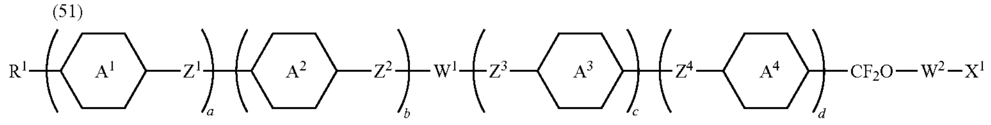

(1-101)

Compound (1-102) in which $Z^5$ is —$CF_2O$—, d=1 and ring $A^4$ is 2,6-difluoro-1,4-phenylene, in formula (1), can also be prepared by the method described below. Compound (53) is obtained by acting N-butyllithium and dibromodifluoromethane on compound (52) prepared according to a known method. Then, compound (1-101) can be derived from compound (51) by being allowed to react with compound (53) in the presence of a base such as potassium carbonate. In addition, a compound in which a=1, $Z^1$ is —$CF_2O$— and ring $A^1$ is 2,6-difluoro-1,4-phenylene, a compound in which b=1, $Z^2$ is —$CF_2O$— and ring $A^2$ is 2,6-difluoro-1,4-phenylene, a compound in which c=1, d=0, $Z^5$ is —$CF_2O$— and ring $A^3$ is 2,6-difluoro-1,4-phenylene, and a compound in which c=1, d=1, $Z^4$ is —$CF_2O$— and ring $A^3$ is 2,6-difluoro-1,4-phenylene can also be prepared by a similar method.

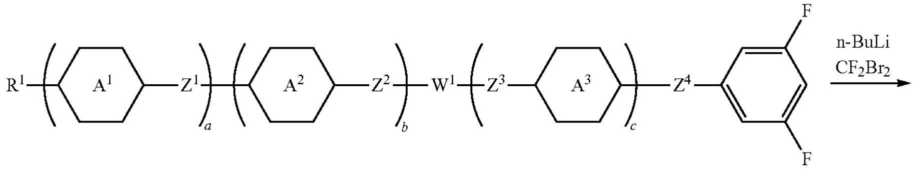

(52)

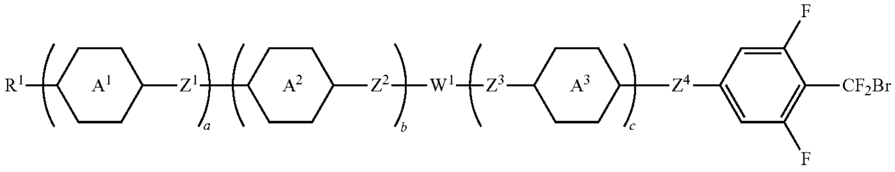

(53)

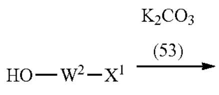

(51)

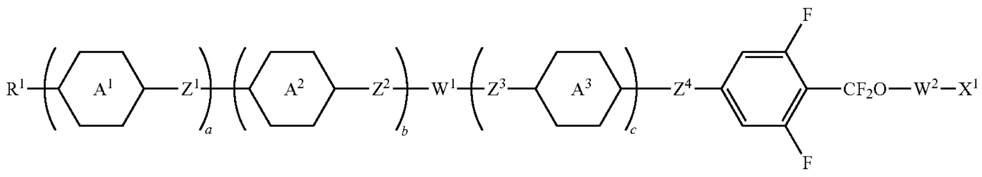

(1-102)

Compound (1-103) in which d=1, $Z^5$ is —$CF_2O$— and ring $A^4$ is 1,4-cyclohexenylene, or compound (1-104) in which d=1, $Z^5$ is —$CF_2O$— and ring $A^4$ is 1,4-cyclohexylene, in formula (1), can also be prepared by the method described below. Compound (55) is obtained by acting tris(diethylamino)phosphine and dibromodifluoromethane on compound (54) prepared according to a known method. Then, compound (56) is obtained by acting bromine on compound (55). Then, compound (1-103) can be obtained by allowing compound (51) to react with compound (56) in the presence of a base such as potassium carbonate. Then, compound (1-104) can be derived from compound (1-103) being subjected to catalytic hydrogenation using a catalyst containing palladium carbon catalyst or the like. In addition, a compound in which a=1, $Z^1$ is —$CF_2O$— and ring $A^1$ is 1,4-cyclohexenylene, or a=1, $Z^1$ is —$CF_2O$— and ring $A^1$ is 1,4-cyclohexylene, or a compound in which b=1, $Z^2$ is —$CF_2O$— and ring $A^2$ 1,4-cyclohexenylene, or b=1, $Z^2$ is —$CF_2O$— and ring $A^2$ is 1,4-cyclohexylene, or a compound in which c=1, d=0, $Z^5$ is —$CF_2O$— and ring $A^3$ is 1,4-cyclohexenylene, or a compound in which c=1, d=0, $Z^5$ is —$CF_2O$— and ring $A^3$ is 1,4-cyclohexylene, or a compound in which c=1, d=1, $Z^4$ is —$CF_2O$— and ring $A^3$ is 1,4-cyclohexenylene, or a compound in which c=1, d=1, $Z^4$ is —$CF_2O$— and ring $A^3$ is 1,4-cyclohexylene can also be prepared by a similar method.

Compound (1-105) in which $W^1$ is represented by formula (1b) and $Y^3$, $Y^4$ and $Y^5$ are fluorine in formula (1) can be prepared by the method described below, for example. Compound (58) is obtained by acting thionyl chloride on compound (57) prepared according to a known method, and then compound (59) is obtained by acting an ethylene gas on the resulting product in the presence of aluminum chloride. Then, compound (60) is obtained by acting an oxidizing agent such as bromine on compound (59), and then compound (61) is obtained by methylating a phenolic hydroxyl group in the resulting product. Then, compound (61) is treated with n-butyllithium, and then compound (62) is obtained by acting bromine on the resulting product. Then, compound (64) is obtained by coupling compound (62) with, for example, compound (63). Then, compound (65) is obtained by acting boron tribromide or the like on compound (64), and then compound (66) is obtained by acting N,N'-difluoro-2,2'-bipyridiniumbis(tetrafluoroborate) on compound (65). Then, compound (67) is obtained by adding a palladium/carbon catalyst to compound (66) and mixing the resulting mixture under a hydrogen atmosphere, and then compound (68) is obtained by acting trifluoromethanesulfonic anhydride on compound (67). Objective compound (1-105) can be obtained by coupling compound (68) with, for example, compound (69).

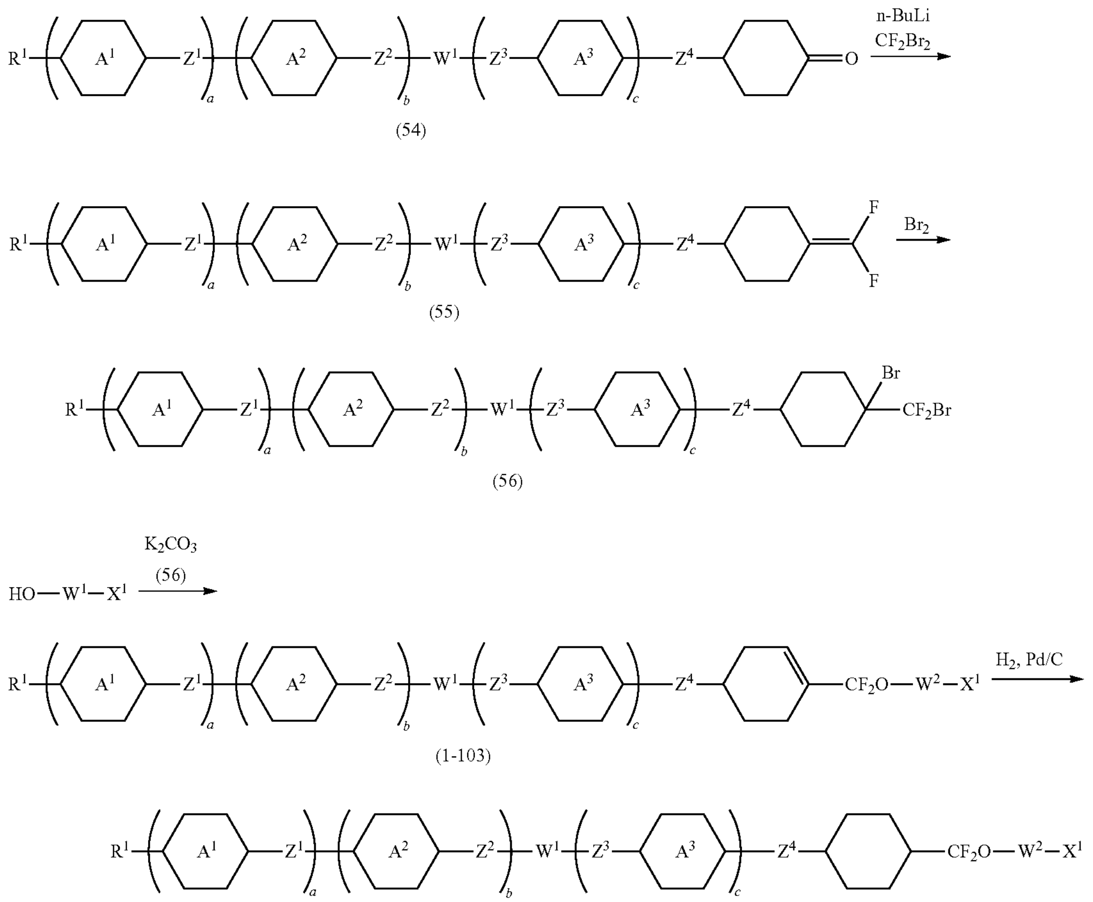

(54)

(55)

(56)

(1-103)

(1-104)

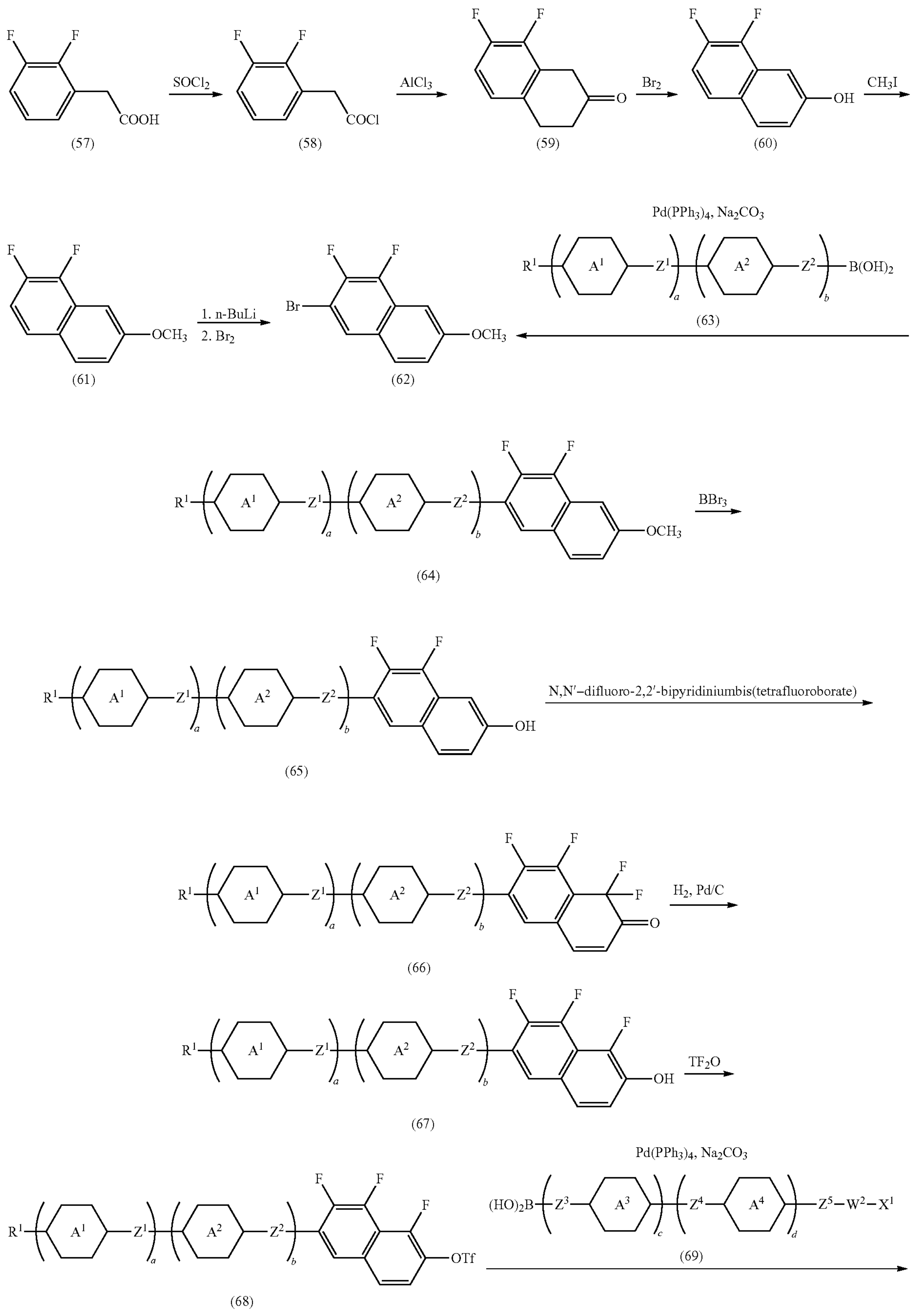
SOCl2
AlCl3
Br2
CH3I
(57)
(58)
(59)
(60)
1. n-BuLi
2. Br2
Pd(PPh3)4, Na2CO3
(61)
(62)
(63)
BBr3
(64)
N,N′-difluoro-2,2′-bipyridiniumbis(tetrafluoroborate)
(65)
H2, Pd/C
(66)
TF2O
(67)
Pd(PPh3)4, Na2CO3
(68)
(69)

-continued

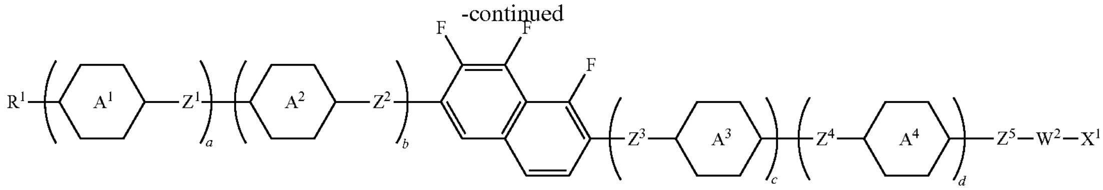

(1-105)

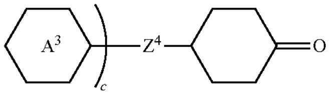

Compound (1-106) in which $W^2$ is represented by formula (1d) and $L^3$, $L^4$, $L^5$ and $X^1$ are fluorine in formula (1) can be prepared by the method described below, for example. Compound (71) is obtained by acting aluminum chloride on compound (70) prepared according to a known method, and then compound (72) is obtained by acting a fluorinating agent such as diethylamino sulfur trifluoride (DAST) on the resulting product. Subsequently, compound (73) is obtained by acting a reducing agent such as potassium tert-butoxide on compound (72), and then compound (74) is obtained by acting bromine on the resulting product. Objective compound (1-106) can be obtained by coupling compound (74) with, for example, compound (75).

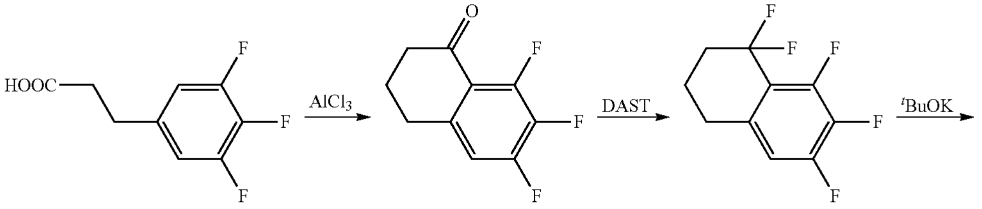

(70) (71) (72)

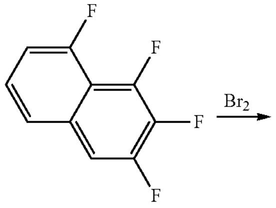

(73)

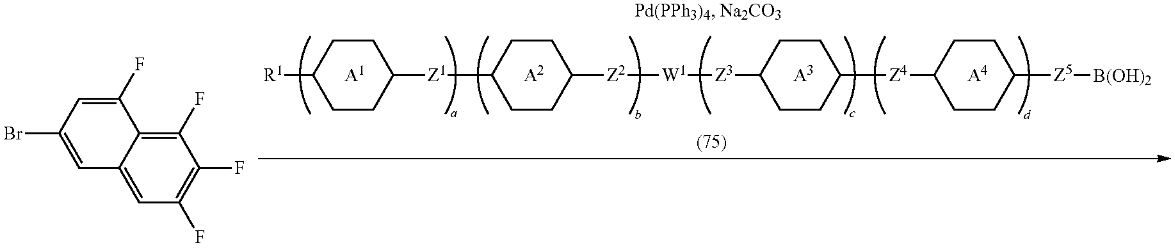

(75)

(74)

-continued

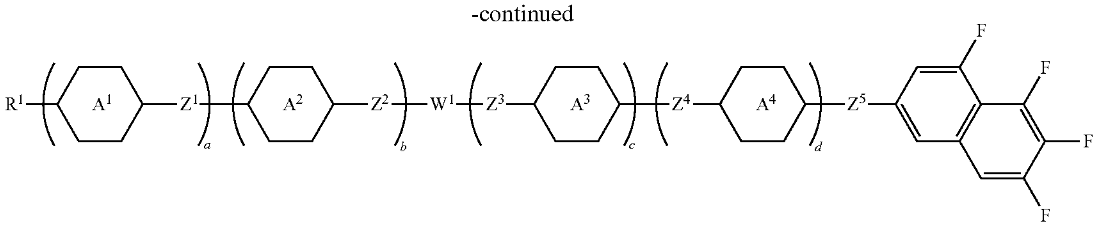

(1-106)

2. Composition (1)

Composition (1) of the invention is described. The composition (1) contains at least one compound (1) as component A. The composition (1) may contain two or more compounds (1). The component of the liquid crystal compound may include only compound (1). In order to obtain excellent physical properties, the composition (1) preferably contains at least one compound (1) in the range of approximately 1 to approximately 99% by weight. In a composition having a positive dielectric anisotropy, a preferred content of compound (1) is in the range of approximately 5 to approximately 60% by weight. In a composition having a negative dielectric anisotropy, the preferred content of compound (1) is approximately 30% by weight or less. The composition (1) may also contain compound (1) and various kinds of liquid crystal compounds that are not described herein.

A preferred composition contains a compound selected from components B, C, D and E shown below. When composition (1) is prepared, the component can be selected, for example, in consideration of the dielectric anisotropy of compound (1). When the composition having the positive dielectric anisotropy is prepared for the mode such as TFT, IPS and FFS, a main component thereof includes components A, B and E. When the composition having the positive dielectric anisotropy is prepared for the mode such as STN and TN, a main component thereof includes components A, C and E. When the composition having the negative dielectric anisotropy is prepared for the mode such as the VA and PSA, a main component thereof includes component D and component E, and component A is added for the purpose of adjusting a voltage-transmittance curve of the device. The composition in which the component is suitably selected has a high maximum temperature, a low minimum temperature, a small viscosity, a suitable optical anisotropy, a large dielectric anisotropy and a suitable elastic constant.

Component B includes compounds (2) to (4). Component C includes compound (5). Component D includes compounds (6) to (12). Component E includes compounds (13) to (15). The components are described, one by one.

Component B is a compound having a halogen-containing or fluorine-containing group at a right terminal. Specific preferred examples of component B include compounds (2-1) to (2-16), compounds (3-1) to (3-113) and compounds (4-1) to (4-57). In the compounds, $R^{11}$ and $X^{11}$ are defined in a manner identical with the definitions in item 10 as described above.

(2-1)

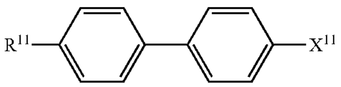

-continued (2-2)

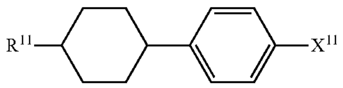

(2-3)

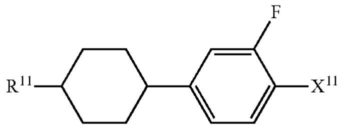

(2-4)

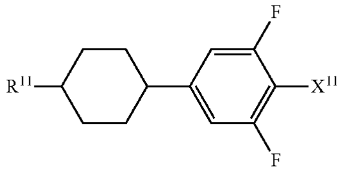

(2-5)

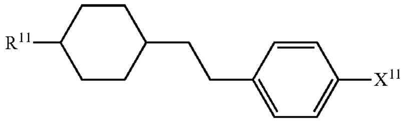

(2-6)

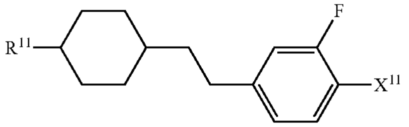

(2-7)

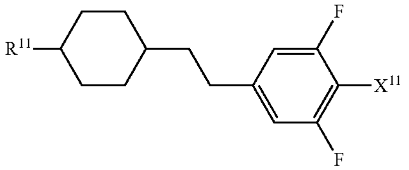

(2-8)

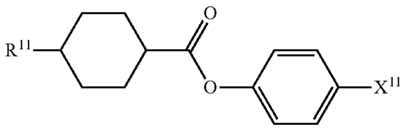

(2-9)

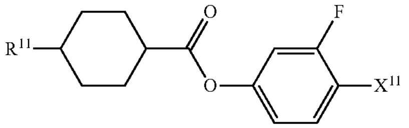

-continued
(2-10)
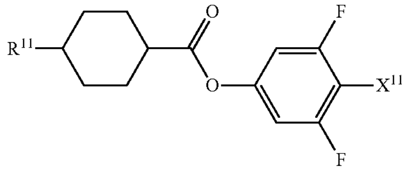
(2-11)
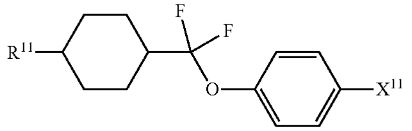
(2-12)
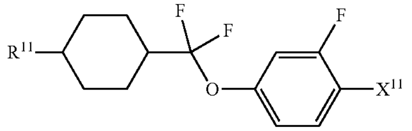
(2-13)
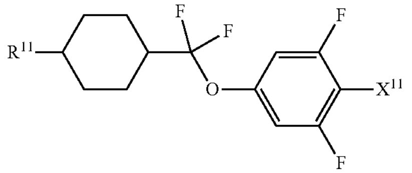
(2-14)
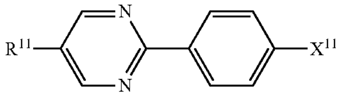
(2-15)
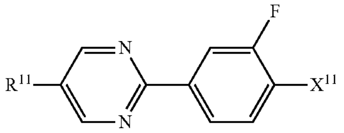
(2-16)
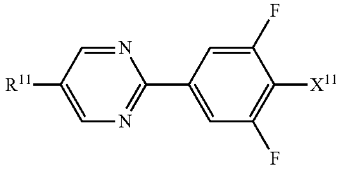
(3-1)
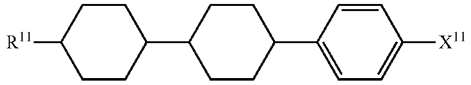
(3-2)
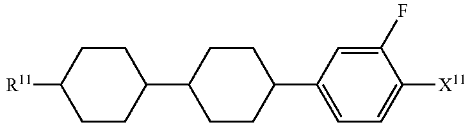
(3-3)
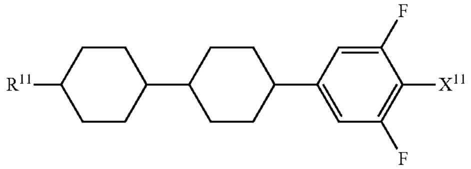
-continued
(3-4)
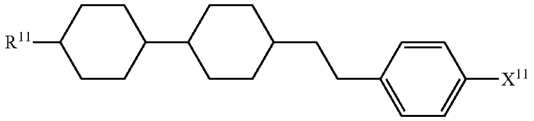
(3-5)
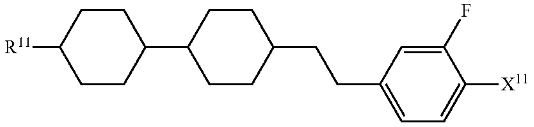
(3-6)
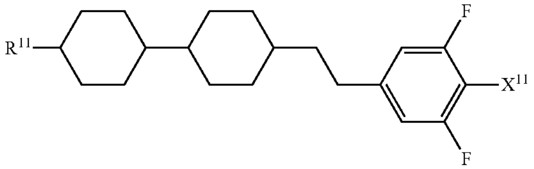
(3-7)
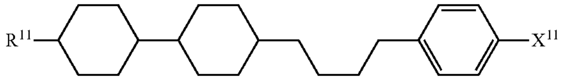
(3-8)
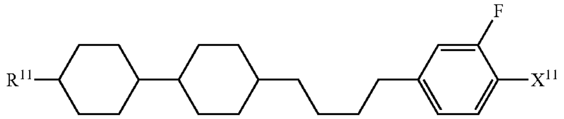
(3-9)
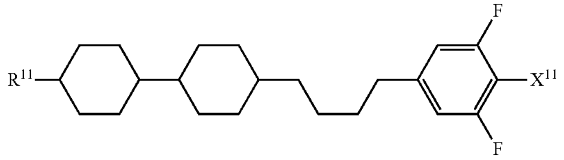
(3-10)
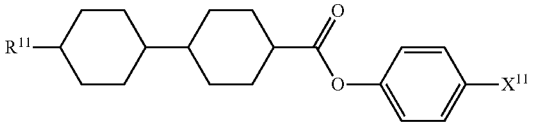
(3-11)
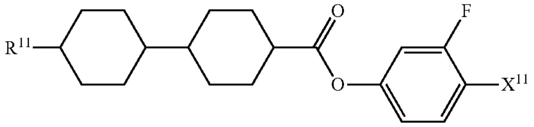
(3-12)
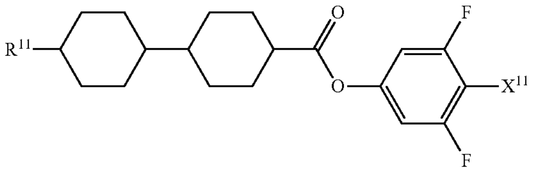

-continued
(3-13)
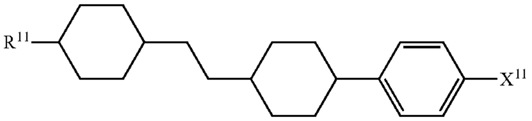
(3-14)
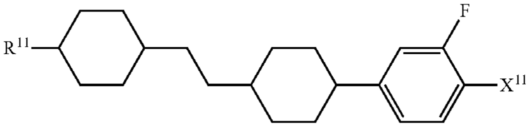
(3-15)
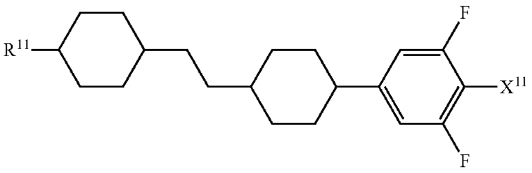
(3-16)
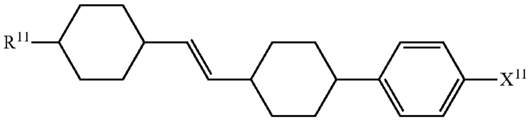
(3-17)
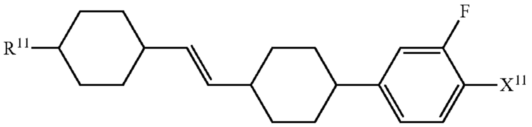
(3-18)
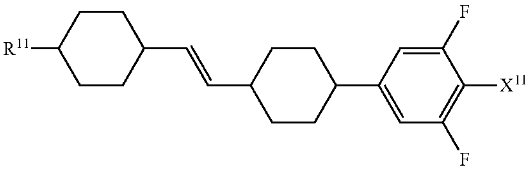
(3-19)
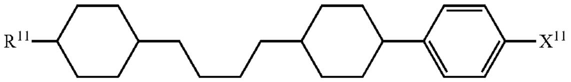
(3-20)
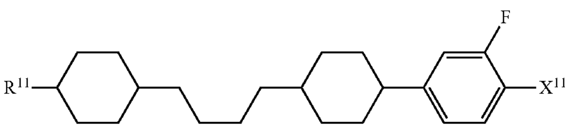
(3-21)
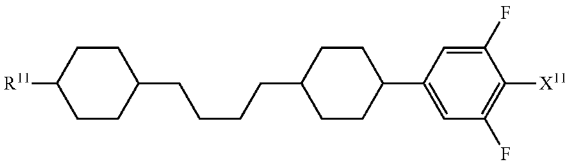
(3-22)
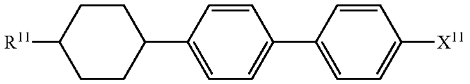
-continued
(3-23)
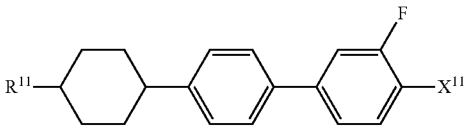
(3-24)
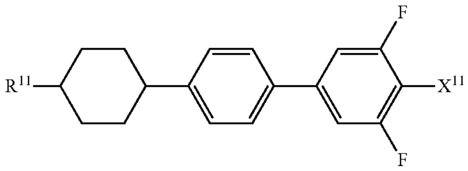
(3-25)
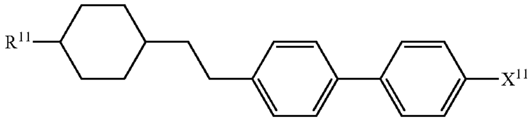
(3-26)
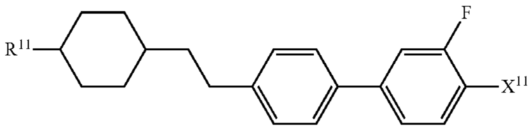
(3-27)
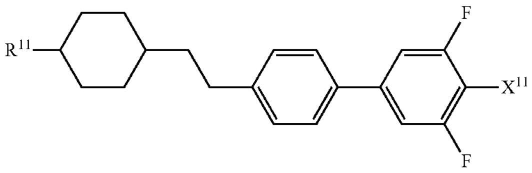
(3-28)
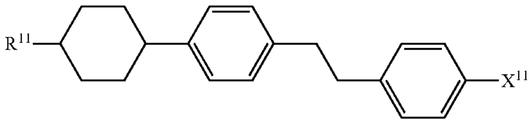
(3-29)
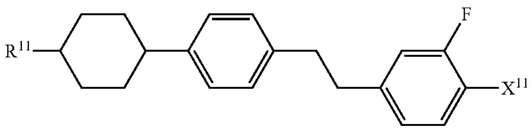
(3-30)
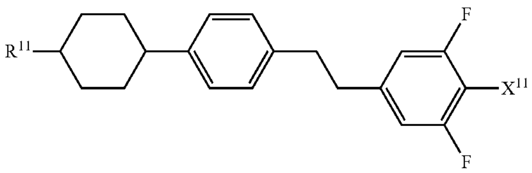
(3-31)
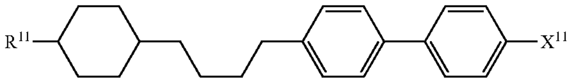

-continued
(3-32)
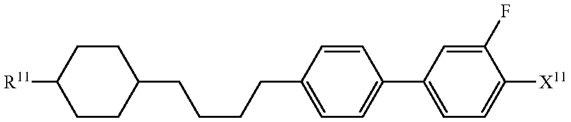
(3-33)
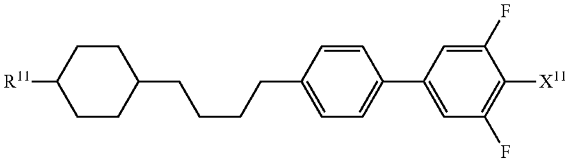
(3-34)
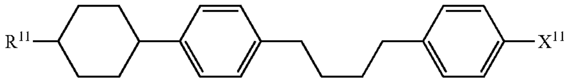
(3-35)
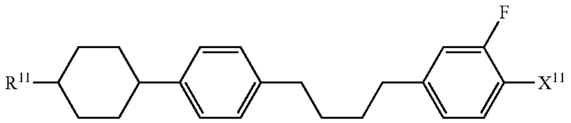
(3-36)
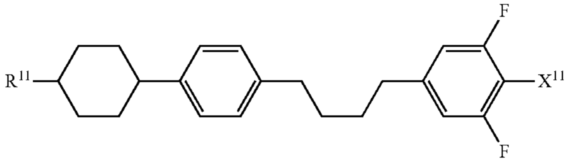
(3-37)
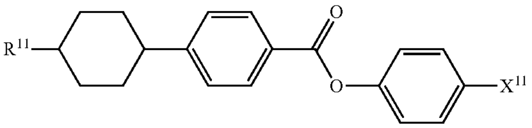
(3-38)
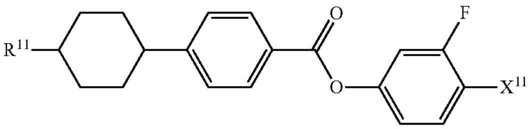
(3-39)
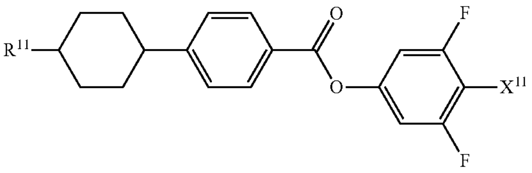
(3-40)
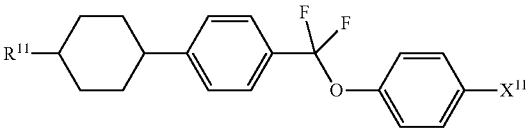
-continued
(3-41)
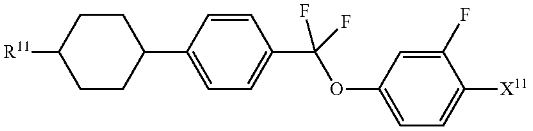
(3-42)
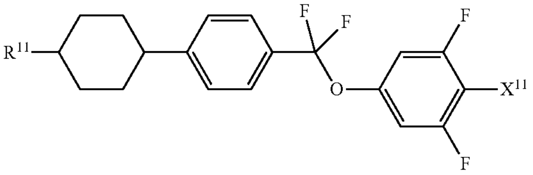
(3-43)
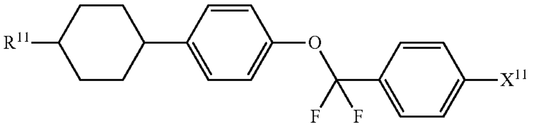
(3-44)
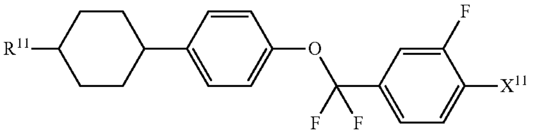
(3-45)
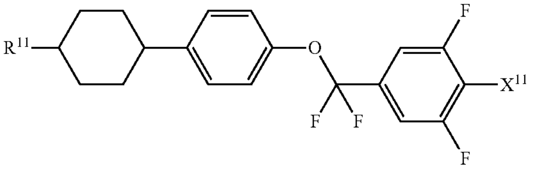
(3-46)
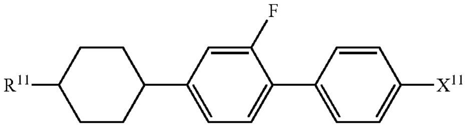
(3-47)
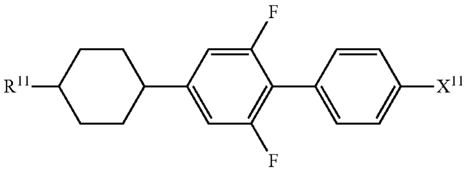
(3-48)
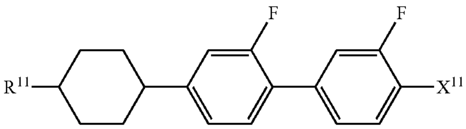
(3-49)
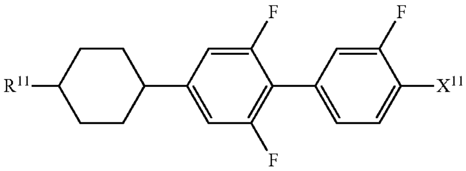

-continued
(3-50)
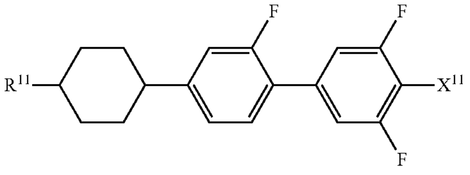
(3-51)
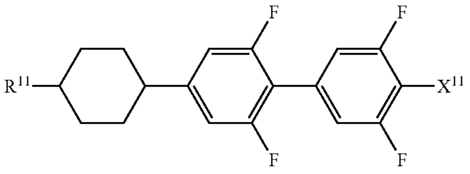
(3-52)
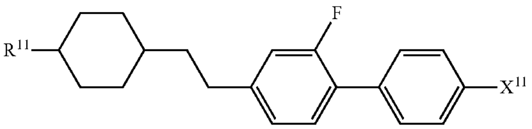
(3-53)
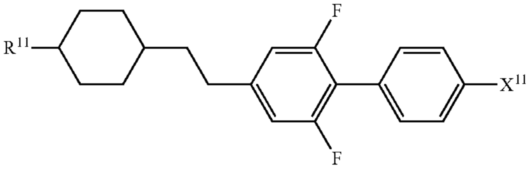
(3-54)
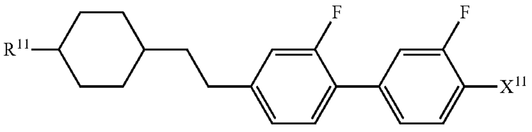
(3-55)
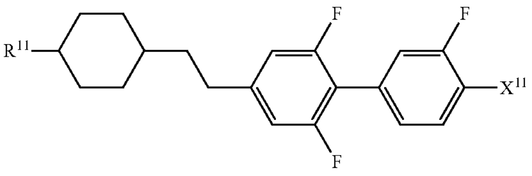
(3-56)
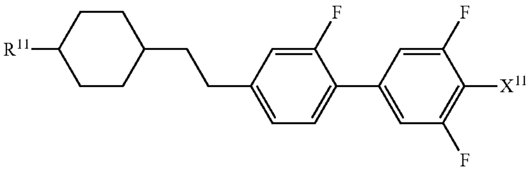
(3-57)
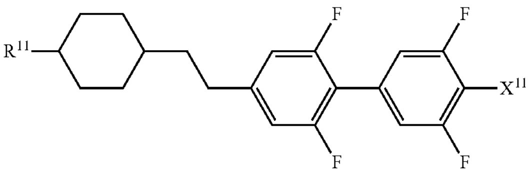
-continued
(3-58)
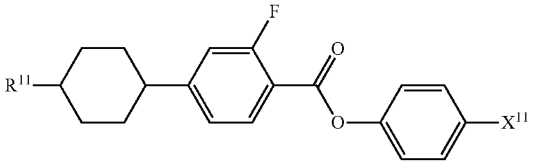
(3-59)
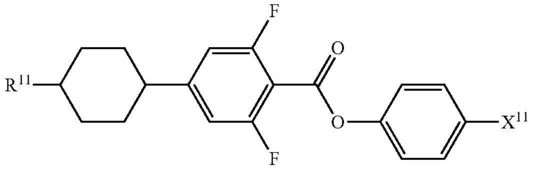
(3-60)
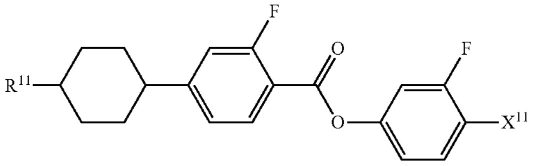
(3-61)
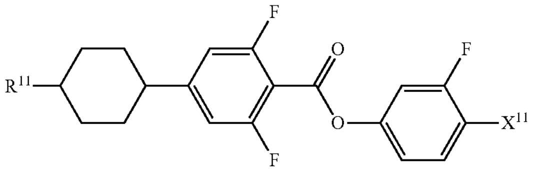
(3-62)
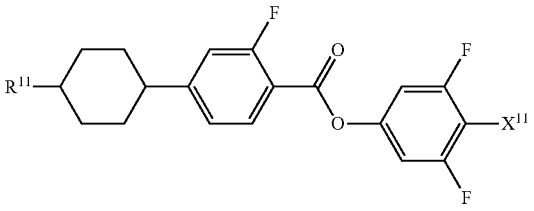
(3-63)
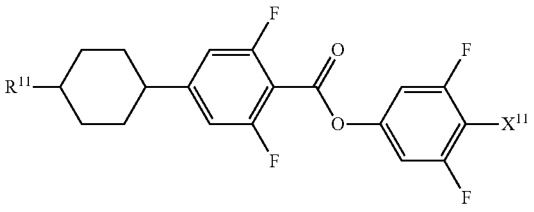
(3-64)
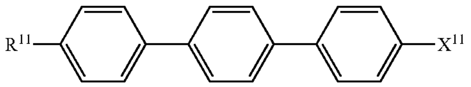
(3-65)
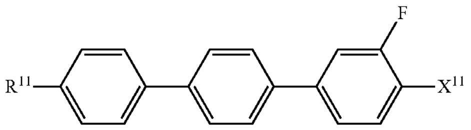

-continued
(3-66)
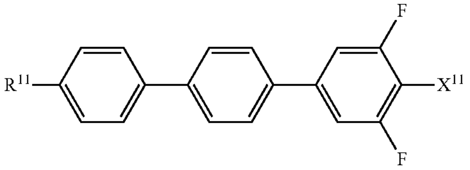
(3-67)
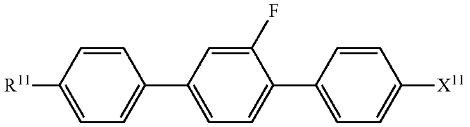
(3-68)
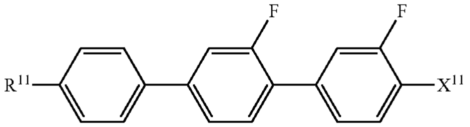
(3-69)
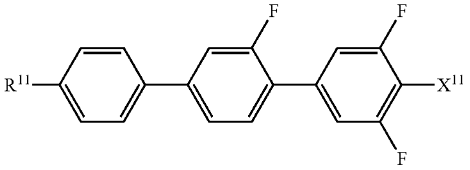
(3-70)
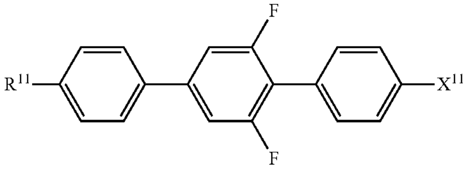
(3-71)
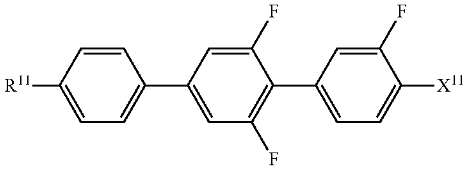
(3-72)
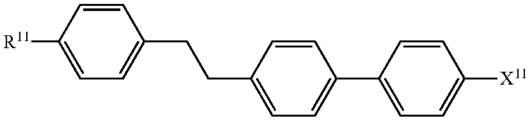
(3-73)
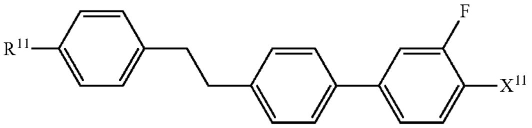
(3-74)
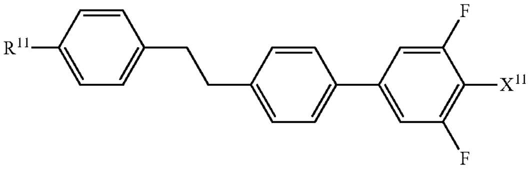
-continued
(3-75)
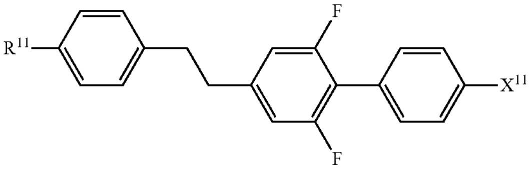
(3-76)
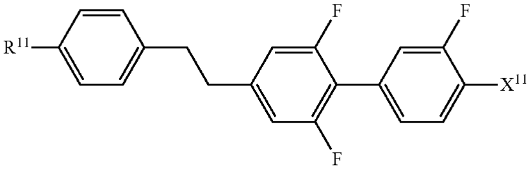
(3-77)
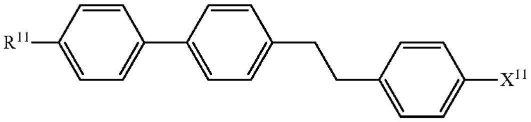
(3-78)
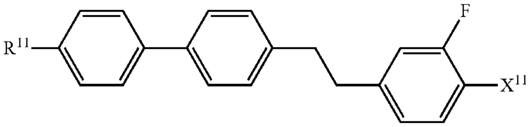
(3-79)
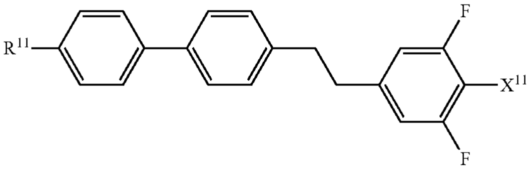
(3-80)
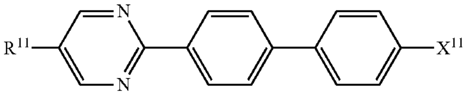
(3-81)
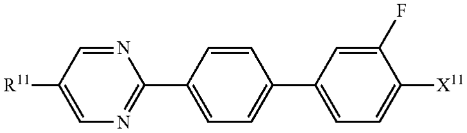
(3-82)
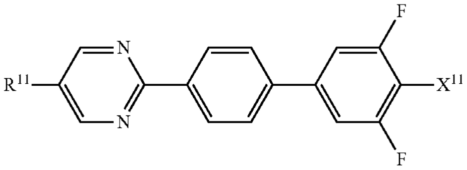
(3-83)
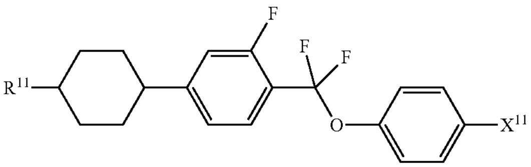

-continued
(3-84)
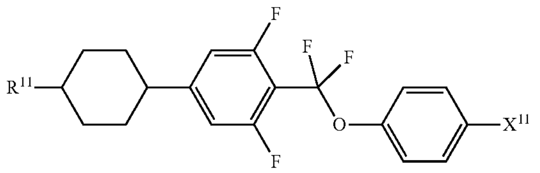
(3-85)
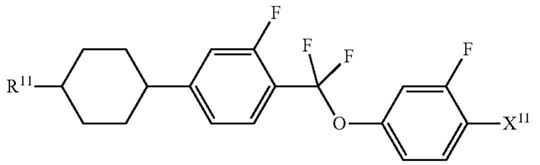
(3-86)
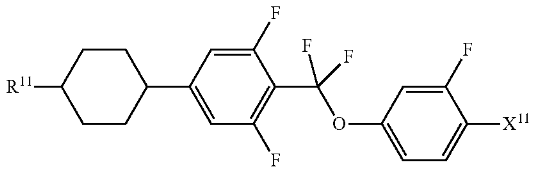
(3-87)
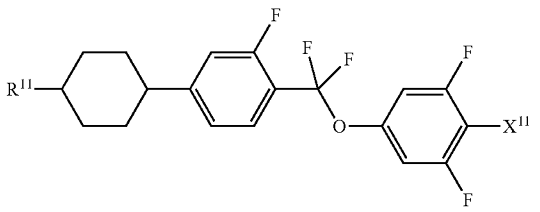
(3-88)
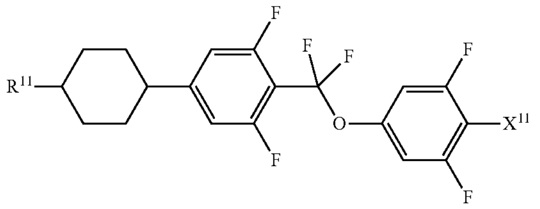
(3-89)
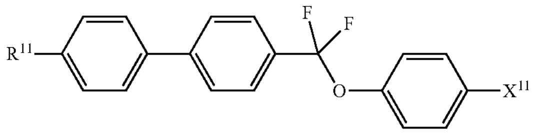
(3-90)
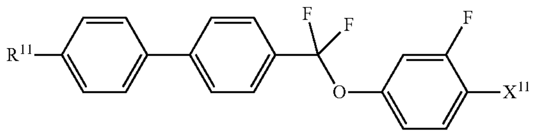
(3-91)
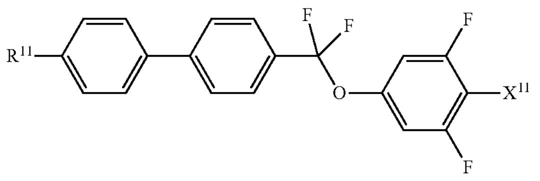
-continued
(3-92)
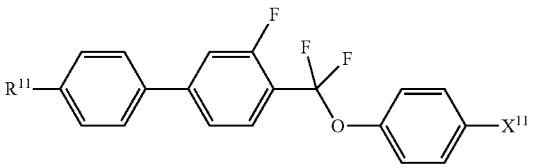
(3-93)
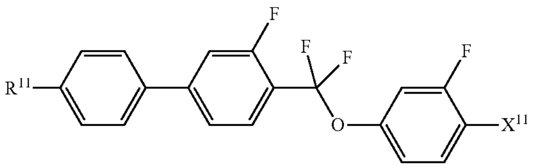
(3-94)
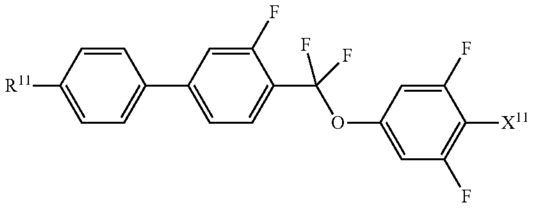
(3-95)
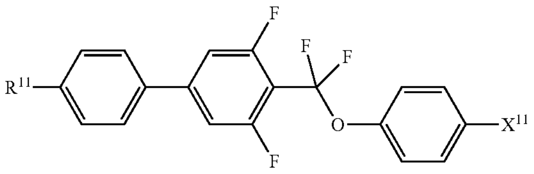
(3-96)
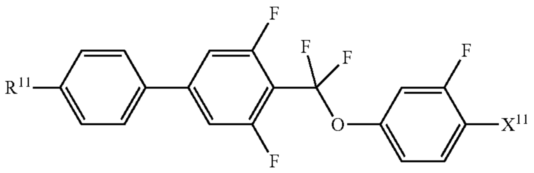
(3-97)
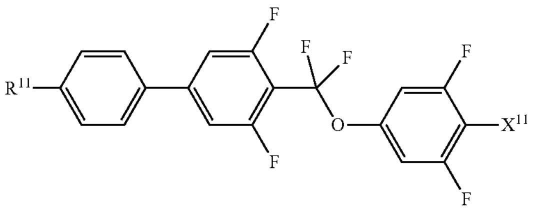
(3-98)
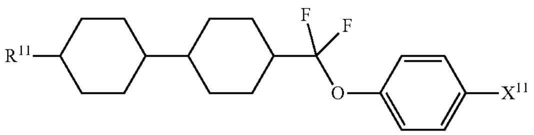
(3-99)
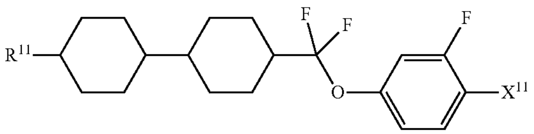

-continued
(3-100)
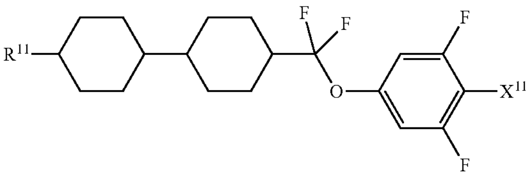
(3-101)
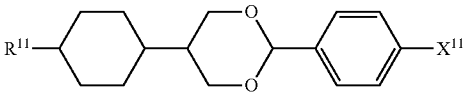
(3-102)
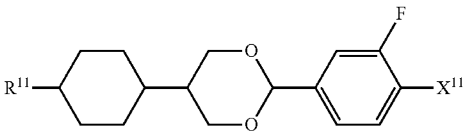
(3-103)
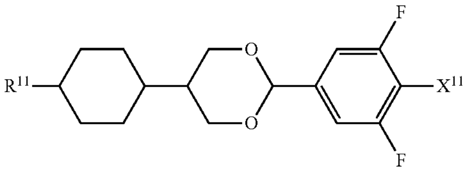
(3-104)
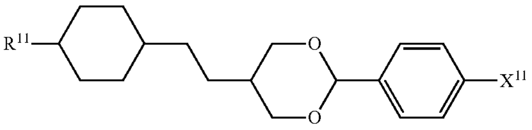
(3-105)
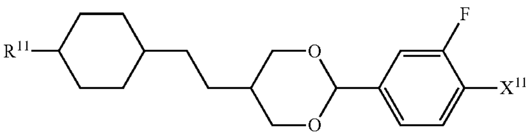
(3-106)
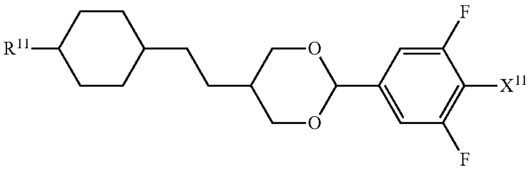
(3-107)
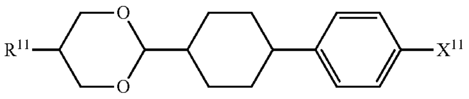
(3-108)
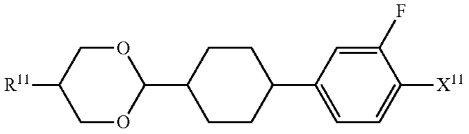
(3-109)
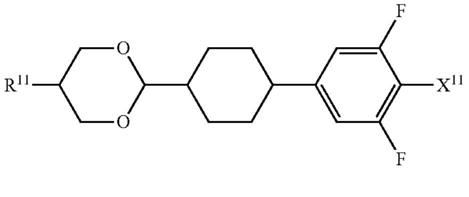
-continued
(3-110)
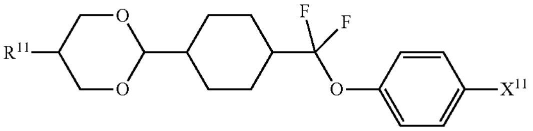
(3-111)
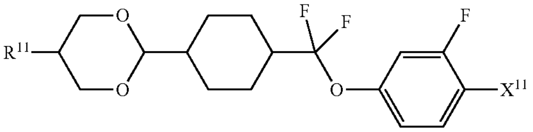
(3-112)
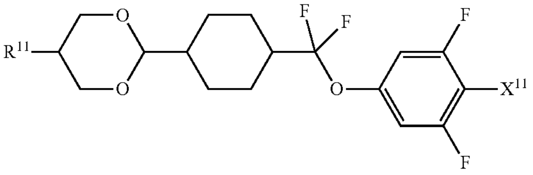
(3-113)
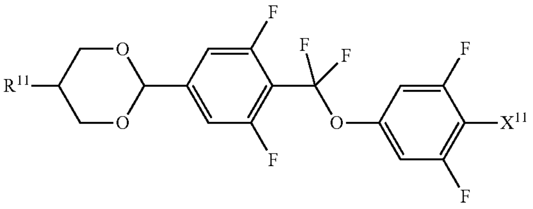
(4-1)
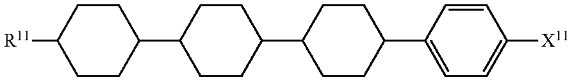
(4-2)
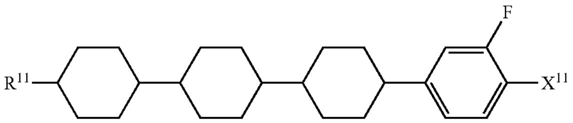
(4-3)
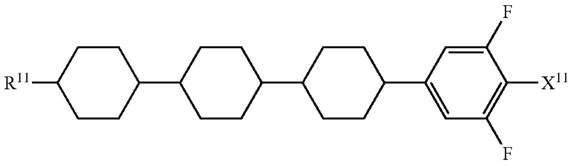
(4-4)
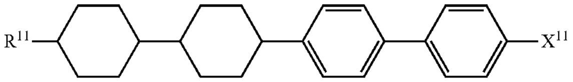
(4-5)
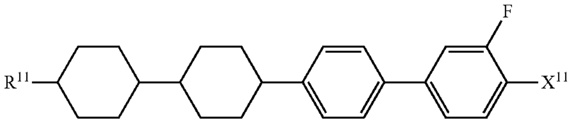

-continued
(4-6)
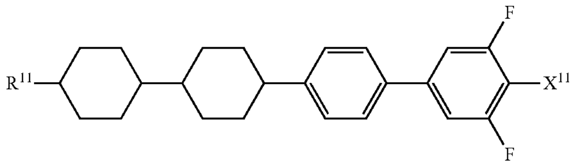
(4-7)
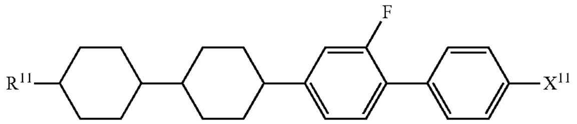
(4-8)
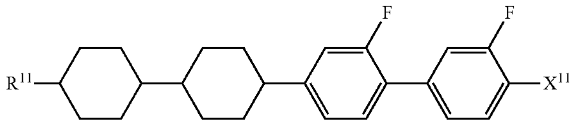
(4-9)
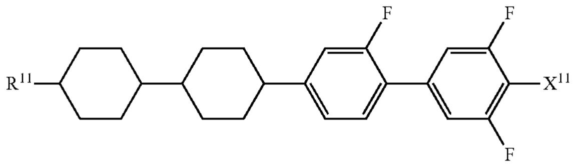
(4-10)
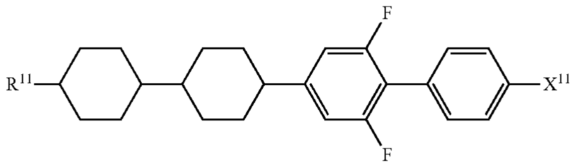
(4-11)
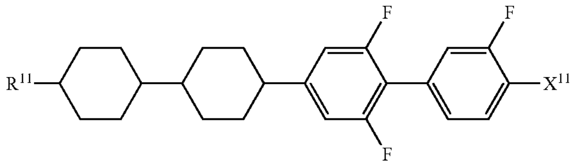
(4-12)
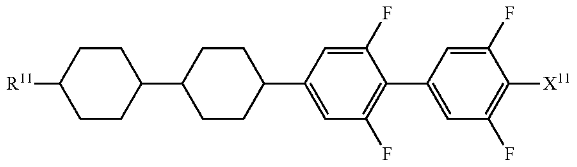
(4-13)
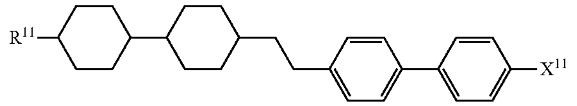
(4-14)
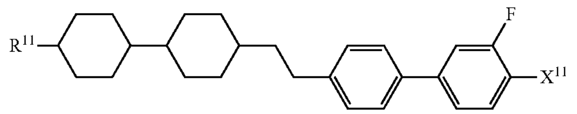
-continued
(4-15)
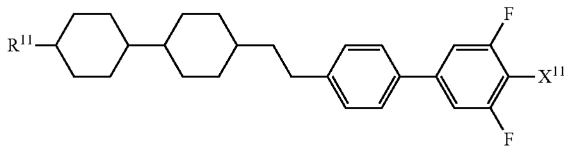
(4-16)
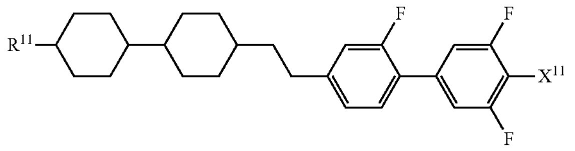
(4-17)
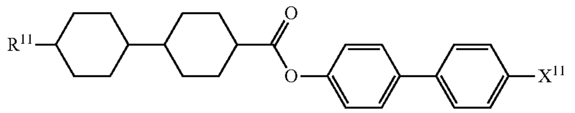
(4-18)
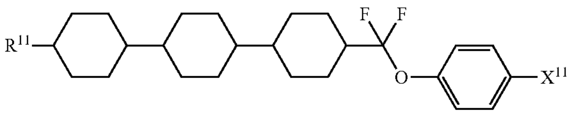
(4-19)
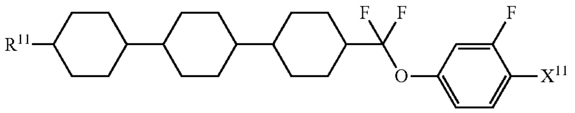
(4-20)
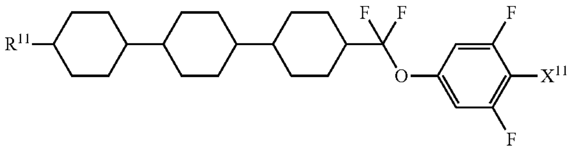
(4-21)
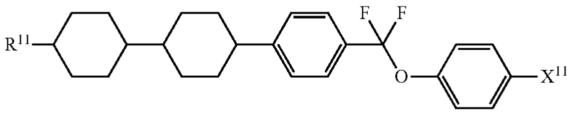
(4-22)
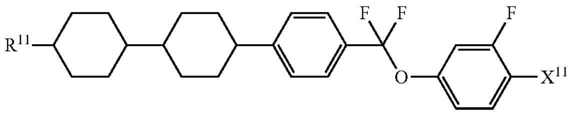
(4-23)
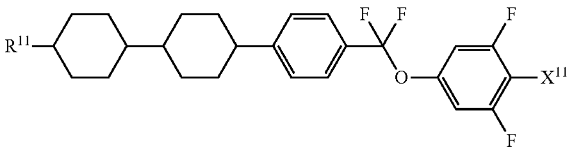
(4-24)
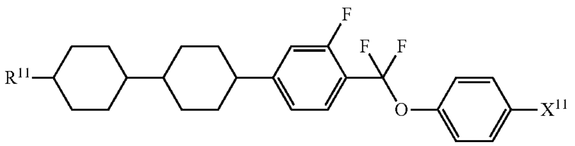

-continued
(4-25)
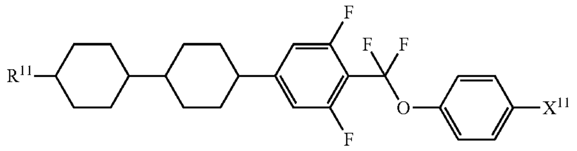
(4-26)
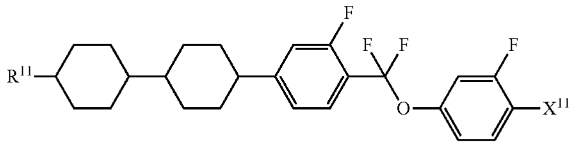
(4-27)
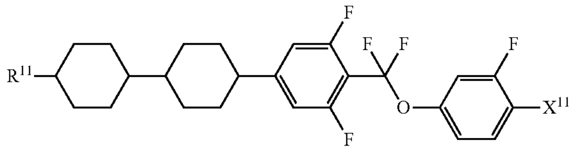
(4-28)
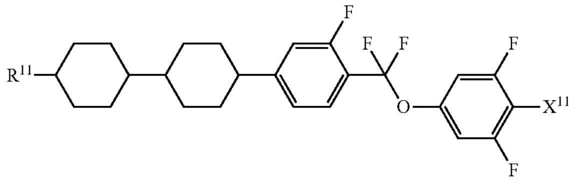
(4-29)
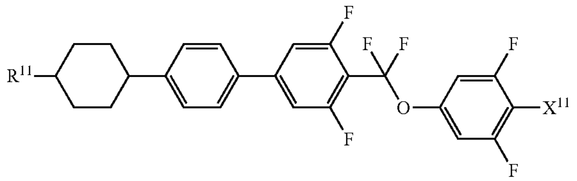
(4-30)
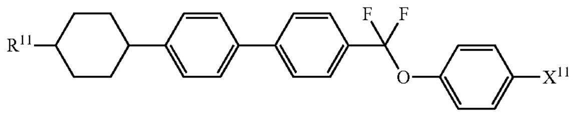
(4-31)
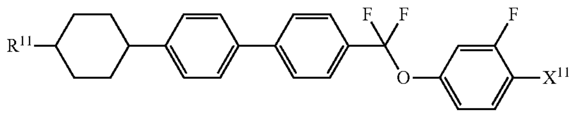
(4-32)
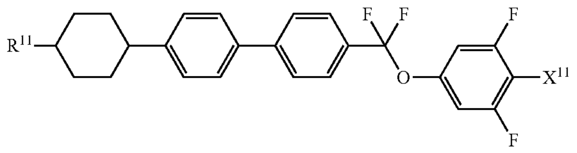
(4-33)
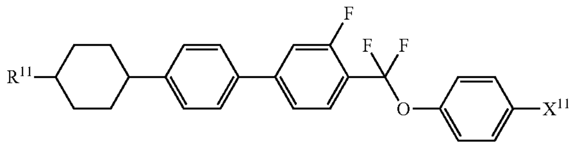
-continued
(4-34)
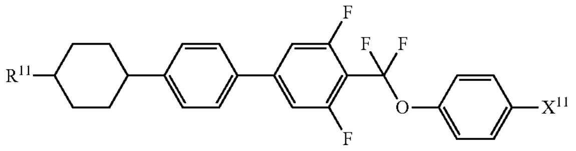
(4-35)
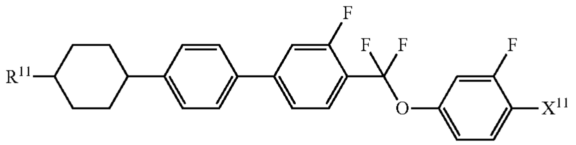
(4-36)
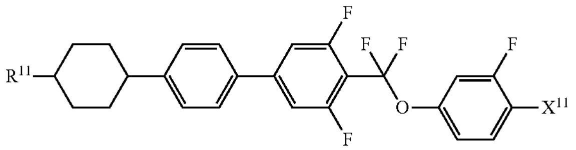
(4-37)
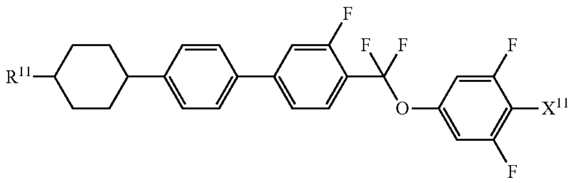
(4-38)
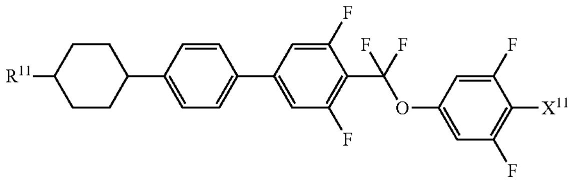
(4-39)
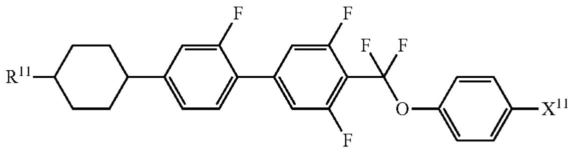
(4-40)
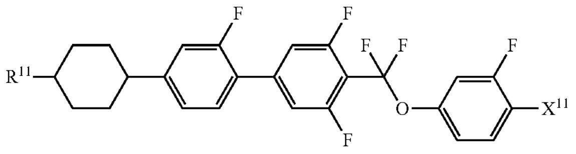
(4-41)
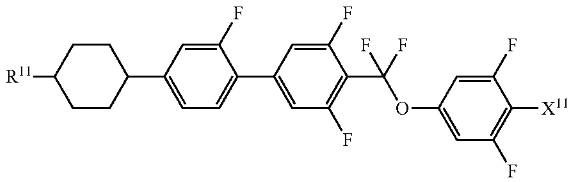

-continued
(4-42)
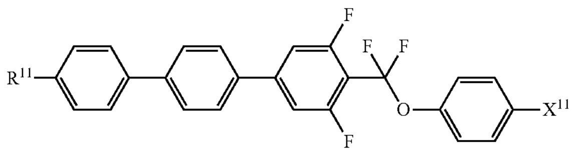
(4-43)
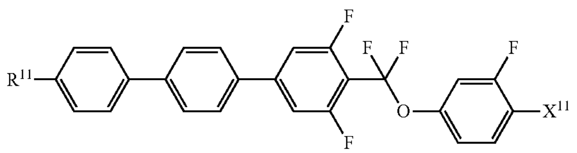
(4-44)
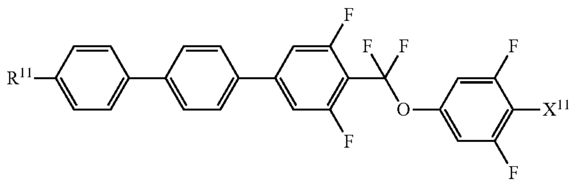
(4-45)
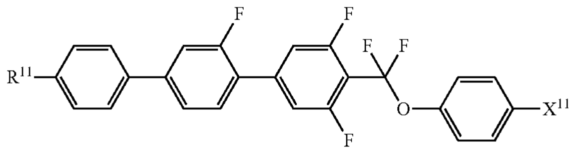
(4-46)
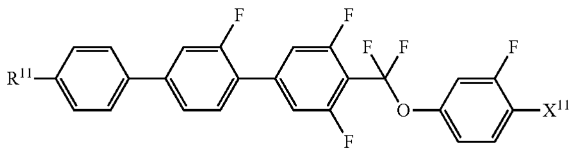
(4-47)
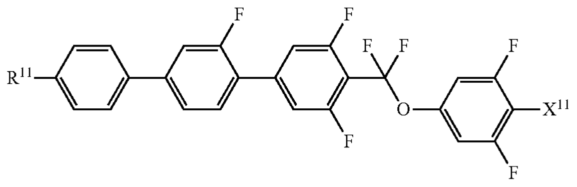
(4-48)
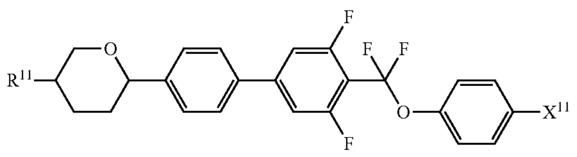
(4-49)
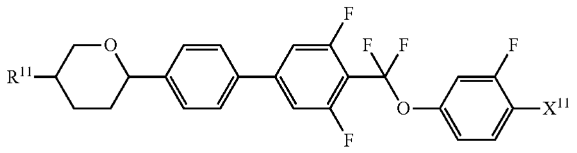
-continued
(4-50)
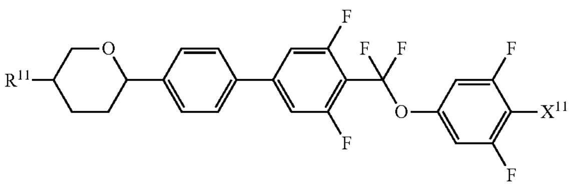
(4-51)
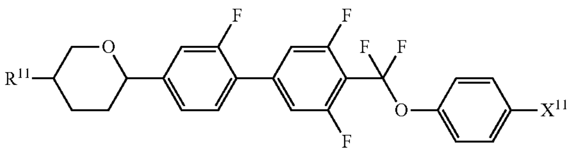
(4-52)
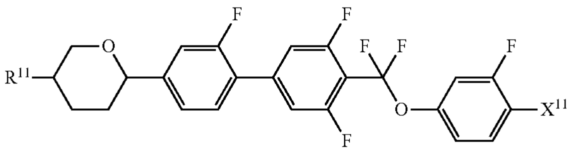
(4-53)
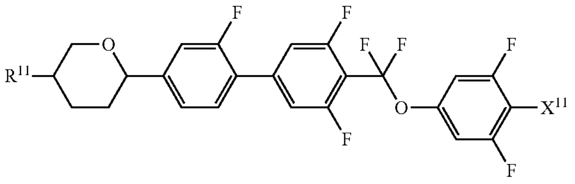
(4-54)
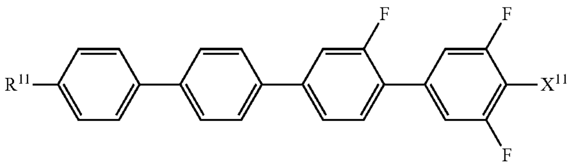
(4-55)
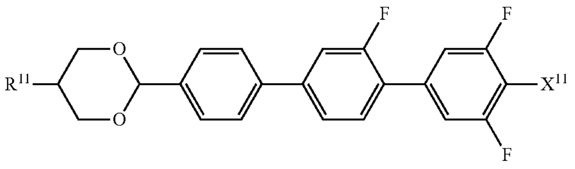
(4-56)
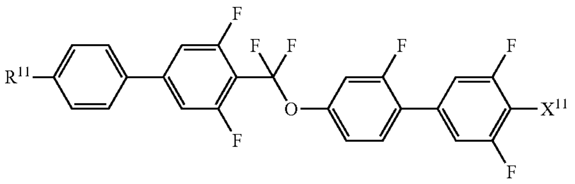
(4-57)
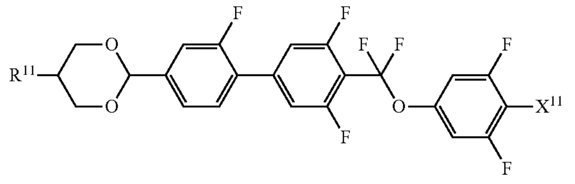
Component B has the positive dielectric anisotropy and a superb stability to heat, light and so forth, and therefore is used when a composition for the mode such as TFT, IPS and FFS is prepared. A content of component B is suitably in the range of approximately 1 to approximately 99% by weight, preferably in the range of approximately 10 to approximately 97% by weight, and further preferably in the range of approximately 40 to approximately 95% by weight, based on the weight of the composition. In the composition, the viscosity can be adjusted by further adding compounds (13) to (15) (component E).

Component C is compound (5) in which a right-terminal group is $-C\equiv N$ or $-C\equiv C-C\equiv N$. Specific preferred examples of component C include compounds (5-1) to (5-64). In the compounds (component C), $R^{12}$ and $X^{12}$ are defined in a manner identical with the definitions in item 11 described above.

(5-1)

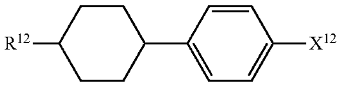

(5-2)

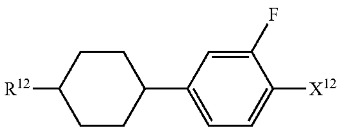

(5-3)

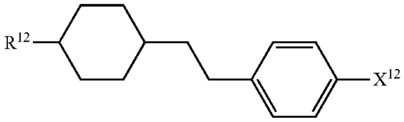

(5-4)

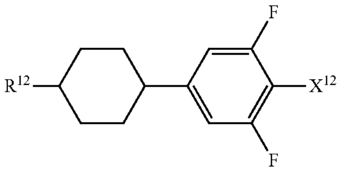

(5-5)

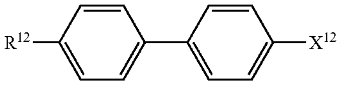

(5-6)

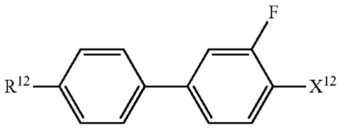

(5-7)

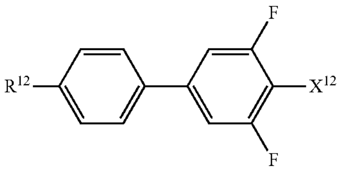

(5-8)

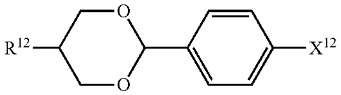

(5-9)

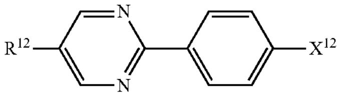

-continued (5-10)

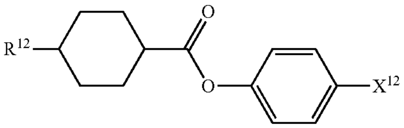

(5-11)

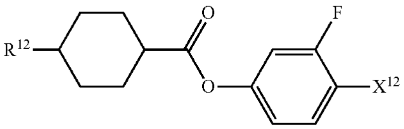

(5-12)

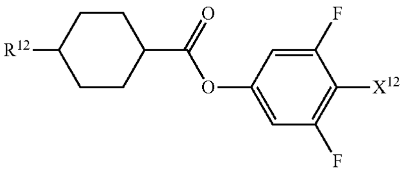

(5-13)

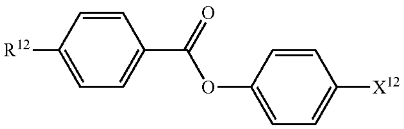

(5-14)

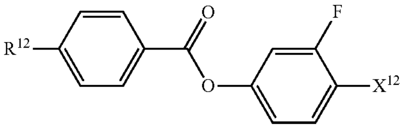

(5-15)

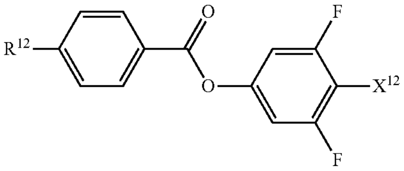

(5-16)

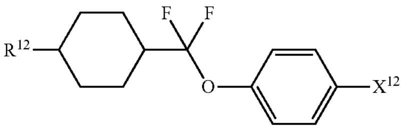

(5-17)

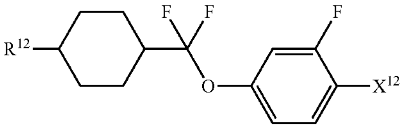

(5-18)

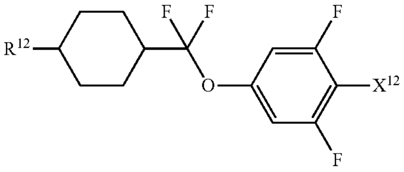

(5-19)

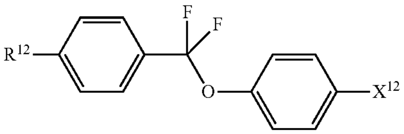

-continued
(5-20)
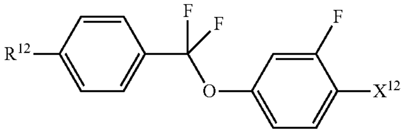
(5-21)
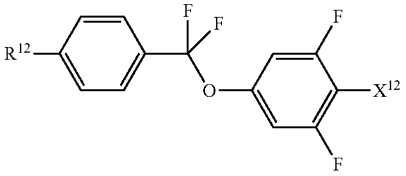
(5-22)
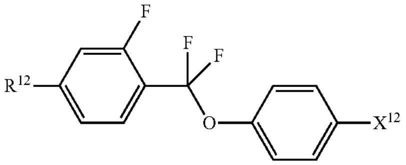
(5-23)
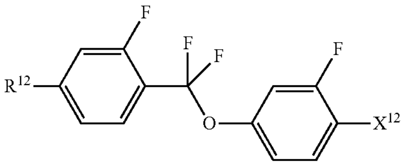
(5-24)
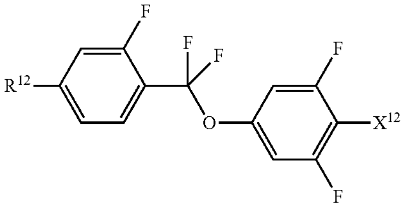
(5-25)
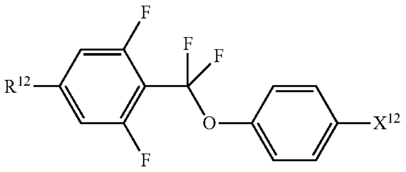
(5-26)
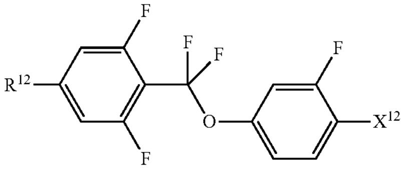
(5-27)
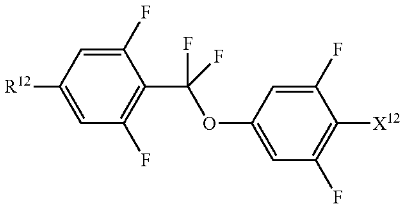
(5-28)
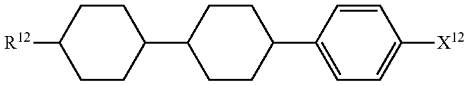
-continued
(5-29)
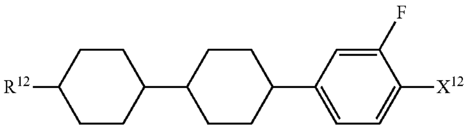
(5-30)
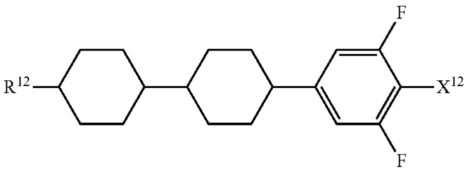
(5-31)
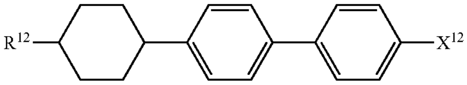
(5-32)
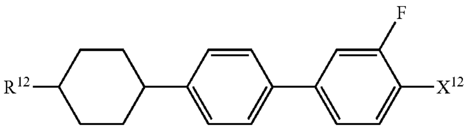
(5-33)
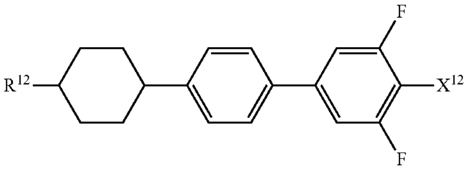
(5-34)
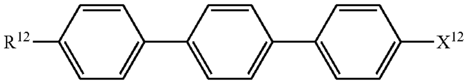
(5-35)
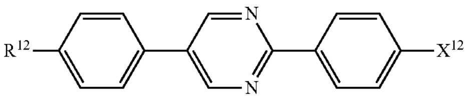
(5-36)
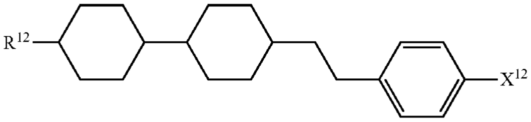
(5-37)
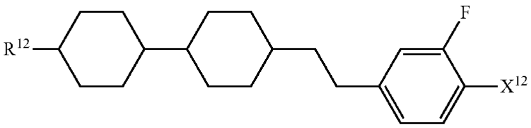
(5-38)
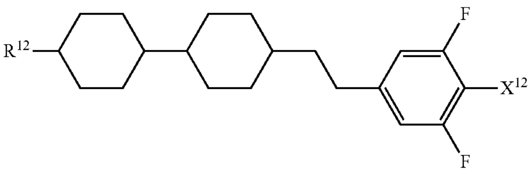

-continued
(5-39)
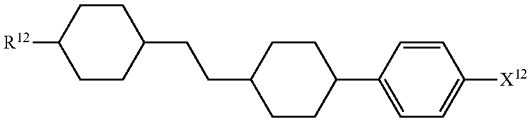
(5-40)
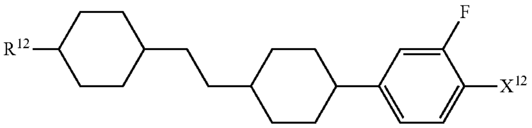
(5-41)
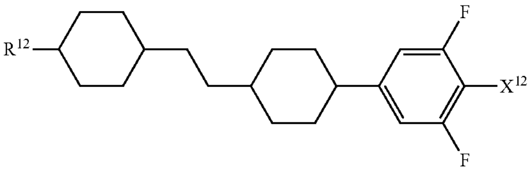
(5-42)
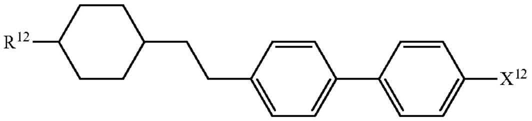
(5-43)
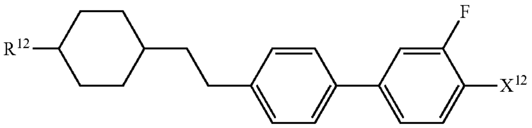
(5-44)
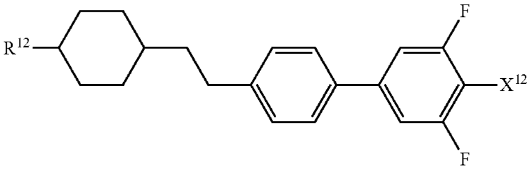
(5-45)
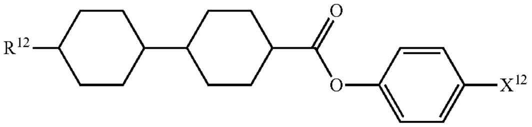
(5-46)
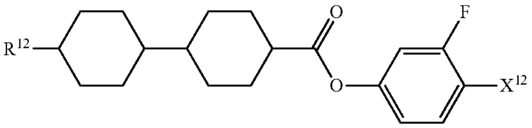
(5-47)
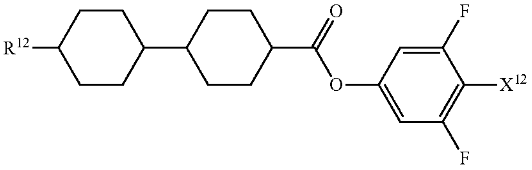
-continued
(5-48)
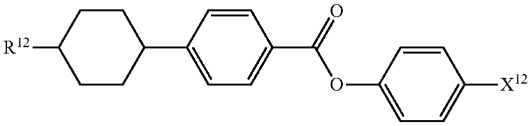
(5-49)
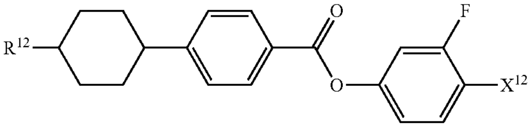
(5-50)
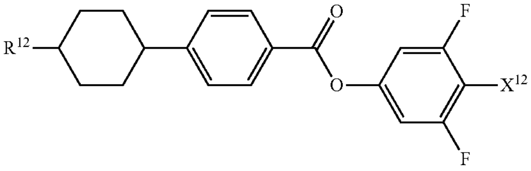
(5-51)
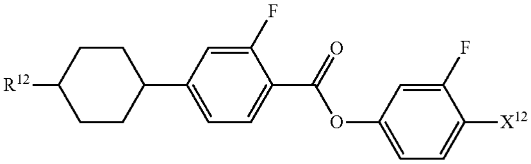
(5-52)
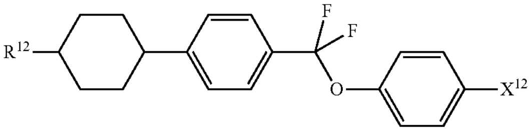
(5-53)
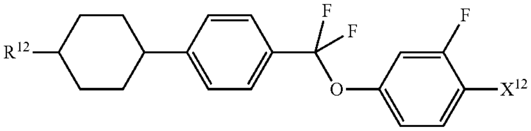
(5-54)
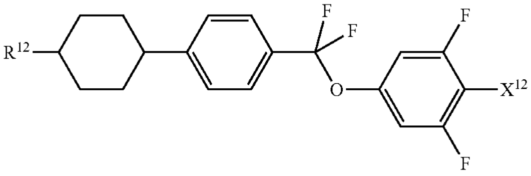
(5-55)
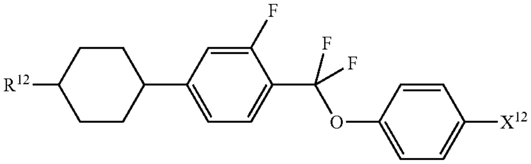
(5-56)
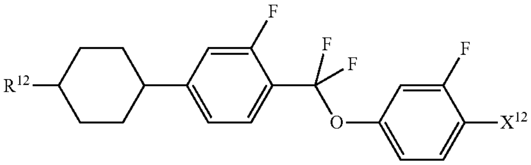

-continued (5-57)

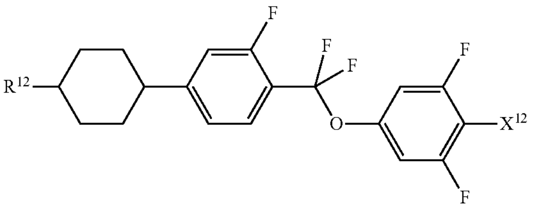

(5-58)

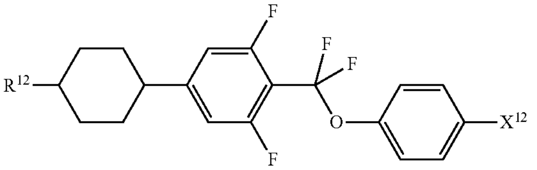

(5-59)

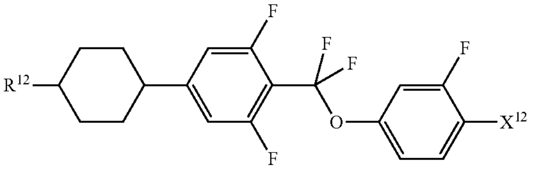

(5-60)

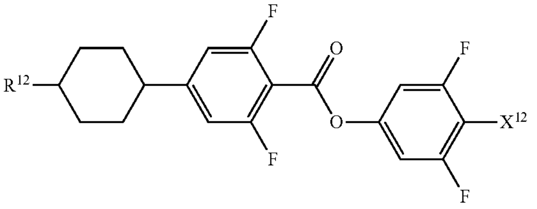

(5-61)

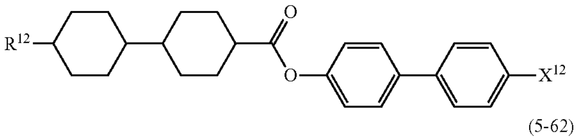

(5-62)

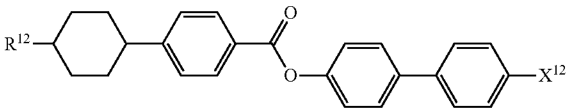

(5-63)

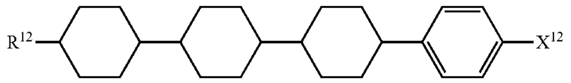

(5-64)

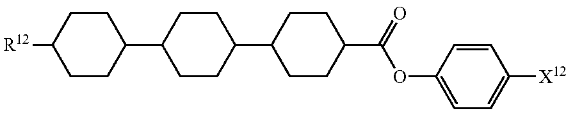

Component C has the positive dielectric anisotropy, and a value thereof is large, and therefore is mainly used when a composition for the STN mode, the TN mode or the PSA mode is prepared. The dielectric anisotropy of the composition can be increased by adding component C. Component C is effective in extending the temperature range of the liquid crystal phase, adjusting the viscosity or the optical anisotropy. Component C is also useful in adjusting the voltage-transmittance curve of the device.

When the composition for the STN mode or the TN mode is prepared, a content of component C is suitably in the range of approximately 1 to approximately 99% by weight, preferably in the range of approximately 10 to approximately 97% by weight, and further preferably in the range of approximately 40 to approximately 95% by weight, based on the weight of the composition. In the composition, the temperature range of the liquid crystal phase, the viscosity, the optical anisotropy, the dielectric anisotropy and so forth can be adjusted by adding component E.

Component D includes compounds (6) to (12). The compounds have a benzene ring in which two of hydrogen in a lateral position thereof is replaced by two of halogen, such as 2,3-difluoro-1,4-phenylene. Specific preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3). In the compounds (component D), $R^{13}$, $R^{14}$ and $R^{15}$ are defined in a manner identical with the definitions in item 12 described above.

(6-1)

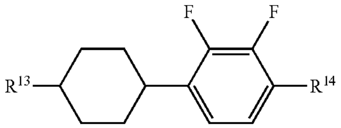

(6-2)

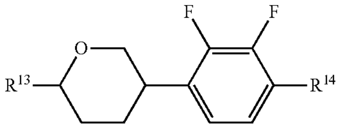

(6-3)

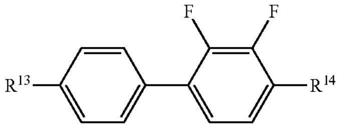

(6-4)

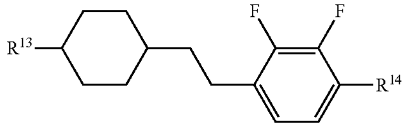

(6-5)

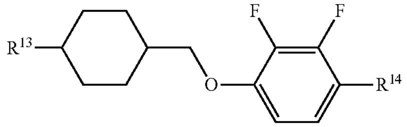

(6-6)

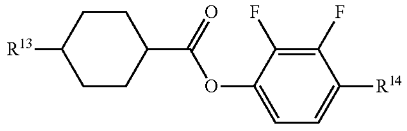

(6-7)

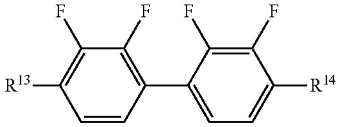

-continued
(6-8)
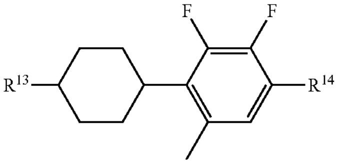
(7-1)
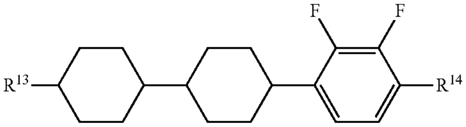
(7-2)
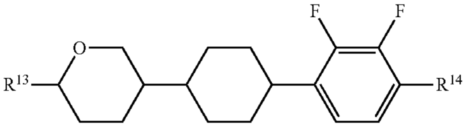
(7-3)
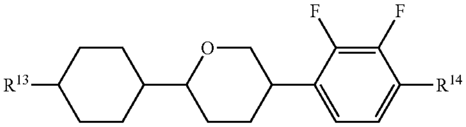
(7-4)
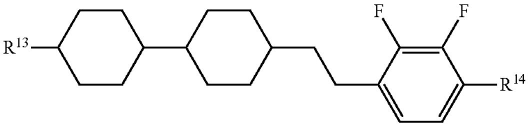
(7-5)
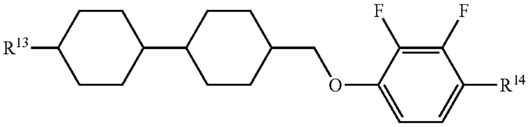
(7-6)
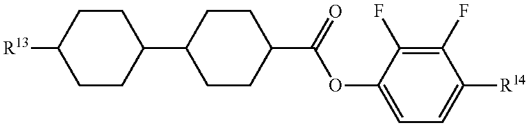
(7-7)
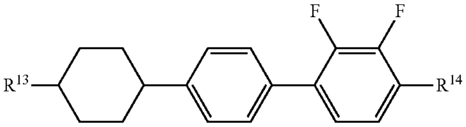
(7-8)
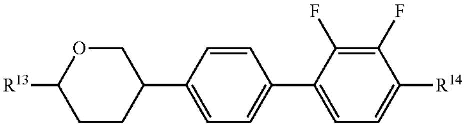
(7-9)
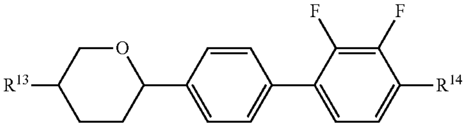
-continued
(7-10)
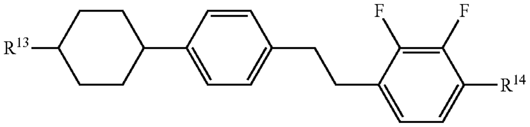
(7-11)
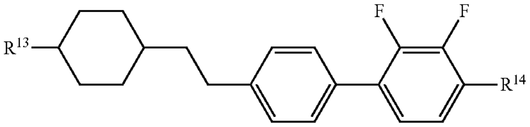
(7-12)
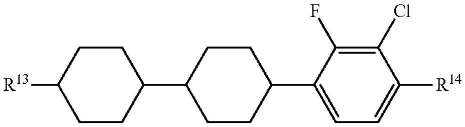
(7-13)
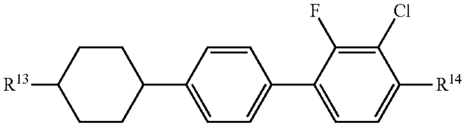
(7-14)
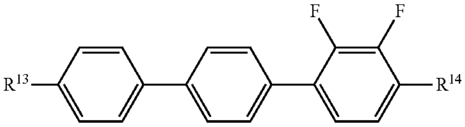
(7-15)
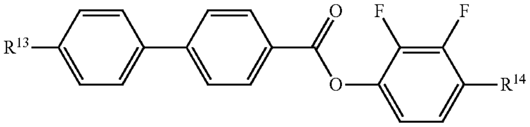
(7-16)
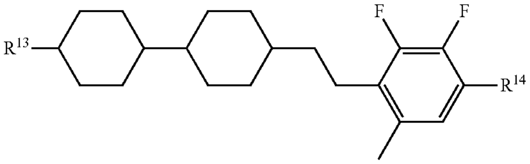
(7-17)
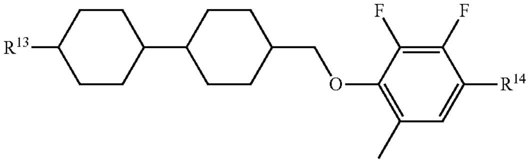
(8-1)
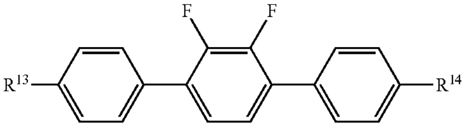
(9-1)
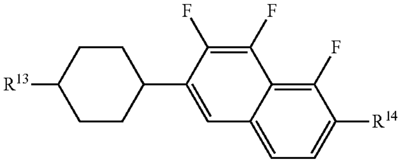

-continued
(9-2)
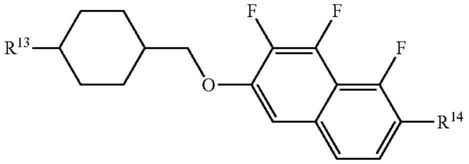
(9-3)
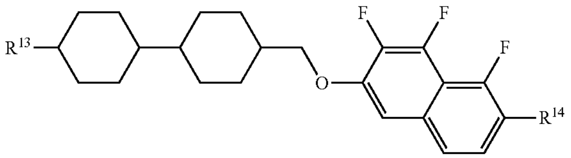
(10-1)
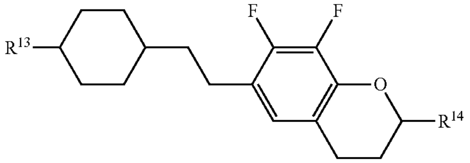
(10-2)
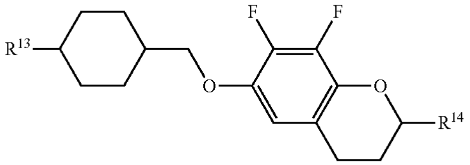
(10-3)
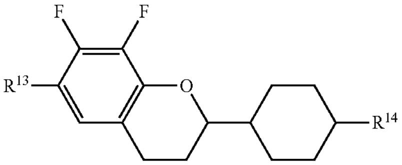
(10-4)
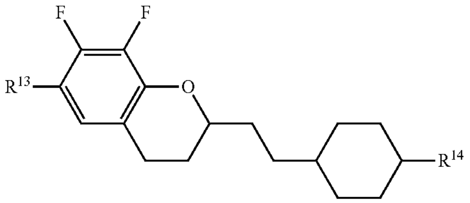
(10-5)
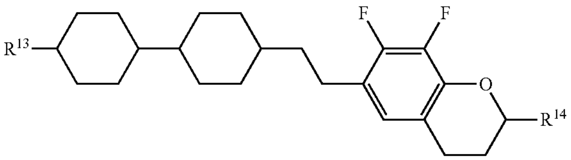
(10-6)
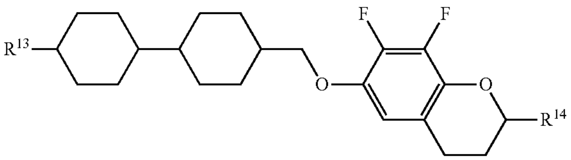
-continued
(10-7)
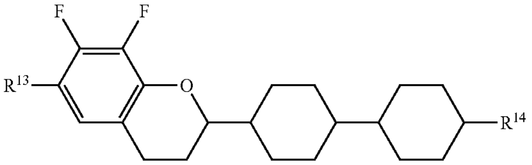
(10-8)
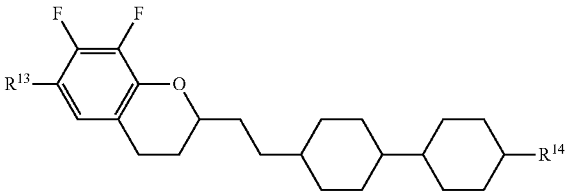
(10-9)
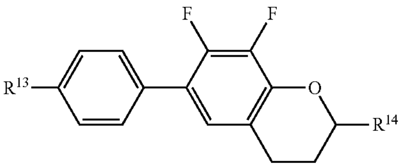
(10-10)
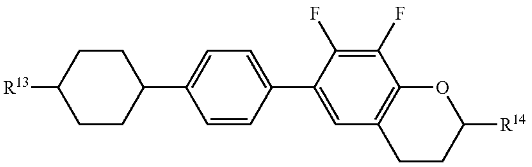
(10-11)
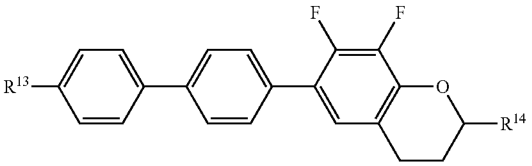
(11-1)
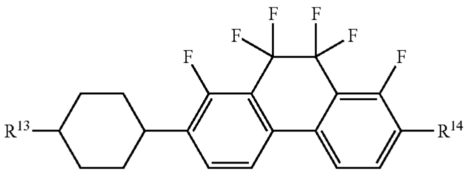
(11-2)
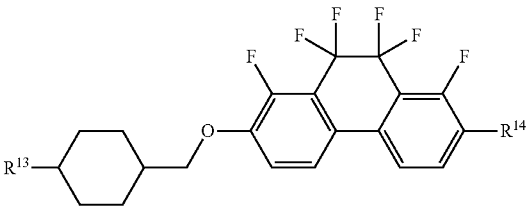

-continued (11-3)

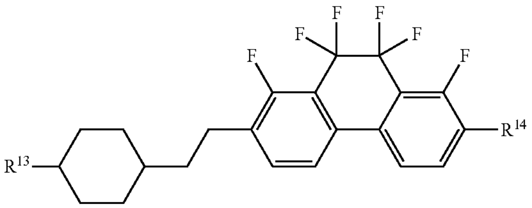

(12-1)

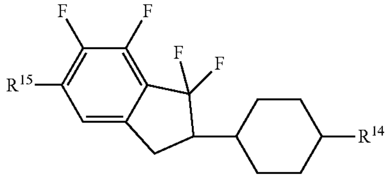

(12-2)

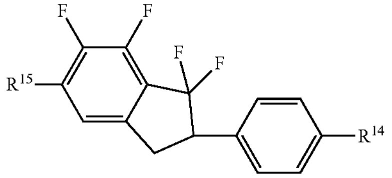

(12-3)

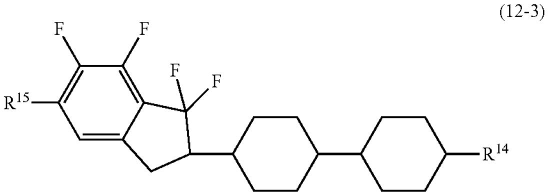

Component D is a compound having the negative dielectric anisotropy. Component D is mainly used when a composition for the VA mode or the PSA mode is prepared. Among types of component D, compound (6) is a bicyclic compound, and therefore is effective mainly in adjusting the viscosity, the optical anisotropy or the dielectric anisotropy. Compounds (7) and (8) are a tricyclic compound, and therefore are effective in increasing the maximum temperature, the optical anisotropy or the dielectric anisotropy. Compounds (9) to (12) are effective in increasing the dielectric anisotropy.

When the composition for the VA mode or the PSA mode is prepared, a content of component D is preferably approximately 40% by weight or more, and further preferably in the range of approximately 50 to approximately 95% by weight, based on the weight of the composition. When component D is added to the composition having the positive dielectric anisotropy, the content of component D is preferably approximately 30% by weight or less based on the weight of the composition. The voltage-transmittance curve of the device can be adjusted by adding component D.

Component E is a compound in which two terminal groups are alkyl or the like. Specific preferred examples of component E include compounds (13-1) to (13-11), compounds (14-1) to (14-19) and compounds (15-1) to (15-7). In the compounds (component E), $R^{16}$ and $R^{17}$ are defined in a manner identical with the definitions in item 13 described above.

(13-1)

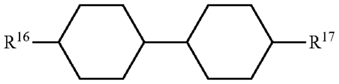

(13-2)

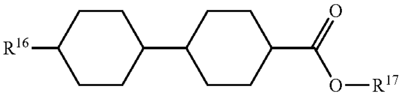

(13-3)

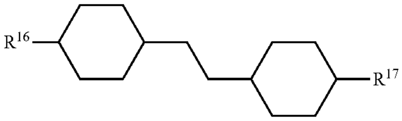

(13-4)

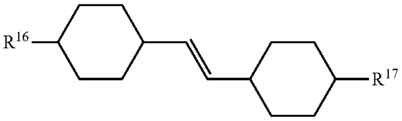

(13-5)

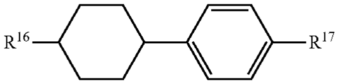

(13-6)

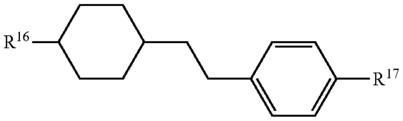

(13-7)

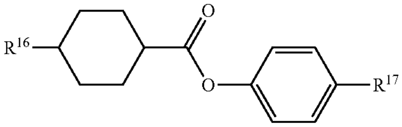

(13-8)

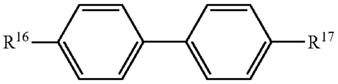

(13-9)

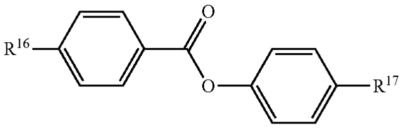

(13-10)

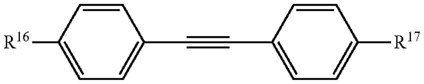

-continued
(13-11)
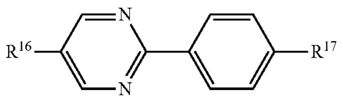
(14-1)
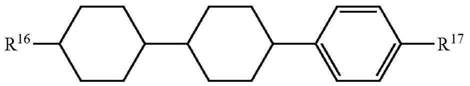
(14-2)
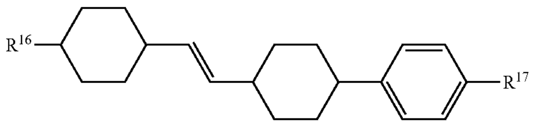
(14-3)
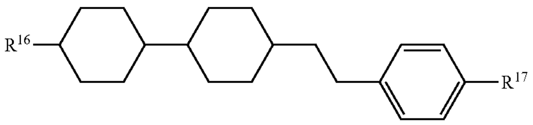
(14-4)
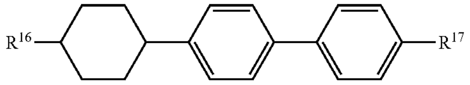
(14-5)
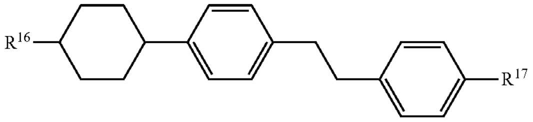
(14-6)
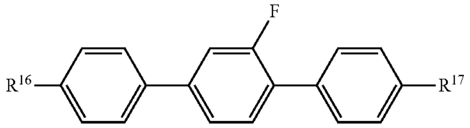
(14-7)
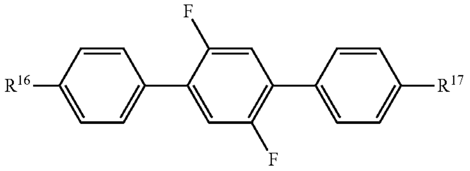
(14-8)
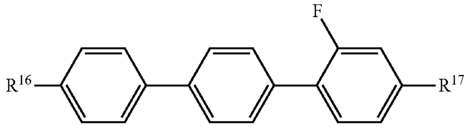
(14-9)
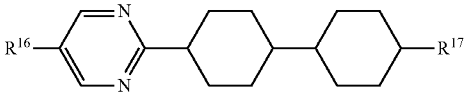
(14-10)
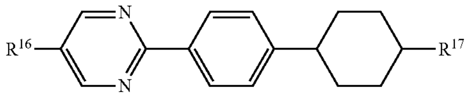
(14-11)
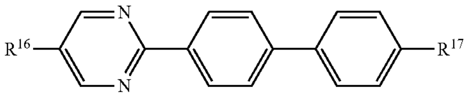
(14-12)
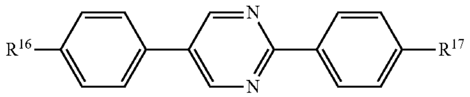
(14-13)
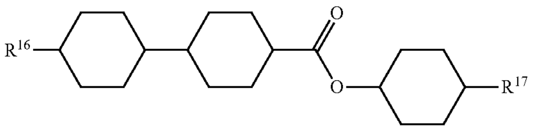
(14-14)
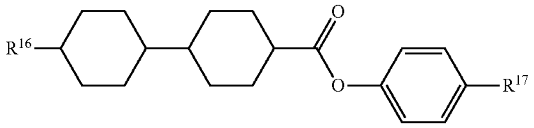
(14-15)
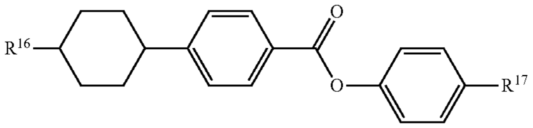
(14-16)
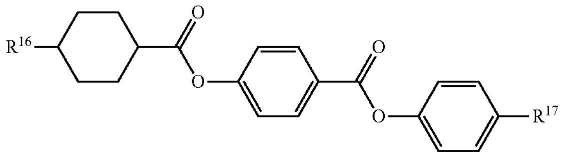
(14-17)
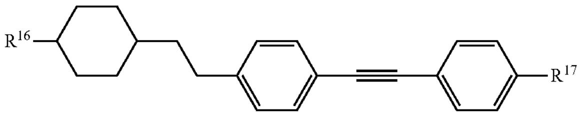
(14-18)
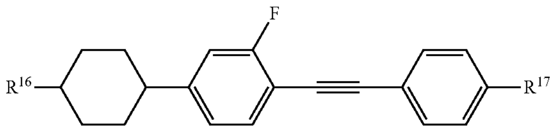
(14-19)
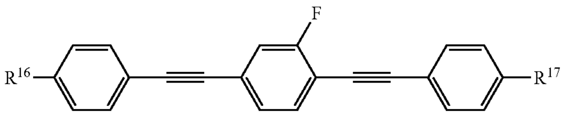

-continued (15-1)

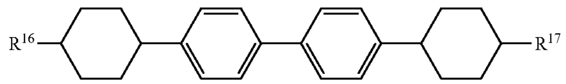

(15-2)

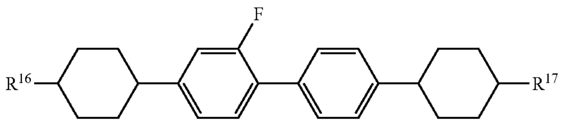

(15-3)

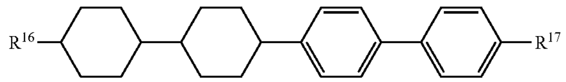

(15-4)

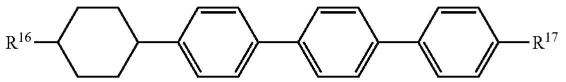

(15-5)

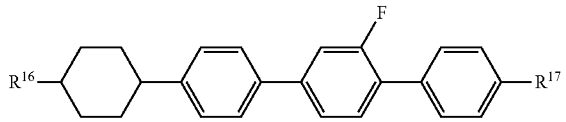

(15-6)

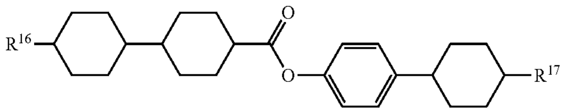

(15-7)

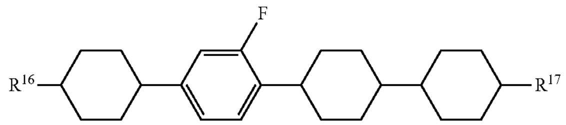

Component (E) has a small absolute value of dielectric anisotropy, and therefore is a compound close to neutrality. Compound (13) is effective mainly in adjusting the viscosity or the optical anisotropy. Compounds (14) and (15) are effective in extending the temperature range of the nematic phase by increasing the maximum temperature, or adjusting the optical anisotropy.

If a content of component E is increased, the dielectric anisotropy of the composition decreases, but the viscosity decreases. Therefore, the content is preferably as large as possible, as long as the composition meets a desired value of threshold voltage of the device. Accordingly, when the composition is prepared, the content of component (E) is preferably approximately 30% by weight or more, and further preferably approximately 40% by weight or more, based on the weight of the liquid crystal composition.

Preparation of composition (1) is performed by a method of dissolving required components at a high temperature or the like. According to an application, the additive may be added to the composition. Specific examples of the additive include an optically active compound, a polymerizable compound, a polymerization initiator, an antioxidant, an ultraviolet light absorber, a light stabilizer, a heat stabilizer, an antifoaming agent and a dye. Such additives are well known to those skilled in the art, and described in literature.

Composition (1) may further contain at least one optically active compound. The optically active compound is effective in inducing a helical structure in liquid crystal molecules to give a required twist angle, thereby preventing a reverse twist. Specific preferred examples of the optically active compound include compounds (Op-1) to (Op-18) described below.

(Op-1)

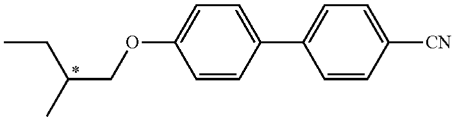

(Op-2)

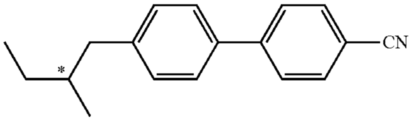

(Op-3)

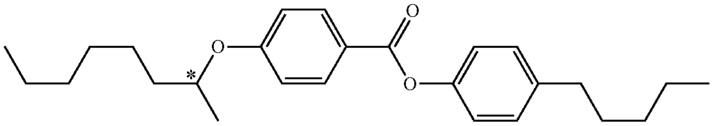

(Op-4)

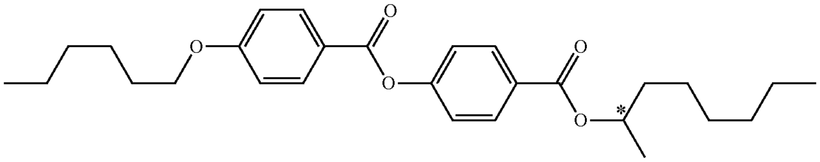

-continued
(Op-5)
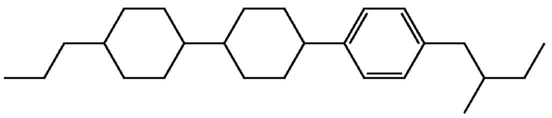
(Op-6)
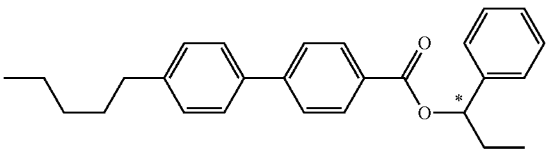
(Op-7)
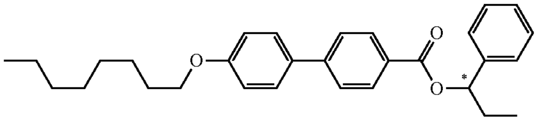
(Op-8)
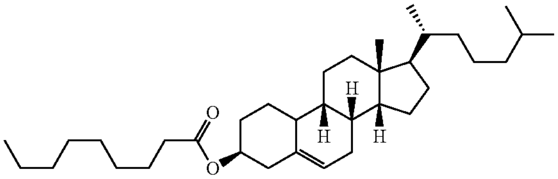
(Op-9)
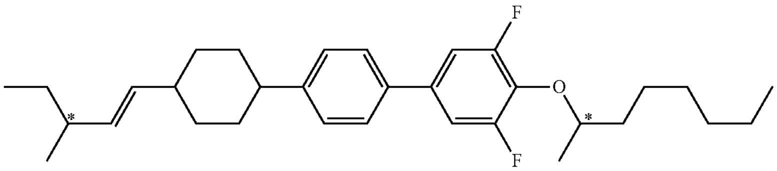
(Op-10)
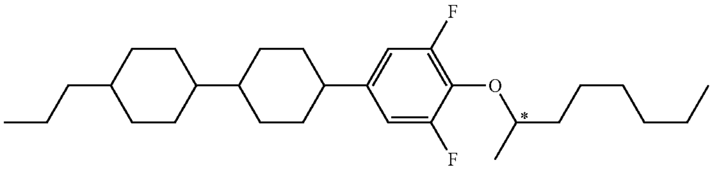
(Op-11)
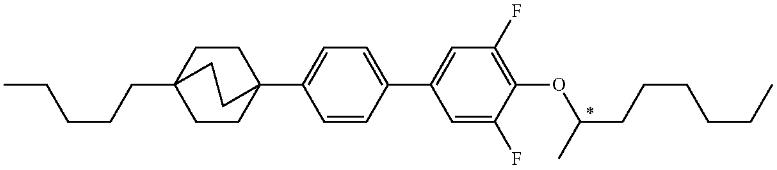
(Op-12)
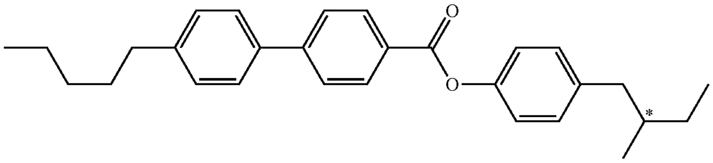
(Op-13)
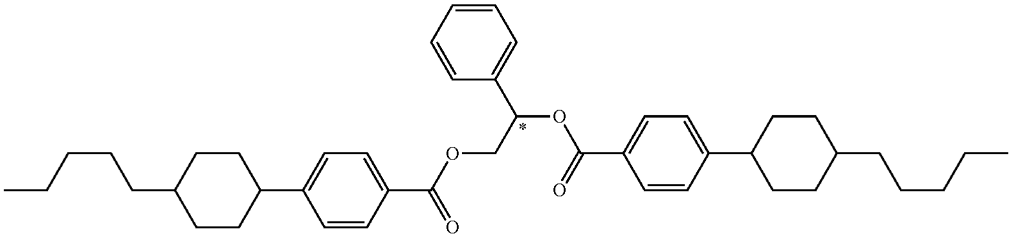
(Op-14)
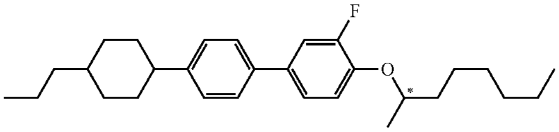
(Op-15)
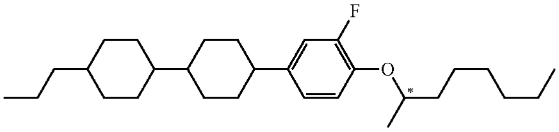

-continued (Op-16)

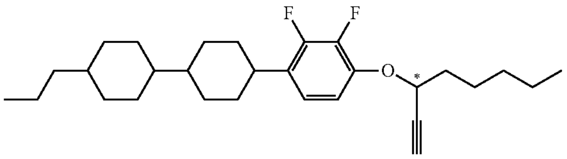

(Op-17)

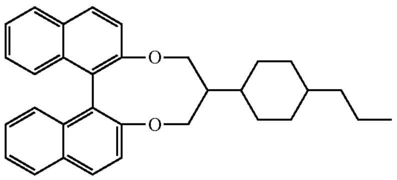

(Op-18)

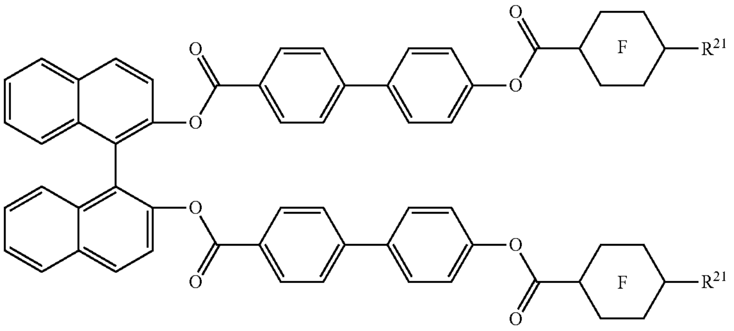

In compound (Op-18), ring F is 1,4-cyclohexylene or 1,4-phenylene, and $R^{21}$ is alkyl having 1 to 10 carbons.

In composition (1), a helical pitch is adjusted by adding such an optically active compound thereto. The helical pitch is preferably adjusted in the range of approximately 40 to approximately 200 micrometers in a composition for the TFT mode and the TN mode. In a composition for the STN mode, the helical pitch is preferably adjusted in the range of approximately 6 to approximately 20 micrometers. In the case of a composition for a BTN mode, the helical pitch is preferably adjusted in the range of approximately 1.5 to approximately 4 micrometers. Two or more optically active compounds may be added thereto for the purpose of adjusting temperature dependence of the helical pitch.

Composition (1) can also be used for the PSA mode by adding the polymerizable compound. Specific examples of the polymerizable compound include an acrylate, a methacrylate, a vinyl compound, a vinyloxy compound, a propenyl ether, an epoxy compound (oxirane, oxetane) and a vinyl ketone. The polymerizable compound is polymerized by irradiation with ultraviolet light or the like. An initiator such as a photopolymerization initiator may be added thereto. Suitable conditions for polymerization, a suitable type of the initiator, and a suitable amount thereof are known to those skilled in the art and are described in literature. Specific preferred examples of the polymerizable compound include compounds (M-1) to (M-16).

(M-1)

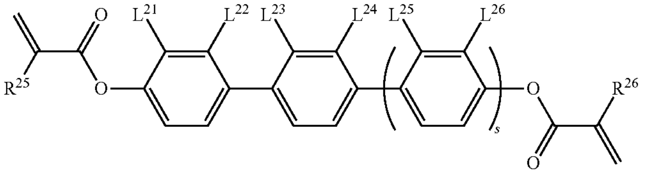

(M-2)

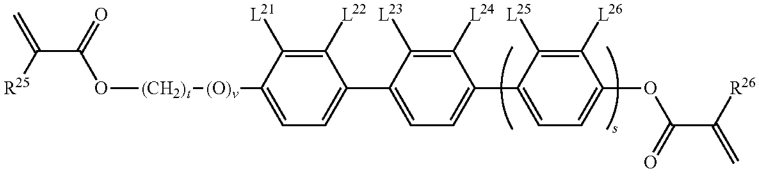

(M-3)

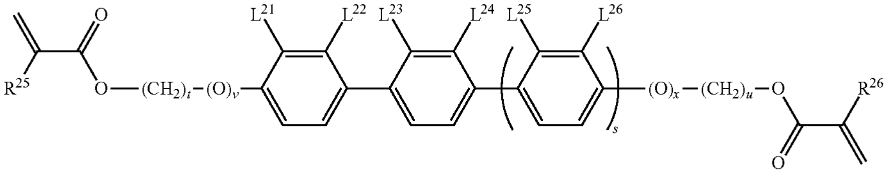

-continued
(M-4)
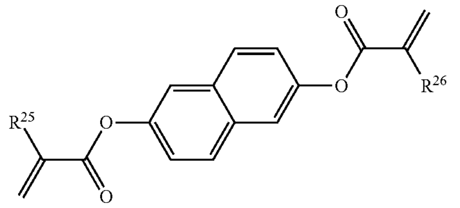
(M-5)
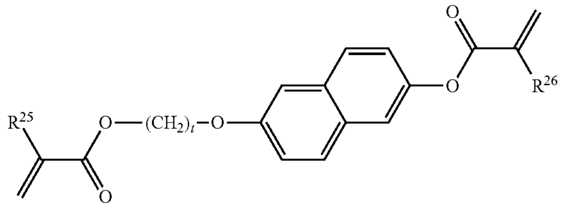
(M-6)
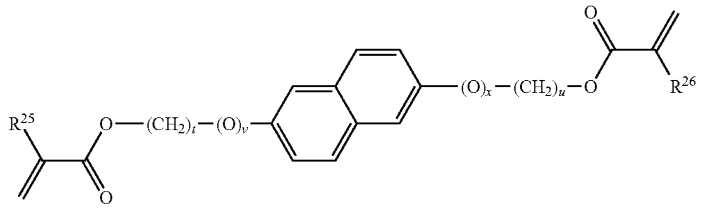
(M-7)
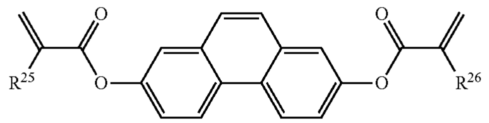
(M-8)
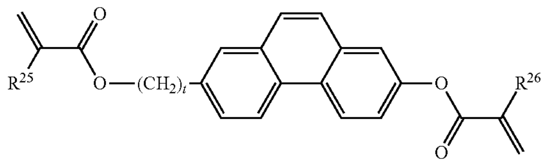
(M-9)
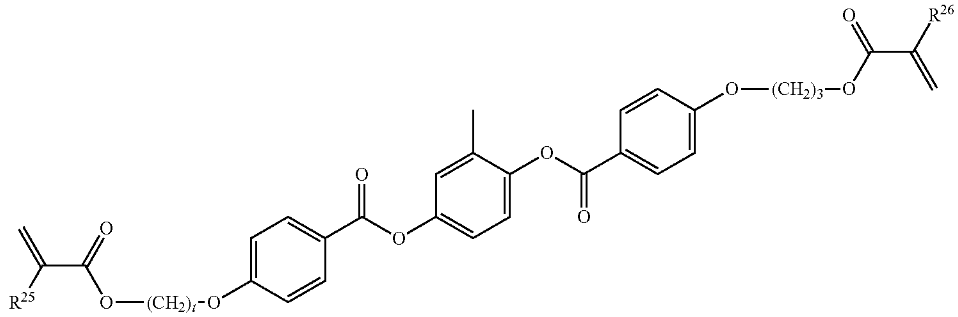
(M-10)
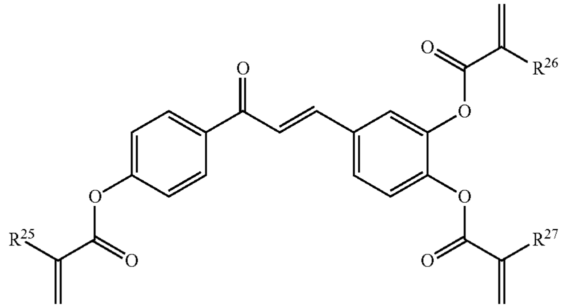
(M-11)
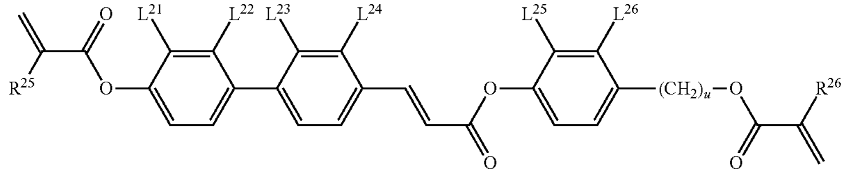

-continued (M-12)

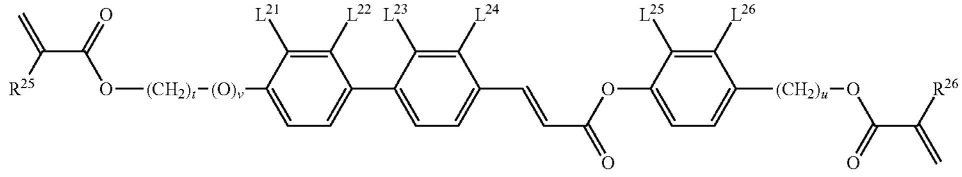

(M-13)

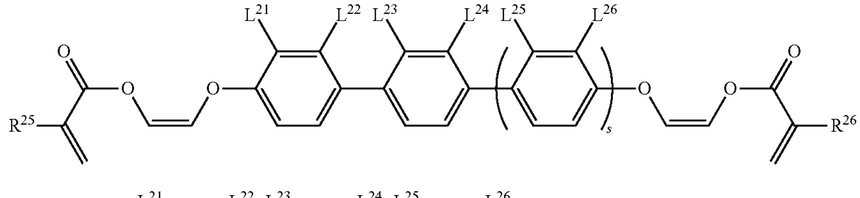

(M-14)

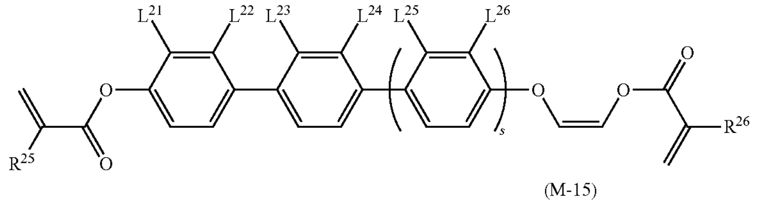

(M-15)

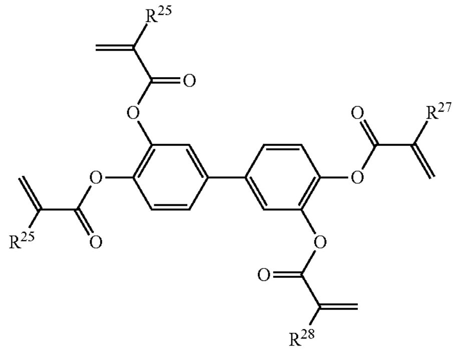

(M-16)

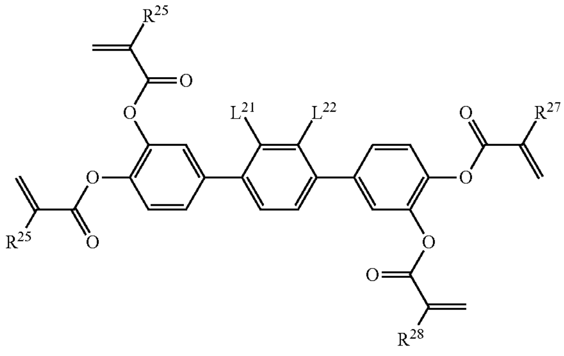

In compounds (M-1) to (M-16), $R^{25}$, $R^{26}$, $R^{27}$ and $R^{28}$ are independently hydrogen or methyl; s, v and x are independently 0 or 1; and t and u are independently an integer from 1 to 10. $L^{21}$, $L^{22}$, $L^{23}$, $L^{24}$, $L^{25}$ and $L^{26}$ are independently hydrogen or fluorine.

The antioxidant is effective for maintaining a large voltage holding ratio. Specific preferred examples of the antioxidant include compounds (AO-1) and (AO-2) described below, IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease of the maximum temperature. Specific preferred examples of the ultraviolet light absorber include a benzophenone derivative, a benzoate derivative and a triazole derivative. Specific examples include (AO-3) and (AO-4) described below, TINUVIN329, TINUVIN P, TINUVIN 326, TINUVIN 234, TINUVIN 213, TINUVIN 400, TINUVIN 328, TINUVIN 99-2 (trade name: BASF SE), and 1,4-diazabicyclo[2.2.2]octane (DABCO). A light stabilizer such as amine having steric hindrance is preferred for maintaining the large voltage holding ratio. Specific preferred examples of the light stabilizer include (AO-5) and (AO-6) described below, TINUVIN 144, TINUVIN 765, and TINUVIN 770DF (trade name: BASF SE). The heat stabilizer is also effective for maintaining the large voltage holding ratio, and preferred examples include IRGAFOS 168 (trade name: BASF SE). The defoaming agent is effective for preventing foam formation. Specific preferred examples of the defoaming agent include dimethyl silicone oil and methylphenyl silicone oil.

(AO-1)

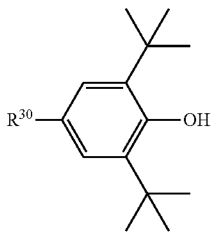

(AO-2)

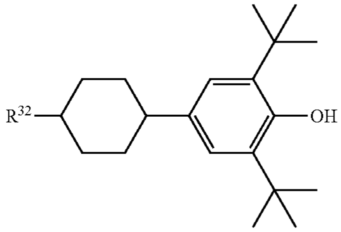

-continued (AO-3)

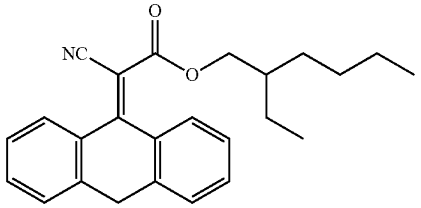

(AO-4)

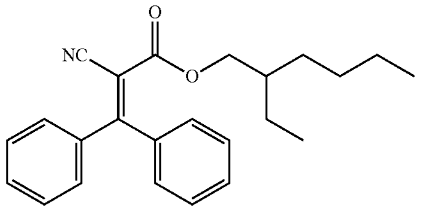

(AO-5)

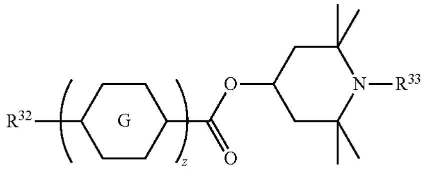

(AO-6)

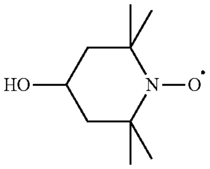

In compound (AO-1), $R^{30}$ is alkyl having 1 to 20 carbons, alkoxy having 1 to 20 carbons, —$COOR^{31}$ or —$CH_2CH_2COOR^{31}$, and $R^{31}$ is alkyl having 1 to 20 carbons. In compound (AO-2), $R^{32}$ is alkyl having 1 to 20 carbons. In compound (AO-5), $R^{32}$ is alkyl having 1 to 20 carbons; $R^{33}$ is hydrogen, methyl, or a (oxygen radical); ring G is 1,4-cyclohexylene or 1,4-phenylene; and z is 1, 2 or 3.

The composition can also be used for a liquid crystal composition for a guest host (GH) mode by addition of a dichroic dye such as a merocyanine, stylyl, azo, azomethine, azoxy, quinophthalone, anthraquinone or tetrazine dye thereto.

3. Liquid Crystal Display Device

Composition (1) can also be used for a liquid crystal display device having the operating mode such as the PC mode, the TN mode, the STN mode, the OCB mode and the PSA mode, and driven by an active matrix (AM) mode. Composition (1) can also be used for a liquid crystal display device having the operating mode such as the PC mode, the TN mode, the STN mode, the OCB mode, the VA mode and the IPS mode, and driven by a passive matrix (PM) mode. The AM mode device and the PM mode device can be applied to any of a reflective type, a transmissive type and transflective type.

Composition (1) can also be used for a nematic curvilinear aligned phase (NCAP) device prepared by microencapsulating a nematic liquid crystal, and a polymer dispersed liquid crystal display device (PDLCD) and a polymer network liquid crystal display device (PNLCD), in which a three-dimensional network polymer is formed in the liquid crystal.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. However, the invention is not limited by the Examples.

1-1. Example of Compound (1)

Compound (1) was synthesized by procedures described below. The thus prepared compound was identified by a method such as an NMR analysis. Physical properties of the compound were measured by methods described below.

NMR Analysis

For measurement, DRX-500 made by Bruker BioSpin Corporation was used. In $^{1}$H-NMR measurement, a sample was dissolved in a deuterated solvent such as $CDCl_3$, and measurement was carried out under conditions of room temperature, 500 MHz and 16 times of accumulation. Tetramethylsilane (TMS) was used as an internal standard. In $^{19}$F-NMR measurement, $CFCl_3$ was used as an internal standard, and measurement was carried out under conditions of 24 times of accumulation. In the explanation of nuclear magnetic resonance spectra, symbols s, d, t, q, quin, sex, m and br stand for a singlet, a doublet, a triplet, a quartet, a quintet, a sextet, a multiplet and being broad, respectively.

Sample for Measurement

When phase structure and a transition temperature were measured, a liquid crystal compound itself was used as a sample. When physical properties such as a maximum temperature of a nematic phase, viscosity, optical anisotropy and dielectric anisotropy were measured, a composition prepared by mixing the compound with a base liquid crystal was used as the sample.

In a case where a sample prepared by mixing the compound with the base liquid crystal was used, measurement was carried out according to the method described below. The sample was prepared by mixing 15% by weight of the compound and 85% by weight of the base liquid crystal. Then, extrapolated values were calculated from measured values of the sample, according to an extrapolation method, represented by an equation below, and the extrapolated values were described. {Extrapolated value}={100×(measured value of a sample)−(% by weight of a base liquid crystal)×(measured value of the base liquid crystal)}/(% by weight of the compound).

When crystals (or a smectic phase) precipitated at 25° C. even at the ratio of the compound to the base liquid crystal, a ratio of the compound to the base liquid crystal was changed in the order of (10% by weight: 90% by weight), (5% by weight: 95% by weight) and (1% by weight: 99% by weight), and physical properties of the sample at the ratio at which no crystals (or the smectic phase) precipitated at 25° C. were measured. In addition, unless otherwise noted, the ratio of the compound to the base liquid crystal was 15% by weight: 85% by weight.

As the base liquid crystal, base liquid crystal (i) described below was used. Ratios of components of the base liquid crystal (i) were expressed in terms of weight percent (% by weight).

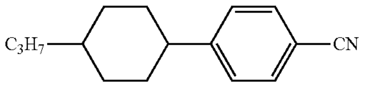
24%

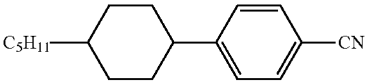
36%

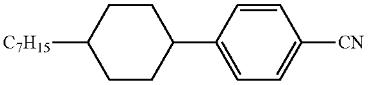
25%

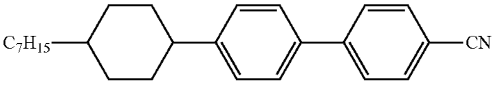
15%

Measuring Methods

Physical properties were measured according to the methods described below. Most of the measuring methods were applied as described in the Standard of the Japan Electronics and Information Technology Industries Association (hereinafter abbreviated as JEITA) (JEITA EIAJ ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc. or a high sensitivity differential scanning calorimeter, X-DSC7000, made by SII NanoTechnology, Inc. were used. A sample was heated and then cooled at a rate of 3° C. per minute, and a starting point of an endothermic peak or an exothermic peak caused by a phase change of the sample was determined by extrapolation, and thus the transition temperature was determined. Temperature at which a compound undergoes transition from a solid to a liquid crystal phase such as a smectic phase and a nematic phase may be occasionally abbreviated as "minimum temperature of the liquid crystal phase." Temperature at which the compound undergoes transition from the liquid crystal phase to an isotropic liquid may be occasionally abbreviated as "clearing point."

The crystals were expressed as C. When kinds of the crystals were distinguishable, each of the crystals was expressed as C1 or C2. The smectic phase or the nematic phase was expressed as S or N. When smectic A phase, smectic B phase, smectic C phase or smectic F phase was distinguishable among the smectic phases, the phases were expressed as SA, SB, SC or SF, respectively. A liquid (isotropic) was expressed as I. The transition temperature was expressed as "C 50.0 N 100.0 I," for example. The expression indicates that the transition temperature from the crystals to the nematic phase was 50.0° C., and the transition temperature from the nematic phase to the liquid was 100.0° C.

(3) Compatibility at a Low Temperature

Samples in which the base liquid crystal and the compound were mixed for the compound to be 20% by weight, 15% by weight, 10% by weight, 5% by weight, 3% by weight and 1% by weight were prepared, and placed in glass vials. After the glass vials were kept in freezers at −10° C. or −20° C. for a predetermined period, whether or not crystals (or the smectic phase) precipitated was observed.

(4) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from the nematic phase to the isotropic liquid was measured. A higher limit of the temperature range of the nematic phase may be occasionally abbreviated as "maximum temperature." When the sample was a mixture of a compound and a base liquid crystal, the maximum temperature was expressed in terms of a symbol $T_{NI}$. When the sample was a mixture of the compound and component B or the like, the maximum temperature was expressed in terms of a symbol NI.

(5) Minimum Temperature of the Nematic Phase ($T_c$; ° C.)

Samples each having the nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., Tc was expressed as $T_c$-20° C. A lower limit of the temperature range of the nematic phase may be occasionally abbreviated as "minimum temperature."

(6) Viscosity (Bulk Viscosity; η; Measured at 20° C.; mPa·s)

A cone-plate (E type) rotational viscometer made by Tokyo Keiki, Inc. was used for measurement.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and a calculation equation (8) described on page 40 of the paper presented by M. Imai et al. A value of a dielectric anisotropy required for the calculation was determined using the device by which the rotational viscosity was measured and by the method described below.

(8) Optical Anisotropy (Refractive Index Anisotropy; Δn; Measured at 25° C.)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(9) Dielectric Constant (∈⊥) in Minor Axis Direction and Dielectric Anisotropy (Δ∈; Measured at 25° C.)

A sample was put in a TN device in which a distance (cell gap) between two glass substrates was 9 micrometers and the twist angle was 80 degrees. Sine waves (10 V, 1 kHz) were applied to the device, and after 2 seconds, a dielectric constant ($\in\|$) in the major axis direction of liquid crystal molecules was measured. Sine waves (0.5 V, 1 kHz) were applied to the device, and after 2 seconds, a dielectric constant ($\in\perp$) in the minor axis direction of the liquid crystal molecules was measured. A value of dielectric anisotropy was calculated from an equation:

$$\Delta\in=\in\|-\in\perp.$$

(10) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. Measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K^{11}$ and $K^{33}$ were obtained from equation (2.99). Next, $K^{22}$ was calculated using the previously determined values of $K^{11}$ and $K^{33}$ in formula (3.18) on page 171. Elastic constant K was expressed in terms of a mean value of the thus determined $K^{11}$, $K^{22}$ and $K^{33}$.

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was approximately 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of a voltage at 90% transmittance.

(12) Voltage Holding Ratio (VHR-1; Measured at 25° C.; %)

A TN device used for measurement had a polyimide alignment film, and a distance (cell gap) between two glass substrates was 5 micrometers. A sample was put in the device, and the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(13) Voltage Holding Ratio (VHR-2; Measured at 80° C.; %)

A voltage holding ratio (VHR-2) was determined in a manner similar to the method for measuring VHF-1 except that measurement was carried out at 80° C.

Raw Material

Solmix A-11 (trade name) was a mixture of ethanol (85.5%), methanol (13.4%) and isopropanol (1.1%), and was purchased from Japan Alcohol Trading Co., Ltd.

Synthesis of Liquid Crystal Compound

Example 1

Synthesis of Compound (1-2-48)

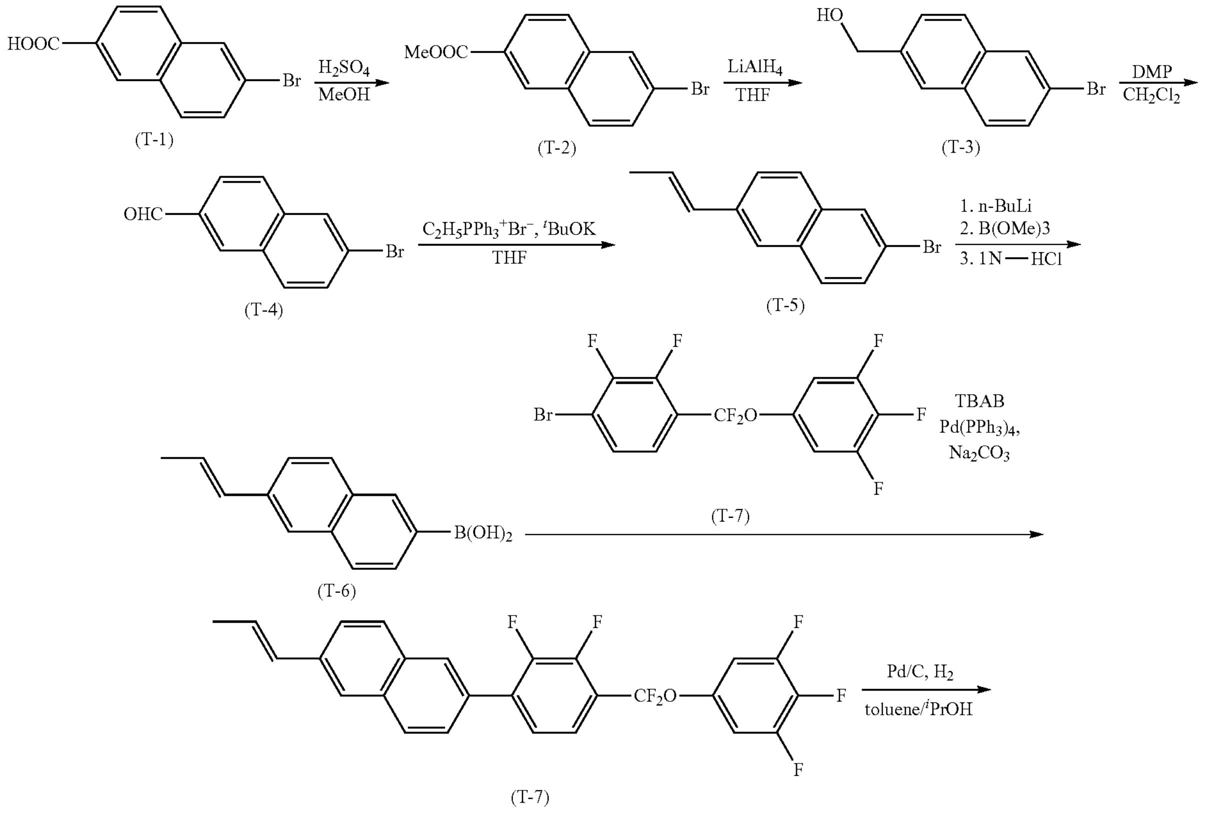

-continued

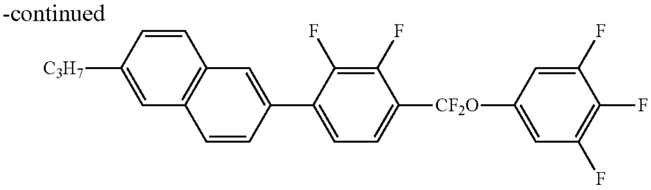

(1-2-48)

First Step 6-bromo-2-naphthalenecarboxylic acid (T-1, made by Tokyo Chemical Industry Co., Ltd.) (25 g, 99.6 mmol), a concentrated sulfuric acid (5.4 mL, 99.6 mmol) and methanol (80 mL) were placed in a reaction vessel. The resulting mixture was stirred and refluxed under heating for 7 hours. The resulting reaction mixture was cooled to room temperature, and then water was further added thereto, and the resulting mixture was extracted with dichloromethane. The combined organic layers were one by one, washed with water, a aqueous solution of sodium carbonate, water and saturated brine, and dried over anhydrous magnesium sulfate. Then, the resulting solution was concentrated under reduced pressure to obtain compound (T-2) (26.4 g, 99.6 mmol). Compound (T-2) was used for a next reaction without purification.

Second Step

Under a nitrogen atmosphere, lithium aluminum hydride (5.67 g, 149.4 mmol) and THF (100 mL) were placed in a reaction vessel, and the resulting mixture was cooled with ice water. Thereto, (T-2) (26.4 g, 99.6 mmol) obtained in the first step and a THF (100 mL) solution were added dropwise thereto in the temperature range of −0° C. to −10° C., and the resulting mixture was further stirred for 2 hours while returning to room temperature. The resulting reaction mixture was cooled with ice water, and ethyl acetate (50 mL) was added dropwise thereto in the temperature range of 0° C. to −10° C., and the resulting mixture was poured into 2N-hydrochloric acid (300 mL) in a vessel, and the resulting mixture was stirred for 15 minutes. The resulting mixture was separated into an organic layer and an aqueous layer, and the aqueous layer was extracted with ethyl acetate. The combined organic layers were washed with water, a saturated aqueous solution of sodium hydrogencarbonate, water and saturated brine, one by one, and dried over anhydrous magnesium sulfate. Then, the resulting solution was concentrated under reduced pressure and compound (T-3) (23.6 g, 99.6 mmol) was obtained. Compound (T-3) was used for a next reaction without purification.

Third Step

Under a nitrogen atmosphere, methylene chloride (250 mL) were put into compound (T-3) (23.6 g, 99.6 mmol) obtained by the second step, in a reaction vessel, The resulting solution was cooled to 0° C., and Three divided portions of Dess-Martin periodinane (DMP; 42.2 g, 99.6 mmol) were added thereto. The resulting mixture was stirred for additional 2 hours while returning to room temperature. The resulting reaction mixture was poured into a saturated aqueous solution of sodium hydrogencarbonate (300 mL) in a vessel, and the resulting mixture was filtered, and the filtered was extracted with ethyl acetate. The combined organic layers were sequentially washed with water, a sodium sulfite aqueous solution, water and saturated brine, and dried over anhydrous magnesium sulfate. Then, the resulting solution was concentrated under reduced pressure, and the residue was purified by silica gel chromatography to obtain compound (T-4) (19.05 g, 81.0 mmol; 81%).

Fourth Step

Under a nitrogen atmosphere, ethyltriphenyl phosphonium bromide (45.13 g, 121.56 mmol) and a THF (150 mL) solution were put in a reaction vessel, and the resulting mixture was cooled to −30° C. or lower. Potassium-tert-butoxide (12.73 g, 113.45 mmol) was added thereto dropwise in the temperature range of −40° C. to −30° C., and the resulting mixture was further stirred for 2 hours. A THF (150 mL) solution of compound (T-4) (19.05 g, 81.0 mmol) obtained in the third step was added dropwise thereto in the temperature range of −40° C. to −30° C., and the resulting mixture was stirred for 2 hours while returning to room temperature. The resulting reaction mixture was poured into ice water in a vessel, and then the resulting mixture was stirred for 30 minutes, and extracted with toluene. The combined organic layers were sequentially washed with water and saturated brine, and dried over anhydrous magnesium sulfate. The resulting solution was concentrated under reduced pressure, and the resulting residue was purified by silica gel chromatography to obtain compound (T-5) (17.88 g, 57.37 mmol; 71%).

Fifth Step

Under a nitrogen atmosphere, compound (T-5) (17.88 g, 57.37 mmol) obtained in the fourth step and a THF (100 mL) solution were put in a reaction vessel, and the resulting mixture was cooled to −60° C. or lower. Thereto, n-butyllithium (1.63 M; n-hexane solution; 38.7 mL, 63.1 mmol) was added dropwise in the temperature range of −70° C. to −60° C., and the resulting mixture was additionally stirred for 1 hour. A THF (20 mL) solution of trimethyl borate (7.15 g, 68.8 mmol) was added dropwise thereto in the temperature range of −70° C. to −60° C., and the resulting mixture was stirred for 1 hour, and then the resulting mixture was additionally stirred for 6 hour while returning to room temperature. The resulting reaction mixture was poured into 1 N hydrochloric acid (63 mL) in a vessel, and then the resulting mixture was stirred for 30 minutes, and was extracted with ethyl acetate. The combined organic layers were sequentially rinsed with water and saturated brine, one by one, and dried over anhydrous magnesium sulfate. The resulting solution was concentrated under reduced pressure, and the resulting residue was washed with heptane, and compound (T-6) (10.2 g, 48.1 mmol; 84%) was obtained.

Sixth Step

In a reaction vessel, compound (T-6) (5.0 g, 23.58 mmol) obtained in the fifth step, compound (T-7) (9.17 g, 23.58 mmol) obtained by a known synthesis method, tetrakistriphenyl phosphine palladium (1.09 g, 0.94 mmol), tetrabutylammonium bromide (1.90 g, 5.89 mmol), sodium carbonate (4.99 g, 47.16 mmol), toluene (120 mL), ethanol (25 mL) and water (25 mL) were put. The resulting mixture was stirred and refluxed under heating for 2 hours. The reaction mixture was cooled to room temperature, and extracted with toluene. The combined organic layers were washed with water and with saturated brine, one by one, and dried over anhydrous magnesium sulfate. The resulting solution was concentrated under reduced pressure, and the resulting residue was purified by silica gel chromatography (heptane) to obtain compound (T-8) (10.53 g, 22.1 mmol; 94%).

Seventh Step

In a reaction vessel, compound (T-8) (10.53 g, 22.1 mmol) obtained in the sixth step, palladium carbon (0.5 g), toluene (50 mL) and ethanol (50 mL) were put. The resulting mixture was stirred under hydrogen atmosphere for 19 hours. The resulting reaction mixture was filtered, and then the resulting filtered was concentrated under reduced pressure. The resulting residue was purified by silica gel chromatography (heptane: toluene=4:1 in a volume ratio), and recrystallized (solvent; heptane) to obtain target compound (1-2-48) (6.37 g, 13.3 mmol; 60%).

$^1$H-NMR (δ ppm; $CDCl_3$): 8.00 (s, 1H), 7.88 (d, 1H), 7.83 (d, 1H), 7.65 (s, 1H), 7.61 (dt, 1H), 7.51 (td, 1H), 7.42-7.39 (m, 2H), 7.02-6.99 (m, 2H), 2.78 (t, 2H), 1.79-1.72 (m, 2H), 0.99 (t, 3H).

Physical properties of compound (No. 1-2-48) were as described below.

Transition temperature: C 82.1 N 84.5 I

Maximum temperature ($T_{NI}$)=67.0; optical anisotropy (Δn)=0.184; dielectric anisotropy (Δ∈)=21.43; dielectric constant in a minor axis direction (∈⊥)=7.17.

According to the synthetic method of compound (1) described above and the synthetic procedures described in Example 1, compounds (No. 1-1-1) to (No. 1-1-20), compounds (No. 1-2-1) to (No. 1-2-100), compounds (No. 1-3-1) to (No. 1-3-100). Compounds (No. 1-4-1) to (No. 1-4-48), compounds (No. 1-5-1) to (No. 1-5-20), compounds (No. 1-6-1) to (No. 1-6-20), compounds (No. 1-7-1) to (No. 1-7-8) and compounds (No. 1-8-1) to (No. 1-8-8) shown below can be prepared.

(1-1-1)

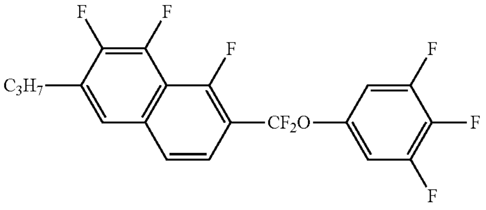

(1-1-2)

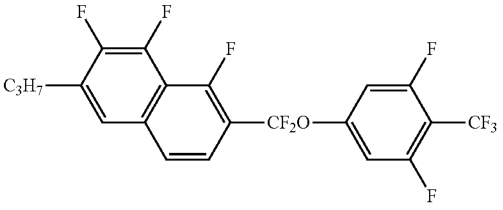

(1-1-3)

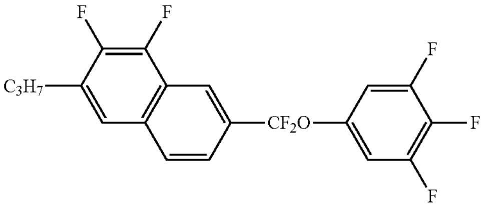

(1-1-4)

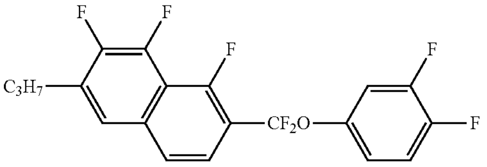

(1-1-5)

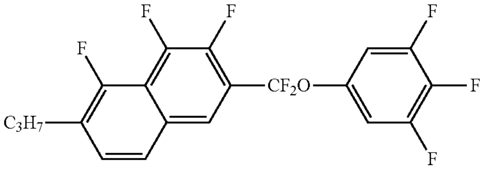

(1-1-6)

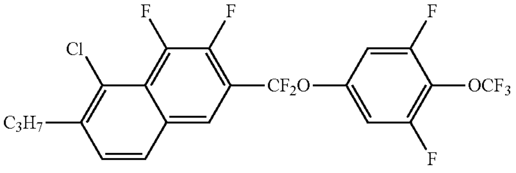

(1-1-7)

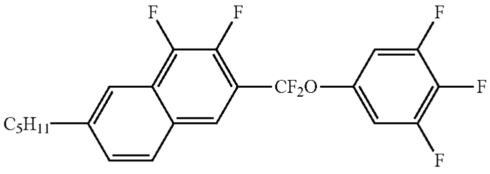

(1-1-8)

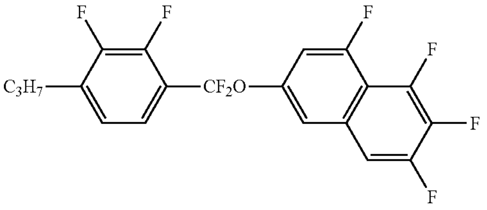

(1-1-9)

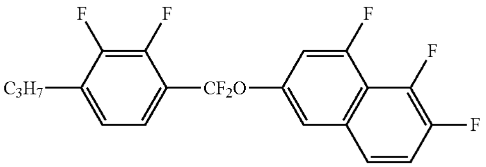

(1-1-10)

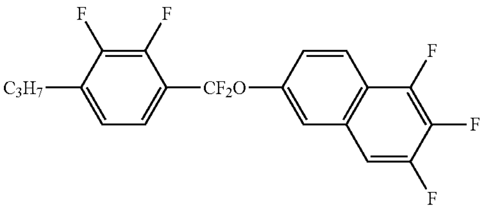

-continued
(1-1-11)
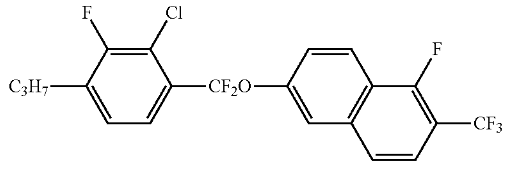
(1-1-12)
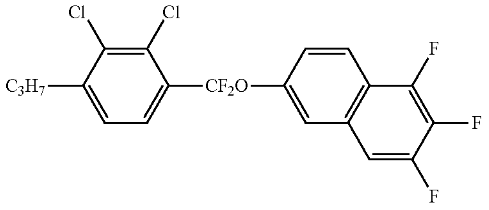
(1-1-13)
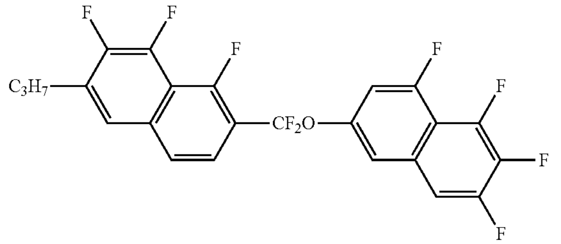
(1-1-14)
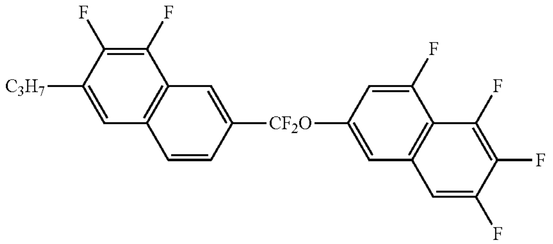
(1-1-15)
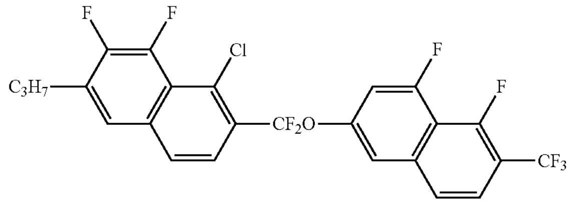
(1-1-16)
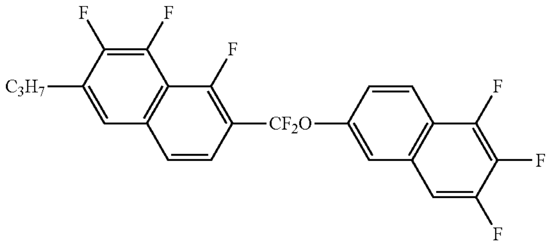
(1-1-17)
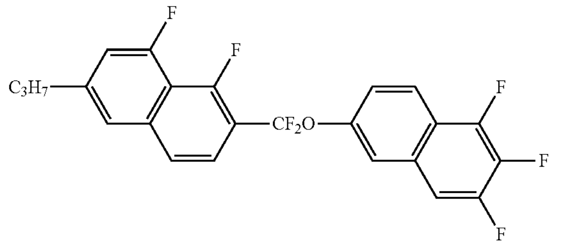
(1-1-18)
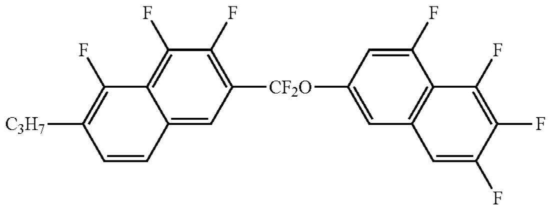
(1-1-19)
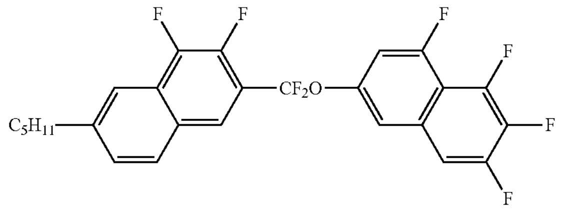
(1-1-20)
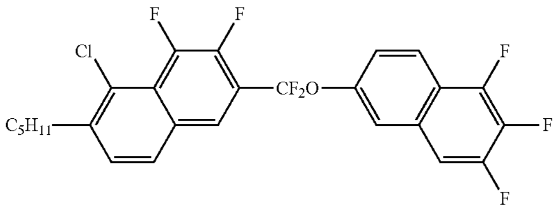
(1-2-1)
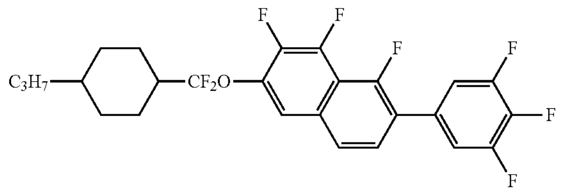
(1-2-2)
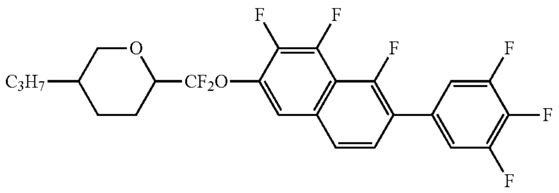

-continued
(1-2-3)
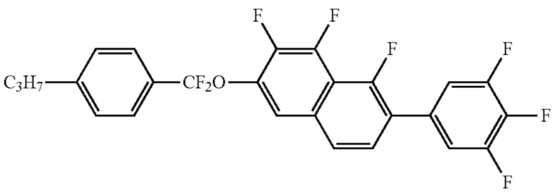
(1-2-4)
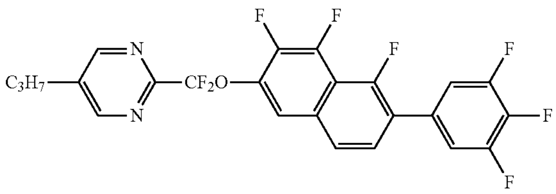
(1-2-5)
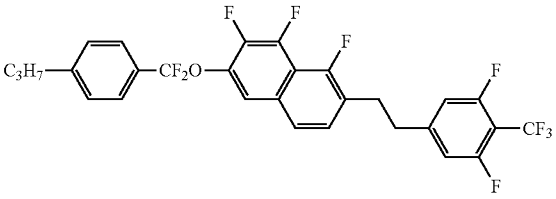
(1-2-6)
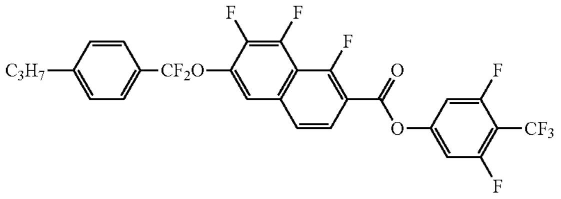
(1-2-7)
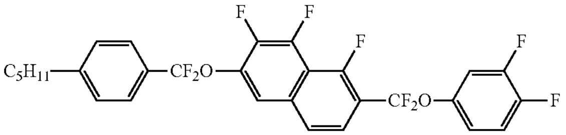
(1-2-8)
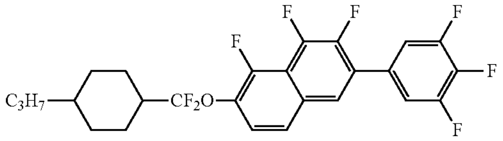
(1-2-9)
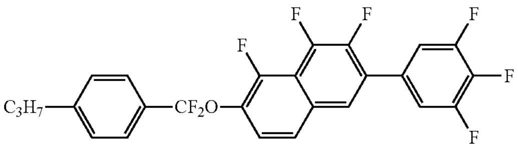
(1-2-10)
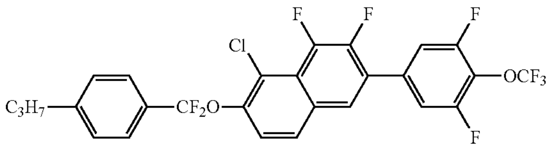
(1-2-11)
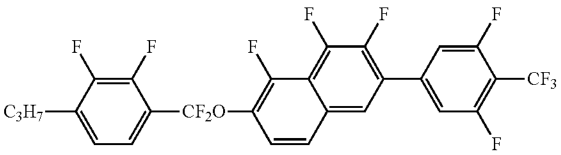
(1-2-12)
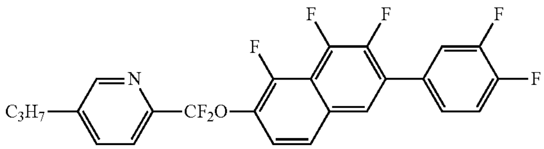
(1-2-13)
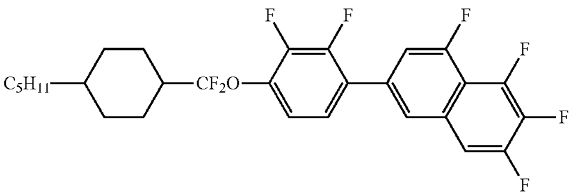
(1-2-14)
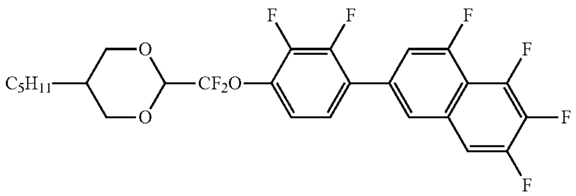
(1-2-15)
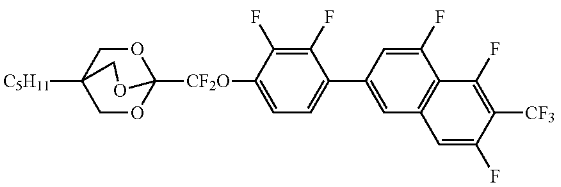
(1-2-16)
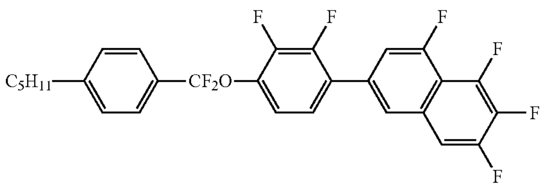
(1-2-17)
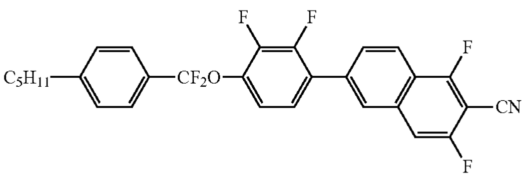
(1-2-18)
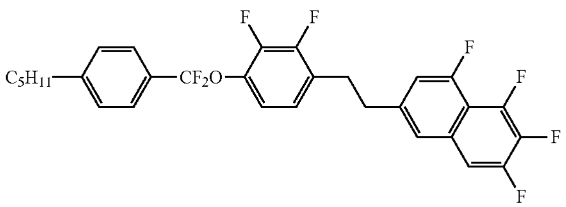

-continued
(1-2-19)
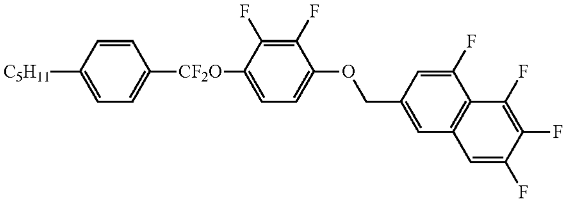
(1-2-20)
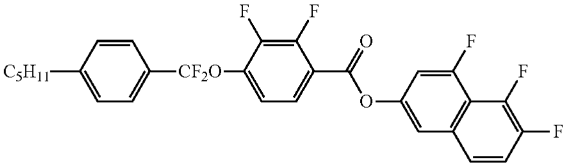
(1-2-21)
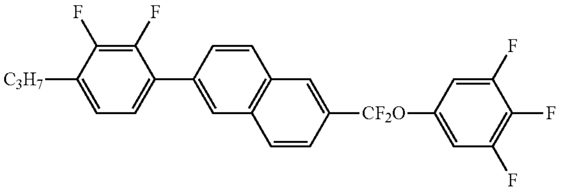
(1-2-22)
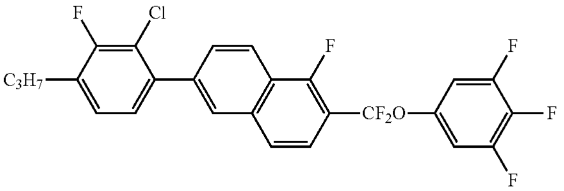
(1-2-23)
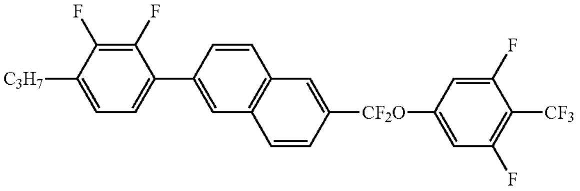
(1-2-24)
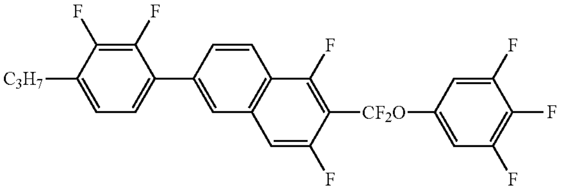
(1-2-25)
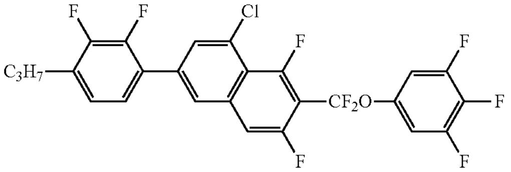
(1-2-26)
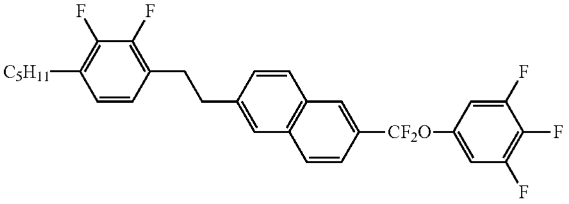
(1-2-27)
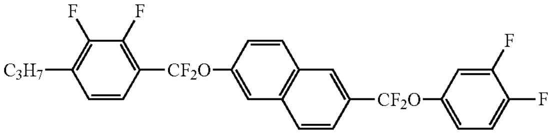
(1-2-28)
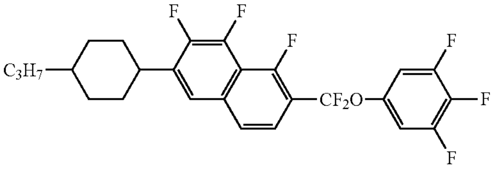
(1-2-29)
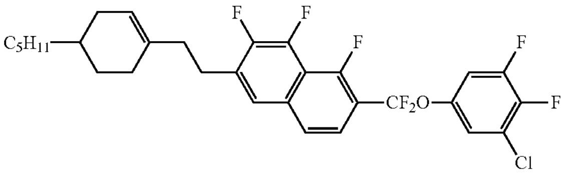
(1-2-30)
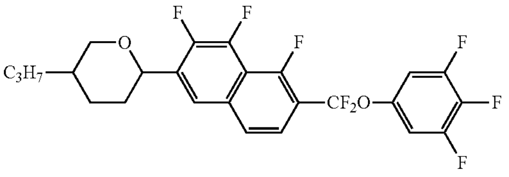
(1-2-31)
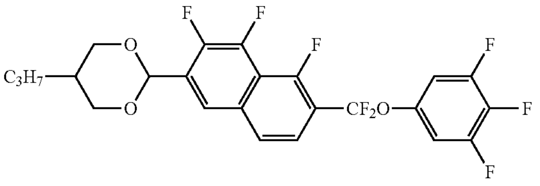
(1-2-32)
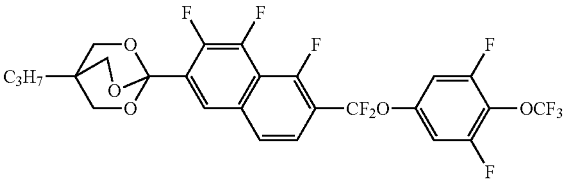

-continued
(1-2-33)
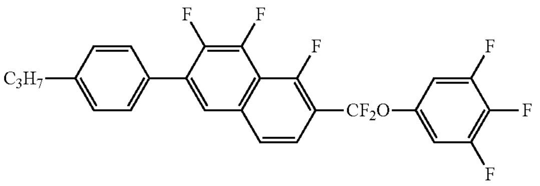
(1-2-34)
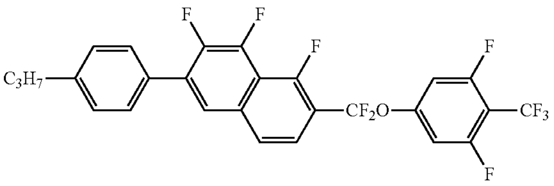
(1-2-35)
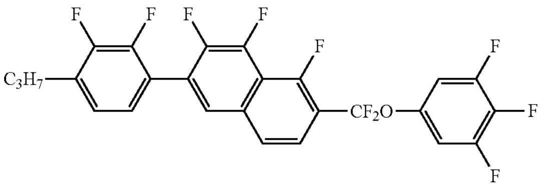
(1-2-36)
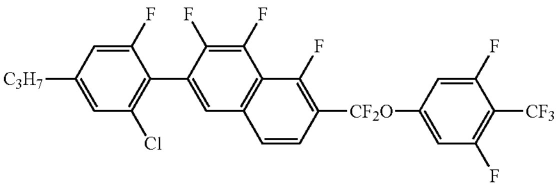
(1-2-37)
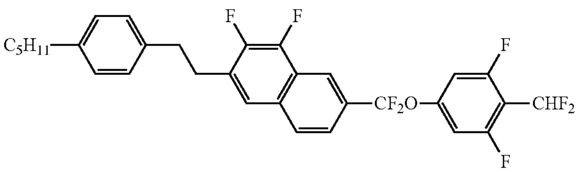
(1-2-38)
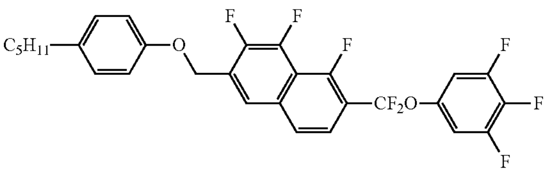
(1-2-39)
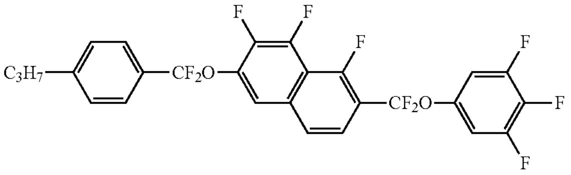
(1-2-40)
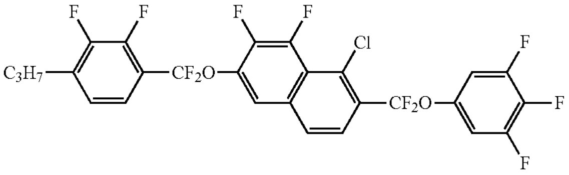
(1-2-41)
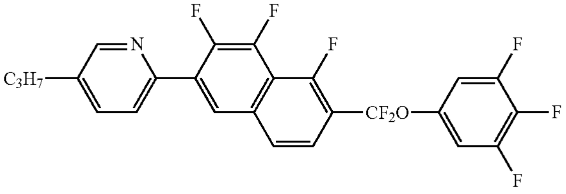
(1-2-42)
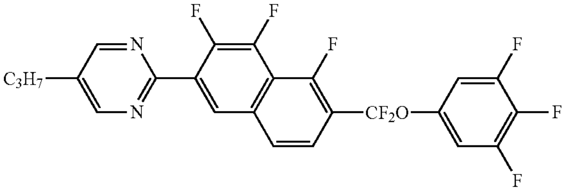
(1-2-43)
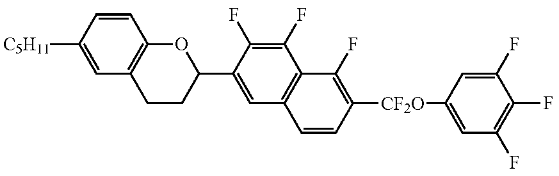
(1-2-44)
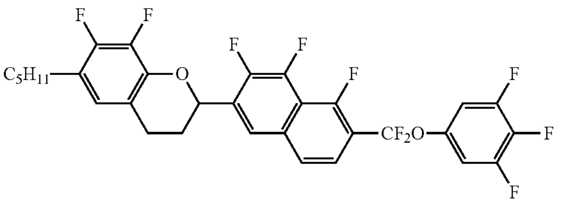
(1-2-45)
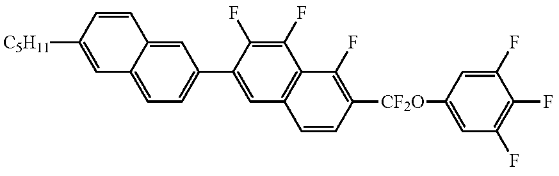
(1-2-46)
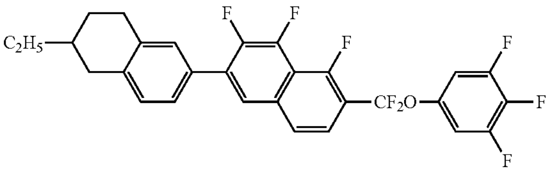

-continued
(1-2-47)
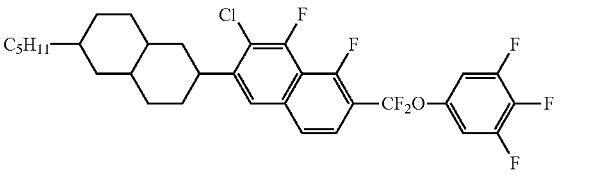
(1-2-48)
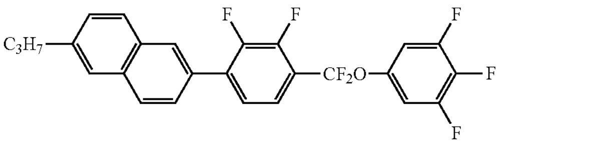
(1-2-49)
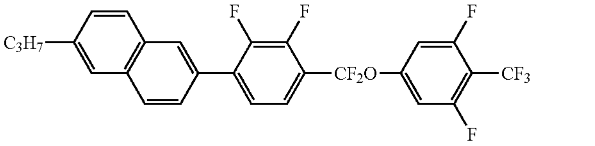
(1-2-50)
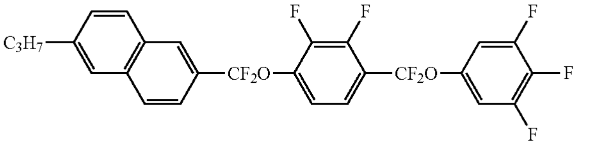
(1-2-51)
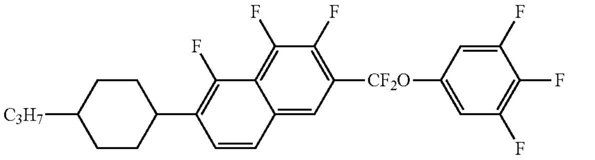
(1-2-52)
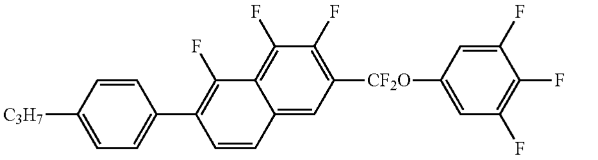
(1-2-53)
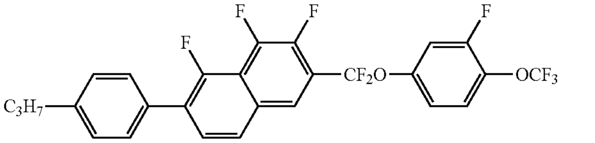
(1-2-54)
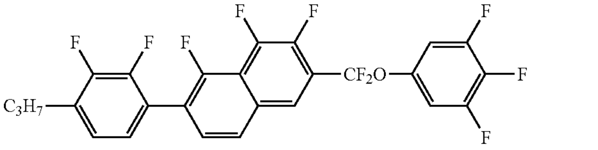
(1-2-55)
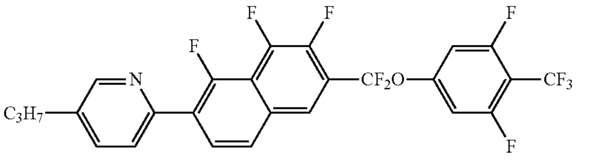
(1-2-56)
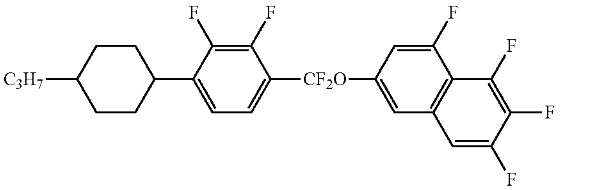
(1-2-57)
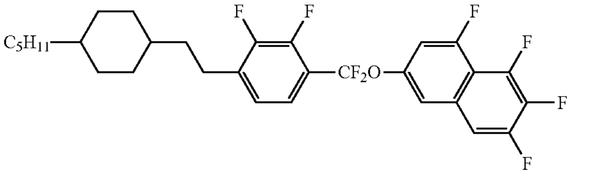
(1-2-58)
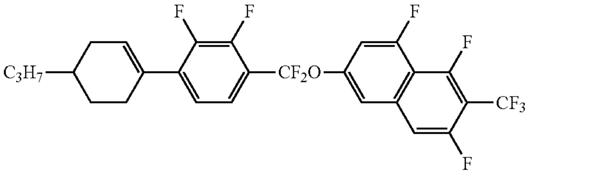
(1-2-59)
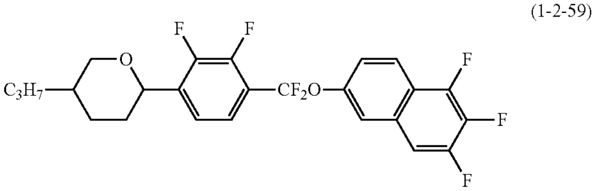
(1-2-60)
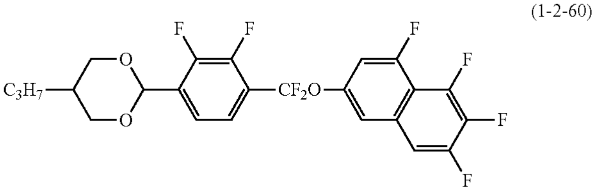
(1-2-61)
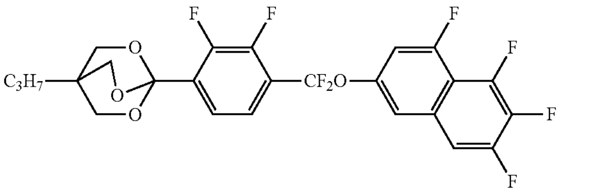
(1-2-62)
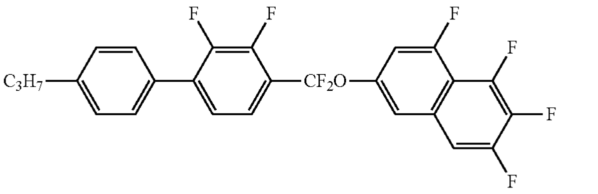

-continued
(1-2-63)
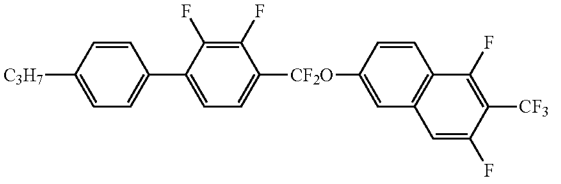
(1-2-64)
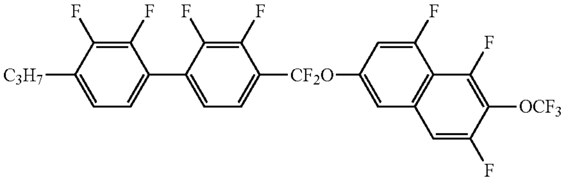
(1-2-65)
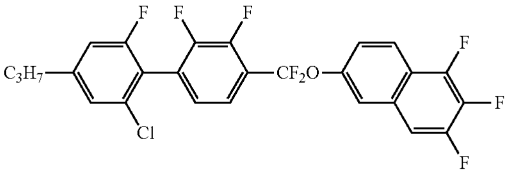
(1-2-66)
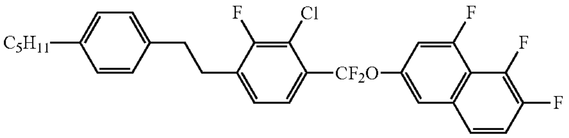
(1-2-67)
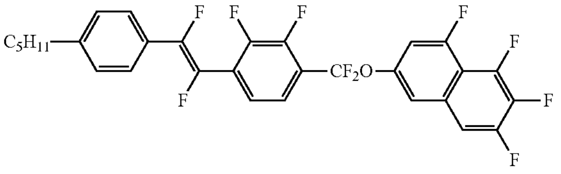
(1-2-68)
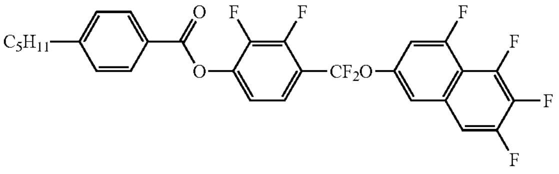
(1-2-69)
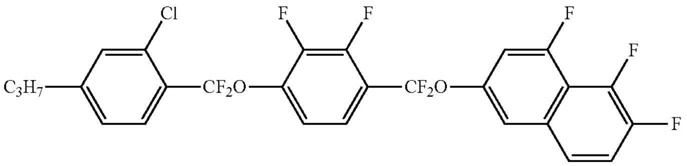
(1-2-70)
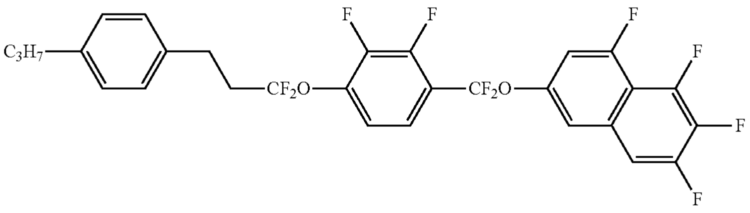
(1-2-71)
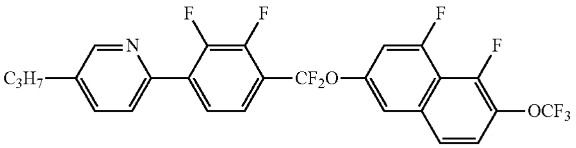
(1-2-72)
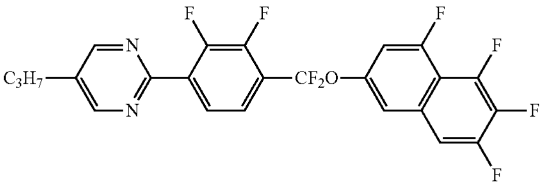
(1-2-73)
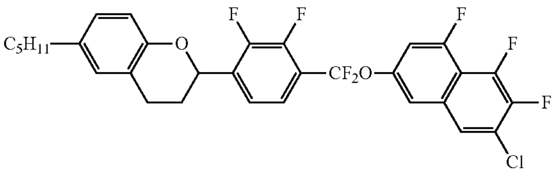
(1-2-74)
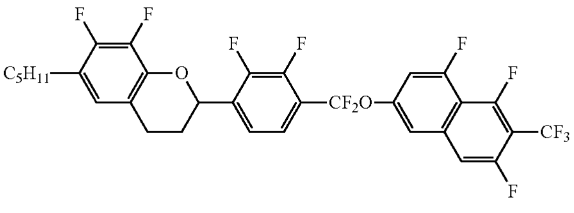

-continued
(1-2-75)
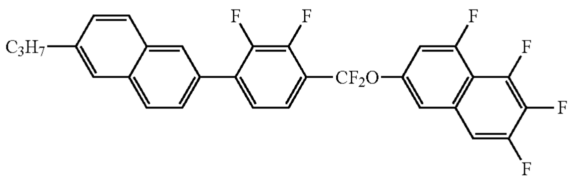
(1-2-76)
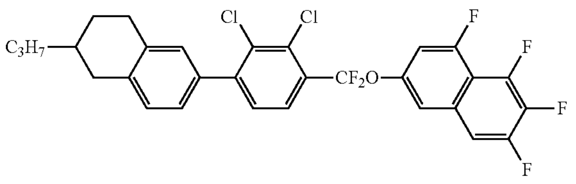
(1-2-77)
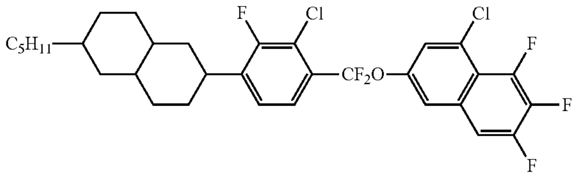
(1-2-78)
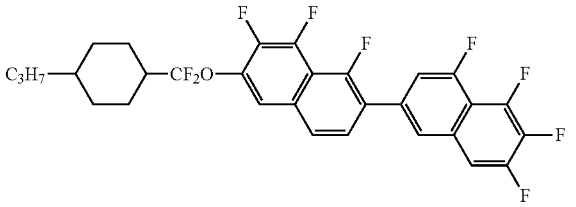
(1-2-79)
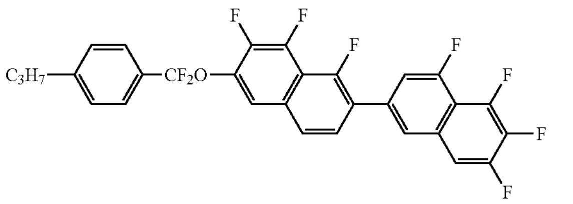
(1-2-80)
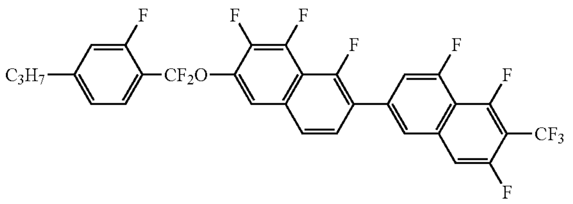
(1-2-81)
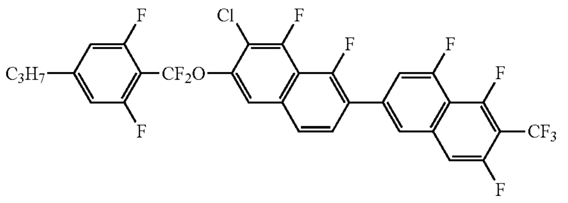
(1-2-82)
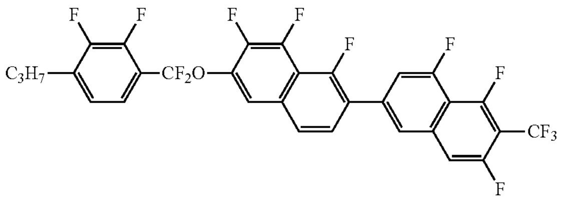
(1-2-83)
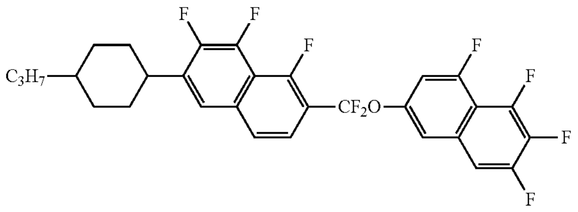
(1-2-84)
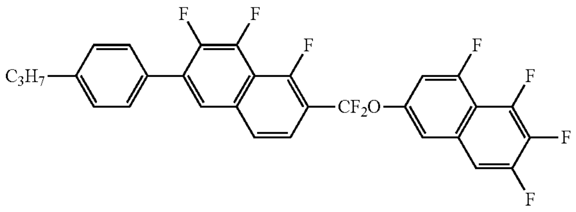
(1-2-85)
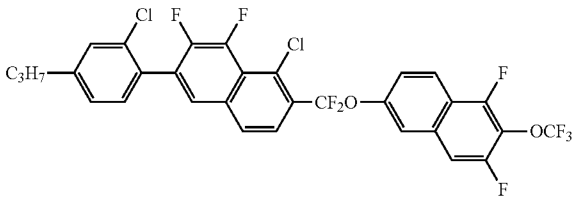
(1-2-86)
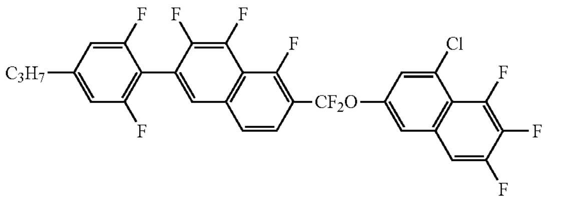
(1-2-87)
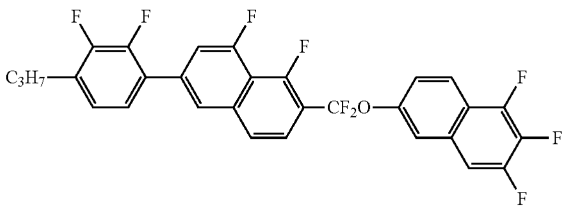
(1-2-88)
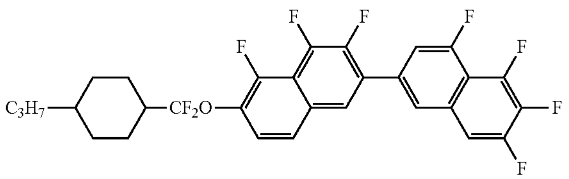

-continued
(1-2-89)
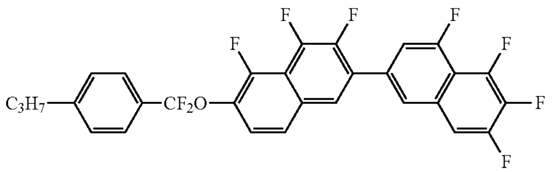
(1-2-90)
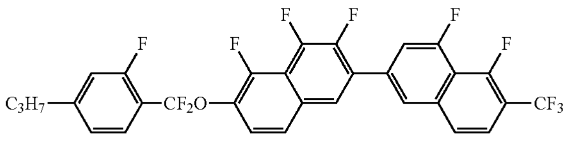
(1-2-91)
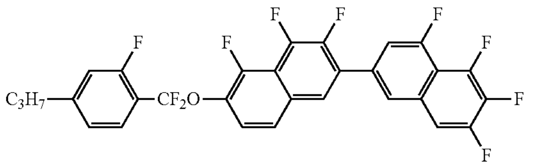
(1-2-92)
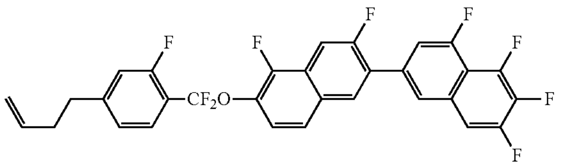
(1-2-93)
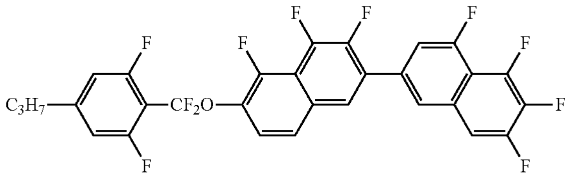
(1-2-94)
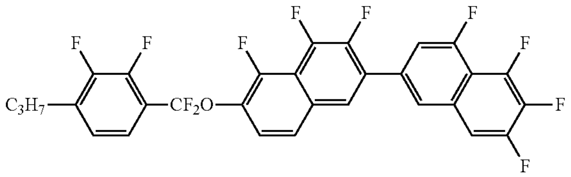
(1-2-95)
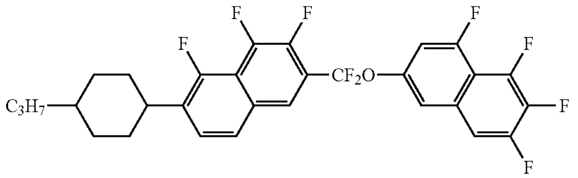
(1-2-96)
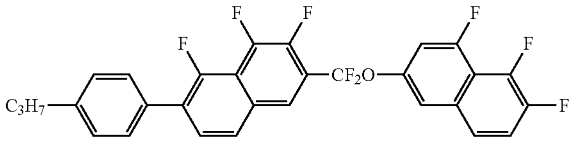
(1-2-97)
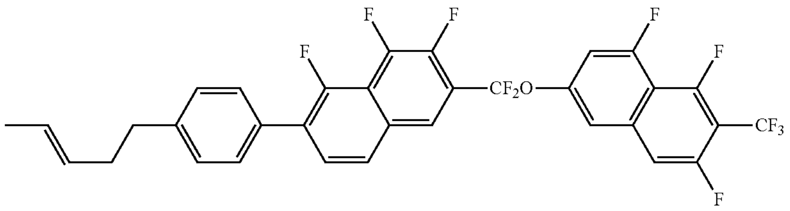
(1-2-98)
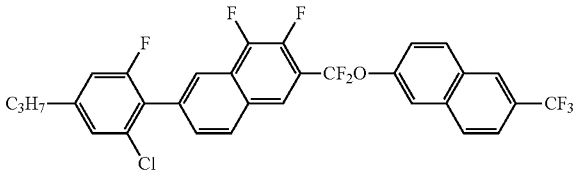
(1-2-99)
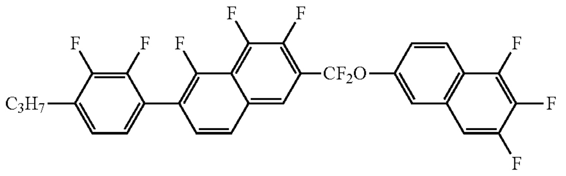
(1-2-100)
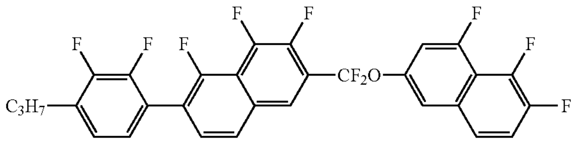
(1-3-1)
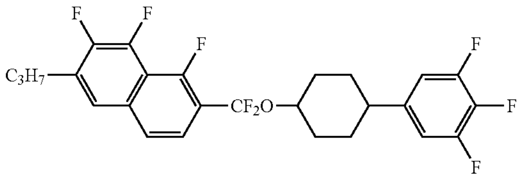
(1-3-2)
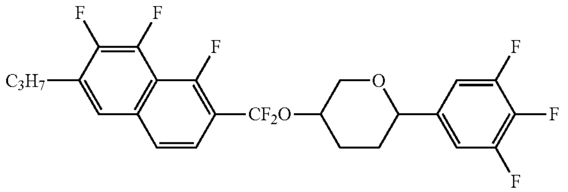
(1-3-3)
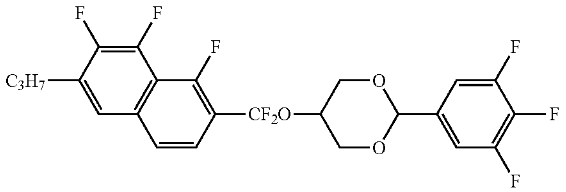

-continued
(1-3-4)
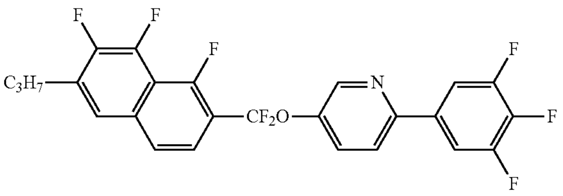
(1-3-5)
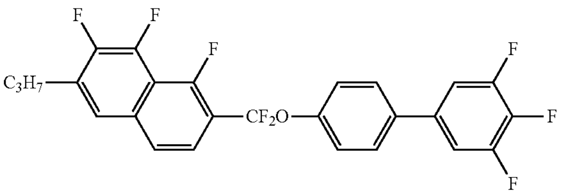
(1-3-6)
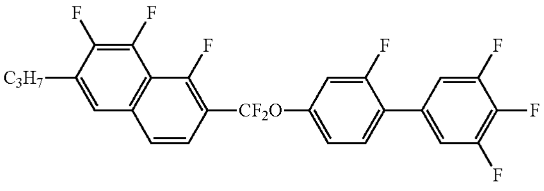
(1-3-7)
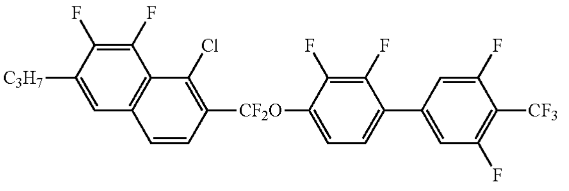
(1-3-8)
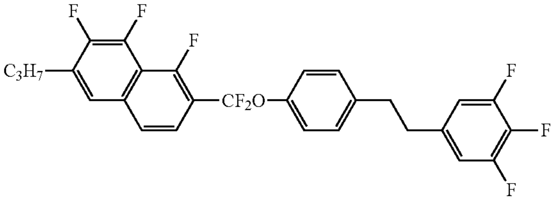
(1-3-9)
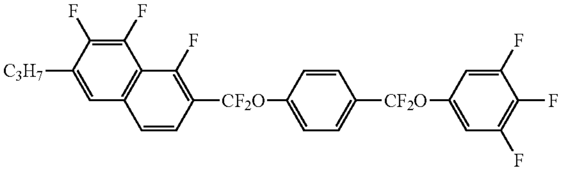
(1-3-10)
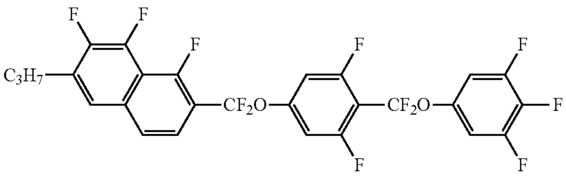
(1-3-11)
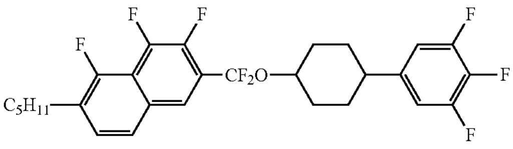
(1-3-12)
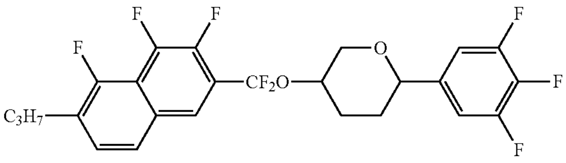
(1-3-13)
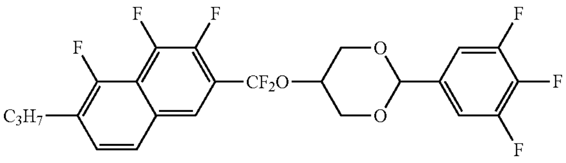
(1-3-14)
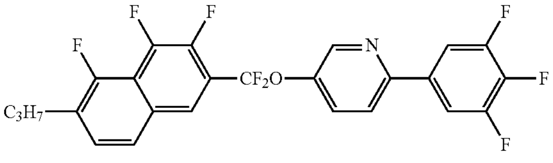
(1-3-15)
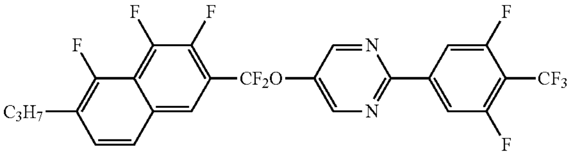
(1-3-16)
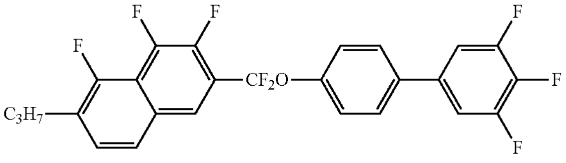
(1-3-17)
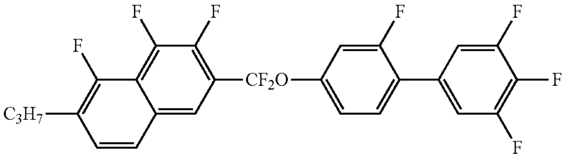
(1-3-18)
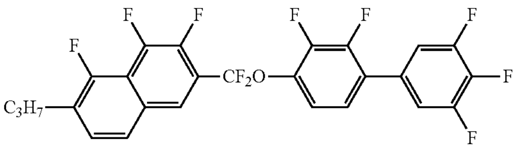
(1-3-19)
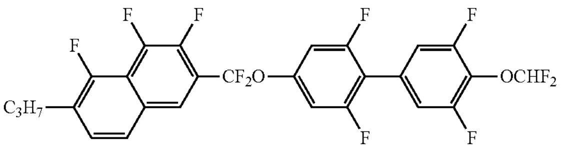

-continued
(1-3-20)
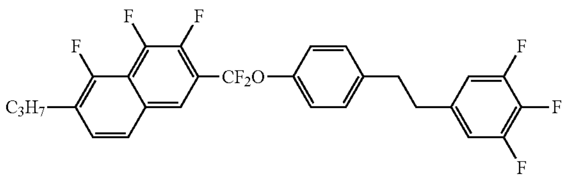
(1-3-21)
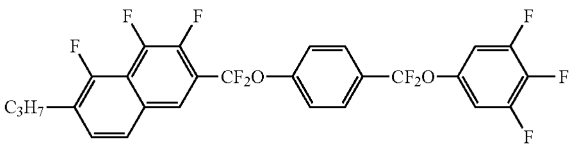
(1-3-22)
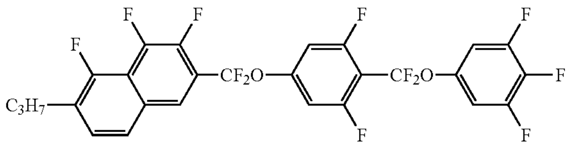
(1-3-23)
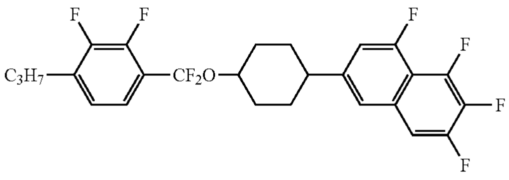
(1-3-24)
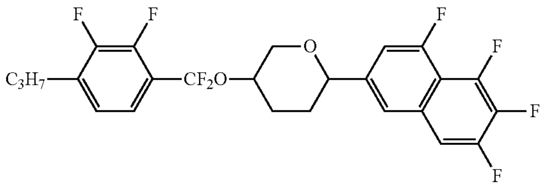
(1-3-25)
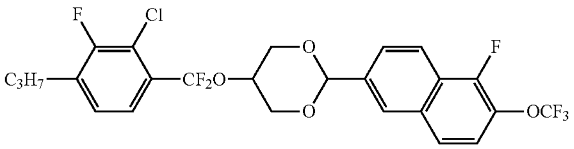
(1-3-26)
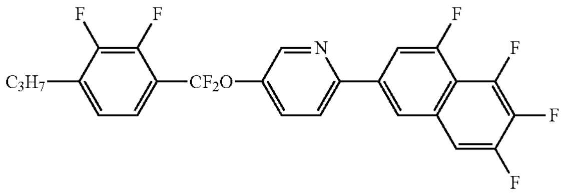
(1-3-27)
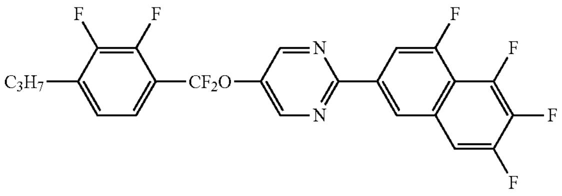
(1-3-28)
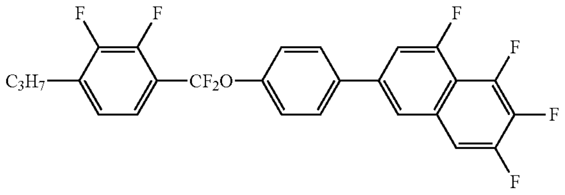
(1-3-29)
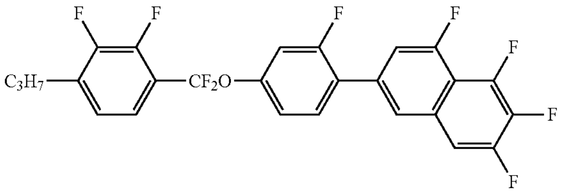
(1-3-30)
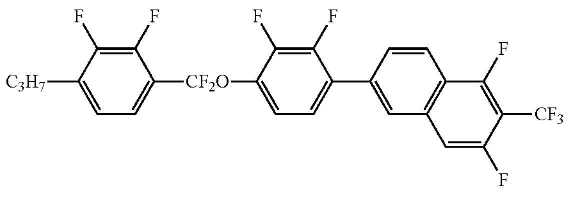
(1-3-31)
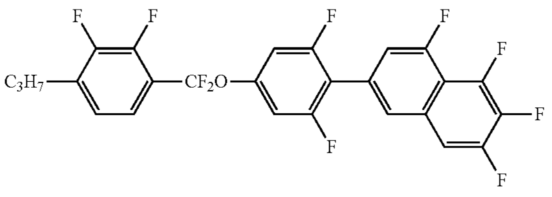
(1-3-32)
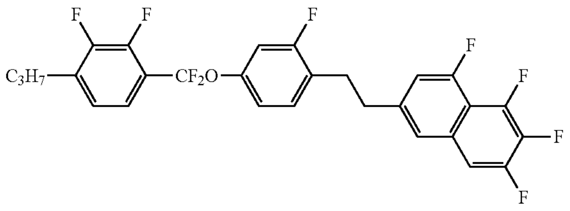
(1-3-33)
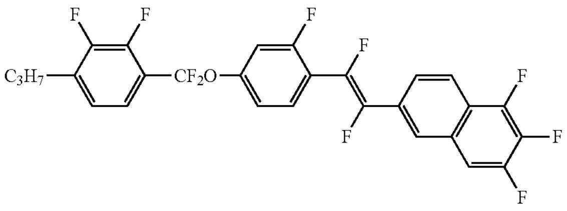

-continued
(1-3-34)
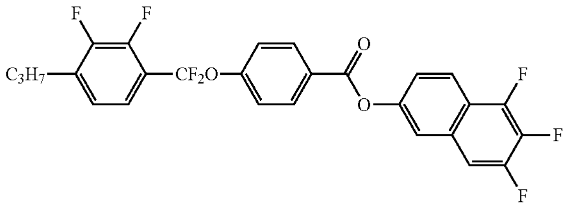
(1-3-35)
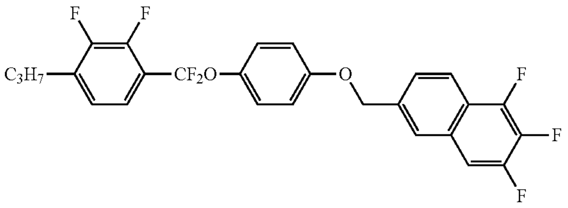
(1-3-36)
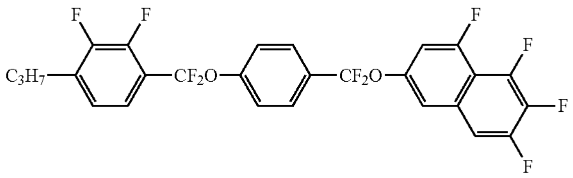
(1-3-37)
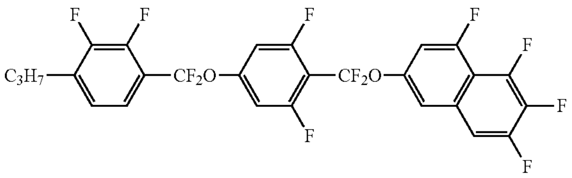
(1-3-38)
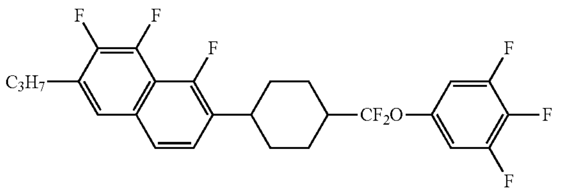
(1-3-39)
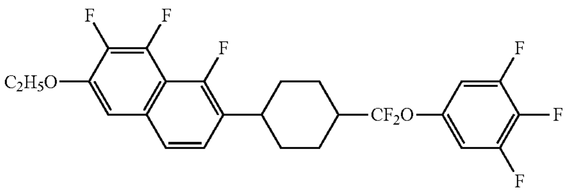
(1-3-40)
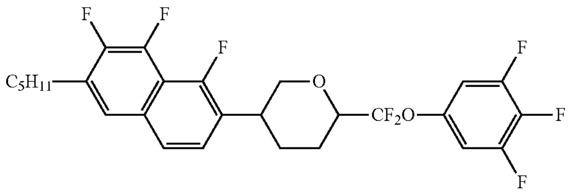
(1-3-41)
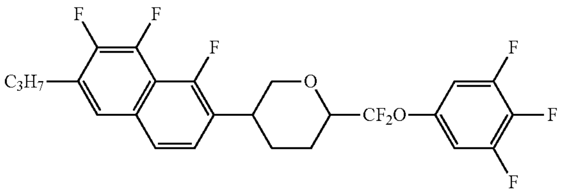
(1-3-42)
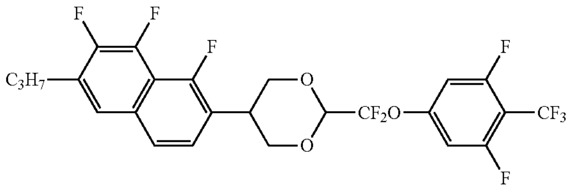
(1-3-43)
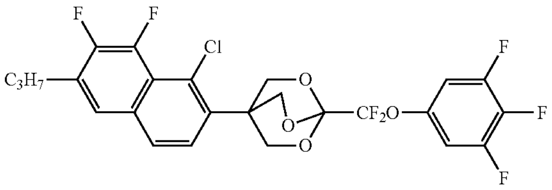
(1-3-44)
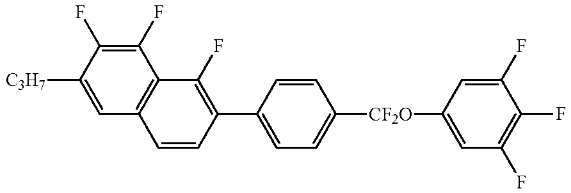
(1-3-45)
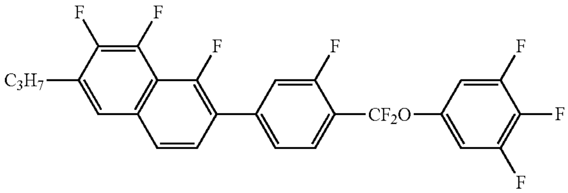
(1-3-46)
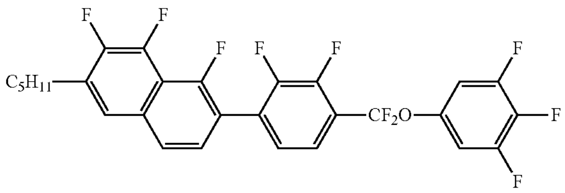
(1-3-47)
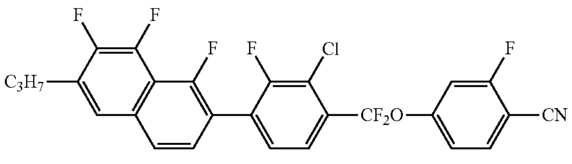

-continued
(1-3-48)
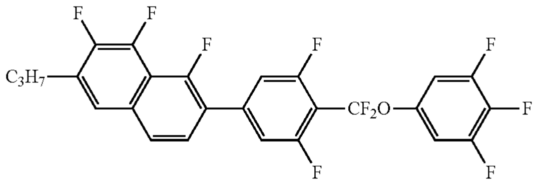
(1-3-49)
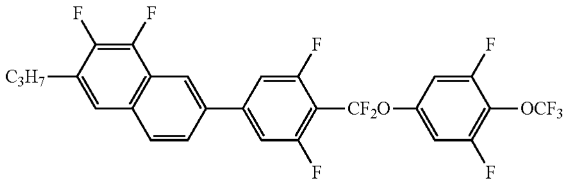
(1-3-50)
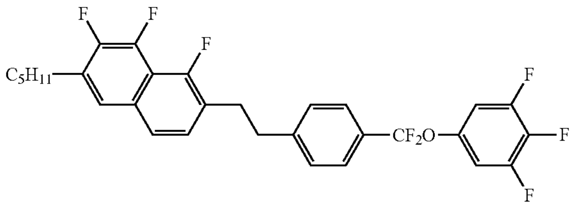
(1-3-51)
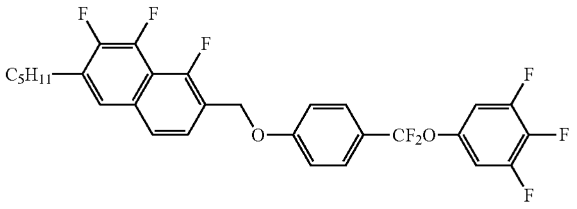
(1-3-52)
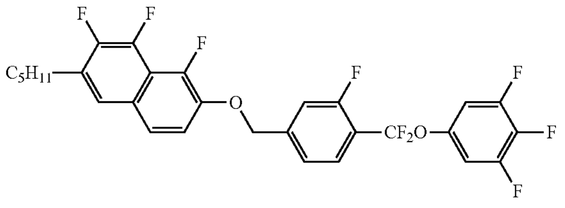
(1-3-53)
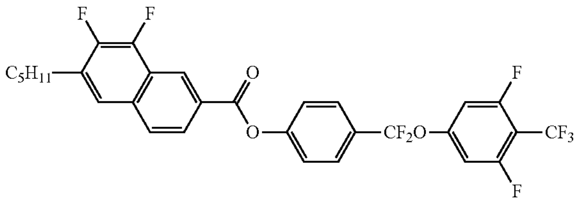
(1-3-54)
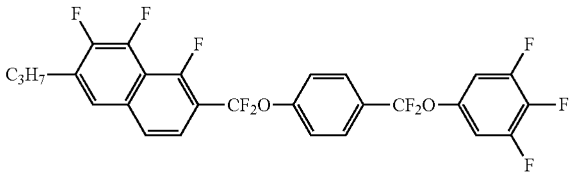
(1-3-55)
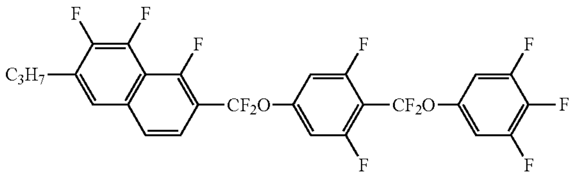
(1-3-56)
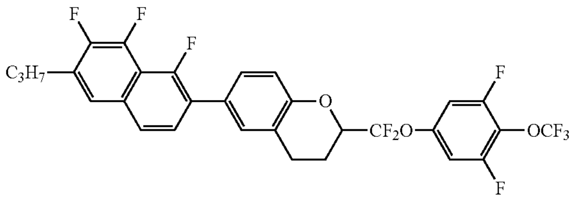
(1-3-57)
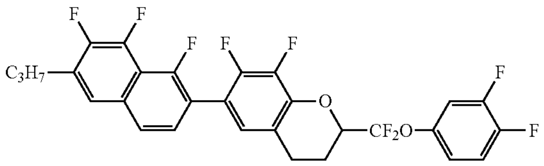
(1-3-58)
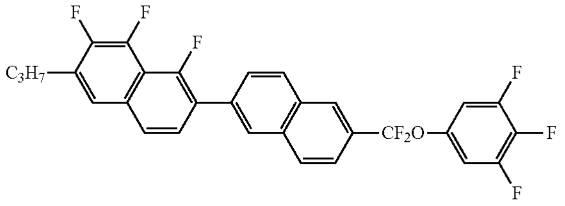
(1-3-59)
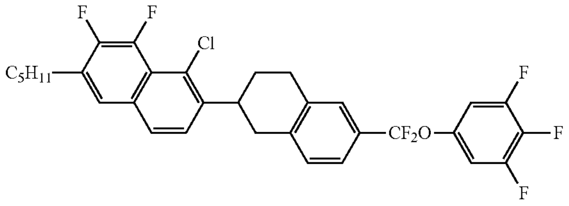
(1-3-60)
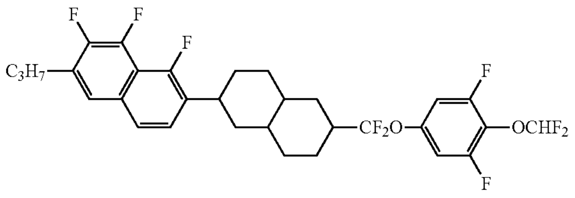
(1-3-61)
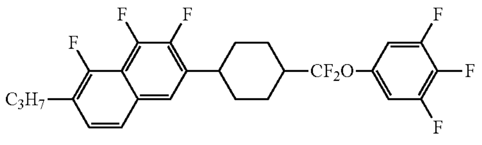

-continued
(1-3-62)
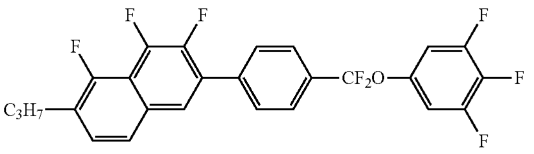
(1-3-63)
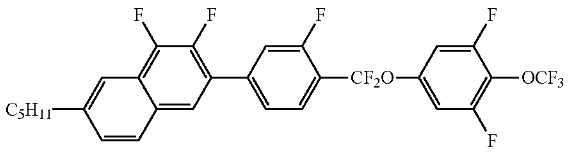
(1-3-64)
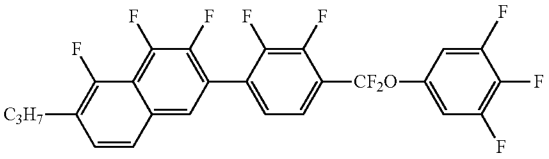
(1-3-65)
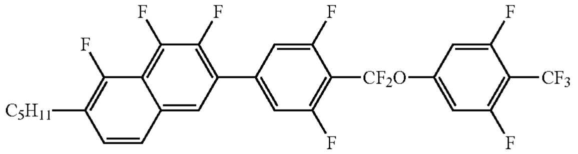
(1-3-66)
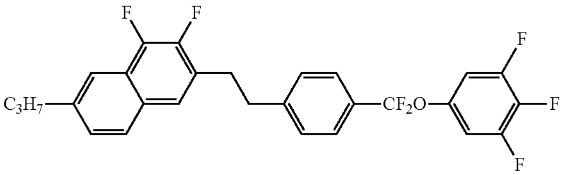
(1-3-67)
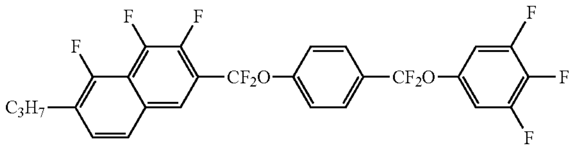
(1-3-68)
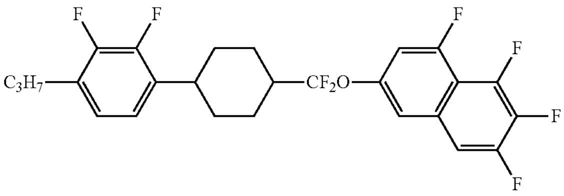
(1-3-69)
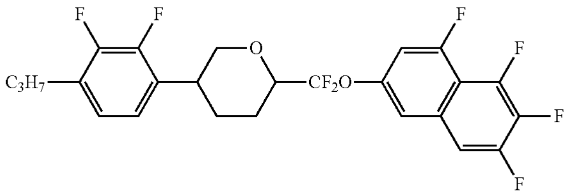
(1-3-70)
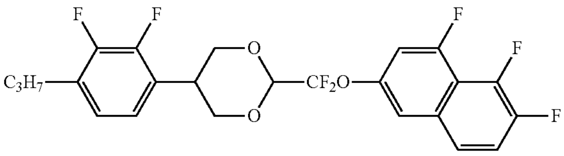
(1-3-71)
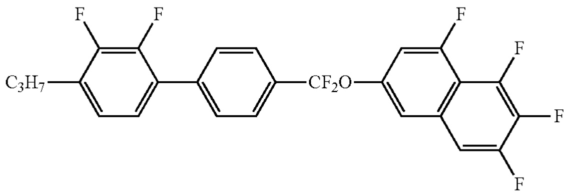
(1-3-72)
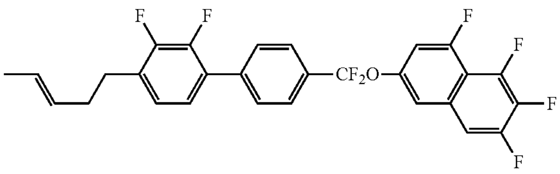
(1-3-73)
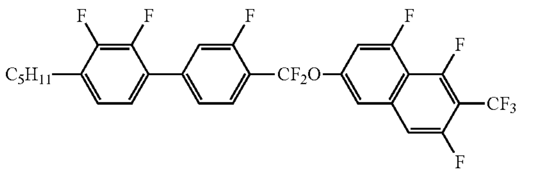
(1-3-74)
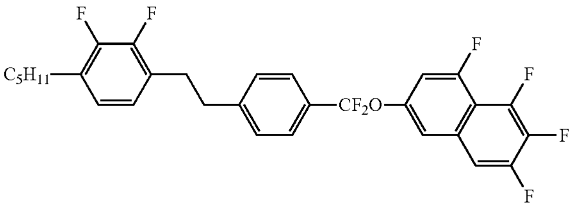
(1-3-75)
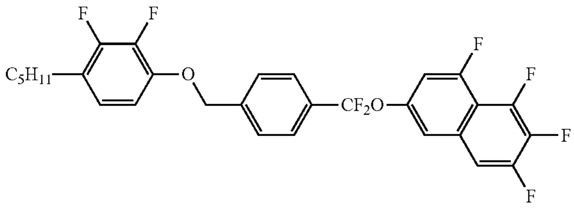

-continued
(1-3-76)
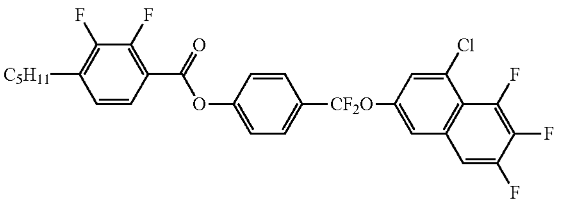
(1-3-78)
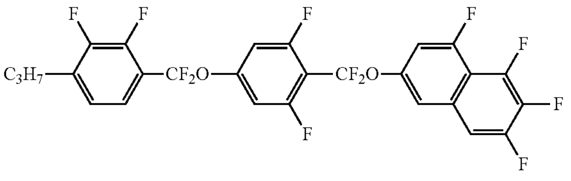
(1-3-80)
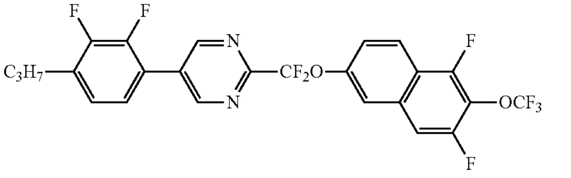
(1-3-82)
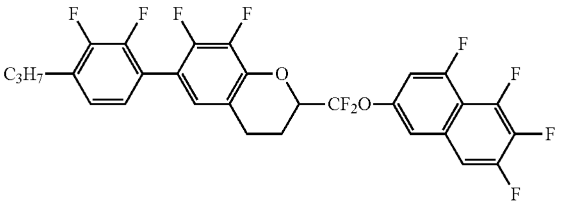
(1-3-84)
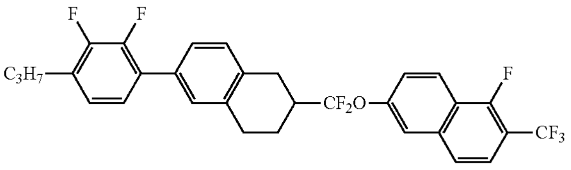
(1-3-86)
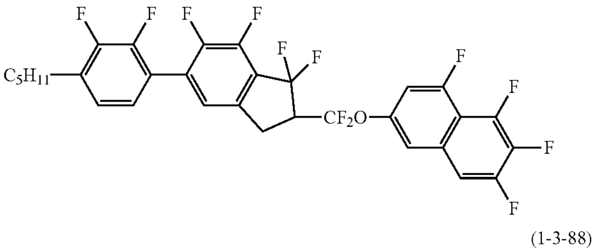
(1-3-88)
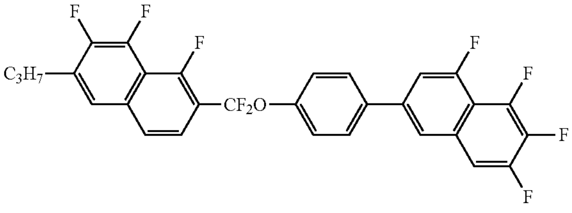
(1-3-77)
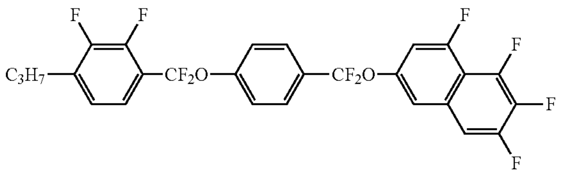
(1-3-79)
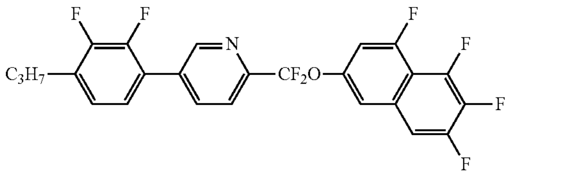
(1-3-81)
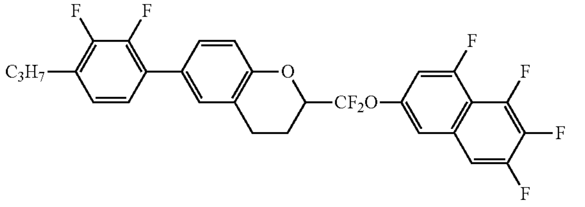
(1-3-83)
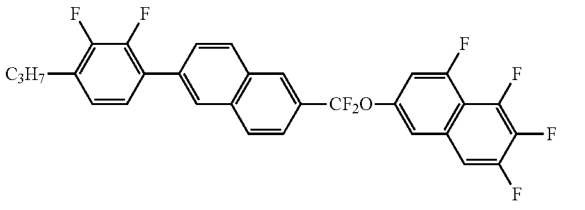
(1-3-85)
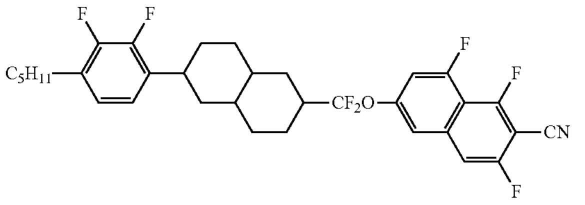
(1-3-87)
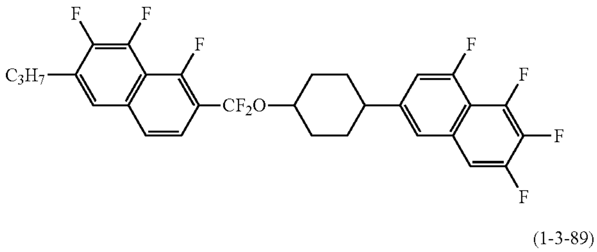
(1-3-89)
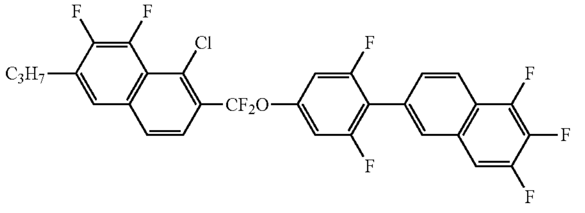

-continued
(1-3-90)
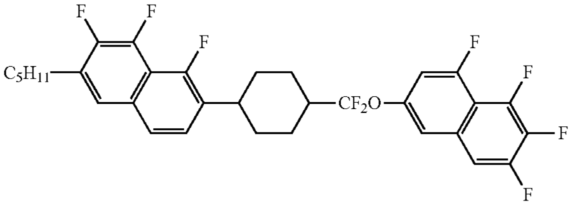
(1-3-91)
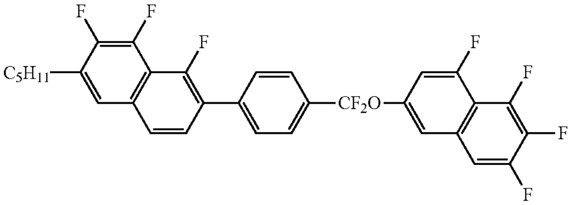
(1-3-92)
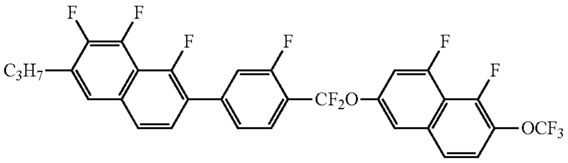
(1-3-93)
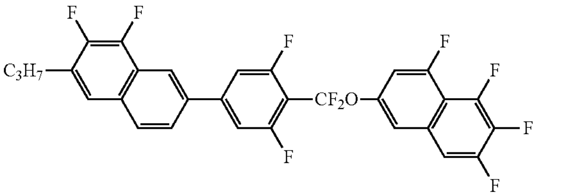
(1-3-94)
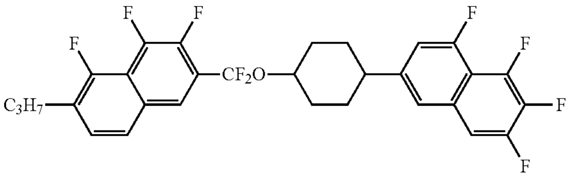
(1-3-95)
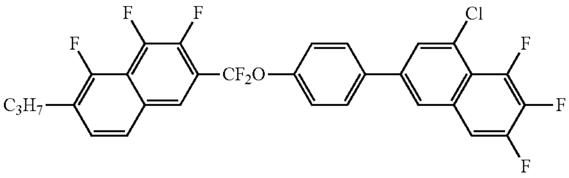
(1-3-96)
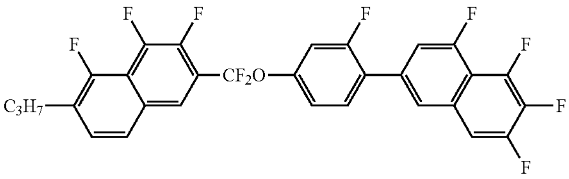
(1-3-97)
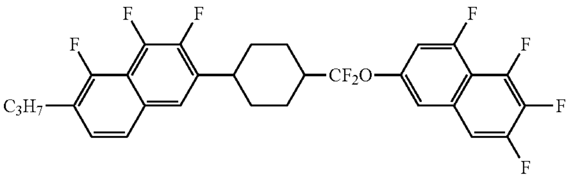
(1-3-98)
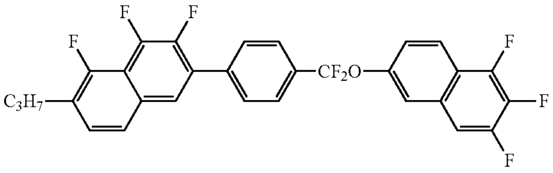
(1-3-99)
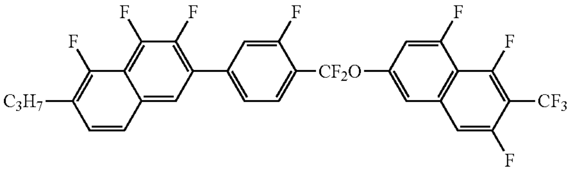
(1-3-100)
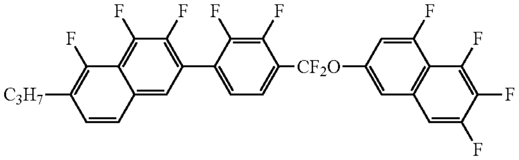
(1-4-1)
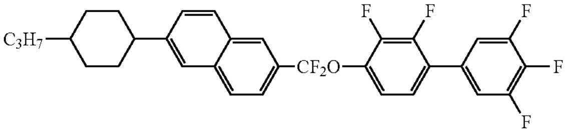
(1-4-2)
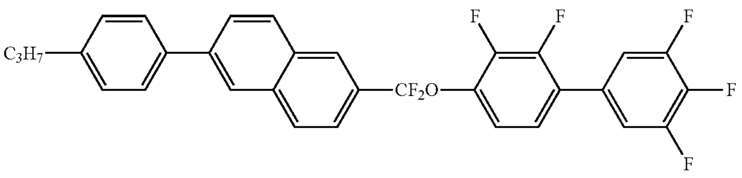

-continued
(1-4-3)
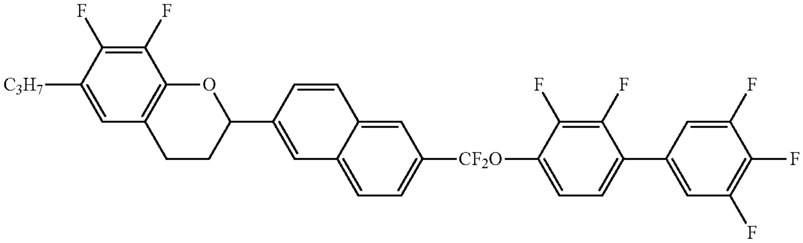
(1-4-4)
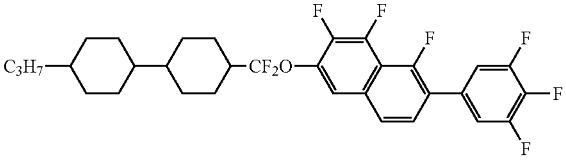
(1-4-5)
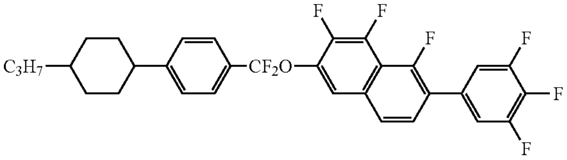
(1-4-6)
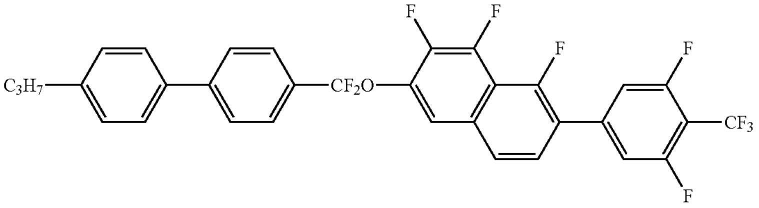
(1-4-7)
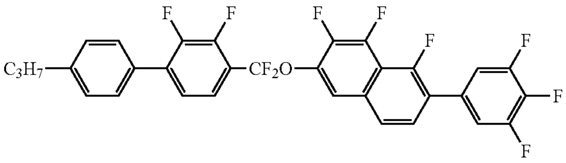
(1-4-8)
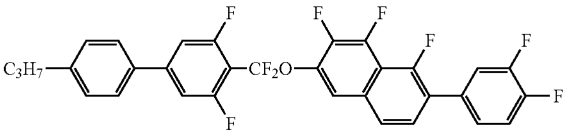
(1-4-9)
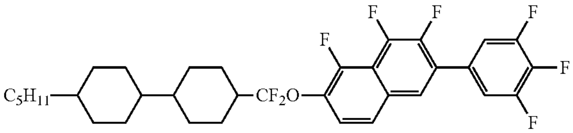
(1-4-10)
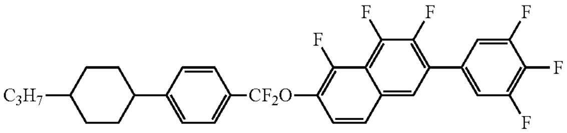
(1-4-11)
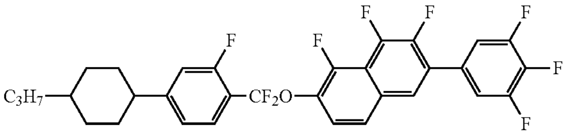
(1-4-12)
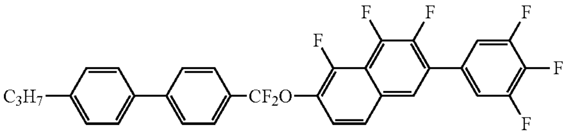
(1-4-13)
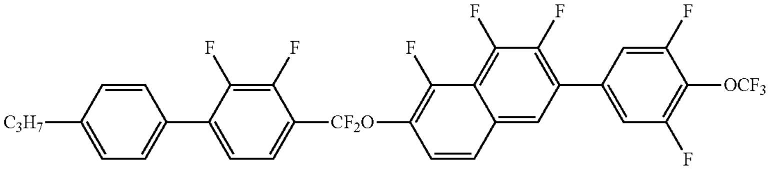
(1-4-14)
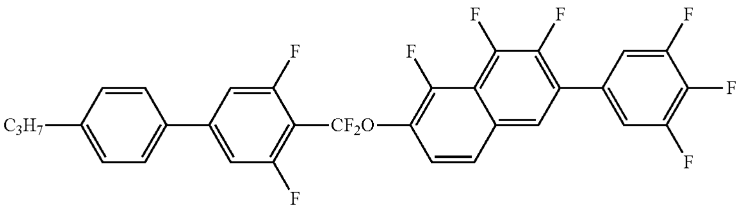

-continued
(1-4-15)
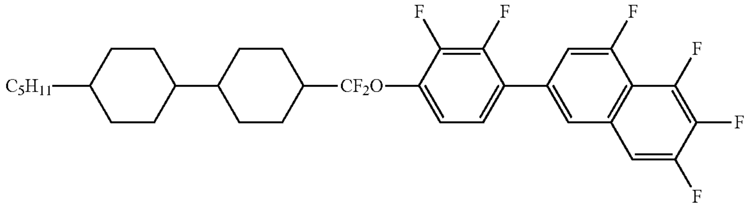
(1-4-16)
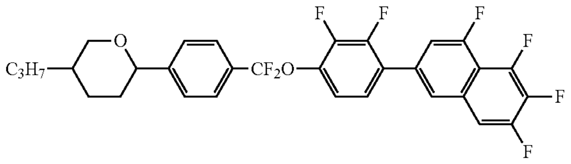
(1-4-17)
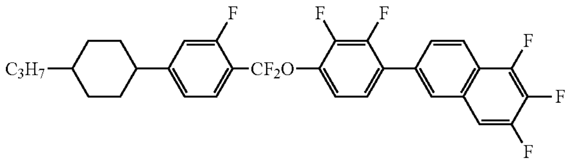
(1-4-18)
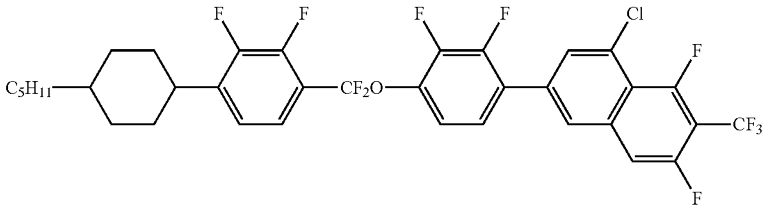
(1-4-19)
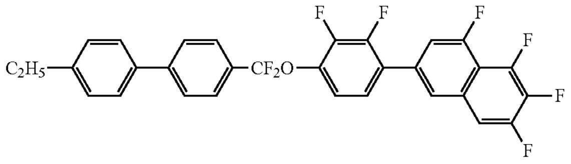
(1-4-20)
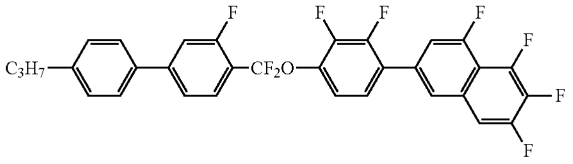
(1-4-21)
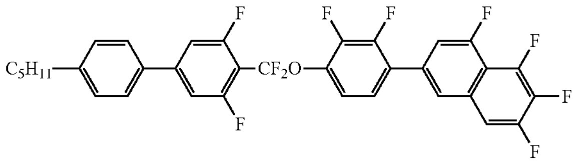
(1-4-22)
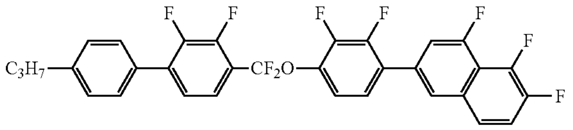
(1-4-23)
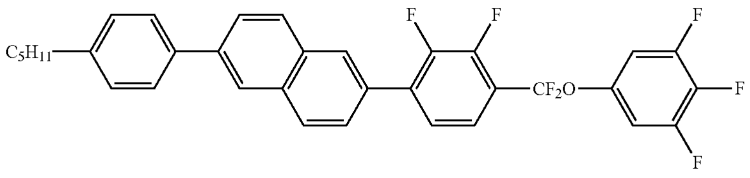
(1-4-24)
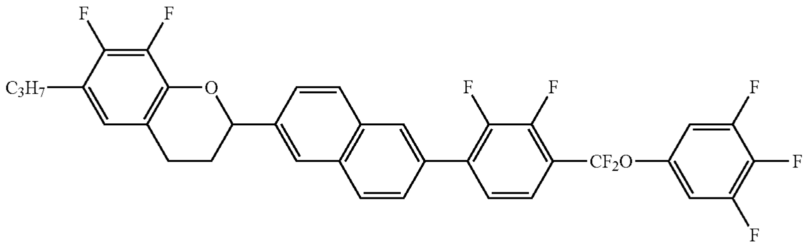

-continued
(1-4-25)
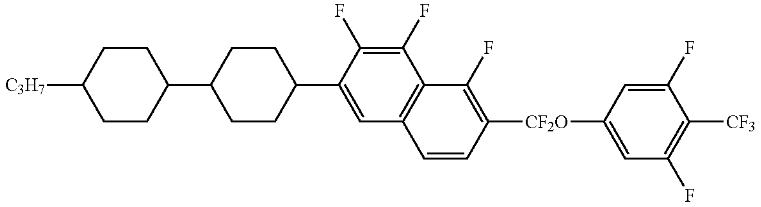
(1-4-26)
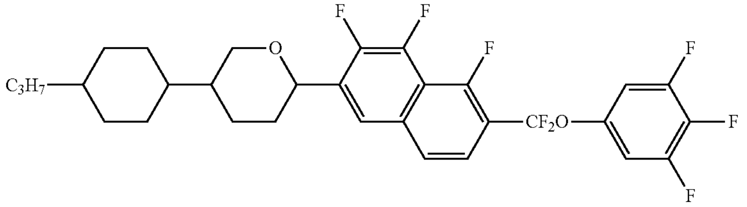
(1-4-27)
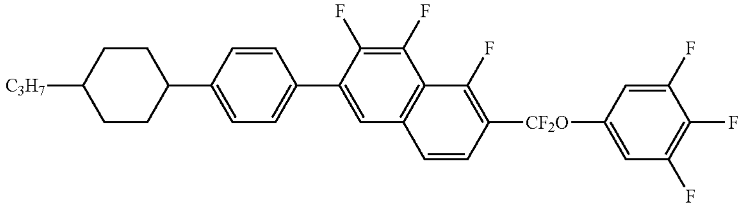
(1-4-28)
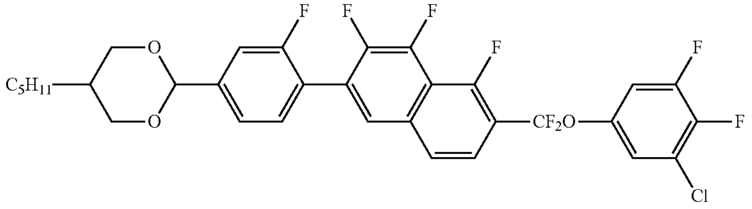
(1-4-29)
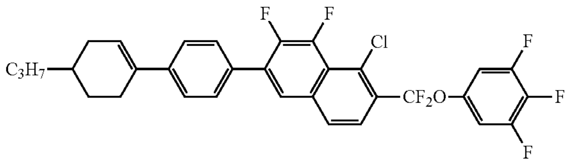
(1-4-30)
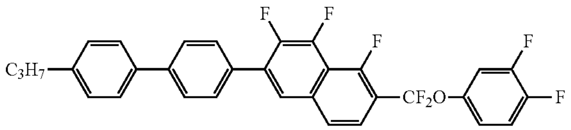
(1-4-31)
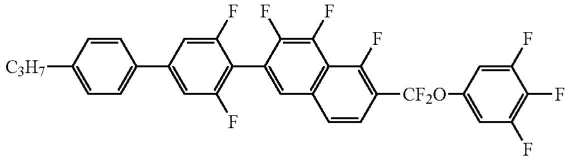
(1-4-32)
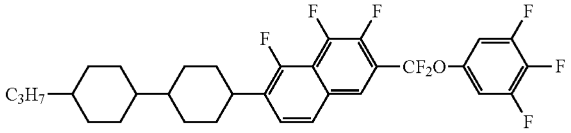
(1-4-33)
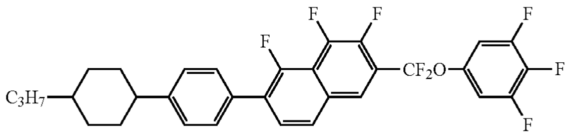
(1-4-34)
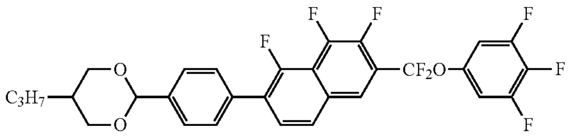
(1-4-35)
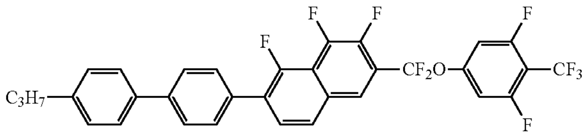
(1-4-36)
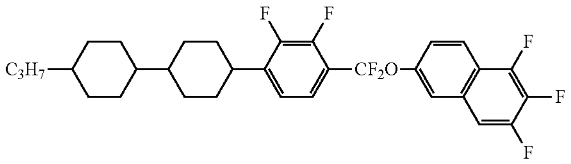

-continued
(1-4-37)
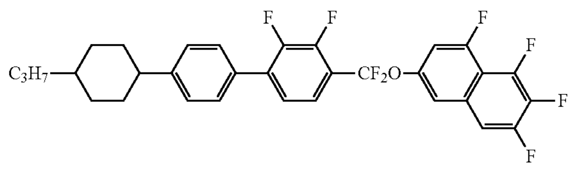
(1-4-38)
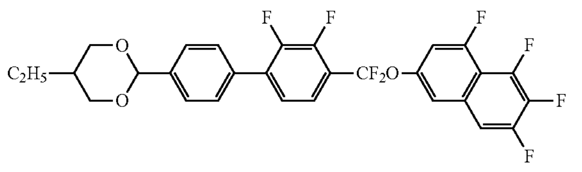
(1-4-39)
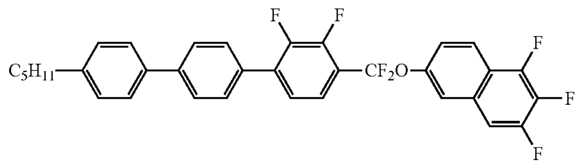
(1-4-40)
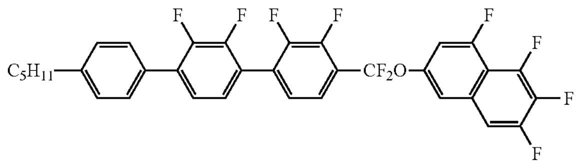
(1-4-41)
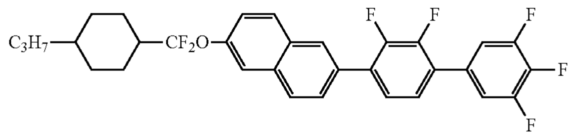
(1-4-42)
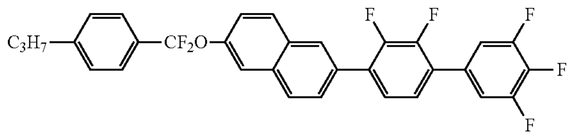
(1-4-43)
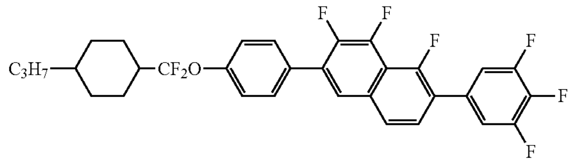
(1-4-44)
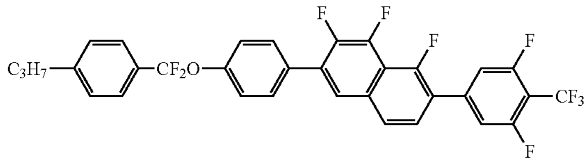
(1-4-45)
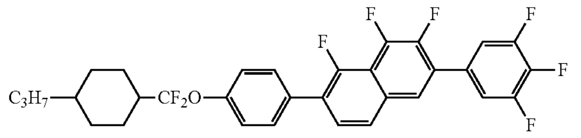
(1-4-46)
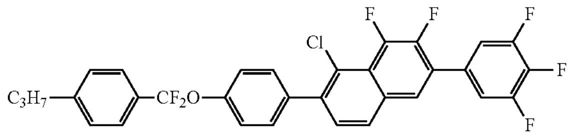
(1-4-47)
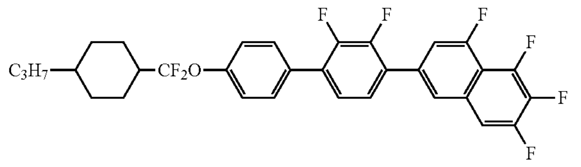
(1-4-48)
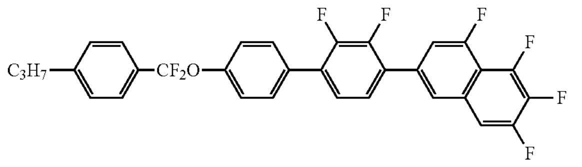
(1-5-1)
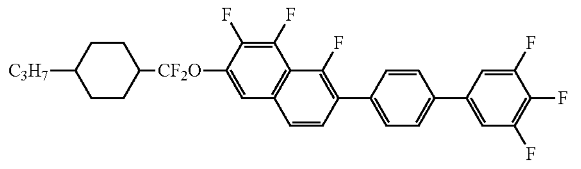
(1-5-2)
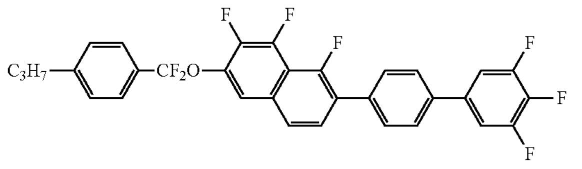
(1-5-3)
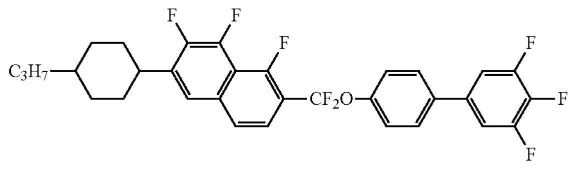
(1-5-4)
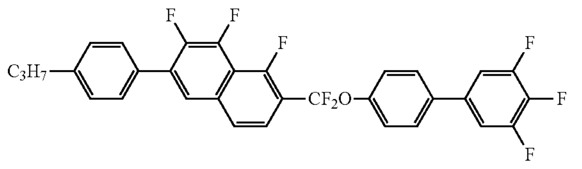

-continued
(1-5-5)
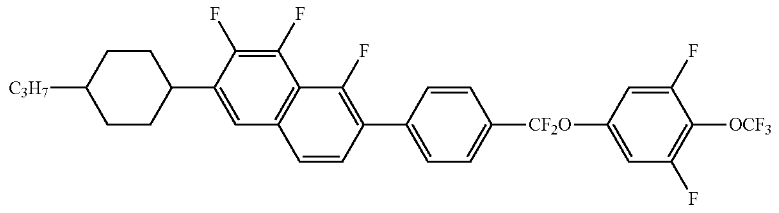
(1-5-6)
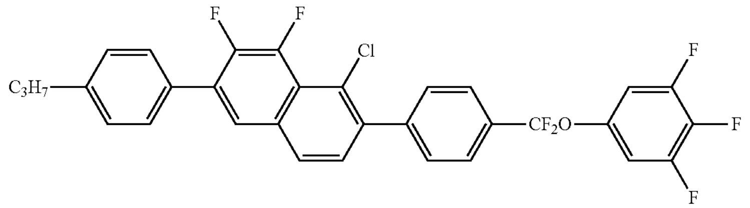
(1-5-7)
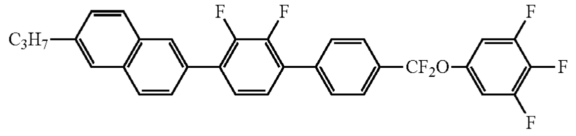
(1-5-8)
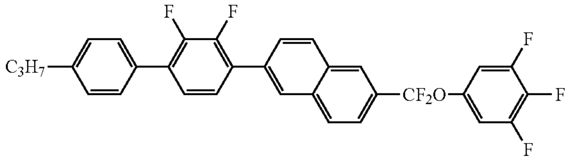
(1-5-9)
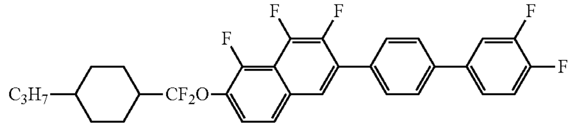
(1-5-10)
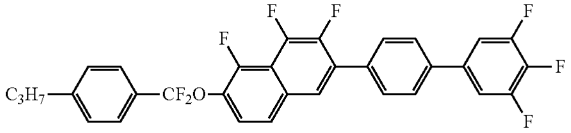
(1-5-11)
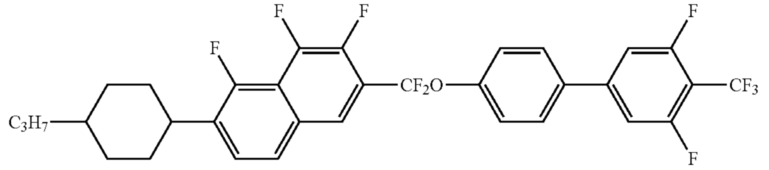
(1-5-12)
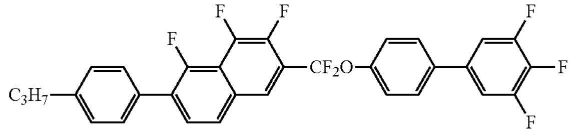
(1-5-13)
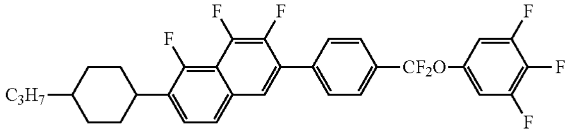
(1-5-14)
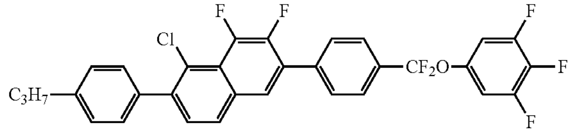
(1-5-15)
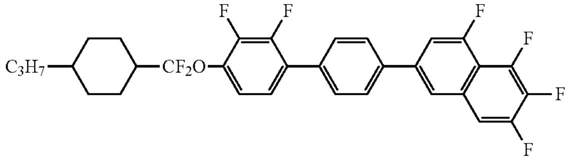
(1-5-16)
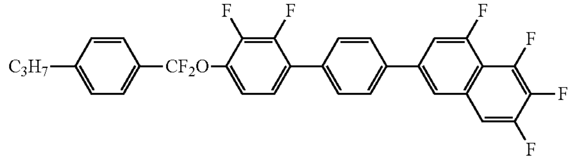
(1-5-17)
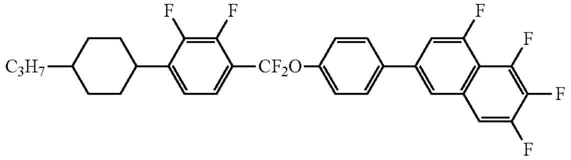

-continued
(1-5-18)
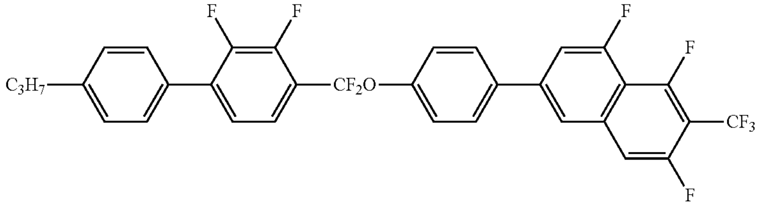
(1-5-19)
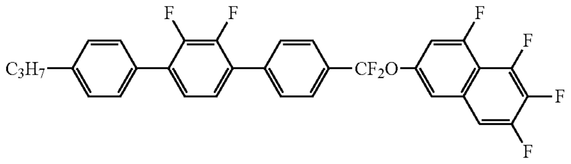
(1-5-20)
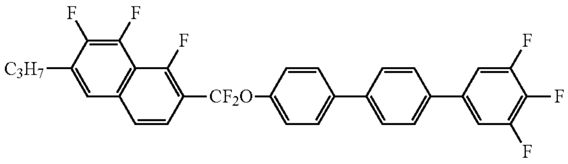
(1-6-1)
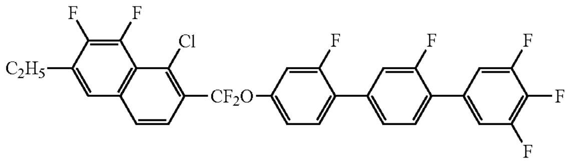
(1-6-2)
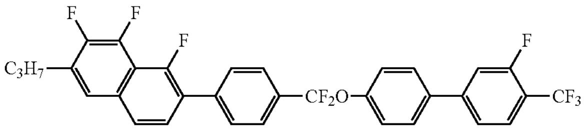
(1-6-3)
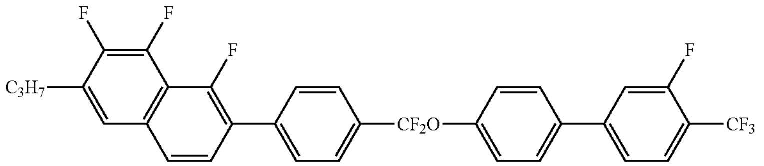
(1-6-4)
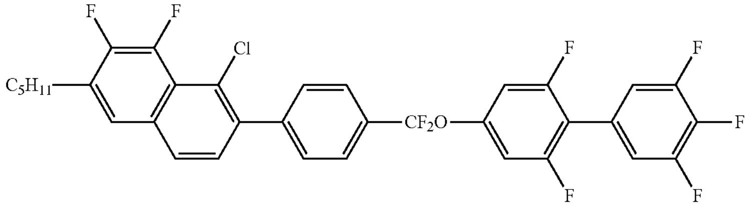
(1-6-5)
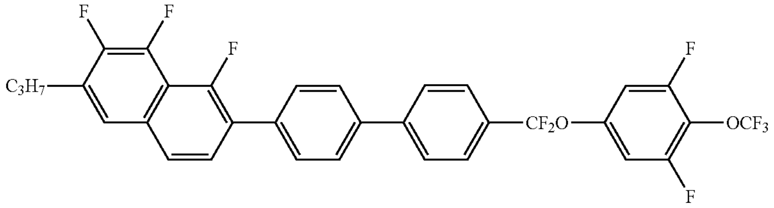
(1-6-6)
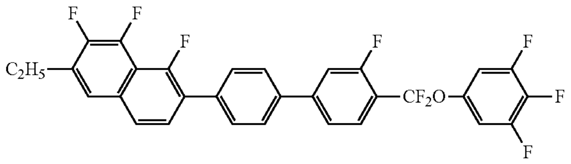
(1-6-7)
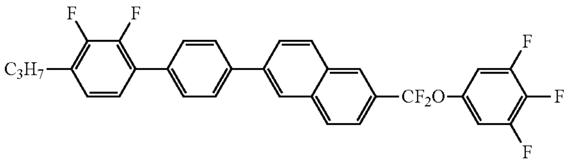
(1-6-8)
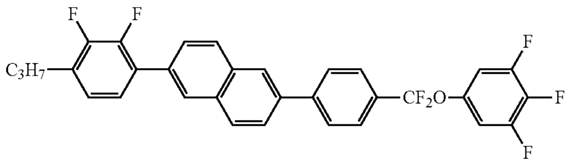
(1-6-9)
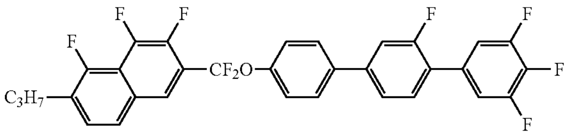

-continued
(1-6-10)
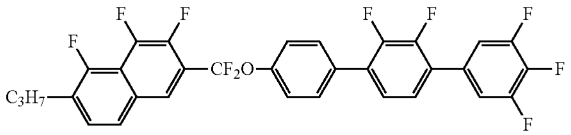
(1-6-11)
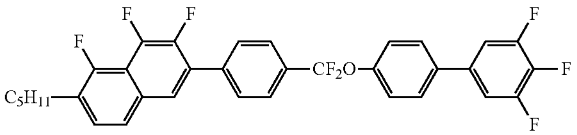
(1-6-12)
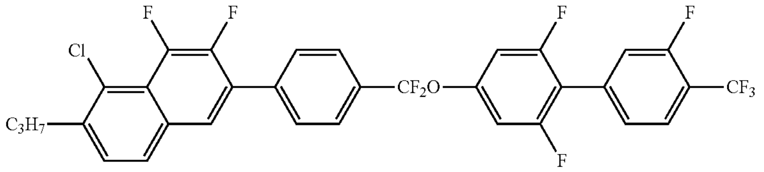
(1-6-13)
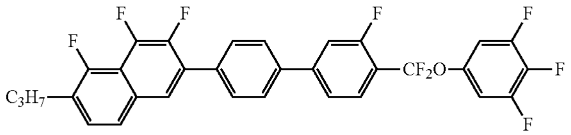
(1-6-14)
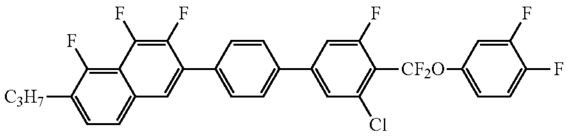
(1-6-15)
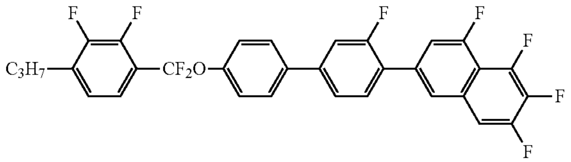
(1-6-16)
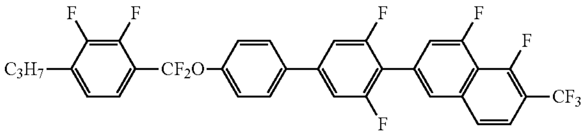
(1-6-17)
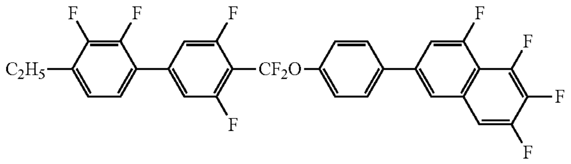
(1-6-18)
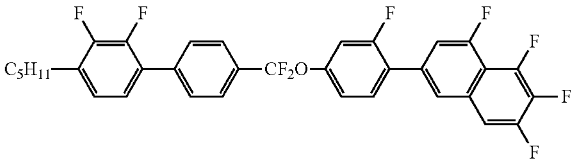
(1-6-19)
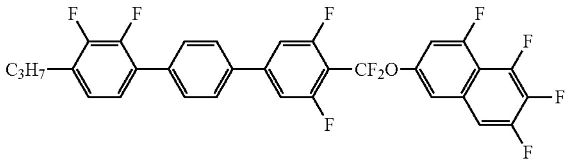
(1-6-20)
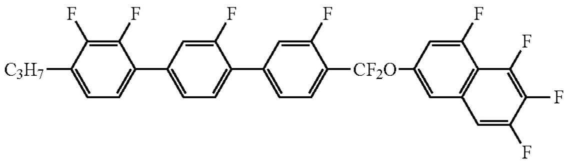
(1-7-1)
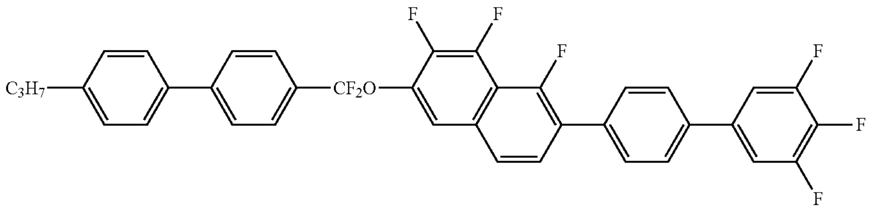
(1-7-2)
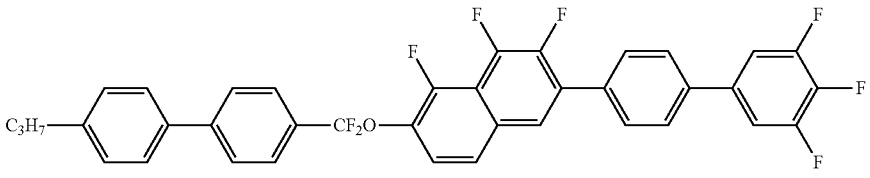

-continued
(1-7-3)
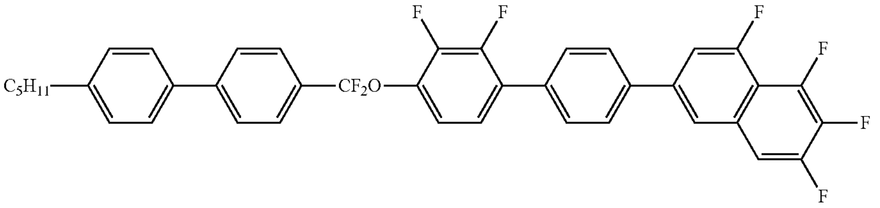
(1-7-4)
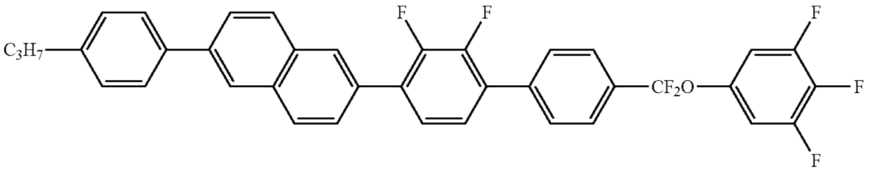
(1-7-5)
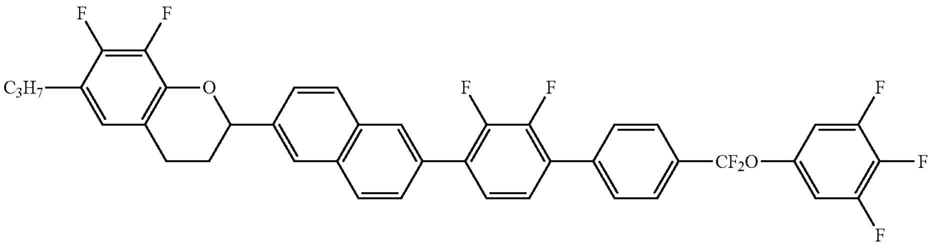
(1-7-6)
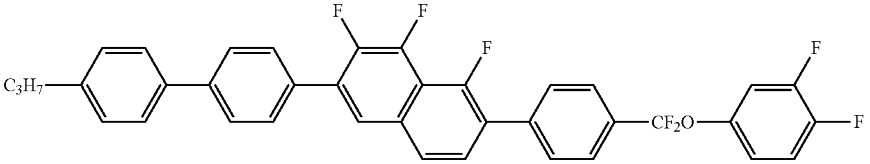
(1-7-7)
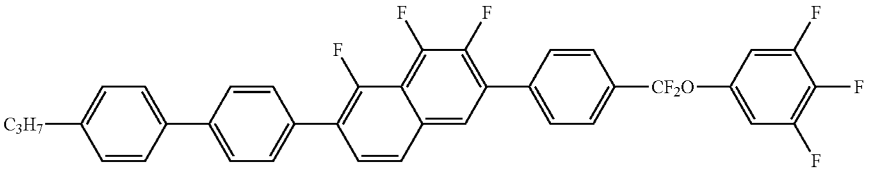
(1-7-8)
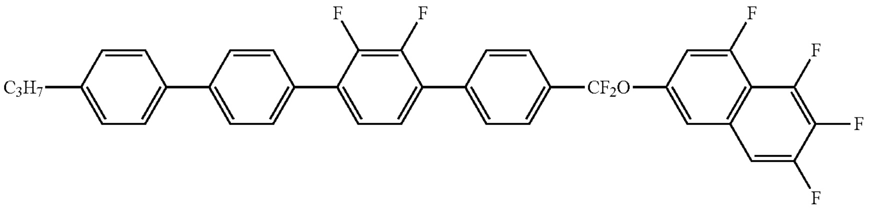
(1-8-1)
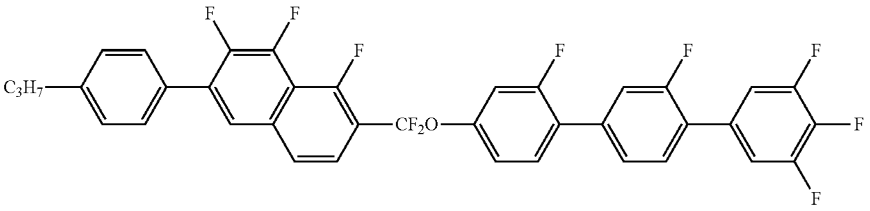
(1-8-2)
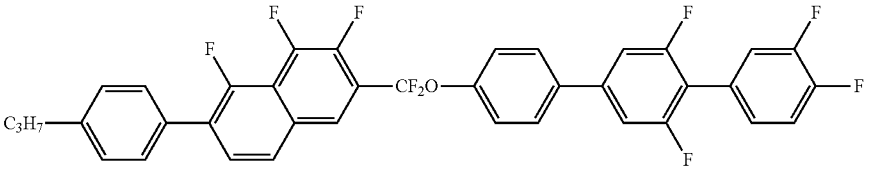

-continued (1-8-3)

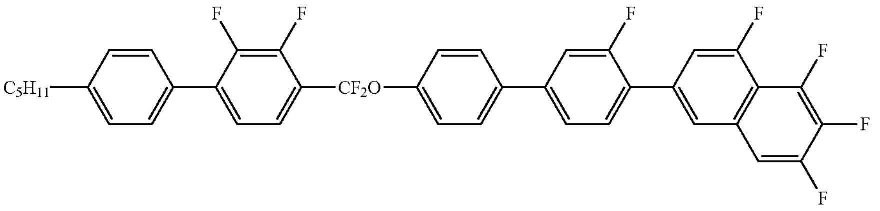

(1-8-4)

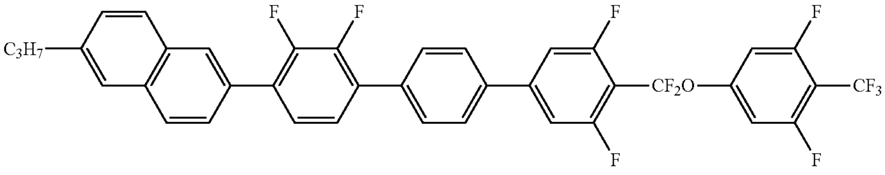

(1-8-5)

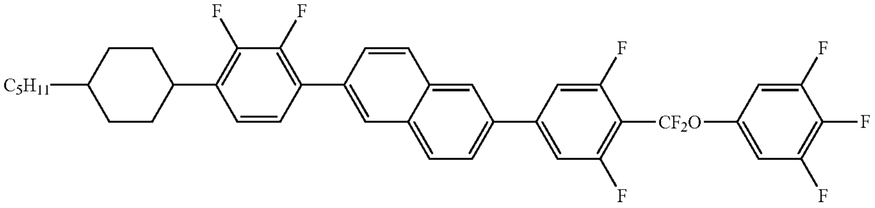

(1-8-6)

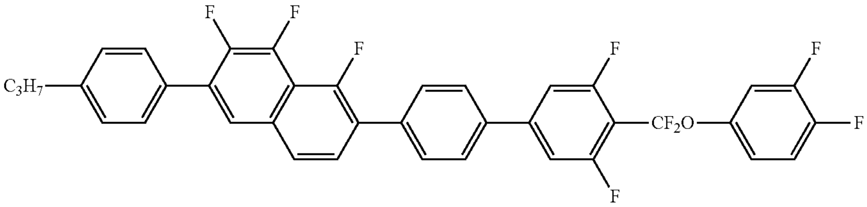

(1-8-7)

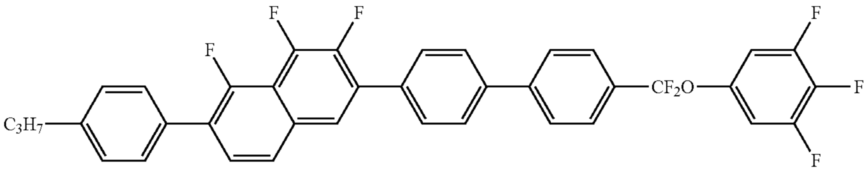

(1-8-8)

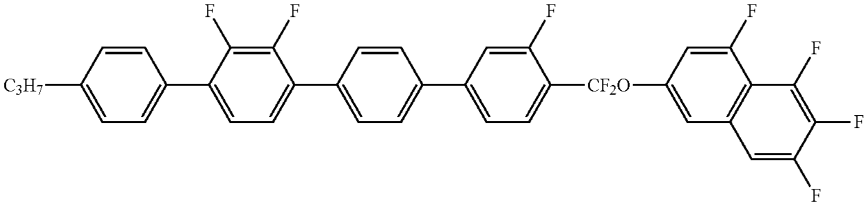

1-2. Example of Liquid Crystal Composition (1)

The invention will be described in greater detail by way of Examples. Compounds in Examples were described using symbols according to definitions in Table 1 below. In Table 1, a configuration of 1,4-cyclohexylene was trans. A parenthesized number next to a symbolized compound in Examples corresponds to the number of a compound. A symbol (-) means any other liquid crystal compound. A ratio (percentage) of the liquid crystal compound was expressed in terms of weight percent (% by weight) based on the weight of the liquid crystal composition.

TABLE 1

| Method of Description of Compound using Symbols | |
|---|---|
| $R-(A_1)-Z_1- \ldots -Z_n-(A_n)-R'$ | Symbol |
| 2) Left-terminal Group R— | |
| $C_nH_{2n+1}-$ | n- |
| $C_nH_{2n+1}O-$ | nO- |
| $C_mH_{2m+1}OC_nH_{2n}-$ | mOn- |

TABLE 1-continued

| Method of Description of Compound using Symbols | |
|---|---|
| R—($A_1$)—$Z_1$— . . . —$Z_n$—($A_n$)—R' | Symbol |
| $CH_2$═CH— | V- |
| $C_nH_{2n+1}$—CH═CH— | nV- |
| $CH_2$═CH—$C_nH_{2n}$— | Vn- |
| $C_mH_{2m+1}$—CH═CH—$C_nH_{2n}$— | mVn- |
| $CF_2$═CH— | VFF- |
| $CF_2$═CH—$C_nH_{2n}$— | VFFn- |
| 2) Right-terminal Group —R' | |
| —$C_nH_{2n+1}$ | -n |
| —$OC_nH_{2n+1}$ | -On |
| —$COOCH_3$ | -EMe |
| —CH═$CH_2$ | -V |
| —CH═CH—$C_nH_{2n+1}$ | -Vn |
| —$C_nH_{2n}$—CH═$CH_2$ | -nV |
| —$C_mH_{2m}$—CH═CH—$C_nH_{2n+1}$ | -mVn |
| —CH═$CF_2$ | -VFF |
| —F | -F |
| —Cl | -CL |
| —$OCF_3$ | -OCF3 |
| —$OCF_2H$ | -OCF2H |
| —$CF_3$ | -CF3 |
| —OCH═CH—$CF_3$ | -OVCF3 |
| —C≡N | -C |
| 3) Bonding Group —Zn— | |
| —$C_nH_{2n}$— | n |
| —COO— | E |
| —CH═CH— | V |
| —$CH_2O$— | 1O |
| —$OCH_2$— | O1 |
| —$CF_2O$— | X |
| —C≡C— | T |
| 4) Ring Structure —An— | |
| 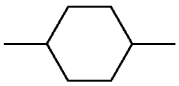 | H |
| 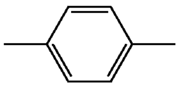 | B |
| 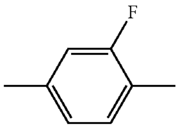 | B(F) |
| 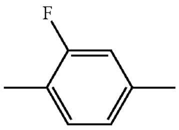 | B(2F) |
| 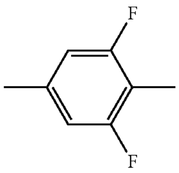 | B(F,F) |

TABLE 1-continued

| Method of Description of Compound using Symbols | |
|---|---|
| R—($A_1$)—$Z_1$— . . . —$Z_n$—($A_n$)—R' | Symbol |
| 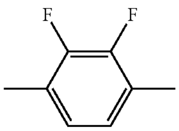 | B(2F,3F) |
| 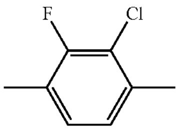 | B(2F,3CL) |
| 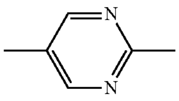 | Py |
| 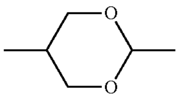 | G |
| 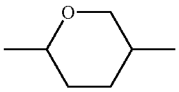 | Dh |
| 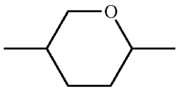 | dh |
| 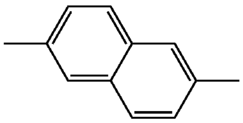 | Np |
| 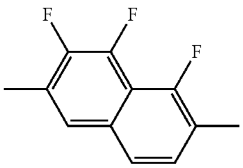 | Np(3F,4F,5F) |
| 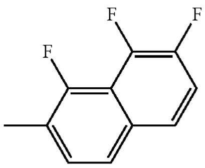 | Np(1F,7F,8F) |
| 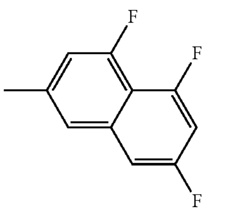 | Np(4F,5F,7F) |

TABLE 1-continued

| Method of Description of Compound using Symbols | |
|---|---|
| R—($A_1$)—$Z_1$— . . . —$Z_n$—($A_n$)—R' | Symbol |
| 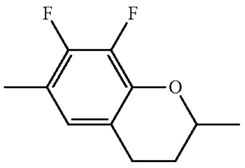 | Cro(7F,8F) |

5) Examples of Description

Example 1. 3-NpB(2F,3F)XB(F,F)-F

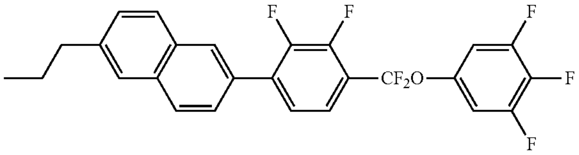

Example 2. 5-HHBB(F,F)-F

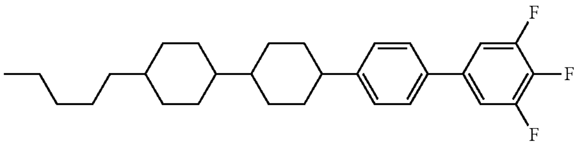 [SMILES: CCCCCC1CCC(C2CCC(c3ccc(-c4cc(F)c(F)c(F)c4)cc3)CC2)CC1]

Example 2

| | | |
|---|---|---|
| 3-NpB(2F,3F)XB(F,F)-F | (1-2-48) | 4% |
| 3-HB-O2 | (13-5) | 10% |
| 5-HB-CL | (2-2) | 13% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 8% |
| 5-PyBB-F | (3-80) | 10% |
| 5-HBB(F)B-2 | (15-5) | 8% |
| 5-HBB(F)B-3 | (15-5) | 10% |

Example 3

| | | |
|---|---|---|
| 3-Np(3F,4F,5F)XB(F,F)-F | (1-1-1) | 3% |
| 2-HB-C | (5-1) | 5% |
| 3-HB-C | (5-1) | 11% |
| 3-HB-O2 | (13-5) | 12% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 5% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

Example 4

| | | |
|---|---|---|
| 3-Np(1F,7F,8F)XB(F,F)-F | (1-1-5) | 3% |
| 7-HB(F,F)-F | (2-4) | 3% |
| 3-HB-O2 | (13-5) | 7% |
| 2-HHB(F)-F | (3-2) | 9% |
| 3-HHB(F)-F | (3-2) | 10% |
| 5-HHB(F)-F | (3-2) | 10% |
| 2-HBB(F)-F | (3-23) | 9% |
| 3-HBB(F)-F | (3-23) | 9% |
| 5-HBB(F)-F | (3-23) | 15% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 9% |

Example 5

| | | |
|---|---|---|
| 3-B(2F,3F)XNp(4F,5F,7F)-F | (1-1-8) | 5% |
| 5-HB-CL | (2-2) | 16% |
| 3-HH-4 | (13-1) | 12% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 7% |
| 5-HHB(F)-F | (3-2) | 8% |
| 7-HHB(F)-F | (3-2) | 7% |
| 5-HBB(F)-F | (3-23) | 3% |
| 1O1-HBBH-5 | (15-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

Example 6

| | | |
|---|---|---|
| 3-Np(3F,4F,5F)XNp(4F,5F,7F)-F | (1-1-13) | 1% |
| 3-B(2F,3F)NpXB(F,F)-F | (1-2-21) | 3% |
| 3-HHB(F,F)-F | (3-3) | 9% |
| 3-H2HB(F,F)-F | (3-15) | 7% |
| 4-H2HB(F,F)-F | (3-15) | 8% |
| 5-H2HB(F,F)-F | (3-15) | 8% |
| 3-HBB(F,F)-F | (3-24) | 19% |
| 5-HBB(F,F)-F | (3-24) | 20% |
| 3-H2BB(F,F)-F | (3-27) | 10% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 3% |
| 1O1-HBBH-5 | (15-1) | 4% |

Example 7

| | | |
|---|---|---|
| 3-BNp(3F,4F,5F)XB(F,F)-F | (1-2-33) | 4% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 4% |

-continued

| | | |
|---|---|---|
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 4% |
| 3-HH2B(F)-F | (3-5) | 3% |
| 3-HBB(F)-F | (3-23) | 8% |
| 5-HBB(F)-F | (3-23) | 10% |
| 5-HBBH-3 | (15-1) | 3% |
| 3-HB(F)BH-3 | (15-2) | 3% |

Example 8

| | | |
|---|---|---|
| 3-HNp(3F,4F,5F)XNp(4F,5F,7F)-F | (1-2-83) | 1% |
| 3-BNp(1F,7F,8F)XB(F)-OCF3 | (1-2-53) | 2% |
| 5-HB-CL | (13-5) | 11% |
| 3-HH-4 | (13-1) | 8% |
| 3-HHB-1 | (14-1) | 5% |
| 3-HHB(F,F)-F | (3-3) | 8% |
| 3-HBB(F,F)-F | (3-24) | 18% |
| 5-HBB(F,F)-F | (3-24) | 14% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

Example 9

| | | |
|---|---|---|
| 3-BNp(1F,7F,8F)XNp(4F,5F,7F)-CF3 | (1-2-97) | 1% |
| 3-BB(2F,3F)XNp(4F,5F,7F)-CF3 | (1-2-63) | 2% |
| 3-HB-CL | (2-2) | 6% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 12% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 10% |
| 3-HBEB(F,F)-F | (3-39) | 5% |

Example 10

| | | |
|---|---|---|
| 3-HB(2F,3F)XNp(4F,5F,7F)-F | (1-2-56) | 3% |
| 5-HB-CL | (2-2) | 17% |
| 7-HB(F,F)-F | (2-4) | 3% |
| 3-HH-4 | (13-1) | 10% |
| 3-HH-5 | (13-1) | 5% |
| 3-HB-O2 | (13-5) | 15% |
| 3-HHB-1 | (14-1) | 8% |
| 3-HHB-O1 | (14-1) | 5% |
| 2-HHB(F)-F | (3-2) | 4% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

Example 11

| | | |
|---|---|---|
| 3-Np(3F,4F,5F)BXB(F,F)-F | (1-3-44) | 5% |
| 5-HB-CL | (2-2) | 3% |
| 7-HB(F)-F | (2-3) | 7% |
| 3-HH-4 | (13-1) | 8% |
| 3-HH-EMe | (13-2) | 22% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 4% |
| 4-HGB(F,F)-F | (3-103) | 5% |
| 5-HGB(F,F)-F | (3-103) | 5% |
| 2-H2GB(F,F)-F | (3-106) | 4% |
| 3-H2GB(F,F)-F | (3-106) | 5% |
| 5-GHB(F,F)-F | (3-109) | 6% |

Example 12

| | | |
|---|---|---|
| 3-Np(1F,7F,8F)BXB(F,F)-F | (1-3-62) | 3% |
| 3-HB-O1 | (13-5) | 15% |
| 3-HH-4 | (13-1) | 5% |
| 3-HB(2F,3F)-O2 | (6-1) | 10% |
| 5-HB(2F,3F)-O2 | (6-1) | 11% |
| 2-HHB(2F,3F)-1 | (7-1) | 12% |
| 3-HHB(2F,3F)-1 | (7-1) | 12% |
| 3-HHB(2F,3F)-O2 | (7-1) | 13% |
| 5-HHB(2F,3F)-O2 | (7-1) | 13% |
| 3-HHB-1 | (14-1) | 6% |

Example 13

| | | |
|---|---|---|
| 3-B(2F,3F)BXNp(4F,5F,7F)-F | (1-3-71) | 3% |
| 1V2-B(2F,3F)BXNp(4F,5F,7F)-F | (1-3-72) | 2% |
| 2-HH-5 | (13-1) | 3% |
| 3-HH-4 | (13-1) | 15% |
| 3-HH-5 | (13-1) | 3% |
| 3-HB-O2 | (13-5) | 11% |
| 3-H2B(2F,3F)-O2 | (6-4) | 14% |
| 5-H2B(2F,3F)-O2 | (6-4) | 14% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 9% |
| 5-HBB(2F,3F)-O2 | (7-7) | 8% |
| 3-HHB-1 | (14-1) | 3% |
| 3-HHB-3 | (14-1) | 4% |
| 3-HHB-O1 | (14-1) | 3% |

Example 14

| | | |
|---|---|---|
| 3-HBNp(3F,4F,5F)XB(F,F)-F | (1-4-27) | 2% |
| 3-GBNp(1F,7F,8F)XB(F,F)-F | (1-4-34) | 3% |
| 2-HH-3 | (13-1) | 21% |
| 3-HH-4 | (13-1) | 9% |
| 1-BB-3 | (13-8) | 9% |
| 3-HB-O2 | (13-5) | 2% |
| 3-BB(2F,3F)-O2 | (6-3) | 7% |
| 5-BB(2F,3F)-O2 | (6-3) | 6% |
| 2-HH1OB(2F,3F)-O2 | (7-5) | 12% |
| 3-HH1OB(2F,3F)-O2 | (7-5) | 20% |
| 3-HHB-1 | (14-1) | 4% |
| 3-HHB-O1 | (14-1) | 3% |
| 2-BBB(2F)-5 | (14-8) | 2% |

Example 15

| | | |
|---|---|---|
| 3-NpB(2F,3F)XB(F,F)-F | (1-2-75) | 2% |
| 3-HBB(2F,3F)XNp(4F,5F,7F)-F | (1-4-37) | 2% |
| 2-HH-3 | (13-1) | 14% |
| 7-HB-1 | (13-5) | 10% |
| 5-HB-O2 | (13-5) | 8% |
| 3-HB(2F,3F)-O2 | (6-1) | 7% |
| 5-HB(2F,3F)-O2 | (6-1) | 15% |
| 3-HHB(2F,3CL)-O2 | (7-12) | 3% |
| 4-HHB(2F,3CL)-O2 | (7-12) | 3% |
| 5-HHB(2F,3CL)-O2 | (7-12) | 2% |
| 3-HH1OCro(7F,8F)-5 | (10-6) | 5% |
| 5-HBB(F)B-2 | (15-5) | 10% |
| 5-HBB(F)B-3 | (15-5) | 9% |

Example 16

| | | |
|---|---|---|
| 3-Np(1F,7F,8F)XB(F,F)-F | (1-1-5) | 5% |
| 1-BB-3 | (13-8) | 9% |
| 3-HH-V | (13-1) | 29% |
| 3-BB(2F,3F)-O2 | (6-3) | 11% |
| 2-HH1OB(2F,3F)-O2 | (7-5) | 19% |
| 3-HH1OB(2F,3F)-O2 | (7-5) | 13% |
| 3-HHB-1 | (14-1) | 8% |
| 2-BBB(2F)-5 | (14-8) | 6% |

Example 17

| | | |
|---|---|---|
| 3-B(2F,3F)NpXB(F,F)-F | (1-2-21) | 4% |
| 2-HH-3 | (13-1) | 6% |
| 3-HH-V1 | (13-1) | 10% |
| 1V2-HH-1 | (13-1) | 8% |
| 1V2-HH-3 | (13-1) | 7% |
| 3-BB(2F,3F)-O2 | (6-3) | 8% |
| 5-BB(2F,3F)-O2 | (6-3) | 4% |
| 3-H1OB(2F,3F)-O2 | (6-5) | 7% |
| 2-HH1OB(2F,3F)-O2 | (7-5) | 9% |
| 3-HH1OB(2F,3F)-O2 | (7-5) | 16% |
| 3-HDhB(2F,3F)-O2 | (7-3) | 6% |
| 3-HHB-1 | (14-1) | 3% |
| 3-HHB-3 | (14-1) | 2% |
| 2-BB(2F,3F)B-3 | (8-1) | 10% |

Example 18

| | | |
|---|---|---|
| 3-HNp(3F,4F,5F)XNp(4F,5F,7F)-F | (1-2-83) | 2% |
| 3-BB(2F,3F)XNp(4F,5F,7F)-CF3 | (1-2-63) | 2% |
| 1V2-BEB(F,F)-C | (5-15) | 5% |
| 3-HB-C | (5-1) | 7% |
| 2-BTB-1 | (13-10) | 10% |
| 5-HH-VFF | (13-1) | 30% |
| 3-HHB-1 | (14-1) | 4% |
| VFF-HHB-1 | (14-1) | 8% |
| VFF2-HHB-1 | (14-1) | 10% |
| 3-H2BTB-2 | (14-17) | 4% |
| 3-H2BTB-3 | (14-17) | 4% |
| 3-H2BTB-4 | (14-17) | 4% |

Example 19

| | | |
|---|---|---|
| 3-HB(2F,3F)XNp(4F,5F,7F)-F | (1-2-56) | 3% |
| 5-HB(F)B(F,F)XB(F,F)-F | (4-41) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 38% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-91) | 11% |
| 3-HHBB(F,F)-F | (4-6) | 3% |

Example 20

| | | |
|---|---|---|
| 1V2-B(2F,3F)BXNp(4F,5F,7F)-F | (1-3-72) | 3% |
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 40% |
| 3-HH-V1 | (13-1) | 7% |
| 3-HHEH-5 | (14-13) | 3% |
| 3-HHB-1 | (14-1) | 4% |
| V-HHB-1 | (14-1) | 4% |
| V2-BB(F)B-1 | (14-6) | 5% |
| 1V2-BB-F | (2-1) | 3% |
| 3-BB(F,F)XB(F,F)-F | (3-91) | 5% |
| 3-GB(F,F)XB(F,F)-F | (3-113) | 5% |
| 3-HHBB(F,F)-F | (4-6) | 3% |

Example 21

| | | |
|---|---|---|
| 3-HNp(3F,4F,5F)XNp(4F,5F,7F)-F | (1-2-83) | 2% |
| 3-Cro(7F,8F)NpB(F,F)XB(F,F)-F | (1-4-24) | 2% |
| 1V2-BEB(F,F)-C | (5-15) | 5% |
| 3-HB-C | (5-1) | 17% |
| 2-BTB-1 | (13-10) | 10% |
| 5-HH-VFF | (13-1) | 30% |
| 3-HHB-1 | (14-1) | 4% |
| VFF-HHB-1 | (14-1) | 8% |
| VFF2-HHB-1 | (14-1) | 10% |
| 3-H2BTB-2 | (14-17) | 4% |
| 3-H2BTB-3 | (14-17) | 4% |
| 3-H2BTB-4 | (14-17) | 4% |

Although the invention has been described and illustrated with a certain degree of particularity, it was understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention satisfies at least one of physical properties such as a high stability to heat, light and so forth, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds. A liquid crystal composition of the invention contains the compound, and satisfies at least one of physical properties such as a high maximum temperature, a low minimum temperature, a small viscosity, a suitable optical anisotropy, a large dielectric anisotropy, a large dielectric constant in a minor axis direction and a suitable elastic constant. The composition has a suitable balance regarding at least two of the physical properties. A liquid crystal display device of the invention includes the composition, and has a wide temperature range in which the device can be used, a short response time, a large voltage holding ratio, a low threshold voltage, a large contrast ratio, and a long service life. Accordingly, the device of the invention can be widely utilized in the liquid crystal display device such as a personal computer and a television.

What is claimed is:

1. A compound represented by formula (1):

(1)

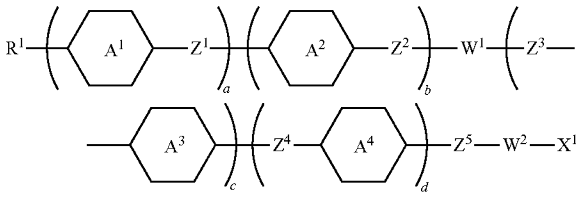

wherein, in formula (1), $R^1$ is alkyl having 1 to 15 carbons, in the alkyl, at least one of —$CH_2$— may be replaced by —O— or —S—, at least one of —$(CH_2)_2$— may be replaced by —CH═CH—, and in the groups, at least one of hydrogen may be replaced by halogen;

ring $A^1$, ring $A^2$, ring $A^3$ and ring $A^4$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, chroman-2,6-diyl, 2,3-dihydro-1H-indene-2,5-diyl, naphthalene-2,6-diyl, decahydronaphthalene-2,6-diyl or 1,2,3,4-tetrahydronaphthalene-2,6-diyl, and at least one of hydrogen directly bonded with the above rings may be replaced by halogen;

$W^1$ is a group represented by formula (1a) or formula (1b);

(1a)

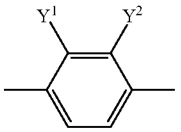

(1b)

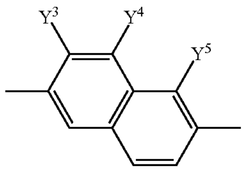

wherein, in formula (1a) and formula (1b), $Y^1$ and $Y^2$ are independently fluorine or chlorine, $Y^3$, $Y^4$ and $Y^5$ are independently hydrogen, fluorine or chlorine, and at least two of $Y^3$, $Y^4$ and $Y^5$ is fluorine or chlorine; and in formula (1), $W^2$ is a group represented by formula (1c) or formula (1d);

(1c)

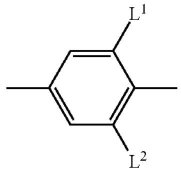

(1d)

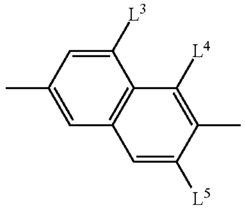

wherein, in formula (1c) and formula (1d), $L^1$, $L^2$, $L^3$, $L^4$ and $L^5$ are independently hydrogen, fluorine or chlorine; and in formula (1), when $W^1$ is represented by formula (1a) and $W^2$ is represented by formula (1c), at least one of ring $A^1$, ring $A^2$, ring $A^3$ and ring $A^4$ is naphthalene-2,6-diyl in which at least one of hydrogen may be replaced by halogen;

$X^1$ is fluorine, —C≡N, —N═C═S or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen was replaced by fluorine, or alkenyloxy having 2 to 9 carbons in which at least one of hydrogen is replaced by fluorine;

a, b, c and d are independently 0 or 1, and a sum of a, b, c and d is 0, 1, 2 or 3;

$Z^1$, $Z^2$, $Z^3$, $Z^4$ and $Z^5$ are independently a single bond or alkylene having 1-6 carbons, in the alkylene, at least one of —$CH_2$— may be replaced by —O—, —S—, —CO— or —$SiH_2$—, one or two of —$CH_2CH_2$— may be replaced by —CH═CH— or —C≡C—, and in the divalent groups, at least one of hydrogen may be replaced by fluorine or chlorine; and at least one of $Z^1$ in the case where a is 1, $Z^2$ in the case where b is 1, $Z^3$ in the case where c is 1, $Z^4$ in the case where d is 1, and $Z^5$ is —$CF_2O$—.

2. The compound according to claim 1, wherein, in formula (1) described in claim 1, $R^1$ is alkyl having 1 to 15 carbons, alkenyl having 2 to 15 carbons, alkoxy having 1 to 14 carbons or alkenyloxy having 2 to 14 carbons, and in the groups, at least one of hydrogen may be replaced by fluorine;

$X^1$ is fluorine, —C≡N, —N═C═S, —CHF, —$CHF_2$, —$CF_3$, —$(CH_2)_2$—F, —$CH_2CF_3$, —$CF_2CF_3$, —$(CH_2)_3$—F, —$(CH_2)_2$—$CF_3$, —$(CF_2)_3$—F, —$(CH_2)_4$—F, —$(CH_2)_3$—$CF_3$, —$(CF_2)_4$—F, —$(CF_2)_5$—F, —$(CF_2)_6$—F, —$(CF_2)_7$—F, —$OCH_2F$, —$OCHF_2$, —$OCF_3$, —O—$(CH_2)_2$—F, —$OCH_2CF_3$, —$OCF_2CF_3$, —O—$(CH_2)_3$—F, —O—$(CH_2)_2$—$CF_3$, —O—$(CF_2)_3$—F, —$O(CH_2)_4$—F, —O—$(CH_2)_3$—$CF_3$, —O—$(CF_2)_4$—F, —O—$(CF_2)_5$—F, —O—

$(CF_2)_6$—F, —CH═CHF, —CH═$CF_2$, —CF═CHF, —CF═$CF_2$, —CH═$CHCH_2F$, —CH═$CHCF_3$, —CF═$CHCF_3$, —CF═$CFCF_3$, —$(CH_2)_2$—CH═$CF_2$, —$(CH_2)_2$—CF═$CF_2$, —$(CH_2)_2$—CH═$CHCF_3$, —$(CH_2)_2$—CF═$CHCF_3$ or —$(CH_2)_2$—CF═$CFCF_3$; and $Z^1$, $Z^2$, $Z^3$, $Z^4$ and $Z^5$ are independently a single bond, —$(CH_2)_2$—, —$(CH_2)_4$—, —COO—, —OCO—, —$CH_2O$—, —$OCH_2$—, —$CF_2O$—, —$OCF_2$—, —CH═CH—, —CF═CF—, —C≡C—, —$(CH_2)_2$COO—, —OCO$(CH_2)_2$—, —$(CH_2)_2CF_2O$—, —$OCF_2(CH_2)_2$—, —$(CH_2)_3O$— or —$O(CH_2)_3$—.

3. The compound according to claim 1, wherein, in formula (1) described in claim 1, $R^1$ is alkyl having 1 to 10 carbons, alkenyl having 2 to 10 carbons, alkoxy having 1 to 9 carbons or alkenyloxy having 2 to 9 carbons, and in the groups, at least one of hydrogen may be replaced by fluorine; and $X^1$ is fluorine, —C≡N, —$CF_3$, —$CHF_2$, —$OCF_3$, —$OCHF_2$, —CH═$CHCF_3$, —CF═$CHCF_3$ or —CF═$CFCF_3$.

4. The compound according to claim 1, represented by any one of formulas (1-1) to (1-8):

(1-1)

$R^1—W^1—Z^5—W^2—X^1$ (1-2)

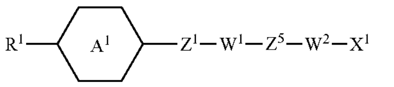

(1-3)

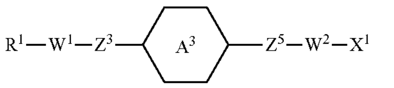

(1-4)

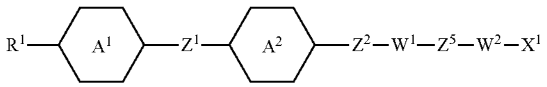

(1-5)

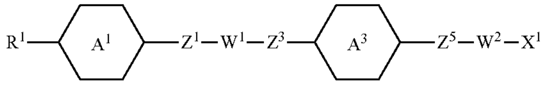

(1-6)

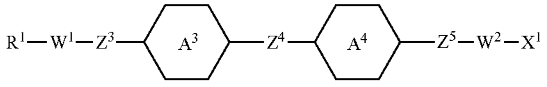

(1-7)

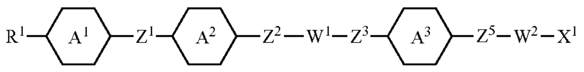

(1-8)

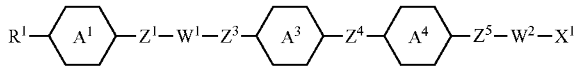

wherein, in formulas (1-1) to (1-8), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$W^1$ is a group represented by formula (1a) or formula (1b);

(1a)

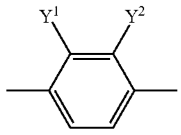

(1b)

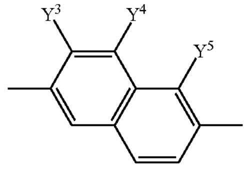

wherein, in formula (1a) and formula (1b), $Y^1$ and $Y^2$ are fluorine, $Y^3$, $Y^4$ and $Y^5$ are independently hydrogen or fluorine, and at least two of $Y^3$, $Y^4$ and $Y^5$ is fluorine; and in formulas (1-1) to (1-8), $W^2$ is a group represented by formula (1c) or formula (1d);

(1c)

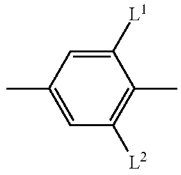

(1d)

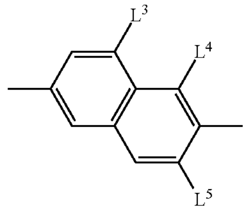

wherein, in formula (1c) and formula (1d), $L^1$, $L^2$, $L^3$, $L^4$ and $L^5$ are independently hydrogen or fluorine; and in formulas (1-1) to (1-8), when $W^1$ is represented by formula (1a) and $W^2$ is represented by formula (1c), at least one of ring $A^1$, ring $A^2$, ring $A^3$ and ring $A^4$ is naphthalene-2,6-diyl in which at least one of hydrogen may be replaced by halogen;

$Z^1$, $Z^2$, $Z^3$, $Z^4$ and $Z^5$ are independently a single bond, —$(CH_2)_2$—, —$(CH_2)_4$—, —COO—, —OCO—, —$CH_2O$—, —$OCH_2$—, —$CF_2O$—, —$OCF_2$—, —CH═CH—, —CF═CF—, —C≡C—, —$(CH_2)_2$COO—, —OCO$(CH_2)_2$—, —$(CH_2)_2CF_2O$—, —$OCF_2(CH_2)_2$—, —$(CH_2)_3O$— or —$O(CH_2)_3$—, and at least one of $Z^1$, $Z^2$, $Z^3$, $Z^4$ and $Z^5$ is —$CF_2O$—; and $X^1$ is fluorine, —$CF_3$, —$CHF_2$, —$OCF_3$ or —$OCHF_2$.

5. The compound according to claim 1, represented by any one of formulas (1-9) to (1-29):

(1-9)
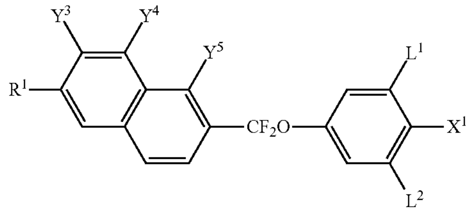
(1-10)
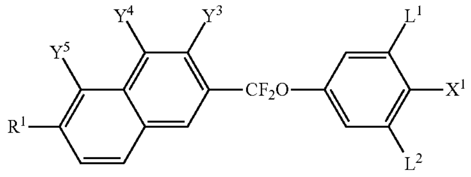
(1-11)
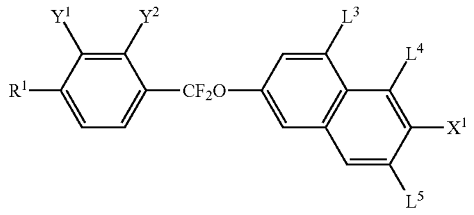
(1-12)
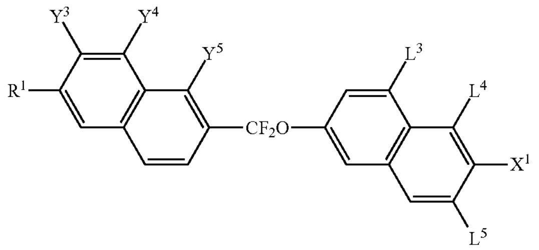
(1-13)
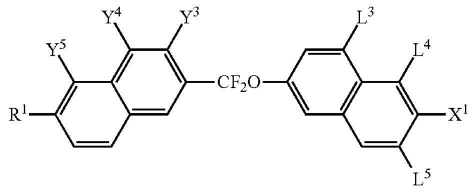
(1-14)
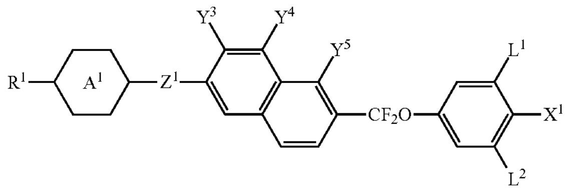
(1-15)
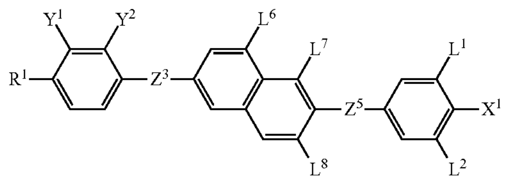
(1-16)
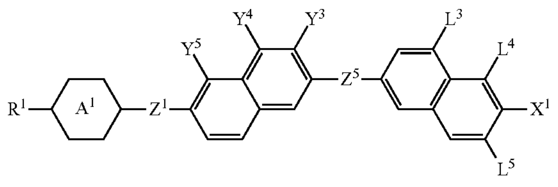
(1-17)
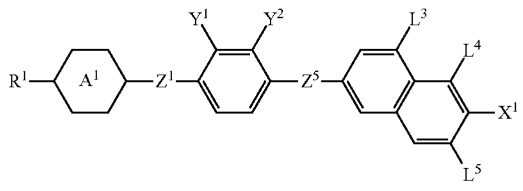
(1-18)
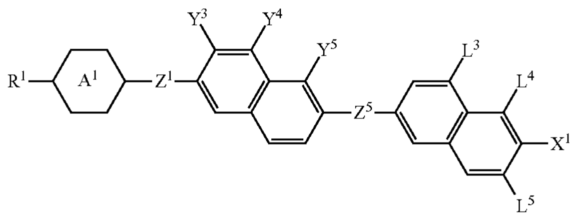
(1-19)
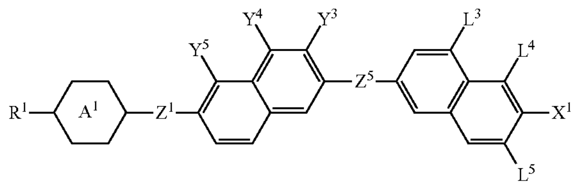
(1-20)
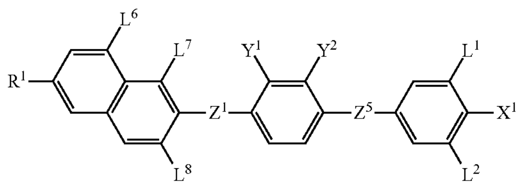
(1-21)
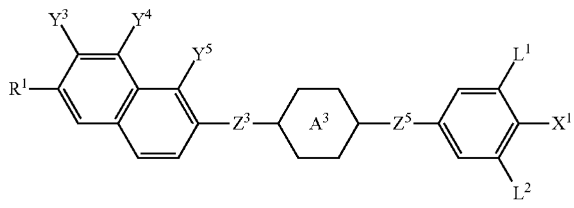
(1-22)
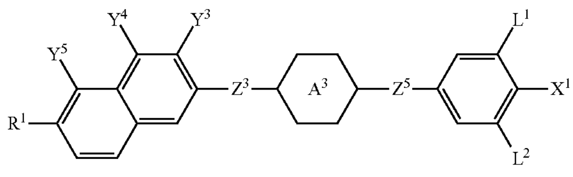

-continued (1-23)

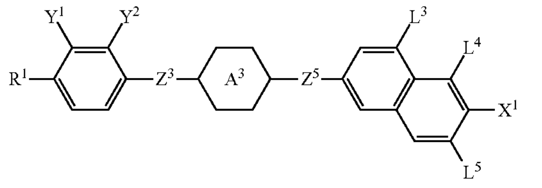

(1-24)

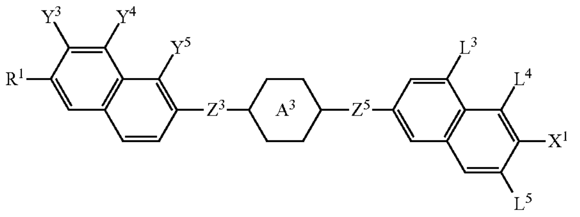

(1-25)

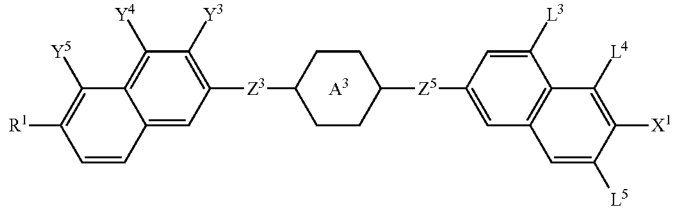

(1-26)

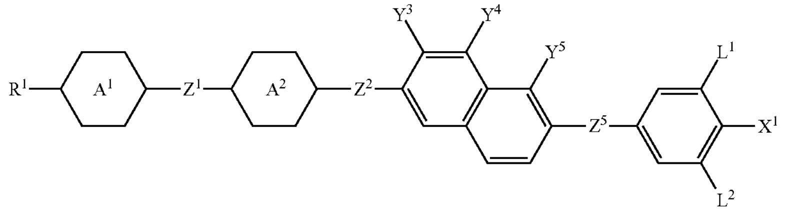

(1-27)

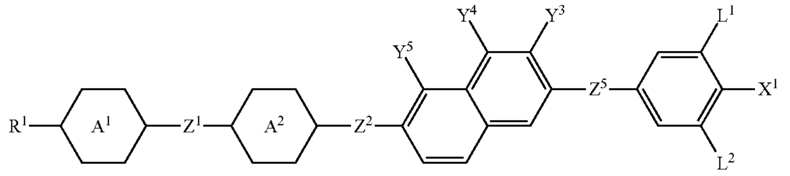

(1-28)

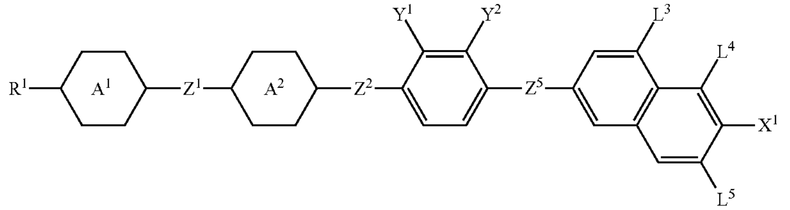

(1-29)

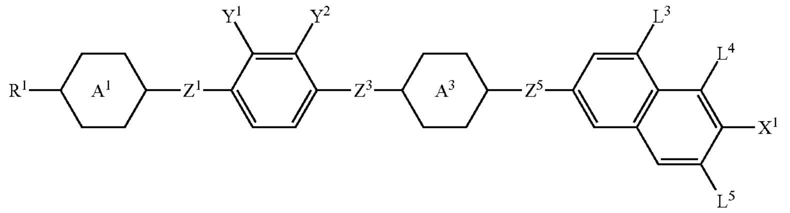

wherein, in formulas (1-9) to (1-29), $R^1$ is alkyl having 1 to 10 carbons or alkenyl having 2 to 10 carbons;

ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$Z^1$, $Z^2$, $Z^3$ and $Z^5$ are independently a single bond, $-(CH_2)_2-$, $-(CH_2)_4-$, $-COO-$, $-OCO-$, $-CH_2O-$, $-OCH_2-$, $-CF_2O-$, $-OCF_2-$, and at least one of $Z^1$, $Z^2$, $Z^3$ and $Z^5$ is $-CF_2O-$;

$X^1$ is fluorine, $-CF_3$ or $-OCF_3$; and $L^1$, $L^2$, $L^3$, $L^4$, $L^5$, $L^6$, $L^7$, $L^8$, $Y^1$, $Y^2$, $Y^3$, $Y^4$ and $Y^5$ are independently hydrogen or fluorine.

6. The compound according to claim 1, represented by any one of formulas (1-30) to (1-54):

(1-30)
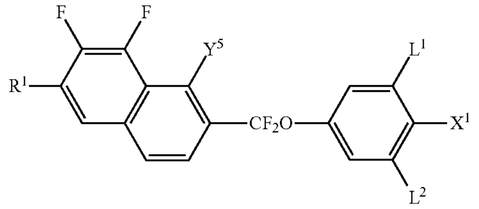
(1-32)
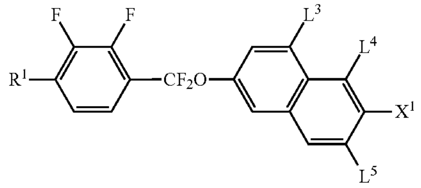
(1-34)
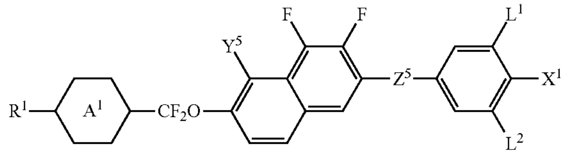
(1-36)
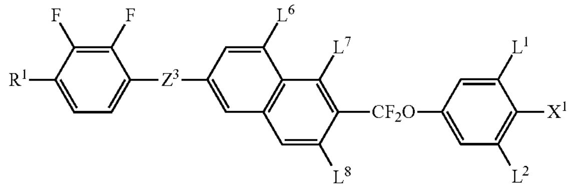
(1-38)
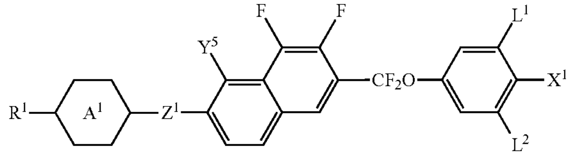
(1-40)
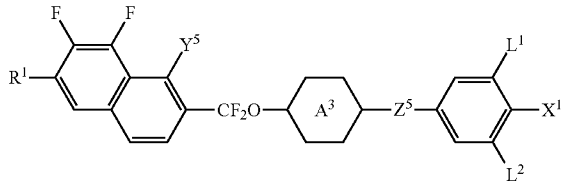
(1-42)
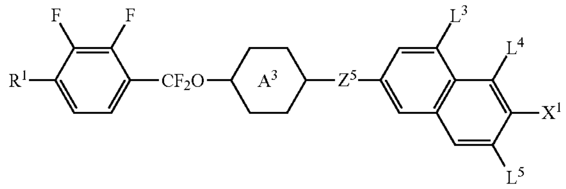
(1-31)
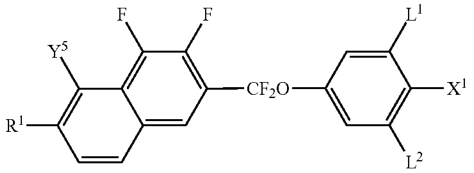
(1-3)
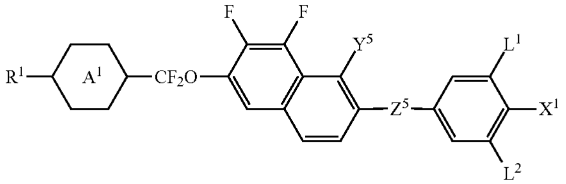
(1-35)
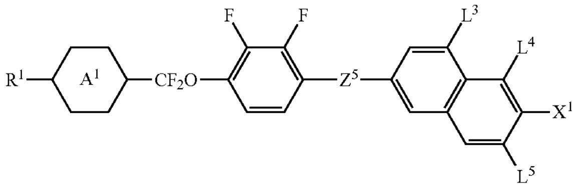
(1-37)
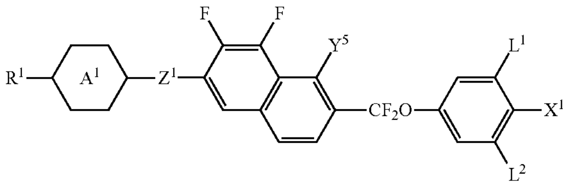
(1-39)
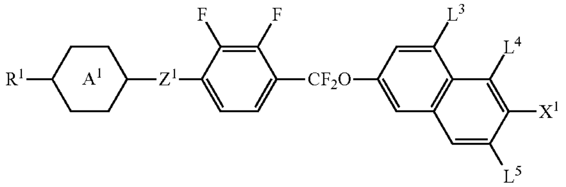
(1-41)
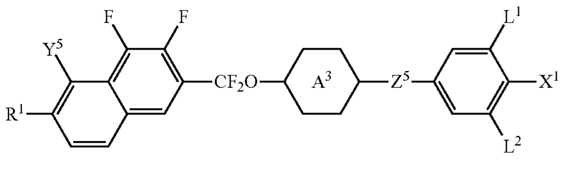
(1-43)
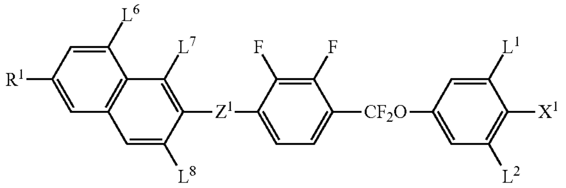

-continued
(1-44)
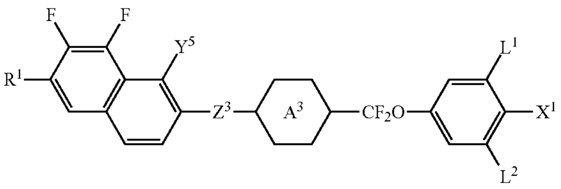
(1-45)
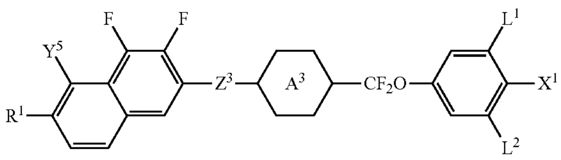
(1-46)
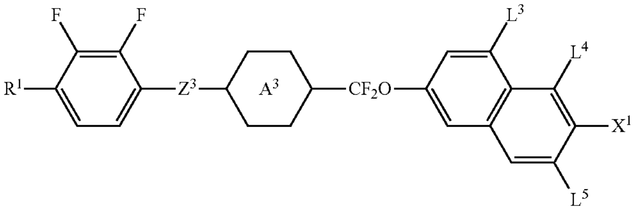
(1-47)
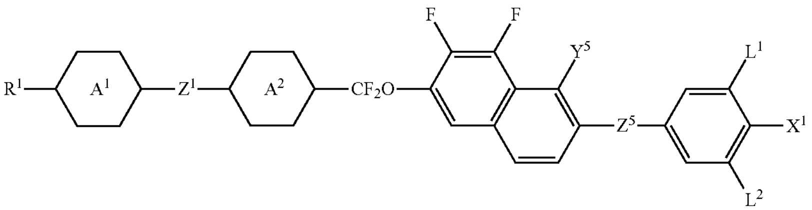
(1-48)
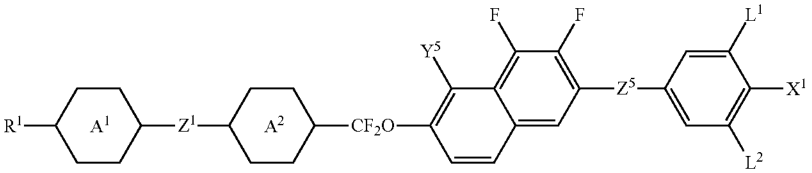
(1-49)
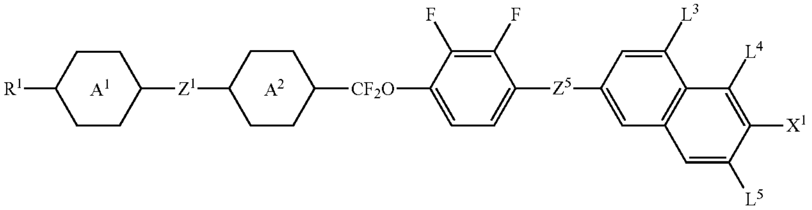
(1-50)
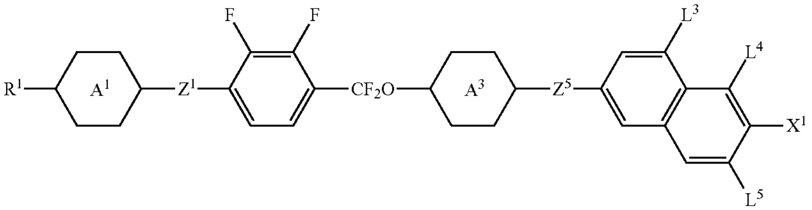
(1-51)
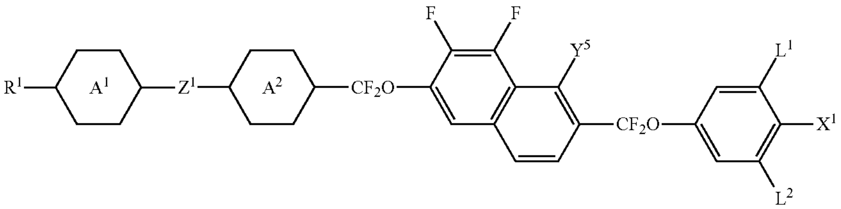

-continued (1-52)

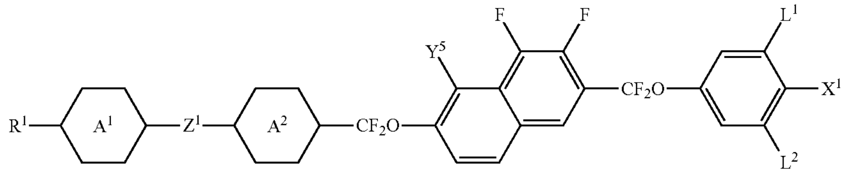

(1-53)

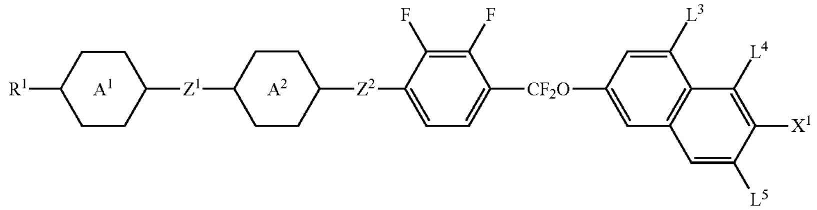

(1-54)

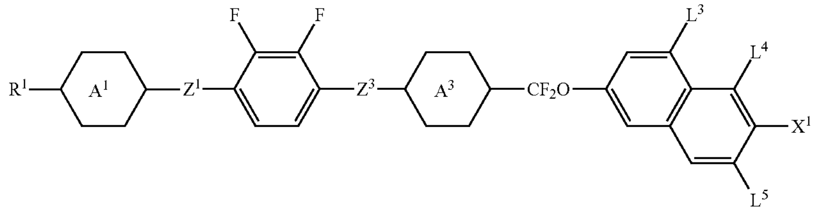

wherein, in formulas (1-30) to (1-54), $R^1$ is alkyl having 1 to 10 carbons or alkenyl having 2 to 10 carbons;

ring $A^1$, ring $A^2$ and ring $A^3$ are independently 1,4-cyclohexylene, 1,4-yclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$Z^1$, $Z^2$, $Z^3$ and $Z^5$ are independently a single bond, $—(CH_2)_2—$, —COO—, —OCO—, $—CH_2O—$, $—OCH_2—$, $—CF_2O—$ and $—OCF_2—$;

$X^1$ is fluorine, $—CF_3$ or $—OCF_3$; and $L^1$, $L^2$, $L^3$, $L^4$, $L^5$, $L^6$, $L^7$, $L^8$ and $Y^5$ are independently hydrogen or fluorine.

7. The compound according to claim 1, represented by any one of formulas (1-55) to (1-78):

(1-55)

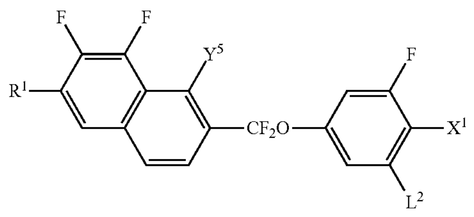

(1-56)

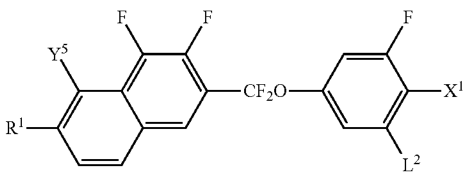

(1-57)

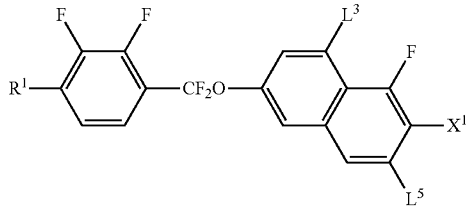

(1-58)

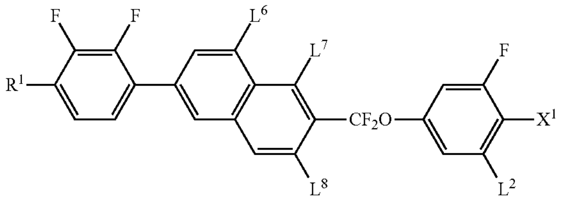

-continued
(1-59)
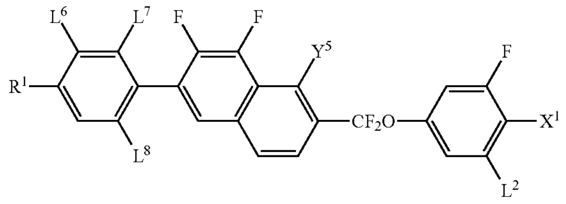
(1-60)
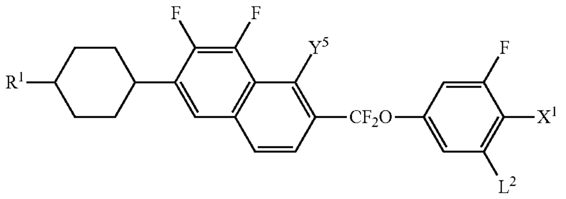
(1-61)
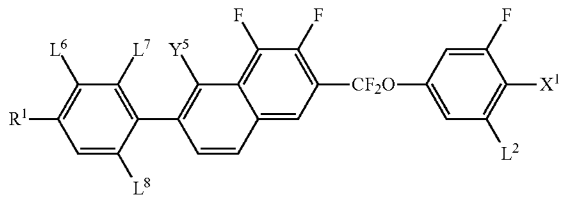
(1-62)
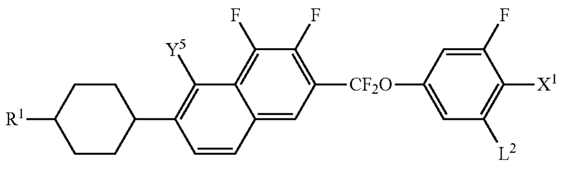
(1-63)
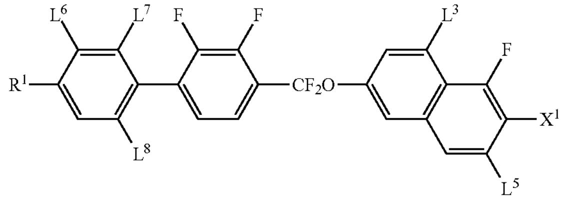
(1-64)
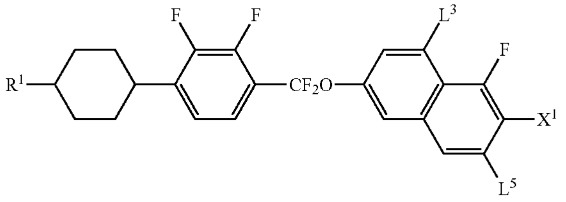
(1-65)
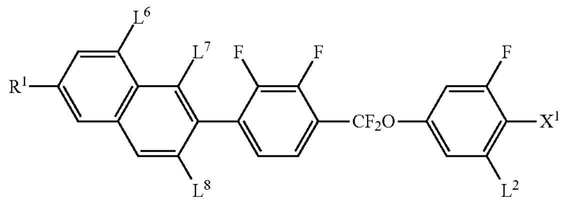
(1-66)
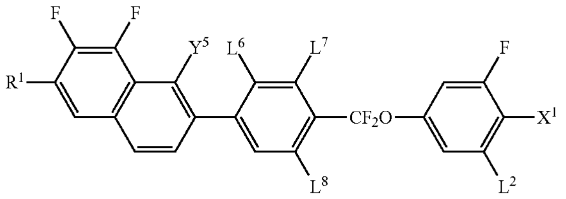
(1-67)
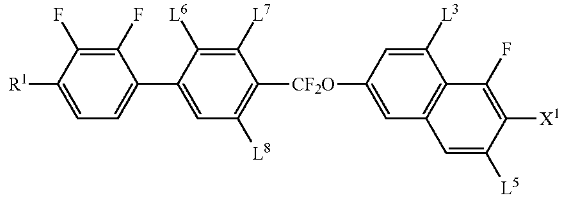
(1-68)
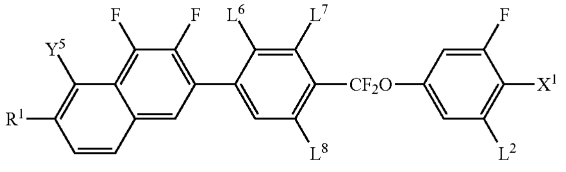
(1-69)
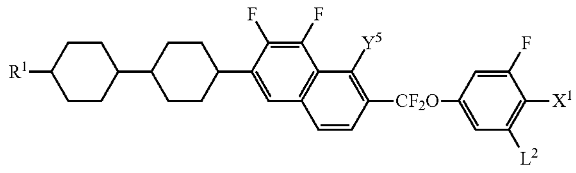
(1-70)
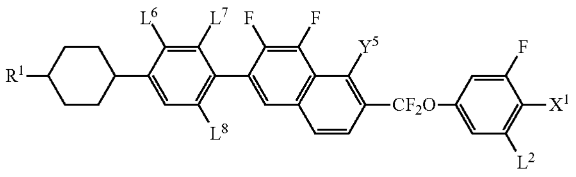
(1-71)
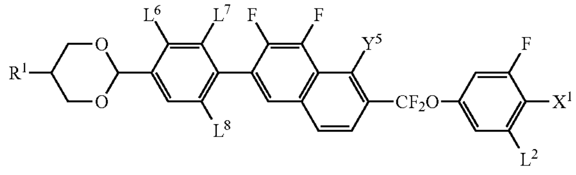
(1-72)
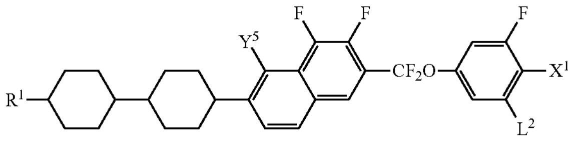

-continued
(1-73)
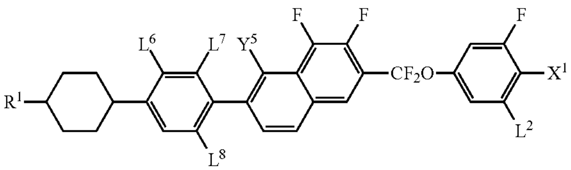
(1-74)
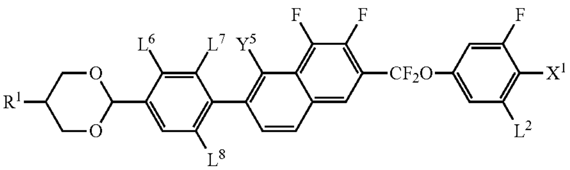
(1-75)
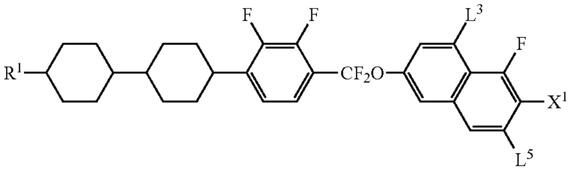
(1-76)
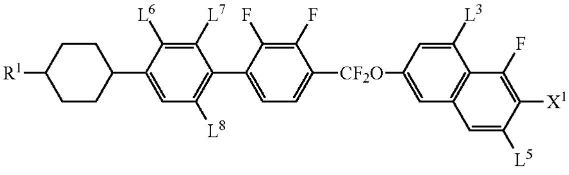
(1-77)
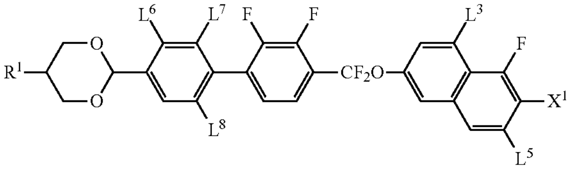
(1-78)
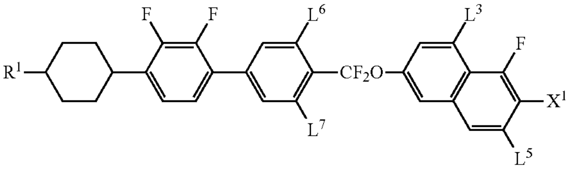
wherein, in formulas (1-55) to (1-78),
$R^1$ is alkyl having 1 to 10 carbons or alkenyl having 2 to 10 carbons;
$X^1$ is fluorine, —$CF_3$ or —$OCF_3$; and
$L^2$, $L^3$, $L^5$, $L^6$, $L^7$, $L^8$ and $Y^5$ are hydrogen or fluorine.
8. The compound according to claim 1, represented by any one of formulas (1-79) to (1-98):
(1-79)
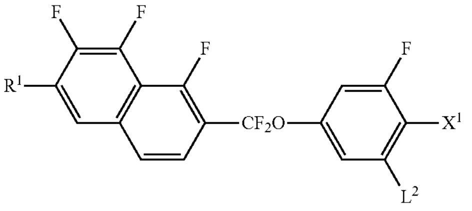
(1-80)
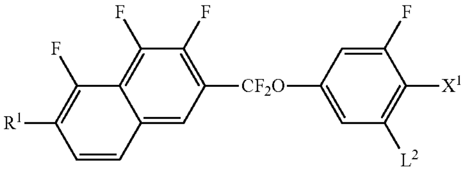
(1-81)
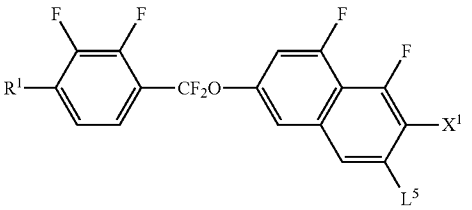
(1-82)
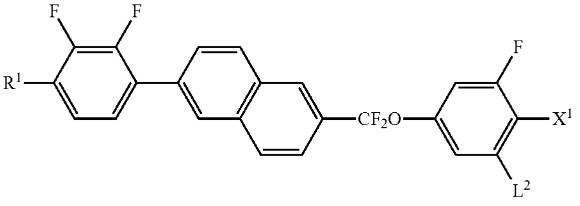
(1-83)
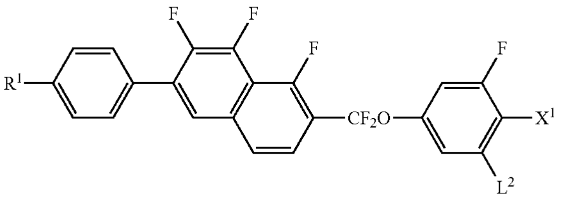
(1-84)
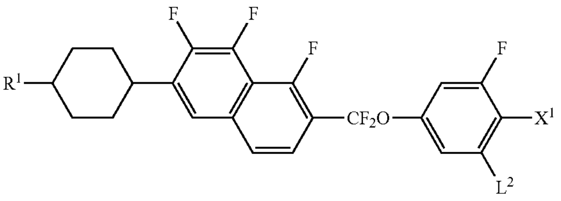

-continued (1-85)

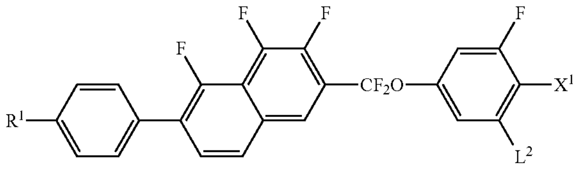

(1-86)

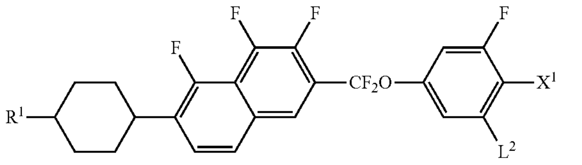

(1-87)

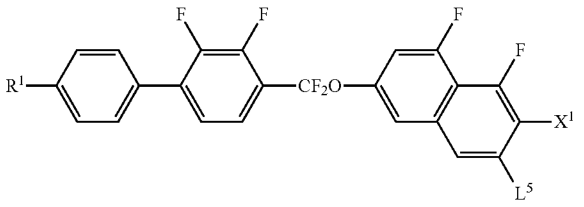

(1-88)

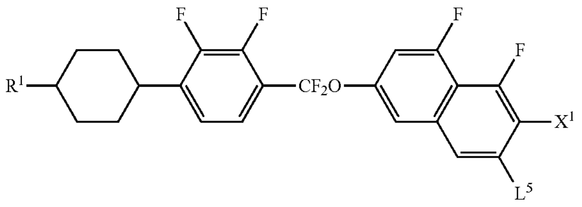

(1-89)

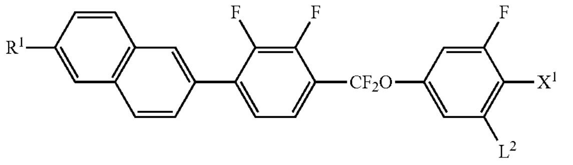

(1-90)

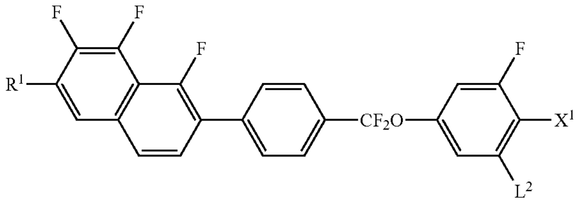

(1-91)

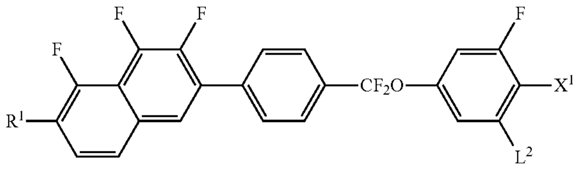

(1-92)

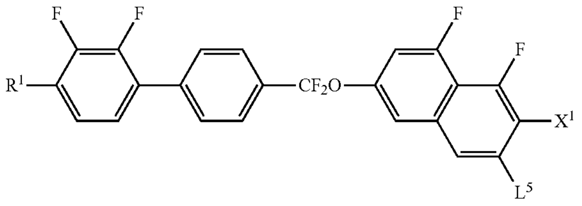

(1-93)

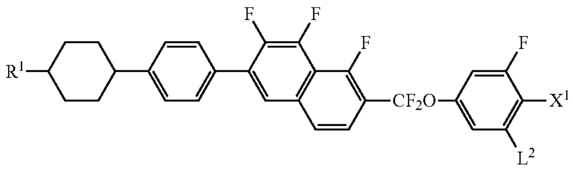

(1-94)

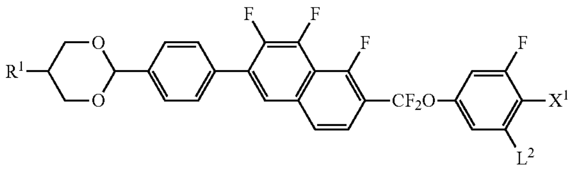

(1-95)

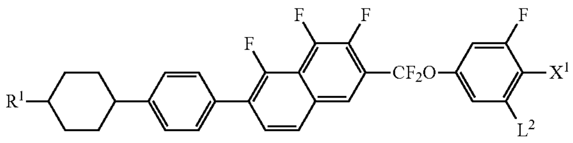

(1-96)

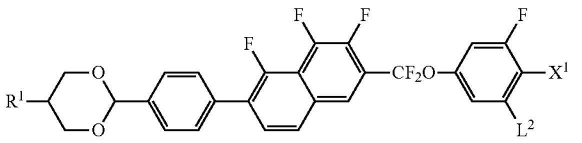

(1-97)

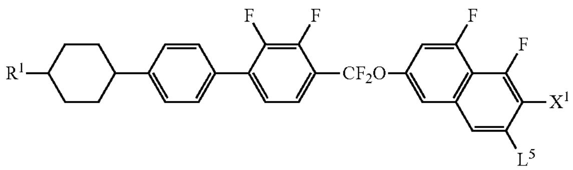

(1-98)

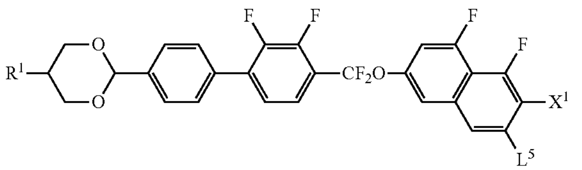

wherein, in formulas (1-79) to (1-98), $R^1$ is alkyl having 1 to 10 carbons or alkenyl having 2 to 10 carbons;

$X^1$ is fluorine, —$CF_3$ or —$OCF_3$; and $L^2$ and $L^5$ are hydrogen or fluorine.

9. A liquid crystal composition, containing at least one compound according to claim 1.

10. The liquid crystal composition according to claim 9, further containing at least one compound selected from the group of compounds represented by formulas (2) to (4):

(2)

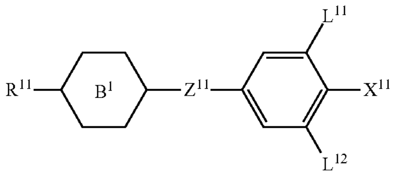

(3)

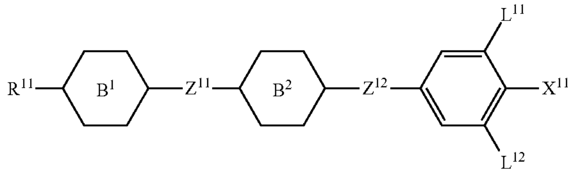

(4)

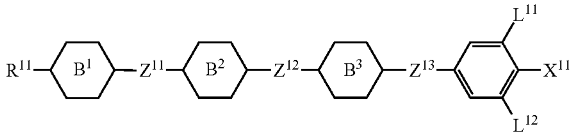

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine and at least one of $—CH_2—$ may be replaced by —O—;

$X^{11}$ is fluorine, chlorine, $—OCF_3$, $—OCHF_2$, $—CF_3$, $—CHF_2$, $—CH_2F$, $—OCF_2CHF_2$ or $—OCF_2CHFCF_3$;

ring $B^1$, ring $B^2$ and ring $B^3$ are independently 1,4-cyclohexylene, 1,4-phenylene, 2-fluoro-1,4-phenylene, 2,5-difluoro-1,4-phenylene, tetrahydropyran-2,5-diyl, 1,3-dioxane-2,5-diyl or pyrimidine-2,5-diyl;

$Z^{11}$, $Z^{12}$ and $Z^{13}$ are independently a single bond, $—CH_2CH_2—$, —CH═CH—, —C≡C—, —COO—, $—CF_2O—$, $—OCF_2—$, $—CH_2O—$ or $—(CH_2)_4—$; and $L^{11}$ and $L^{12}$ are independently hydrogen or fluorine.

11. The liquid crystal composition according to claim 9, further containing at least one compound selected from the group of compounds represented by formula (5):

(5)

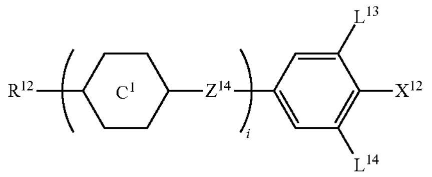

wherein, in formula (5), $R^{12}$ is alkyl having 1 to 10 carbons or alkenyl having 2 to 10 carbons, and in the alkyl and the alkenyl, at least one of hydrogen may be replaced by fluorine and at least one of $—CH_2—$ may be replaced by —O—;

$X^{12}$ is —C≡N or —C≡C—C≡N;

ring $C^1$ is 1,4-cyclohexylene, 1,4-phenylene, 2-fluoro-1,4-phenylene, 2,5-difluoro-1,4-phenylene, tetrahydropyran-2,5-diyl, 1,3-dioxane-2,5-diyl or pyrimidine-2,5-diyl;

$Z^{14}$ is a single bond, $—CH_2CH_2—$, —C≡C—, —COO—, $—CF_2O—$, $—OCF_2—$ or $—CH_2O—$;

$L^{13}$ and $L^{14}$ are independently hydrogen or fluorine; and i is 1, 2, 3 or 4.

12. The liquid crystal composition according claim 9, further containing at least one compound selected from the group of compounds represented by formulas (6) to (12):

(6)

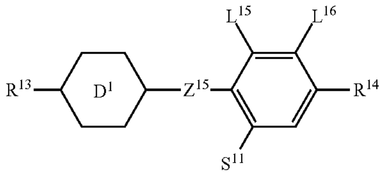

(7)

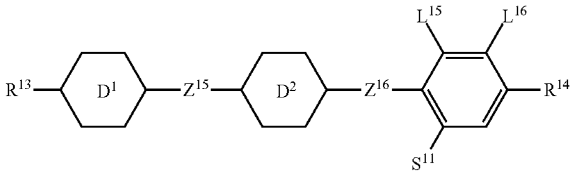

(8)

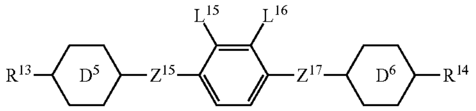

(9)

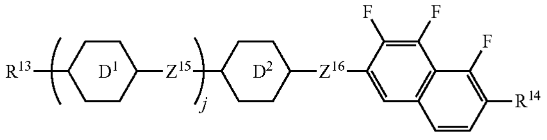

(10)

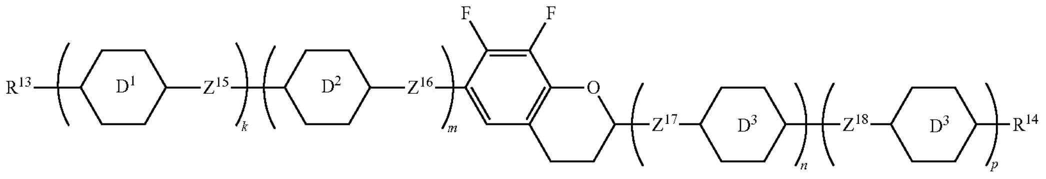

(11)

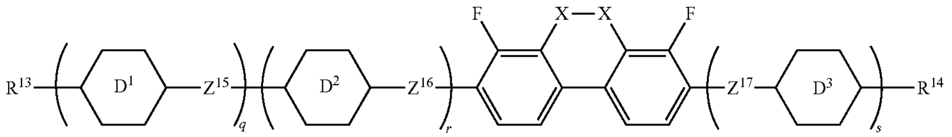

-continued (12)

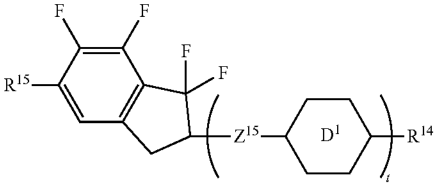

wherein, in formulas (6) to (12), $R^{13}$ and $R^{14}$ are independently alkyl having 1 to 10 carbons or alkenyl having 2 to 10 carbons, and in the alkyl and the alkenyl, at least one of $-CH_2-$ may be replaced by —O—;

$R^{15}$ is hydrogen, fluorine, alkyl having 1 to 10 carbons or alkenyl having 2 to 10 carbons, and in the alkyl and the alkenyl, at least one of $-CH_2-$ may be replaced by —O— and at least one of hydrogen may be replaced by fluorine;

$S^{11}$ is hydrogen or methyl;

X is $-CF_2-$, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, $-CH_2CH_2-$, —COO—, $-CH_2O-$, $-OCF_2-$ or $-OCF_2CH_2CH_2-$;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is independently 1, 2 or 3.

13. The liquid crystal composition according to claim 9, further containing at least one compound selected from the group of compounds represented by formulas (13) to (15):

(13)

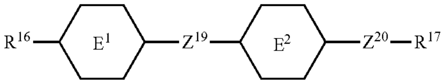

-continued (14)

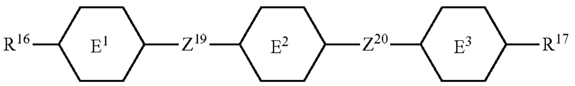

(15)

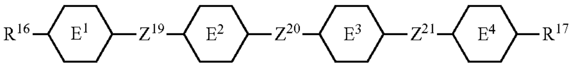

wherein, in formulas (13) to (15), $R^{16}$ and $R^{17}$ are independently alkyl having 1 to 10 carbons or alkenyl having 2 to 10 carbons, and in the alkyl or the alkenyl, at least one of $-CH_2-$ may be replaced by —O— and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, $-CH_2CH_2-$, —CH═CH—, —C≡C— or —COO—.

14. The liquid crystal composition according to claim 9, further containing at least one of a polymerizable compound, an optically active compound, an antioxidant, an ultraviolet light absorber, a light stabilizer, a heat stabilizer and an antifoaming agent.

15. A liquid crystal display device, including the liquid crystal composition according to claim 9.

* * * * *